United States Patent
Lu et al.

(10) Patent No.: US 11,186,830 B2
(45) Date of Patent: Nov. 30, 2021

(54) TUNING BACTERIOPHAGE HOST RANGE

(71) Applicant: Massachusetts Institute of Technology, Cambridge, MA (US)

(72) Inventors: Timothy Kuan-Ta Lu, Cambridge, MA (US); Hiroki Ando, Boston, MA (US); Sebastien Lemire, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/166,523

(22) Filed: Oct. 22, 2018

(65) Prior Publication Data

US 2019/0106683 A1   Apr. 11, 2019

Related U.S. Application Data

(63) Continuation of application No. 15/445,700, filed on Feb. 28, 2017, now abandoned, which is a continuation of application No. 14/478,657, filed on Sep. 5, 2014, now Pat. No. 9,617,522.

(60) Provisional application No. 61/873,901, filed on Sep. 5, 2013.

(51) Int. Cl.
*C12N 7/00* (2006.01)
*C12N 7/02* (2006.01)
*C12N 15/81* (2006.01)

(52) U.S. Cl.
CPC .................. *C12N 7/00* (2013.01); *C12N 7/02* (2013.01); *C12N 15/81* (2013.01); *C12N 2795/00011* (2013.01); *C12N 2795/00021* (2013.01)

(58) Field of Classification Search
None
See application file for complete search history.

(56) References Cited

U.S. PATENT DOCUMENTS

| | | |
|---|---|---|
| 7,485,426 B2 | 2/2009 | Harney et al. |
| 9,617,522 B2 | 4/2017 | Lu et al. |
| 2003/0216338 A1 | 11/2003 | Merril et al. |
| 2013/0122549 A1 | 5/2013 | Lu et al. |
| 2013/0184183 A1 | 7/2013 | Scholl et al. |
| 2017/0183634 A1 | 6/2017 | Lu et al. |

FOREIGN PATENT DOCUMENTS

| | | |
|---|---|---|
| WO | WO 99/24562 A1 | 5/1999 |
| WO | WO 02/07742 A2 | 1/2002 |

OTHER PUBLICATIONS

Yoichi et al., Journal of Biotechnology, 2005, 115:101-107. (Year: 2005).*

Ando et al., Engineering Modular Viral Scaffolds for Targeted Bacterial Population Editing. Cell Systems 2015; 1: 187-96.
Dunn et al., Complete nucleotide sequence of bacteriophage T7 DNA and the locations of T7 genetic elements. J Mol Biol. Jun. 5, 1983;166(4):477-535.
Garcia-Doval et al., Structure of the receptor-binding carboxy-terminal domain of bacteriophage T7 tail fibers. PNAS. 2012; 109(24): 9390-5.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gibson et al., One-step assembly in yeast of 25 overlapping DNA fragments to form a complete synthetic Mycoplasma genitalium genome. PNAS. 2008; 105(51): 20404-9, doi: 10.1073/pnas.0811011106.
Gibson, Oligonucleotide assembly in yeast to produce synthetic DNA fragments. Methods Mol Biol. 2012;852:11-21. doi: 10.1007/978-1-61779-564-0.sub.--2.
Heilpern et al., pIIICTX, a predicted CTXphi minor coat protein, can expand the host range of coliphage fd to include Vibrio cholerae. J Bacteriol. Feb. 2003;185(3):1037-44.
Jaschke et al., A fully decompressed synthetic bacteriophage øX174 genome assembled and archived in yeast. Virology. Dec. 20, 2012;434(2):278-84. doi: 10.1016/j.virol.2012.09.020. Epub Oct. 15, 2012.
Liang et al., Recombination-based DNA assembly and mutagenesis methods for metabolic engineering. Methods Mol Biol. 2012;834:93-109. doi: 10.1007/978-1-61779-483-4_8.
Lin et al., A T3 and T7 Recombinant Phage Acquires Efficient Adsorption and a Broader Host Range. PLoS One. 2012;7(2):e30954. doi: 10.1371/journal.pone.0030954. Epub Feb. 9, 2012.
Ma et al., Plasmid construction by homologous recombination in yeast. Gene. 1987;58(2-3):201-16.
Mahichi et al., Site-specific recombination of T2 phage using IP008 long tail fiber genes provides a targeted method for expanding host range while retaining lytic activity. FEMS Microbiol Lett. Jun. 2009;295(2):211-7. doi: 10.1111/j.1574-6968.2009.01588.x. Epub Apr. 21, 2009.
Marzari et al., Extending filamentous phage host range by the grafting of a heterologous receptor binding domain. Gene. Jan. 31, 1997 ;185(1):27-33.
Molineux, In: The Bacteriophages. Calendar, Ed. Oxford University Press. New York. 2006:277-301.
Overstreet et al., Self-made phage libraries with heterologous inserts in the Mtd of Bordetella bronchiseptica. Protein Eng Des Sel. Apr. 2012;25(4): 145-51. doi: 10.1093/protein/gzr068. Epub Jan. 27, 2012.
Pajunen et al., Complete nucleotide sequence and likely recombinatorial origin of bacteriophage T3. J Mol Biol. Jun. 21, 2002;319(5):1115-32.
Scholl et al., Bacteriophage K1-5 encodes two different tail fiber proteins, allowing it to infect and replicate on both K1 and K5 strains of *Escherichia coli*. J Virol. Mar. 2001;75(6):2509-15.
Steven et al., Molecular substructure of a viral receptor-recognition protein. The gpl7 tail-fiber of bacteriophage T7. J Mol Biol. Mar. 20, 1988;200(2):351-65.

(Continued)

*Primary Examiner* — Nicole Kinsey White
(74) *Attorney, Agent, or Firm* — Wolf, Greenfield & Sacks, P.C.

(57) ABSTRACT

Disclosed here are recombinant bacteriophages with tail fibers encoded by at least two subsets of genomic fragments from different bacteriophage having different host ranges.

12 Claims, 9 Drawing Sheets

Specification includes a Sequence Listing.

(56) References Cited

OTHER PUBLICATIONS

Sulakvelidze et al., Bacteriophage therapy. Antimicrob Agents Chemother. Mar. 2001;45(3):649-59.
Trojet et al., The gp38 adhesins of the T4 superfamily: a complex modular determinant of the phage's host specificity. Genome Biol Evol. 2011;3:674-86. doi: 10.1093/gbe/evr059. Epub Jul. 11, 2011.
Yoichi et al., Alteration of tail fiber protein gp38 enables T2 phage to infect *Escherichia coli* O157:H7. J Biotechnol. Jan. 12, 2005;115(1):101-7.
Yu et al., Leveraging the power of next-generation sequencing to generate interactome datasets. Nat Methods. 2011; 8(6): 478-80. Doi: 10.1038/nmeth.l597. Author manuscript.

\* cited by examiner adsorption efficiency (%) =
[1-(pfu of unadsorbed phage/ original pfu in the BL21-phage mixture)] × 100

Synthetic phages from PCR products:
synT3_WT    synT3_T7tail
synT7_WT    synT7_T3tail

SEQUENCE LISTING

<160> NUMBER OF SEQ ID NOS: 90

<210> SEQ ID NO 1
<211> LENGTH: 39937
<212> TYPE: DNA
<213> ORGANISM: Artificial Sequence
<220> FEATURE:
<223> OTHER INFORMATION: Synthetic Polynucleotide

<400> SEQUENCE: 1

```
tctcacagtg tacggaccta aagttccccc ataggggta cctaaagccc agccaatcac      60
ctaaagtcaa ccttcggttg accttgaggg ttccctaagg gttggggatg acccttgggt     120
```

```
ttgtctttgg gtgttacctt gagtgtctct ctgtgtccct atctgttaca gtctcctaaa      180
gtatcctcct aaagtcacct cctaacgtcc atcctaaagc caacacctaa agcctacacc      240
taaagaccca tcaagtcaac gcctatctta aagtttaaac ataaagacca gacctaaaga      300
ccagacctaa agacactaca taaagaccag acctaaagac gccttgttgt tagccataaa      360
gtgataacct ttaatcattg tctttattaa tacaactcac tataaggaga gacaacttaa      420
agagacttaa aagattaatt taaaatttat caaaaagagt attgacttaa agtctaacct      480
ataggatact tacagccatc gagagggaca cggcgaatag ccatcccaat cgacaccggg      540
gtcaaccgga taagtagaca gcctgataag tcgcacgaaa aacaggtatt gacaacatga      600
agtaacatgc agtaagatac aaatcgctag gtaacactag cagcgtcaac cgggcgcaca      660
gtgccttcta ggtgacttaa gcgcaccacg gcacataagg tgaaacaaaa cggttgacaa      720
catgaagtaa acacggtacg atgtaccaca tgaaacgaca gtgagtcacc acactgaaag      780
gtgatgcggt ctaacgaaac ctgacctaag acgctcttta acaatctggt aaatagctct      840
tgagtgcatg actagcggat aactcaaggg tatcgcaagg tgccctttat gatattcact      900
aataactgca cgaggtaaca caagatggct atgtctaaca tgacttacaa caacgttttc      960
gaccacgctt acgaaatgct gaaagaaaac atccgttatg atgacatccg tgacactgat     1020
gacctgcacg atgctattca catggctgcc gataatgcag ttccgcacta ctacgctgac     1080
atctttagcg taatggcaag tgagggcatt gaccttgagt tcgaagactc tggtctgatg     1140
cctgacacca aggacgtaat ccgcatcctg caagcgcgta tctatgagca attaacgatt     1200
gacctctggg aagacgcaga agacttgctc aatgaatact tggaggaagt cgaggagtac     1260
gaggaggatg aagagtaatg tctactacca acgtgcaata cggtctgacc gctcaaactg     1320
tacttttcta tagcgacatg gtgcgctgtg gctttaactg gtcactcgca atggcacagc     1380
tcaaagaact gtacgaaaac aacaaggcaa tagctttaga atctgctgag tgatagactc     1440
aaggtcgctc ctagcgagtg gcctttatga ttatcacttt acttatgagg gagtaatgta     1500
tatgcttact atcggtctac tcaccgctct aggtctagct gtaggtgcat cctttgggaa     1560
ggctttaggt gtagctgtag gttcctactt taccgcttgc atcatcatag gaatcatcaa     1620
agggcactta cgcaaatgat gaagcactac gttatgccaa tccacacgtc caacggggca     1680
accgtatgta cacctgatgg gttcgcaatg aaacaacgaa tcgaacgcct taagcgtgaa     1740
ctccgcatta accgcaagat taacaagata ggttccggct atgacagaac gcactgatgg     1800
cttaaagaaa ggttatatgc ccaatggcac actatacgct gcaaatcggc gaatagtgag     1860
aacttggcga gagaacaacc tcgaacgccg caaggacaag agagggcggc gtggcataga     1920
cgaaaggaaa aggttaaagc caagaaactc gccgcacttg aacaggcact agccaacaca     1980
ctgaacgcta tctcataacg aacataaagg acacaatgca atgaacatta ccgacatcat     2040
gaacgctatc gacgcaatca aagcactgcc aatctgtgaa cttgacaagc gtcaaggtat     2100
gcttatcgac ttactggtcg agatggtcaa cagcgagacg tgtgatggcg agctaaccga     2160
actaaatcag gcacttgagc atcaagattg gtggactacc ttgaagtgtc tcacggctga     2220
cgcagggttc aagatgctcg gtaatggtca cttctcggct gcttatagtc acccgctgct     2280
acctaacaga gtgattaagg tgggctttaa gaaagaggat tcaggcgcag cctataccgc     2340
attctgccgc atgtatcagg gtcgtcctgg tatccctaac gtctacgatg tacagcgcca     2400
cgctggatgc tatacggtgg tacttgacgc acttaaggat tgcgagcgtt tcaacaatga     2460
```

-continued

```
tgcccattat aaatacgctg agattgcaag cgacatcatt gattgcaatt cggatgagca    2520
tgatgagtta actggatggg atggtgagtt tgttgaaact tgtaaactaa tccgcaagtt    2580
ctttgagggc atcgcctcat tcgacatgca tagcgggaac atcatgttct caaatggaga    2640
cgtaccatac atcaccgacc cggtatcatt ctcgcagaag aaagacggtg gcgcattcag    2700
catcgaccct gaggaactca tcaaggaagt cgaggaagtc gcacgacaga aagaaattga    2760
ccgcgctaag gcccgtaaag aacgtcacga ggggcgctta gaggcacgca gattcaaacg    2820
tcgcaaccgc aaggcacgta agcacacaa agctaagcgc gaaagaatgc ttgctgcgtg    2880
gcgatgggct gaacgtcaag aacggcgtaa ccatgaggta gctgtagatg tactaggaag    2940
aaccaataac gctatgctct gggtcaacat gttctctggg gactttaagg cgcttgagga    3000
acgaatcgcg ctgcactggc gtaatgctga ccggatggct atcgctaatg gtcttacgct    3060
caacattgat aagcaacttg acgcaatgtt aatgggctga tagtcttatc ttacaggtca    3120
tctgcgggtg gcctgaatag gtacgattta ctaactggaa gaggcactaa atgaacacga    3180
ttaacatcgc taagaacgac ttctctgaca tcgaactggc tgctatcccg ttcaacactc    3240
tggctgacca ttacggtgag cgtttagctc gcgaacagtt ggcccttgag catgagtctt    3300
acgagatggg tgaagcacgc ttccgcaaga tgtttgagcg tcaacttaaa gctggtgagg    3360
ttgcggataa cgctgccgcc aagcctctca tcactaccct actccctaag atgattgcac    3420
gcatcaacga ctggtttgag gaagtgaaag ctaagcgcgg caagcgcccg acagccttcc    3480
agttcctgca agaaatcaag ccggaagccg tagcgtacat caccattaag accactctgg    3540
cttgcctaac cagtgctgac aatacaaccg ttcaggctgt agcaagcgca atcggtcggg    3600
ccattgagga cgaggctcgc ttcggtcgta tccgtgacct tgaagctaag cacttcaaga    3660
aaaacgttga ggaacaactc aacaagcgcg tagggcacgc ctacaagaaa gcatttatgc    3720
aagttgtcga ggctgacatg ctctctaagg gtctactcgg tggcgaggcg tggtcttcgt    3780
ggcataagga agactctatt catgtaggag tacgctgcat cgagatgctc attgagtcaa    3840
ccggaatggt tagcttacac cgccaaaatg ctggcgtagt aggtcaagac tctgagacta    3900
tcgaactcgc acctgaatac gctgaggcta tcgcaacccg tgcaggtgcg ctggctggca    3960
tctctccgat gttccaacct tgcgtagttc ctcctaagcc gtggactggc attactggtg    4020
gtggctattg ggctaacggt cgtcgtcctc tggcgctggt gcgtactcac agtaagaaag    4080
cactgatgcg ctacgaagac gtttacatgc ctgaggtgta caaagcgatt aacattgcgc    4140
aaaacaccgc atgaaaatc aacaagaaag tcctagcggt cgccaacgta atcaccaagt    4200
ggaagcattg tccggtcgag gacatccctg cgattgagcg tgaagaactc ccgatgaaac    4260
cggaagacat cgacatgaat cctgaggctc tcaccgcgtg gaaacgtgct gccgctgctg    4320
tgtaccgcaa ggacaaggct cgcaagtctc gccgtatcag ccttgagttc atgcttgagc    4380
aagccaataa gtttgctaac cataaggcca tctggttccc ttacaacatg gactggcgcg    4440
gtcgtgttta cgctgtgtca atgttcaacc cgcaaggtaa cgatatgacc aaaggactgc    4500
ttacgctggc gaaaggtaaa ccaatcggta aggaaggtta ctactggctg aaaatccacg    4560
gtgcaaactg tgcgggtgtc gataaggttc cgttccctga cgcatcaag ttcattgagg    4620
aaaaccacga gaacatcatg gcttgcgcta agtctccact ggagaacact ggtgggctg    4680
agcaagattc tccgttctgc ttccttgcgt tctgctttga gtacgctggg gtacagcacc    4740
acggcctgag ctataactgc tcccttccgc tggcgtttga cgggtcttgc tctgcatcc    4800
agcacttctc cgcgatgctc cgagatgagg taggtggtcg cgcggttaac ttgcttccta    4860
```

```
gtgaaaccgt tcaggacatc tacgggattg ttgctaagaa agtcaacgag attctacaag   4920
cagacgcaat caatgggacc gataacgaag tagttaccgt gaccgatgag aacactggtg   4980
aaatctctga gaaagtcaag ctgggcacta aggcactggc tggtcaatgg ctggcttacg   5040
gtgttactcg cagtgtgact aagcgttcag tcatgacgct ggcttacggg tccaaagagt   5100
tcggcttccg tcaacaagtg ctggaagata ccattcagcc agctattgat tccggcaagg   5160
gtctgatgtt cactcagccg aatcaggctg ctggatacat ggctaagctg atttgggaat   5220
ctgtgagcgt gacggtggta gctgcggttg aagcaatgaa ctggcttaag tctgctgcta   5280
agctgctggc tgctgaggtc aaagataaga agactggaga gattcttcgc aagcgttgcg   5340
ctgtgcattg ggtaactcct gatggtttcc ctgtgtggca ggaatacaag aagcctattc   5400
agacgcgctt gaacctgatg ttcctcggtc agttccgctt acagcctacc attaacacca   5460
acaaagatag cgagattgat gcacacaaac aggagtctgg tatcgctcct aactttgtac   5520
acagccaaga cggtagccac cttcgtaaga ctgtagtgtg ggcacacgag aagtacggaa   5580
tcgaatcttt tgcactgatt cacgactcct tcggtaccat tccggctgac gctgcgaacc   5640
tgttcaaagc agtgcgcgaa actatggttg acacatatga gtcttgtgat gtactggctg   5700
atttctacga ccagttcgct gaccagttgc acgagtctca attggacaaa atgccagcac   5760
ttccggctaa aggtaacttg aacctccgtg acatcttaga gtcggacttc gcgttcgcgt   5820
aacgccaaat caatacgact cactatagag ggacaaactc aaggtcattc gcaagagtgg   5880
cctttatgat tgaccttctt ccggttaata cgactcacta taggagaacc ttaaggttta   5940
actttaagac ccttaagtgt taattagaga tttaaattaa agaattacta agagaggact   6000
ttaagtatgc gtaacttcga aaagatgacc aaacgttcta accgtaatgc tcgtgacttc   6060
gaggcaacca aaggtcgcaa gttgaataag actaagcgtg accgctctca caagcgtagc   6120
tgggagggtc agtaagatgg gacgtttata tagtggtaat ctggcagcat tcaaggcagc   6180
aacaaacaag ctgttccagt tagacttagc ggtcatttat gatgactggt atgatgccta   6240
tacaagaaaa gattgcatac ggttacgtat tgaggacagg agtggaaacc tgattgatac   6300
tagcaccttc taccaccacg acgaggacgt tctgttcaat atgtgtactg attggttgaa   6360
ccatatgtat gaccagttga aggactggaa gtaatacgac tcagtatagg acaatgctt    6420 aaggtcgctc tctaggagtg gccttagtca tttaaccaat aggagataaa cattatgatg   6480
aacattaaga ctaacccgtt taaagccgtg tctttcgtag agtctgccat taagaaggct   6540
ctggataacg ctgggtatct tatcgctgaa atcaagtacg atggtgtacg cgggaacatc   6600 tgccgtagaca atactgctaa cagttactgg ctctctcgtg tatctaaaac gattccggca   6660
ctggagcact taaacgggtt tgatgttcgc tggaagcgtc tactgaacga tgaccgttgc   6720
ttctacaaag atggctttat gcttgatggg gaactcatgg tcaagggcgt agactttaac   6780
acagggtccg gcctactgcg taccaaatgg actgacacga agaaccaaga gttccatgaa   6840
gagttattcg ttgaaccaat ccgtaagaaa gataaagttc cctttaagct gcacactgga   6900
caccttcaca taaaactgta cgctatcctc ccgctgcaca tcgtggagtc tggagaagac   6960
tgtgatgtca tgacgttgct catgcaggaa cacgttaaga acatgctgcc tctgctacag   7020
gaatacttcc ctgaaatcga atggcaagcg gctgaatctt acgaggtcta cgatatggta   7080
gaactacagc aactgtacga gcagaagcga gcagaaggcc atgagggtct cattgtgaaa   7140
gacccgatgt gtatctataa gcgcggtaag aaatctggct ggtggaaaat gaaacctgag   7200
```

```
aacgaagctg acggtatcat tcagggtctg gtatggggta caaaaggtct ggctaatgaa    7260
ggtaaagtga ttggttttga ggtgcttctt gagagtggtc gtttagttaa cgccacgaat    7320
atctctcgcg ccttaatgga tgagttcact gagacagtaa aagaggccac cctaagtcaa    7380
tggggattct ttagcccata cggtattggc gacaacgatg cttgtactat taacccttac    7440
gatggctggg cgtgtcaaat tagctacatg gaggaaacac ctgatggctc tttgcggcac    7500
ccatcgttcg taatgttccg tggcaccgag gacaaccctc aagagaaaat gtaatcacac    7560
tggctcacct tcgggtgggc cttttctgcgt ttataaggag acactttatg tttaagaagg    7620
ttggtaaatt ccttgcggct ttggcagcta tcctgacgct tgcgtatatt cttgcggtat    7680
accctcaagt agcactagta gtagttggcg cttgttactt agcggcagtg tgtgcttgcg    7740
tgtggagtat agttaactgg taatacgact cactaaagga ggtacacacc atgatgtact    7800
taatgccatt actcatcgtc attgtaggat gccttgcgct ccactgtagc gatgatgata    7860
tgccagatgg tcacgcttaa tacgactcac taaaggagac actatatgtt tcgacttcat    7920
tacaacaaaa gcgttaagaa tttcacggtt cgccgtgctg accgttcaat cgtatgtgcg    7980
agcgagcgcc gagctaagat acctcttatt ggtaacacag ttcctttggc accgagcgtc    8040
cacatcatta tcacccgtgg tgactttgag aaagcaatag acaagaaacg tccggttctt    8100
agtgtggcag tgacccgctt cccgttcgtc cgtctgttac tcaaacgaat caaggaggtg    8160
ttctgatggg actgttagat ggtgaagcct gggaaaaaga aaacccgcca gtacaagcaa    8220
ctgggtgtat agcttgctta gagaaagatg accgttatcc acacacctgt aacaaaggag    8280
ctaacgatat gaccgaacgt gaacaagaga tgatcattaa gttgatagac aataatgaag    8340
gtcgcccaga tgatttgaat ggctgcggta ttctctgctc caatgtccct tgccacctct    8400
gccccgcaaa taacgatcaa aagataaacct taggtgaaat ccgagcgatg gacccacgta    8460
aaccacatct gaataaacct gaggtaactc ctacagatga ccagccttcc gctgagacaa    8520
tcgaaggtgt cactaagcct tcccactaca tgctgtttga cgacattgag gctatcgaag    8580
tgattgctcg ttcaatgacc gttgagcagt tcaagggata ctgcttcggt aacatcttaa    8640
agtacagact acgtgctggt aagaagtcag agttagcgta cttagagaaa gacctagcga    8700
aagcagactt ctataaagaa ctctttgaga aacataagga taaatgttat gcataacttc    8760
aagtcaaccc cacctgccga cagcctatct gatgacttca catcttgctc agagtggtgc    8820
cgaaagatgt gggaagagac attcgacgat gcgtacatca agctgtatga actttggaaa    8880
tcgagaggtc aatgactatg tcaaacgtaa atacaggttc acttagtgtg gacaataaga    8940
agttttgggc taccgtagag tcctcggagc attccttcga ggttccaatc tacgctgaga    9000
ccctagacga agctctggag ttagccgaat ggcaatacgt tccggctggc tttgaggtta    9060
ctcgtgtgcg tccttgtgta gcaccgaagt aatacgactc actattaggg aagactccct    9120
ctgagaaacc aaacgaaacc taaggagat taacattatg gctaagaaga ttttcacctc    9180
tgcgctgggt accgctgaac cttacgctta catcgccaag ccggactacg gcaacgaaga    9240
gcgtggcttt gggaaccctc gtggtgtcta taagttgac ctgactattc caacaaaga    9300
cccgcgctgc cagcgtatgg tcgatgaaat cgtgaagtgt cacgaagagg cttatgctgc    9360
tgccgttgag gaatacgaag ctaatccacc tgctgtagct cgtggtaaga accgctgaa    9420
accgtatgag ggtgacatgc cgttcttcga taacggtgac ggtacgacta cctttaagtt    9480
caaatgctac gcgtctttcc aagacaagaa gaccaaagag accaagcaca tcaatctggt    9540
tgtggttgac tcaaaaggta agaagatgga agacgttccg attatcggtg gtggctctaa    9600
```

```
gctgaaagtt aaatattctc tggttccata caagtggaac actgctgtag gtgcgagcgt   9660
taagctgcaa ctggaatccg tgatgctggt cgaactggct acctttggtg gcggtgaaga   9720
cgattgggct gacgaagttg aagagaacgg ctatgttgcc tctggttctg ccaaagcgag   9780
caaaccacgc gacgaagaaa gctgggacga agacgacgaa gagtccgagg aagcagacga   9840
agacggagac ttctaagtgg aactgcggga gaaaatcctt gagcgaatca aggtgacttc   9900
ctctgggtgt tgggagtggc agggcgctac gaacaataaa gggtacgggc aggtgtggtg   9960
cagcaatacc ggaaaggttg tctactgtca tcgcgtaatg tctaatgctc cgaaaggttc  10020
taccgtcctg cactcctgtg ataatccatt atgttgtaac cctgaacacc tatccatagg  10080
aactccaaaa gagaactcca ctgacatggt aaataagggt cgctcacaca aggggtataa  10140
actttcagac gaagacgtaa tggcaatcat ggagtccagc gagtccaatg tatccttagc  10200
tcgcacctat ggtgtctccc aacagactat ttgtgatata cgcaaaggga ggcgacatgg  10260
caggttacgg cgctaaagga atccgaaagg ttggagcgtt tcgctctggc ctagaggaca  10320
aggtttcaaa gcagttggaa tcaaaaggta ttaaattcga gtatgaagag tggaaagtgc  10380
cttatgtaat tccggcgagc aatcacactt acactccaga cttcttactt ccaaacggta  10440
tattcgttga gacaaagggt ctgtgggaaa gcgatgatag aaagaagcac ttattaatta  10500
gggagcagca ccccgagcta gacatccgta ttgtcttctc aagctcacgt actaagttat  10560
acaaaggttc tccaacgtct tatggagagt tctgcgaaaa gcatggtatt aagttcgctg  10620
ataaactgat acctgctgag tggataaagg aacccaagaa ggaggtcccc tttgatagat  10680 taaaaggaa aggaggaaag aaataatggc tcgtgtacag tttaaacaac gtgaatctac  10740
tgacgcaatc tttgttcact gctcggctac caagccaagt cagaatgttg gtgtccgtga  10800
gattcgccag tggcacaaag agcagggttg gctcgatgtg ggataccact ttatcatcaa  10860
gcgagacggt actgtggagg caggacgaga tgagatggct gtaggctctc acgctaaggg  10920
ttacaaccac aactctatcg gcgtctgcct tgttggtggt atcgacgata aggtaagtt  10980 cgacgctaac tttacgccag cccaaatgca atcccttcgc tcactgcttg tcacactgct  11040
ggctaagtac gaaggcgctg tgcttcgcgc ccatcatgag gtggcgccga aggcttgccc  11100
ttcgttcgac cttaagcgtt ggtgggagaa gaacgaactg gtcacttctg accgtggata  11160
attaattgaa ctcactaaag ggagaccaca gcggtttccc tttgttcgca ttggaggtca  11220
aataatgcgc aagtcttata aacaattcta taggctccg aggaggcata tccaagtgtg  11280
ggaggcagcc aatgggccta taccaaaagg ttattatata gaccacattg acggcaatcc  11340
actcaacgac gccttagaca atctccgtct ggctctccca aaagaaaact catggaacat  11400
gaagactcca aagagcaata cctcaggact aaagggactg agttggagca aggaaaggga  11460
gatgtggaga ggcactgtaa cagctgaggg taaacagcat aactttcgta gtagagatct  11520
attggaagtc gttgcgtgga tttatagaac taggagggaa ttgcatggac aattcgcacg  11580
attccgatag tgtatttctt taccacattc cttgtgacaa ctgtgggagt agtgatggga  11640
actcgctgtt ctctgacgga cacacgttct gctacgtatg cgagaagtgg actgctggta  11700
atgaagacac taaagagagg gcttcaaaac ggaaaccctc aggaggtaaa ccaatgactt  11760
acaacgtgtg gaacttcggg gaatccaatg gacgctactc cgcgttaact gcgagaggaa  11820
tctccaagga aacctgtcag aaggctggct actggattgc caaagtagac ggtgtgatgt  11880
accaagtggc tgactatcgg gaccagaacg gcaacattgt gagtcagaag gttcgagata  11940
```

```
aagataagaa ctttaagacc actggtagtc acaagagtga cgctctgttc gggaagcact    12000
tgtggaatgg tggtaagaag attgtcgtta cagaaggtga aatcgacatg cttaccgtga    12060
tggaacttca agactgtaag tatcctgtag tgtcgttggg tcacggtgcc tctgccgcta    12120
agaagacatg cgctgccaac tacgaatact ttgaccagtt cgaacagatt atcttaatgt    12180
tcgatatgga cgaagcaggg cgcaaagcag tcgaagaggc tgcacaggtt ctacctgctg    12240
gtaaggtacg agtggcagtt cttccgtgta aggatgcaaa cgagtgtcac ctaaatggtc    12300
acgaccgtga aatcatggag caagtgtgga atgctggtcc ttggattcct gatggtgtgg    12360
tatcggctct ttcgttacgt gaacgaatcc gtgagcacct atcgtccgag gaatcagtag    12420
gtttactttt cagtggctgc actggtatca acgataagac cttaggtgcc cgtggtggtg    12480
aagtcattat ggtcacttcc ggttccggta tgggtaagtc aacgttcgtc cgtcaacaag    12540
ctctacaatg gggcacagcg atgggcaaga aggtaggctt agcgatgctt gaggagtccg    12600
ttgaggagac cgctgaggac cttataggtc tacacaaccg tgtccgactg agacaatccg    12660
actcactaaa gagagagatt attgagaacg gtaagttcga ccaatggttc gatgaactgt    12720
tcggcaacga tacgttccat ctatatgact cattcgccga ggctgagacg datagactgc    12780
tcgctaagct ggcctacatg cgctcaggct tgggctgtga cgtaatcatt ctagaccaca    12840
tctcaatcgt cgtatccgct tctggtgaat ccgatgagcg taagatgatt gacaacctga    12900
tgaccaagct caaagggttc gctaagtcaa ctggggtggt gctggtcgta atttgtcacc    12960
ttaagaaccc agacaaaggt aaagcacatg aggaaggtcg ccccgtttct attactgacc    13020
tacgtggttc tggcgcacta cgccaactat ctgatactat tattgccctt gagcgtaatc    13080
agcaaggcga tatgcctaac cttgtcctcg ttcgtattct caagtgccgc tttactggtg    13140
atactggtat cgctggctac atggaataca acaaggaaac cggatggctt gaaccatcaa    13200
gttactcagg ggaagaagag tcacactcag agtcaacaga ctggtccaac gacactgact    13260
tctgacagga ttcttgatga ctttccagac gactacgaga agtttcgctg gagagtccca    13320
ttctaatacg actcactaaa ggagacacac catgttcaaa ctgattaaga agttaggcca    13380
actgctggtt cgtatgtaca acgtggaagc caagcgactg aacgatgagg ctcgtaaaga    13440
ggccacacag tcacgcgctc tggcgattcg ctccaacgaa ctggctgaca gtgcatccac    13500
taaagttacc gaggctgccc gtgtggcaaa ccaagctcaa cagcttttcca aattctttga    13560 gtaatcaaac aggagaaacc attatgtcta acgtagctga aactatccgt ctatccgata    13620
cagctgacca gtggaaccgt cgagtccaca tcaacgttcg caacggtaag gcgactatgg    13680
tttaccgctg gaaggactct aagtcctcta agaatcacac tcagcgtatg acgttgacag    13740
atgagcaagc actgcgtctg gtcaatgcgc ttaccaaagc tgccgtgaca gcaattcatg    13800
aagctggtcg cgtcaatgaa gctatggcta tcctcgacaa gattgataac taagagtggt    13860
atcctcaagg tcgccaaagt ggtggccttc atgaatacta ttcgactcac tataggagat    13920
attaccatgc gtgaccctaa agttatccaa gcagaaatcg ctaaactgga agctgaactg    13980
gaggacgtta agtaccatga agctaagact cgctccgctg ttcacatctt gaagaactta    14040
ggctggactt ggacaagaca gactggctgg aagaaaccag aagttaccaa gctgagtcat    14100
aaggtgttcg ataaggacac tatgacccac atcaaggctg gtgattgggt taaggttgac    14160
atgggagttg ttggtggata cggctacgtc cgctcagtta gtggcaaata tgcacaagtg    14220
tcatacatca caggtgttac tccacgcggt gcaatcgttg ccgataagac caacatgatt    14280
cacacaggtt tcttgacagt tgtttcatat gaagagattg ttaagtcacg ataatcaata    14340
```

```
ggagaaatca atatgatcgt ttctgacatc gaagctaacg ccctcttaga gagcgtcact    14400
aagttccact gcggggttat ctacgactac tccaccgctg agtacgtaag ctaccgtccg    14460
agtgacttcg gtgcgtatct ggatgcgctg gaagccgagg ttgcacgagg cggtcttatt    14520
gtgttccaca acggtcacaa gtatgacgtt cctgcattga ccaaactggc aaagttgcaa    14580
ttgaaccgag agttccacct tcctcgtgag aactgtattg acacccttgt gttgtcacgt    14640
ttgattcatt ccaacctcaa ggacaccgat atgggtcttc tgcgttccgg caagttgccc    14700
ggaaaacgct ttgggtctca cgctttggag gcgtggggtt atcgcttagg cgagatgaag    14760
ggtgaataca aagacgactt taagcgtatg cttgaagagc agggtgaaga atacgttgac    14820
ggaatggagt ggtggaactt caacgaagag atgatggact ataacgttca ggacgttgtg    14880
gtaactaaag ctctccttga gaagctactc tctgacaaac attacttccc tcctgagatt    14940
gactttacgg acgtaggata cactacgttc tggtcagaat cccttgaggc cgttgacatt    15000
gaacatcgtg ctgcatggct gctcgctaaa caagagcgca acgggttccc gtttgacaca    15060
aaagcaatcg aagagttgta cgtagagtta gctgctcgcc gctctgagtt gctccgtaaa    15120
ttgaccgaaa cgttcggctc gtggtatcag cctaaaggtg gcactgagat gttctgccat    15180
ccgcgaacag gtaagccact acctaaatac cctcgcatta agacacctaa agttggtggt    15240
atctttaaga agcctaagaa caaggcacag cgagaaggcc gtgagccttg cgaacttgat    15300
acccgcgagt acgttgctgg tgctccttac accccagttg aacatgttgt gtttaaccct    15360
tcgtctcgtg accacattca gaagaaactc aagaggctg ggtgggtccc gaccaagtac    15420
accgataagg gtgctcctgt ggtggacgat gaggtactcg aaggagtacg tgtagatgac    15480
cctgagaagc aagccgctat cgacctcatt aaagagtact tgatgattca gaagcgaatc    15540
ggacagtctg ctgagggaga caaagcatgg cttcgttatg ttgctgagga tggtaagatt    15600
catggttctg ttaaccctaa tggagcagtt acgggtcgtg cgacccatgc gttcccaaac    15660
cttgcgcaaa ttccgggtgt acgttctcct tatggagagc agtgtcgcgc tgcttttggc    15720
gctgagcacc atttggatgg gataactggt aagccttggg ttcaggctgg catcgacgca    15780
tccggtcttg agctacgctg cttggctcac ttcatggctc gctttgataa cggcgagtac    15840
gctcacgaga ttcttaacgg cgacatccac actaagaacc agatagctgc tgaactacct    15900
acccgagata acgctaagac gttcatctat gggttcctct atggtgctgg tgatgagaag    15960
attggacaga ttgttggtgc tggtaaagag cgcggtaagg aactcaagaa gaaattcctt    16020
gagaacaccc ccgcgattgc agcactccgc gagtctatcc aacagacact tgtcgagtcc    16080
tctcaatggg tagctggtga gcaacaagtc aagtggaaac gccgctggat taaaggtctg    16140
gatggtcgta aggtacacgt tcgtagtcct cacgctgcct tgaatacccct actgcaatct    16200 gctggtgctc tcatctgcaa actgtggatt atcaagaccg aagagatgct cgtagagaaa    16260
ggcttgaagc atggctggga tggggacttt gcgtacatgg catgggtaca tgatgaaatc    16320
caagtaggct gccgtaccga agagattgct caggtggtca ttgagaccgc acaagaagcg    16380
atgcgctggg ttggagacca ctggaacttc cggtgtcttc tggataccga aggtaagatg    16440
ggtcctaatt gggcgatttg ccactgatac aggaggctac tcatgaacga aagacactta    16500
acaggtgctg cttctgaaat gctagtagcc tacaaattta ccaaagctgg gtacactgtc    16560
tattacccta tgctgactca gagtaaagag gacttggttg tatgtaagga tggtaaattt    16620
agtaaggttc aggttaaaac agccacaacg gttcaaacca acacaggaga tgccaagcag    16680
```

```
gttaggctag gtggatgcgg taggtccgaa tataaggatg gagactttga cattcttgcg    16740
gttgtggttg acgaagatgt gcttattttc acatgggacg aagtaaaagg taagacatcc    16800
atgtgtgtcg gcaagagaaa caaaggcata aaactatagg agaaattatt atggctatga    16860
caaagaaatt taaagtgtcc ttcgacgtta ccgcaaagat gtcgtctgac gttcaggcaa    16920
tcttagagaa agatatgctg catctatgta agcaggtcgg ctcaggtgcg attgtcccca    16980
atggtaaaca gaaggaaatg attgtccagt tcctgacaca cggtatggaa ggattgatga    17040
cattcgtagt acgtacatca tttcgtgagg ccattaagga catgcacgaa gagtatgcag    17100
ataaggactc tttcaaacaa tctcctgcaa cagtacggga ggtgttctga tgtctgacta    17160
cctgaaagtg ctgcaagcaa tcaaaagttg ccctaagact ttccagtcca actatgtacg    17220
gaacaatgcg agcctcgtag cggaggccgc ttcccgtggt cacatctcgt gcctgactac    17280
tagtggacgt aacggtggcg cttgggaaat cactgcttcc ggtactcgct ttctgaaacg    17340
aatgggagga tgtgtctaat gtctcgtgac cttgtgacta ttccacgcga tgtgtggaac    17400
gatatacagg gctacatcga ctctctggaa cgtgagaacg atagccttaa gaatcaacta    17460
atggaagctg acgaatacgt agcggaacta gaggagaaac ttaatggcac ttcttgacct    17520
taaacaattc tatgagttac gtgaaggctg cgacgacaag ggtatccttg tgatggacgg    17580
cgactggctg gtcttccaag ctatgagtgc tgctgagttt gatgcctctt gggaggaaga    17640
gatttggcac cgatgctgtg accacgctaa ggcccgtcag attcttgagg attccattaa    17700
gtcctacgag acccgtaaga aggcttgggc aggtgctcca attgtccttg cgttcaccga    17760
tagtgttaac tggcgtaaag aactggttga cccgaactat aaggctaacc gtaaggccgt    17820
gaagaaacct gtagggtact ttgagttcct tgatgctctc tttgagcgcg aagagttcta    17880
ttgcatccgt gagcctatgc ttgagggtga tgacgttatg ggagttattg cttccaatcc    17940
gtctgccttc ggtgctcgta aggctgtaat catctcttgc gataaggact ttaagaccat    18000
ccctaactgt gacttcctgt ggtgtaccac tggtaacatc ctgactcaga ccgaagagtc    18060
cgctgactgg tggcacctct ccagaccat caagggtgac atcactgatg gttactcagg    18120
gattgctgga tggggtgata ccgccgagga cttcttgaat aacccgttca taaccgagcc    18180
taaaacgtct gtgcttaagt ccggtaagaa caaaggccaa gaggttacta atgggttaa    18240 acgcgaccct gagcctcatg agacgctttg ggactgcatt aagtccattg gcgcgaaggc    18300
tggtatgacc gaagaggata ttatcaagca gggccaaatg gctcgaatcc tacggttcaa    18360
cgagtacaac tttattgaca aggagattta cctgtggaga ccgtagcgta tattggtctg    18420
ggtctttgtg ttctcggagt gtgcctcatt tcgtgggcc tttgggactt agccagaata    18480
atcaagtcgt tacacgacac taagtgataa actcaaggtc cctaaattaa tacgactcac    18540
tatagggaga tagggggcctt tacgattatt actttaagat ttaactctaa gaggaatctt    18600
tattatgtta acacctatta accaattact taagaaccct aacgatattc cagatgtacc    18660
tcgtgcaacc gctgagtatc tacaggttcg attcaactat gcgtacctcg aagcgtctgg    18720
tcatatagga cttatgcgtg ctaatggttg tagtgaggcc cacatcttgg gtttcattca    18780
gggcctacag tatgcctcta acgtcattga cgagattgag ttacgcaagg aacaactaag    18840
agatgatggg gaggattgac actatgtgtt tctcaccgaa aattaaaact ccgaagatgg    18900
ataccaatca gattcgagcc gttgagccag cgcctctgac ccaagaagtg tcaagcgtgg    18960
agttcggtgg gtcttctgat gagacggata ccgagggcac cgaagtgtct ggacgcaaag    19020
gcctcaaggt cgaacgtgat gattccgtag cgaagtctaa agccagcggc aatggctccg    19080
```

```
ctcgtatgaa atcttccatc cgtaagtccg catttggagg taagaagtga tgtctgagtt    19140
cacatgtgtg gaggctaaga gtcgcttccg tgcaatccgg tggactgtgg aacaccttgg    19200
gttgcctaaa ggattcgaag gacactttgt gggctacagc ctctacgtag acgaagtgat    19260
ggacatgtct ggttgccgtg aagagtacat tctggactct accggaaaac atgtagcgta    19320
cttcgcgtgg tgcgtaagct gtgacattca ccacaaagga gacattctgg atgtaacgtc    19380
cgttgtcatt aatcctgagg cagactctaa gggcttacag cgattcctag cgaaacgctt    19440
taagtacctt gcggaactcc acgattgcga ttgggtgtct cgttgtaagc atgaaggcga    19500
gacaatgcgt gtatacttta aggaggtata agttatgggg aagaaagtta agaaggccgt    19560
gaagaaagtc accaagtccg ttaagaaagt cgttaaggaa ggggctcgtc cggttaaaca    19620
ggttgctggc ggtctagctg gtctggctgg tggtactggt gaagcacaga tggtggaagt    19680
accacaagct gccgcacaga ttgttgacgt acctgagaaa gaggtttcca ctgaggacga    19740
agcacagaca gaaagcggac gcaagaaagc tcgtgctggc ggtaagaaat ccttgagtgt    19800
agcccgtagc tccggtggcg gtatcaacat ttaatcagga ggttatcgtg aagactgca    19860 ttgaatggac cggaggtgtc aactctaagg gttatggtcg taagtgggtt aatggtaaac    19920
ttgtgactcc acataggcac atctatgagg agacatatgg tccagttcca acaggaattg    19980
tggtgatgca tatctgcgat aaccctaggt gctataacat aaagcacctt acgcttggaa    20040
ctccaaagga taattccgag gacatggtta ccaaaggtag acaggctaaa ggagaggaac    20100
taagcaagaa acttacagag tcagacgttc tcgctatacg ctcttcaacc ttaagccacc    20160
gctccttagg agaactgtat ggagtcagtc aatcaaccat aacgcgaata ctacagcgta    20220
agacatggag acacatttaa tggctgagaa acgaacagga cttgcggagg atggcgcaaa    20280
gtctgtctat gagcgtttaa agaacgaccg tgctccctat gagacacgcg ctcagaattg    20340
cgctcaatat accatcccat cattgttccc taaggactcc gataacgcct ctacagatta    20400
tcaaactccg tggcaagccg tgggcgctcg tggtctgaac aatctagcct ctaagctcat    20460
gctggctcta ttccctatgc agacttggat gcgacttact atatctgaat atgaagcaaa    20520
gcagttactg agcgacccg atggactcgc taaggtcgat gagggcctct cgatggtaga    20580
gcgtatcatc atgaactaca ttgagtctaa cagttaccgc gtgactctct ttgaggctct    20640
caaacagtta gtcgtagctg gtaacgtcct gctgtaccta ccggaaccgg aagggtcaaa    20700
ctataatccc atgaagctgt accgattgtc ttcttatgtg gtccaacgag acgcattcgg    20760
caacgttctg caaatggtga ctcgtgacca gatagctttt ggtgctctcc ctgaggacat    20820
ccgtaaggct gtagaaggtc aaggtggtga agaaagct gatgagacaa tcgacgtgta    20880
cactcacatc tatctggatg aggactcagg tgaatacctc cgatacgaag aggtcgaggg    20940
tatggaagtc caaggctccg atgggactta tcctaaagag gcttgcccat acatcccgat    21000
tcggatggtc agactagatg gtgaatccta cggtcgttcg tacattgagg aatacttagg    21060
tgacttacgg tcccttgaaa atctccaaga ggctatcgtc aagatgtcca tgattagctc    21120
taaggttatc ggcttagtga atcctgctgg tatcacccag ccacgccgac tgaccaaagc    21180
tcagactggt gacttcgtta ctggtcgtcc agaagacatc tcgttcctcc aactggagaa    21240
gcaagcagac tttactgtag ctaaagccgt aagtgacgct atcgaggctc gcctttcgtt    21300
tgcctttatg ttgaactctg cggttcagcg tacaggtgaa cgtgtgaccg ccgaagagat    21360
tcggtatgta gcttctgaac ttgaagatac tttaggtggt gtctactcta tcctttctca    21420
```

```
agaattacaa ttgcctctgg tacgagtgct cttgaagcaa ctacaagcca cgcaacagat   21480
tcctgagtta cctaaggaag ccgtagagcc aaccattagt acaggtctgg aagcaattgg   21540
tcgaggacaa gaccttgata agctggagcg tgtgtcact gcgtgggctg cactggcacc   21600
tatgcgggac gaccctgata ttaaccttgc gatgattaag ttacgtattg ccaacgctat   21660
cggtattgac acttctggta ttctactcac cgaagaacag aagcaacaga agatggccca   21720
acagtctatg caaatgggta tggataatgg tgctgctgcg ctggctcaag gtatggctgc   21780
acaagctaca gcttcacctg aggctatggc tgctgccgct gattccgtag gtttacagcc   21840
gggaatttaa tacgactcac tataggagac cctcatcttt gaaatgagcg atgacaagag   21900
gttggagtcc tcggtcttcc tgtagttcaa cttttaaggag acaataataa tggctgaatc   21960
taatgcagac gtatatgcat cttttggcgt gaactccgct gtgatgtctg gtggttccgt   22020
tgaggaacat gagcagaaca tgctggctct tgatgttgct gcccgtgatg gcgatgatgc   22080
aatcgagtta gcgtcagacg aagtggaaac agaacgtgac ctgtatgaca actctgaccc   22140
gttcggtcaa gaggatgacg aaggccgcat tcaggttcgt atcggtgatg gctctgagcc   22200
gaccgatgtg gacactggag aagaaggcgt tgagggcacc gaaggttccg aagagtttac   22260
cccactgggc gagactccag aagaactggt agctgcctct gagcaacttg gtgagcacga   22320
agagggcttc caagagatga ttaacattgc tgctgagcgt ggcatgagtg tcgagaccat   22380
tgaggctatc cagcgtgagt acgaggagaa cgaagagttg tccgccgagt cctacgctaa   22440
gctggctgaa attggctaca cgaaggcttt cattgactcg tatatccgtg gtcaagaagc   22500
tctggtggag cagtacgtaa acagtgtcat tgagtacgct ggtggtcgtg aacgttttga   22560
tgcactgtat aaccaccttg agacgcacaa ccctgaggct gcacagtcgc tggataatgc   22620
gttgaccaat cgtgacttag cgaccgttaa ggctatcatc aacttggctg gtgagtctcg   22680
cgctaaggcg ttcggtcgta agccaactcg tagtgtgact aatcgtgcta ttccggctaa   22740
acctcaggct accaagcgtg aaggctttgc ggaccgtagc gagatgatta agctatgag   22800
tgaccctcgg tatcgcacag atgccaacta tcgtcgtcaa gtcgaacaga agtaatcga   22860
ttcgaacttc tgatagactt cgaaattaat acgactcact atagggagac cacaacggtt   22920
tccctctaga ataattttg tttaacttta agaaggagat atacatatgg ctagcatgac   22980
tggtggacag caaatgggta ctaaccaagg taaaggtgta gttgctgctg gagataaact   23040
ggcgttgttc ttgaaggtat ttggcggtga agtcctgact gcgttcgctc gtacctccgt   23100
gaccacttct cgccacatgg tacgttccat ctccagcggt aaatccgctc agttccctgt   23160
tctgggtcgc actcaggcag cgtatctggc tccgggcgag aaccttgacg ataaacgtaa   23220
ggacatcaaa cacaccgaga aggtaatcac cattgacggt ctcctgacgg ctgacgttct   23280
gatttatgat attgaggacg cgatgaacca ctacgacgtt cgctctgagt atacctctca   23340
gttgggtgaa tctctggcga tggctgcgga tggtgcggtt ctggctgaga ttgccggtct   23400
gtgtaacgtg gaaagcaaat ataatgagaa catcgagggc ttaggtactg ctaccgtaat   23460
tgagaccact cagaacaagg ccgcacttac cgaccaagtt gcgctgggta aggagattat   23520
tgcggctctg actaaggctc gtgcggctct gaccaagaac tatgttccgg ctgctgaccg   23580
tgtgttctac tgtgacccag atagctactc tgcgattctg gcagcactga tgccgaacgc   23640
agcaaactac gctgctctga ttgaccctga agggttctct atccgcaacg ttatgggctt   23700
tgaggttgta gaagttccgc acctcaccgc tggtggtgct ggtaccgctc gtgagggcac   23760
tactggtcag aagcacgtct tccctgccaa taaaggtgag ggtaatgtca aggttgctaa   23820
```

```
ggacaacgtt atcggcctgt tcatgcaccg ctctgcggta ggtactgtta agctgcgtga   23880
cttggctctg gagcgcgctc gccgtgctaa cttccaagcg gaccagatta tcgctaagta   23940
cgcaatgggc cacggtggtc ttcgcccaga agctgctggt gcagtggttt tcaaagtgga   24000
gtaatgctgg gggtggcctc aacggtcgct gctagtcccg aagaggcgag tgttacttca   24060
acagaagaaa ccttaacgcc agcacaggag gccgcacgca cccgcgctgc taacaaagcc   24120
cgaaaggaag ctgagttggc tgctgccacc gctgagcaat aactagcata accccttggg   24180
gcctctaaac gggtcttgag gggttttttg ctgaaggag gaactatatg cgctcatacg    24240
atatgaacgt tgagactgcc gctgagttat cagctgtgaa cgacattctg gcgtctatcg   24300
gtgaacctcc ggtatcaacg ctggaaggtg acgctaacgc agatgcagcg aacgctcggc   24360
gtattctcaa caagattaac cgacagattc aatctcgtgg atggacgttc aacattgagg   24420
aaggcataac gctactacct gatgtttact ccaacctgat tgtatacagt gacgactatt   24480
tatccctaat gtctacttcc ggtcaatcca tctacgttaa ccgaggtggc tatgtgtatg   24540
accgaacgag tcaatcagac cgctttgact ctggtattac tgtgaacatt attcgtctcc   24600
gcgactacga tgagatgcct gagtgcttcc gttactggat tgtcaccaag gcttcccgtc   24660
agttcaacaa ccgattcttt ggggcaccgg aagtagaggg tgtactccaa gaagaggaag   24720
atgaggctag acgtctctgc atggagtatg agatggacta cggtgggtac aatatgctgg   24780
atggagatgc gttcacttct ggtctactga ctcgctaaca ttaataaata aggaggctct   24840
aatggcactc attagccaat caatcaagaa cttgaagggt ggtatcagcc aacagcctga   24900
catccttcgt tatccagacc aagggtcacg ccaagttaac ggttggtctt cggagaccga   24960
gggcctccaa aagcgtccac ctcttgtttt cttaaataca cttggagaca acggtgcgtt   25020
aggtcaagct ccgtacatcc acctgattaa ccgagatgag cacgaacagt attacgctgt   25080
gttcactggt agcggaatcc gagtgttcga cctttctggt aacgagaagc aagttaggta   25140
tcctaacggt tccaactaca tcaagaccgc taatccacgt aacgacctgc gaatggttac   25200
tgtagcagac tatacgttca tcgttaaccg taacgttgtt gcacagaaga acacaaagtc   25260
tgtcaactta ccgaattaca accctaatca agacggattg attaacgttc gtggtggtca   25320
gtatggtagg gaactaattg tacacattaa cggtaaagac gttgcgaagt ataagatacc   25380
agatggtagt caacctgaac acgtaaacaa tacggatgcc caatggttag ctgaagagtt   25440
agccaagcag atgcgcacta acttgtctga ttggactgta aatgtagggc aagggttcat   25500
ccatgtgacc gcacctagtg gtcaacagat tgactccttc acgactaaag atggctacgc   25560
agaccagttg attaaccctg tgacccacta cgctcagtcg ttctctaagc tgccacctaa   25620
tgctcctaac ggctacatgg tgaaaatcgt aggggacgcc tctaagtctg ccgaccagta   25680
ttacgttcgg tatgacgctg agcggaaagt ttggactgag actttaggtt ggaacactga   25740
ggaccaagtt ctatgggaaa ccatgccaca cgctcttgtg cgagccgctg acggtaattt   25800
cgacttcaag tggcttgagt ggtctcctaa gtcttgtggt gacgttgaca ccaacccttg   25860
gccttctttt gttggttcaa gtattaacga tgtgttcttc ttccgtaacc gcttaggatt   25920
ccttagtggg gagaacatca tattgagtcg tacagccaaa tacttcaact tctaccctgc   25980
gtccattgcg aaccttagtg atgacgaccc tatagacgta gctgtgagta ccaaccgaat   26040
agcaatcctt aagtacgccg ttccgttctc agaagagtta ctcatctggt ccgatgaagc   26100
acaattcgtc ctgactgcct cgggtactct cacatctaag tcggttgagt tgaacctaac   26160
```

```
gacccagttt gacgtacagg accgagcgag accttttggg attgggcgta atgtctactt   26220
tgctagtccg aggtccagct tcacgtccat ccacaggtac tacgctgtgc aggatgtcag   26280
ttccgttaag aatgctgagg acattacatc acacgttcct aactacatcc ctaatggtgt   26340
gttcagtatt tgcggaagtg gtacggaaaa cttctgttcg gtactatctc acggggaccc   26400
tagtaaaatc ttcatgtaca aattcctgta cctgaacgaa gagttaaggc aacagtcgtg   26460
gtctcattgg gactttgggg aaaacgtaca ggttctagct tgtcagagta tcagctcaga   26520
tatgtatgtg attcttcgca atgagttcaa tacgttccta gctagaatct ctttcactaa   26580
gaacgccatt gacttacagg gagaacccta tcgtgccttt atggacatga agattcgata   26640
cacgattcct agtggaacat acaacgatga cacattcact acctctattc atattccaac   26700
aatttatggt gcaaacttcg ggaggggcaa aatcactgta ttggagcctg atggtaagat   26760
aaccgtgttt gagcaaccta cggctgggtg gaatagcgac ccttggctga gactcagcgg   26820
taacttggag ggacgcatgg tgtacattgg gttcaacatt aacttcgtat atgagttctc   26880
taagttcctc atcaagcaga ctgccgacga cgggtctacc tccacggaag acattgggcg   26940
cttacagtta cgccgagcgt gggttaacta cgagaactct ggtacgtttg acatttatgt   27000
tgagaaccaa tcgtctaact ggaagtacac aatggctggt gcccgattag gctctaacac   27060
tctgagggct gggagactga acttaggggac cggacaatat cgattccctg tggttggtaa   27120
cgccaagttc aacactgtat acatcttgtc agatgagact accctctga acatcattgg   27180 gtgtggctgg gaaggtaact acttacggag aagttccggt atttaattaa atattctccc   27240
tgtggtggct cgaaattaat acgactcact atagggagaa caatacgact acgggagggt   27300
tttcttatga tgactataag acctactaaa agtacagact ttgaggtatt cactccggct   27360
caccatgaca ttcttgaagc taaggctgct ggtattgagc cgagtttccc tgatgcttcc   27420
gagtgtgtca cgttgagcct ctatgggttc cctctagcta tcggtggtaa ctgcggggac   27480
cagtgctggt tcgttacgag cgaccaagtg tggcgactta gtggaaaggc taagcgaaag   27540
ttccgtaagt taatcatgga gtatcgcgat aagatgcttg agaagtatga tactctttgg   27600
aattacgtat gggtaggcaa tacgtcccac attcgtttcc tcaagactat cggtgcggta   27660
ttccatgaag agtacacacg agatggtcaa tttcagttat ttacaatcac gaaaggagga   27720
taaccatatg tgttgggcag ccgcaatacc tatcgctata tctggcgctc aggctatcag   27780
tggtcagaac gctcaggcca aaatgattgc cgctcagacc gctgctggtc gtcgtcaagc   27840
tatgaaaatc atgaggcaga cgaacatcca gaatgctgac ctatcgttgc aagctcgaag   27900
taaacttgag gaagcgtccg ccgagttgac ctcacagaac atgcagaagg tccaagctat   27960
tgggtctatc cgagcggcta tcggagagag tatgcttgaa ggttcctcaa tggaccgcat   28020
taagcgagtc acagaaggac agttcattcg ggaagccaat atggtaactg agaactatcg   28080
ccgtgactac caagcaatct tcgcacagca acttggtggt actcaaagtg ctgcaagtca   28140
gattgacgaa atctataaga gcgaacagaa acagaagagt aagctacaga tggttctgga   28200
cccactggct atcatggggt cttccgctgc gagtgcttac gcatccggtg cgttcgactc   28260
taagtccaca actaaggcac ctattgttgc cgctaaagga accaagacgg ggaggtaatg   28320
agctatgagt aaaattgaat ctgcccttca agcggcacaa ccgggactct ctcggttacg   28380
tggtggtgct ggaggtatgg gctatcgtgc agcaaccact caggccgaac agccaaggtc   28440
aagcctattg gacaccattg gtcggttcgc taaggctggt gccgatatgt ataccgctaa   28500
ggaacaacga gcacgagacc tagctgatga acgctctaac gagattatcc gtaagctgac   28560
```

```
ccctgagcaa cgtcgagaag ctctcaacaa cgggacccct ctgtatcagg atgacccata    28620
cgctatggaa gcactccgag tcaagactgg tcgtaacgct gcgtatcttg tggacgatga    28680
cgttatgcag aagataaaag agggtgtctt ccgtactcgc gaagagatgg aagagtatcg    28740
ccatagtcgc cttcaagagg gcgctaaggt atacgctgag cagttcggca tcgaccctga    28800
ggacgttgat tatcagcgtg gtttcaacgg ggacattacc gagcgtaaca tctcgctgta    28860
tggtgcgcat gataacttct tgagccagca agctcagaag ggcgctatca tgaacagccg    28920
agtggaactc aacggtgtcc ttcaagaccc tgatatgctg cgtcgtccag actctgctga    28980
cttctttgag aagtatatcg acaacggtct ggttactggc gcaatcccat ctgatgctca    29040
agccacacag cttataagcc aagcgttcag tgacgcttct agccgtgctg gtggtgctga    29100
cttcctgatg cgagtcggtg acaagaaggt aacacttaac ggagccacta cgacttaccg    29160
agagttgatt ggtgaggaac agtggaacgc tctcatggtc acagcacaac gttctcagtt    29220
tgagactgac gcgaagctga cgagcagta tcgcttgaag attaactctg cgctgaacca    29280
agaggaccca aggacagctt gggagatgct tcaaggtatc aaggctgaac tagataaggt    29340
ccaacctgat gagcagatga caccacaacg tgagtggcta atctccgcac aggaacaagt    29400
tcagaatcag atgaacgcat ggacgaaagc tcaggccaag gctctggacg attccatgaa    29460
gtcaatgaac aaacttgacg taatcgacaa gcaattccag aagcgaatca acggtgagtg    29520
ggtctcaacg gattttaagg atatgccagt caacgagaac actggtgagt tcaagcatag    29580
cgatatggtt aactacgcca ataagaagct cgctgagatt gacagtatgg acattccaga    29640
cggtgccaag gatgctatga agttgaagta ccttcaagcg gactctaagg acggagcatt    29700
ccgtacagcc atcggaacca tggtcactga cgctggtcaa gagtggtctg ccgctgtgat    29760
taacggtaag ttaccagaac gaaccccagc tatggatgct ctgcgcagaa tccgcaatgc    29820
tgaccctcag ttgattgctg cgctataccc agaccaagct gagctattcc tgacgatgga    29880
catgatggac aagcagggta ttgaccctca ggttattctt gatgccgacc gactgactgt    29940
taagcggtcc aaagagcaac gctttgagga tgataaagca ttcgagtctg cactgaatgc    30000
atctaaggct cctgagattg cccgtatgcc agcgtcactg cgcgaatctg cacgtaagat    30060
ttatgactcc gttaagtatc gctcggggaa cgaaagcatg gctatggagc agatgaccaa    30120
gttccttaag gaatctacct acacgttcac tggtgatgat gttgacggtg ataccgttgg    30180
tgtgattcct aagaatatga tgcaggttaa ctctgacccg aaatcatggg agcaaggtcg    30240
ggatattctg gaggaagcac gtaagggaat cattgcgagc aacccttgga taaccaataa    30300
gcaactgacc atgtattctc aaggtgactc catttacctt atggacacca caggtcaagt    30360
cagagtccga tacgacaaag agttactctc gaaggtctgg agtgagaacc agaagaaact    30420
cgaagagaaa gctcgtgaga aggctctggc tgatgtgaac aagcgagcac ctatagttgc    30480
cgctacgaag gcccgtgaag ctgctgctaa acgagtccga gagaaacgta acagactcc    30540 taagttcatc tacggacgta aggagtaact aaaggctaca taaggaggcc ctaaatggat    30600
aagtacgata agaacgtacc aagtgattat gatggtctgt tccaaaaggc tgctgatgcc    30660 aacgggtct cttatgacct tttacgtaaa gtcgcttgga cagaatcacg atttgtgcct    30720
acagcaaaat ctaagactgg accattaggc atgatgcaat ttaccaaggc aaccgctaag    30780
gccctcggtc tgcgagttac cgatggtcca gacgacgacc gactgaaccc tgagttagct    30840
attaatgctg ccgctaagca acttgcaggt ctggtaggga agtttgatgg cgatgaactc    30900
```

```
aaagctgccc ttgcgtacaa ccaaggcgag ggacgcttgg gtaatccaca acttgaggcg   30960
tactctaagg gagacttcgc atcaatctct gaggagggac gtaactacat gcgtaacctt   31020
ctggatgttg ctaagtcacc tatggctgga cagttggaaa cttttggtgg cataacccca   31080
aagggtaaag gcattccggc tgaggtagga ttggctggaa ttggtcacaa gcagaaagta   31140
acacaggaac ttcctgagtc cacaagtttt gacgttaagg gtatcgaaca ggaggctacg   31200
gcgaaaccat cgccaagga cttttgggag acccacggag aaacacttga cgagtacaac   31260
agtcgttcaa ccttcttcgg attcaaaaat gctgccgaag ctgaactctc caactcagtc   31320
gctgggatgg cttttccgtgc tggtcgtctc gataatggtt ttgatgtgtt aaagacacc   31380
attacgccga ctcgctggaa ctctcacatc tggactccag aggagttaga aagattcga   31440
acagaggtta agaaccctgc gtacatcaac gttgtaactg gtggttcccc tgagaacctc   31500
gatgacctca ttaaattggc taacgagaac tttgagaatg actcccgcgc tgccgaggct   31560
ggcctaggtg ccaaactgag tgctggtatt attggtgctg gtgtggaccc gcttagctat   31620
gttcctatgg tcggtgtcac tggtaagggc tttaagttaa tcaataaggc tcttgtagtt   31680
ggtgccgaaa gtgctgctct gaacgttgca tccgaaggtc tccgtacctc cgtagctggt   31740
ggtgacgcag actatgcggg tgctgcctta ggtggctttg tgtttggcgc aggcatgtct   31800
gcaatcagtg acgctgtagc tgctggactg aaacgcagta aaccagaagc tgagttcgac   31860
aatgagttca tcggtcctat gatgcgattg gaagcccgtg agacagcacg aaacgccaac   31920
tctgcggacc tctctcggat gaacactgag aacatgaagt ttgaaggtga acataatggt   31980
gtcccttatg aggacttacc aacagagaga ggtgccgtgg tgttacatga tggctccgtt   32040
ctaagtgcaa gcaacccaat caaccctaag actctaaaag agttctccga ggttgaccct   32100
gagaaggctg cgcgaggaat caaactggct gggttcaccg agattggctt gaagaccttg   32160
gggtctgacg atgctgacat ccgtagagtg gctatcgacc tcgttcgctc tcctactggt   32220
atgcagtctg gtgcctcagg taagttcggt gcaacagctt ctgacatcca tgagagactt   32280
catggtactg accagcgtac ttataatgac ttgtacaaag caatgtctga cgctatgaaa   32340
gaccctgagt tctctactgg cggcgctaag atgtcccgtg aagaaactcg atacactatc   32400
taccgtagag cggcactagc tattgagcgt ccagaactac agaaggcact cactccgtct   32460
gagagaatcg ttatggacat cattaagcgt cactttgaca ccaagcgtga acttatggaa   32520
aacccagcaa tattcggtaa cacaaaggct gtgagtatct tccctgagag tcgccacaaa   32580
ggtacttacg ttcctcacgt atatgaccgt catgccaagg cgctgatgat tcaacgctac   32640
ggtgccgaag gtttgcagga agggattgcc cgctcatgga tgaacagcta cgtctccaga   32700
cctgaggtca aggccagagt cgatgagatg cttaaggaat tacacggggt gaaggaagta   32760
acaccagaga tggtagagaa gtacgctatg gataaggctt atggtatctc ccactcagac   32820
cagttcacca acagttccat aatagaagag aacattgagg gcttagtagg tatcgagaat   32880
aactcattcc ttgaggcacg taacttgttt gattcggacc tatccatcac tatgccagac   32940
ggacagcaat tctcagtgaa tgacctaagg gacttcgata tgttccgcat catgccagcg   33000
tatgaccgcc gtgtcaatgg tgacatcgcc atcatggggt ctactggtaa aaccactaag   33060
gaacttaagg atgagatttt ggctctcaaa gcgaaagctg agggagacgg taagaagact   33120
ggcgaggtac atgctttaat ggataccgtt aagattctta ctggtcgtgc tagacgcaat   33180
caggacactg tgtgggaaac ctcactgcgt gccatcaatg acctagggtt cttcgctaag   33240
aacgcctaca tgggtgctca gaacattacg gagattgctg ggatgattgt cactggtaac   33300
```

```
gttcgtgctc tagggcatgg tatcccaatt ctgcgtgata cactctacaa gtctaaacca   33360
gtttcagcta aggaactcaa ggaactccat gcgtctctgt tcgggaagga ggtggaccag   33420
ttgattcggc ctaaacgtgc tgacattgtg cagcgcctaa gggaagcaac tgataccgga   33480
cctgccgtgg cgaacatcgt agggaccttg aagtattcaa cacaggaact ggctgctcgc   33540
tctccgtgga ctaagctact gaacggaacc actaactacc ttctggatgc tgcgcgtcaa   33600
ggtatgcttg gggatgttat tagtgccacc ctaacaggta agactacccg ctgggagaaa   33660
gaaggcttcc ttcgtggtgc ctccgtaact cctgagcaga tggctggcat caagtctctc   33720
atcaaggaac atatggtacg cggtgaggac gggaagttta ccgttaagga caagcaagcg   33780
ttctctatgg acccacgggc tatggactta tggagactgg ctgacaaggt agctgatgag   33840
gcaatgctgc gtccacataa ggtgtcctta caggattccc atgcgttcgg agcactaggt   33900
aagatggtta tgcagtttaa gtctttcact atcaagtccc ttaactctaa gttcctgcga   33960
accttctatg atggatacaa gaacaaccga gcgattgacg ctgcgctgag catcatcacc   34020
tctatgggtc tcgctggtgg tttctatgct atggctgcac acgtcaaagc atacgctctg   34080
cctaaggaga aacgtaagga gtacttggag cgtgcactgg acccaaccat gattgcccac   34140
gctgcgttat ctcgtagttc tcaattgggt gctcctttgg ctatggttga cctagttggt   34200
ggtgttttag ggttcgagtc ctccaagatg gctcgctcta cgattctacc taaggacacc   34260
gtgaaggaac gtgacccaaa caaaccgtac acctctagag aggtaatggg cgctatgggt   34320
tcaaaccttc tggaacagat gccttcggct ggctttgtgg ctaacgtagg ggctaccttg   34380
atgaatgctg ctggcgtggt caactcacct aataaagcaa ccgagcagga cttcatgact   34440
ggtcttatga actccacaaa agagttagta ccgaacgacc cattgactca acagcttgtg   34500
ttgaagattt atgaggcgaa cggtgttaac ttgagggagc gtaggaaata atacgactca   34560
ctatagggag aggcgaaata atcttctccc tgtagtctct tagatttact ttaaggaggt   34620
caaatggcta acgtaattaa aaccgttttg acttaccagt tagatggctc caatcgtgat   34680
tttaatatcc cgtttgagta tctagcccgt aagttcgtag tggtaactct tattggtgta   34740
gaccgaaagg tccttacgat taatacagac tatcgctttg ctacacgtac tactatctct   34800
ctgacaaagg cttggggtcc agccgatggc tacacgacca tcgagttacg tcgagtaacc   34860
tccactaccg accgattggt tgactttacg gatggttcaa tcctccgcgc gtatgacctt   34920
aacgtcgctc agattcaaac gatgcacgta gcggaagagg cccgtgacct cactacggat   34980
actatcggtg tcaataacga tggtcacttg gatgctcgtg gtcgtcgaat tgtgaaccta   35040
gcgaacgccg tggatgaccg cgatgctgtt ccgtttggtc aactaaagac catgaaccag   35100
aactcatggc aagcacgtaa tgaagcctta cagttccgta atgaggctga gacttccaga   35160
aaccaagcgg agggctttaa gaacgagtcc agtaccaacg ctacgaacac aaagcagtgg   35220
cgcgatgaga ccaagggttt ccgagacgaa gccaagcggt tcaagaatac ggctggtcaa   35280
tacgctacat ctgctgggaa ctctgcttcc gctgcgcatc aatctgaggt aaacgctgag   35340
aactctgcca cagcatccgc taactctgct catttggcag aacagcaagc agaccgtgcg   35400
gaacgtgagg cagacaagct ggaaaattac aatggattgg ctggtgcaat tgataaggta   35460
gatggaacca atgtgtactg gaaaggaaat attcacgcta acgggcgcct ttacatgacc   35520
acaaacggtt ttgactgtgg ccagtatcaa cagttctttg gtggtgtcac taatcgttac   35580
tctgtcatgg agtggggaga tgagaacgga tggctgatgt atgttcaacg tagagagtgg   35640
```

```
acaacagcga taggcggtaa catccagtta gtagtaaacg gacagatcat cacccaaggt   35700
ggagccatga ccggtcagct aaaattgcag aatgggcatg ttcttcaatt agagtccgca   35760
tccgacaagg cgcactatat tctatctaaa gatggtaaca ggaataactg gtacattggt   35820
agagggtcag ataacaacaa tgactgtacc ttccactcct atgtacatgg tacgacctta   35880
acactcaagc aggactatgc agtagttaac aaacacttcc acgtaggtca ggccgttgtg   35940
gccactgatg gtaatattca aggtactaag tggggaggta aatggctgga tgcttaccta   36000
cgtgacagct tcgttgcgaa gtccaaggcg tggactcagg tgtggtctgg tagtgctggc   36060 ggtgggtaa gtgtgactgt ttcacaggat ctccgcttcc gcaatatctg gattaagtgt    36120
gccaacaact cttggaactt cttccgtact ggccccgatg gaatctactt catagcctct   36180
gatggtggat ggttacgatt ccaaatacac tccaacggtc tcggattcaa gaatattgca   36240
gacagtcgtt cagtacctaa tgcaatcatg gtggagaacg agtaattggt aaatcacaag   36300
gaaagacgtg tagtccacgg atggactctc aaggaggtac aaggtgctat cattagactt   36360
taacaacgaa ttgattaagg ctgctccaat tgttgggacg ggtgtagcag atgttagtgc   36420
tcgactgttc tttgggttaa gccttaacga atggttctac gttgctgcta tcgcctacac   36480
agtggttcag attggtgcca aggtagtcga taagatgatt gactggaaga aagccaataa   36540
ggagtgatat gtatgaaaaa ggataagagc cttattacat tcttagagat gttggacact   36600
gcgatggctc agcgtatgct tgcggacctt tcggaccatg agcgtcgctc tccgcaactc   36660
tataatgcta ttaacaaact gttagaccgc cacaagttcc agattggtaa gttgcagccg   36720
gatgttcaca tcttaggtgg ccttgctggt gctcttgaag agtacaaaga gaaagtcggt   36780
gataacggtc ttacggatga tgatatttac acattacagt gatatactca aggccactac   36840
agatagtggt ctttatggat gtcattgtct atacgagatg ctcctacgtg aaatctgaaa   36900
gttaacggga ggcattatgc tagaattttt acgtaagcta atcccttggg ttctcgctgg   36960
gatgctattc gggttaggat ggcatctagg gtcagactca atggacgcta aatggaaaca   37020
ggaggtacac aatgagtacg ttaagagagt tgaggctgcg aagagcactc aaagagcaat   37080
cgatgcggta tctgctaagt atcaagaaga ccttgccgcg ctggaaggga gcactgatag   37140
gattatttct gatttgcgta gcgacaataa gcggttgcgc gtcagagtca aaactaccgg   37200
aacctccgat ggtcagtgtg gattcgagcc tgatggtcga gccgaacttg acgaccgaga   37260
tgctaaacgt attctcgcag tgacccagaa gggtgacgca tggattcgtg cgttacagga   37320
tactattcgt gaactgcaac gtaagtagga aatcaagtaa ggaggcaatg tgtctactca   37380
atccaatcgt aatgcgctcg tagtggcgca actgaaagga gacttcgtgg cgttcctatt   37440
cgtcttatgg aaggcgctaa acctaccggt gcccactaag tgtcagattg acatggctaa   37500
ggtgctggcg aatggagaca acaagaagtt catcttacag gctttccgtg gtatcggtaa   37560
gtcgttcatc acatgtgcgt tcgttgtgtg gtccttatgg agagaccctc agttgaagat   37620
acttatcgta tcagcctcta aggagcgtgc agacgctaac tccatcttta ttaagaacat   37680
cattgacctg ctgccattcc tatctgagtt aaagccaaga cccggacagc gtgactcgt   37740 aatcagcttt gatgtaggcc cagccaatcc tgaccactct cctagtgtga aatcagtagg   37800
tatcactggt cagttaactg gtagccgtgc tgacattatc attgcggatg acgttgagat   37860
tccgtctaac agcgcaacta tgggtgcccg tgagaagcta tggactctgg ttcaggagtt   37920
cgctgcgtta cttaaaccgc tgccttcctc tcgcgttatc taccttggta cacctcagac   37980
agagatgact ctctataagg aacttgagga taaccgtggg tacacaacca ttatctggcc   38040
```

```
tgctctgtac ccaaggacac gtgaagagaa cctctattac tcacagcgtc ttgctcctat   38100
gttacgcgct gagtacgatg agaaccctga ggcacttgct gggactccaa cagacccagt   38160
gcgctttgac cgtgatgacc tgcgcgagcg tgagttggaa tacggtaagg ctggctttac   38220
gctacagttc atgcttaacc ctaaccttag tgatgccgag aagtaccgc tgaggcttcg   38280 tgacgctatc gtagcggcct tagacttaga gaaggcccca atgcattacc agtggcttcc   38340
gaaccgtcag aacatcattg aggaccttcc taacgttggc cttaagggtg atgacctgca   38400
tacgtaccac gattgttcca acaactcagg tcagtaccaa cagaagattc tggtcattga   38460
ccctagtggt cgcggtaagg acgaaacagg ttacgctgtg ctgtacacac tgaacggtta   38520
catctacctt atggaagctg gaggtttccg tgatggctac tccgataaga cccttgagtt   38580
actcgctaag aaggcaaagc aatggggagt ccagacggtt gtctacgaga gtaacttcgg   38640
tgacggtatg ttcggtaagg tattcagtcc tatccttctt aaacaccaca actgtgcgat   38700
ggaagagatt cgtgcccgtg gtatgaaaga gatgcgtatt tgcgataccc ttgagccagt   38760
catgcagact caccgccttg taattcgtga tgaggtcatt agggccgact accagtccgc   38820
tcgtgacgta gacggtaagc atgacgttaa gtactcgttg ttctaccaga tgacccgtat   38880
cactcgtgag aaaggcgctc tggctcatga tgaccgattg gatgcccttg cgttaggcat   38940
tgagtatctc cgtgagtcca tgcagttgga ttccgttaag gtcgagggtg aagtacttgc   39000
tgacttcctt gaggaacaca tgatgcgtcc tacggttgct gctacgcata tcattgagat   39060
gtctgtggga ggagttgatg tgtactctga ggacgatgag ggttacggta cgtctttcat   39120
tgagtggtga tttatgcatt aggactgcat agggatgcac tatagaccac ggatggtcag   39180
ttctttaagt tactgaaaag acacgataaa ttaatacgac tcactatagg gagaggaggg   39240
acgaaaggtt actatataga tactgaatga atacttatag agtgcataaa gtatgcataa   39300
tggtgtacct agagtgacct ctaagaatgg tgattatatt gtattagtat caccttaact   39360
taaggaccaa cataaaggga ggagactcat gttccgctta ttgttgaacc tactgcggca   39420
tagagtcacc taccgatttc ttgtggtact ttgtgctgcc cttgggtacg catctcttac   39480
tggagacctc agttcactgg agtctgtcgt ttgctctata ctcacttgta gcgattaggg   39540
tcttcctgac cgactgatgg ctcaccgagg gattcagcgg tatgattgca tcacaccact   39600
tcatccctat agagtcaagt cctaaggtat acccataaag agcctctaat ggtctatcct   39660
aaggtctata cctaaagata ggccatccta tcagtgtcac ctaaagaggg tcttagagag   39720
ggcctatgga gttcctatag ggtcctttaa aatataccat aaaaatctga gtgactatct   39780
cacagtgtac ggacctaaag ttcccccata gggggtacct aaagcccagc caatcaccta   39840
aagtcaacct tcggttgacc ttgagggttc cctaagggtt ggggatgacc cttgggtttg   39900
tctttgggtg ttaccttgag tgtctctctg tgtccct                          39937
```

<210> SEQ ID NO 2
<211> LENGTH: 43769
<212> TYPE: DNA
<213> ORGANISM: Artificial Sequence
<220> FEATURE:
<223> OTHER INFORMATION: Synthetic Polynucleotide

<400> SEQUENCE: 2

```
tctctcggcc tcggcctcgc cgggatgtcc ccataggtg cctgtgggcg ctagggcggc     60
ctgtggaggc ctgagagaag ctcttagtgt gggccaaagg gtaacctgag gcctgccgga   120
```

```
gcgagcgata gggacgcgtg taggccgctt gacagcgtgt gtgggcgtgg gctatctgtt    180
cgtttgctcc gcttacgcta cgcttcactc acggccttgt gtaccttagg gtcttcctta    240
tcgtgtacct tgggacagtc ttagtaacta ccttagtcac ttccttagta gcttccttag    300
tgagtagctt agtggctatc tattgctgtc ttagtgttac cttagtgatt gcatagctac    360
gctataagat gcgaataggt cgcggtcggt agaccgctaa agaaagagaa gaacaataag    420
atgcagtagg agggacacca gaatcctagc cagcctaacc tatcctagct ctgtatctat    480
tgcttttcct tagtccaaca cgttagacaa cctatgatta tcttagtagc tgtgacatgt    540
atcacataaa taatctatct tagtgaaact tagtgttgac acaggcagta gtcggtagta    600
cattacagtc atcgggaggc aacccagccg aacgataggt agctttggct gccttgctct    660
ttaacaatat ggctagtgtc ttgataggct aactaactga ggttactatc atgctcaaag    720
agactcaaat caagcacgaa aacggaaagt attgggtgtt agaggttaag aaaggtatgt    780
atcaggtgat gatatctggc ttaactcact caacttgtga tagtgcttac aacgatctta    840
gcttagctat ttatcggtgc gattatctgg ctaaacgagc ataaggtaag gctggcgtag    900
gctggcctat caaggcacta tccttgctct ttaacaatct gcttagtgta acctatgtaa    960
gccgtggtat tacttattaa cttaatgagg tgatactatg tacgatgaac tgtatgaagc   1020
ttactttaac tctctggatg aaggagaaga ggtactatcc tttgctgatt ttgtagaggc   1080
taggggaggt gctgaatgat gaccttgaat cttagagaag ctagcgcggt ctttactatg   1140
ttatgttgga tgatacgtaa caacgaaatg atgaccgatg acgagctagc gctttaccac   1200
cgcttttcgta atgagggctg ggaagataca gtgaacaatg tgcgcgacat actgaaggag   1260
ataatccatg tttaagcaca cgatatacac gcaatgctgc aattcagtgg gcattatgcg   1320
ttggtgggat gagtctagtg ttaagtgcta caatttgaat gatgatagca ctatgtatga   1380
ggttactctc attaaaagat ataaccacga cacgctgtta tggattctat ctgaatggga   1440
actaacctat gaagatgtga ttacagaaga aatttaaatt aaccattgac taccacggct   1500
tacataggtt acattaagca ccaacaagaa gtaacgatct ttaacaatct ggattgaagc   1560
cgattagata gaggttaaca cataggaggt ttacagagcct cctagatggt aacttactaa   1620
ctaagaggaa atagaaatgg caatgtctaa catgacttac agcgacgttt acaaccacgc   1680
ttacggattg ctgaaagaat acattcgcta cgatgatgta cgcaacgagg acgacctgag   1740
cgataaaatc cacgaggccg ctggtaatgc tgttccgcac tggtacgctg acatctttag   1800
cgtaatggct agtgacggta ttgacttgga gttcgacgac tctggtctga tgcctgacac   1860
taaggacgta acgtacatcc ttcaagctcg catccatgaa caactcacga ttgaccttta   1920
cggggacgct gaagacctgc ttaatgagta tttagaagag attgaagctg aagaagacga   1980
agaagaggac gaataaatga acggcaaaca atataccttt caattttctg atggtattac   2040
cttgaaatgt tctctaaggt tcgccatgat gcgagaggaa acattaggaa ctagttataa   2100
actagttatg tgacactata agatgattaa cagggtattc ttgcgagagt acccgattaa   2160
tctaatttga tgaggcgatt atgagtaaag taacaaacat tttagtctct attgtaatcc   2220
tgttagttgt gctgtggtct gcaataggtt ctaacttcca gtggtttaac acctgctatg   2280
aaggagattt acacactaag cacttacagt ttaatggtgt tacaatatat tccacctttg   2340
aaaaccataa agataaccct tttcataagt aatagcctat agtgtcattc gtggcactat   2400
gtgaaattac ttaataacat atggagaaca taccatgact actgaataca ccattgtaac   2460
tcttcgtgaa gctgcaaccg ctgaaatcaa agcacattta gacaccatcg gcgcttccta   2520
```

```
tatcaagatt ggtacttgct taaacgagct acgcgctgac tttgacggtc aaaaggagtt    2580
tttagcttat gttgaggctg aattctcaat taagaaagca caatgctatc acctgatgaa    2640
tgtagcgcgt gttttcggtg aagatgagcg ctttaaaggt gtggcgatgc gtgtaatgtt    2700
ggcgcttatt ccggtagctg atgaagcctc cgtaatgggt aaggccgcag aactggcggc    2760
taatggtgag ctggatacta aggccgtaaa taaactgctt ggaaagcctc aggccacgcc    2820
taaatctgaa cctaagcaat cacatggcga cgaagagaaa acgcctgaga gcgccgcaca    2880
gggagcgcct cagccattgc agtcagtacc tgaggaagat aaagcgcctt gggatgaaga    2940
caccacgcaa actgtgaaag atgattcaca gaaagcacct gagacagccg cgccgcgcct    3000
ggataacgct gagaccgcag acagtgcggc tatggctagc ctgttagacc agattagcaa    3060
gctgacagaa caactaacat tagctaacaa ccgcatcgcg gagttaacaa gcgctcgtga    3120
atccaagaaa gcaagcgctc caatgctccc acagtttaaa tcttcatgtt tctatgctcg    3180
cttaggtctg agcgcggagg aagcaaccaa gaaaacagca gttaacaagg ctaagcgtga    3240
acttgttaag ctagggtatg gtgaaggtca tgaagcgtgg gccttgatta gcgaagcagt    3300
agaatcctta actaaataaa gttgacttat agagcgtcat taagtaagat ggcgctcaat    3360
taagttttct agtaccgcat gaggatacaa gatgcaagat ttacacgcta tccagcttca    3420
attagaagaa gagatgttta atggtggcat tcgtcgcttc gaagcagatc aacaacgcca    3480
gattgcagca ggtagcgaga gcgacacagc atggaaccgc cgcctgttgt cagaacttat    3540
tgcacctatg gctgaaggca ttcaggctta taagaagag tacgaaggta agaaaggtcg    3600
tgcacctcgc gcattggctt tcttacaatg tgtagaaaat gaagttgcag catacatcac    3660
tatgaaagtt gttatggata tgctgaatac ggatgctacc cttcaggcta ttgcaatgag    3720
tgtagcagaa cgcattgaag accaagtgcg cttttctaag ctagaaggtc acgccgctaa    3780
atactttgag aaggttaaga agtcactcaa ggctagccgt actaagtcat atcgtcacgc    3840
tcataacgta gctgtagttg ctgaaaaatc agttgcagaa aaggacgcgg actttgaccg    3900
ttgggaggcg tggccaaaag aaactcaatt gcagattggt actaccttgc ttgaaatctt    3960
agaaggtagc gttttctata atggtgaacc tgtatttatg cgtgctatgc gcacttatgg    4020
cggaaagact atttactact tacaaacttc tgaaagtgta ggccagtgga ttagcgcatt    4080
caaagagcac gtagcgcaat taagcccagc ttatgcccct tgcgtaatcc ctcctcgtcc    4140
ttggagaact ccatttaatg gagggttcca tactgagaag gtagctagcc gtatccgtct    4200
tgtaaaaggt aaccgtgagc atgtacgcaa gttgactcaa aagcaaatgc caaggttta     4260 taaggctatc aacgcattac aaaatacaca atggcaaatc aacaaggatg tattagcagt    4320
tattgaagaa gtaatccgct tagaccttgg ttatggtgta ccttccttca gccactgat    4380 tgacaaggag aacaagccag ctaacccggt acctgttgaa ttccaacacc tgcgcggtcg    4440
tgaactgaaa gagatgctat cacctgagca gtggcaacaa ttcattaact ggaaaggcga    4500
atgcgcgcgc ctatataccg cagaaactaa gcgcggttca aagtccgccg ccgttgttcg    4560
catggtagga caggcccgta aatatagcgc ctttgaatcc atttacttcg tgtacgcaat    4620
ggatagccgc agccgtgtct atgtgcaatc tagcacgctc tctccgcagt ctaacgactt    4680
aggtaaggca ttactccgct ttaccgaggg acgccctgtg aatggcgtag aagcgcttaa    4740
atggttctgc atcaatggtg ctaaccttg gggatgggaa agaaaactt ttgatgtgcg     4800 cgtgtctaac gtattagatg aggaattcca agatatgtgt cgagacatcg ccgcagaccc    4860
```

```
tctcacattc acccaatggg ctaaagctga tgcaccttat gaattcctcg cttggtgctt    4920
tgagtatgct caataccttg atttggtgga tgaaggaagg gccgacgaat tccgcactca    4980
cctaccagta catcaggacg ggtcttgttc aggcattcag cactatagtg ctatgcttcg    5040
cgacgaagta ggggccaaag ctgttaacct gaaaccctcc gatgcaccgc aggatatcta    5100
tggggcggtg gcgcaagtgg ttatcaagaa gaatgcgcta tatatggatg cggacgatgc    5160
aaccacgttt acttctggta gcgtcacgct gtccggtaca gaactgcgag caatggctag    5220
cgcatgggat agtattggta ttacccgtag cttaaccaaa aagcccgtga tgaccttgcc    5280
atatggttct actcgcttaa cttgccgtga atctgtgatt gattacatcg tagacttaga    5340
ggaaaaagag gcgcagaagg cagtagcaga agggcggacg gcaaacaagg tacatccttt    5400
tgaagacgat cgtcaagatt acttgactcc gggcgcagct tacaactaca tgacggcact    5460
aatctggcct tctatttctg aagtagttaa ggcaccgata gtagctatga agatgatacg    5520
ccagcttgca cgctttgcag cgaaacgtaa tgaaggcctg atgtacaccc tgcctactgg    5580
cttcatctta gaacagaaga tcatggcaac cgagatgcta cgcgtgcgta cctgtctgat    5640
gggtgatatc aagatgtccc ttcaggttga aacggatatc gtagatgaag ccgctatgat    5700
gggagcagca gcacctaatt tcgtacacgg tcatgcgaca agtcaccttg tccttaccgt    5760
atgtgaattg gtagacaagg gcgtaactag tatcgctgta atccacgact cttttggtac    5820
tcatgcagac aacaccctca ctcttagagt ggcacttaaa gggcagatgg ttgcaatgta    5880
tattgatggt aatgcgcttc agaaactact ggaggagcat gaagagcgct ggatggttga    5940
tacaggtatc gaagtacctg agcaagggga gttcgacctt aacgaaatca tggattctga    6000
atacgtattt gcctaataga acaataaata tacaggtcag ccttcgggct ggccttttct    6060
tttaactatt acctgtaaca tttaattaac aagtccaacg tgttggacac gatgcggatt    6120
taagggacac tataggacta cccgtcggag acggaaagta ataggtaata ataggaagta    6180
gtaggtaagt aaggtaatta taggttactt aggttactcc ttcctattac ctccttctta    6240
ataggaaggg cagacactag gttgtctaac gtgttggaca gaacttattt acgtgacact    6300
attgaactaa tcaacattca attcattgga gaattaatca tgcgtaactt tgagaaactg    6360
acccgtaagc ctgctaatcg tttttggcatg gaggaaggga agacaggcgc caagcgtaac    6420
aagcctaccc gtgaccgtgt atctaagcgt gcagtgtggg agtactaagt tatggctatt    6480
attaacaata ttccgtgccc tgcctgtcaa aagaatggac atgataaatc tggcaatcat    6540
cttatgatat ttgatgatgg cgctggttac tgcaatcgtg gacacttcca tgatagtggc    6600
aagccttact accataagcc ggaaggtggc atcgaaatca ccgagctacc catcactggc    6660
aatatcaaat atacaccttc tcaattcaaa gaaatggaga aggaagggaa gataagtgac    6720
cctaaacttc gtgctatcgc cttgggtggt atgcgtatga agatcgttg ggaggtgatg    6780
aatgcggaag aaagggcgga gcaagaatct gaatggcagc ttgacgttga gtggttcctt    6840
gaacttaaaa ggaagaacct tgtatcacga cacattcgcg gagacatttg tgcgctttat    6900
gacgtccgag taggtcatga tggagaaggg aaggttaata ggcactacta ccctcgcttc    6960
gaaggtggca aacttgtggg agctaagtgc cggacgctac ctaaagattt caagtttgga    7020
catctaggta aactgtttgg caaccaagac atgttcggta tgaataccat gtctaacgtg    7080
ttggacaagg gacgaaggaa agacaccctg cttatcgtgg gaggtgaact ggatgcacta    7140
gcagcacagc agatgcttct ggattctgcc aaaggtacga agtgggaagg tcagccttac    7200
catgtgtggt ctatcaacaa gggtgaggct tgccttgaag agatagtaca gaaccgtgag    7260
```

```
cacatctctc agttcaagaa gattatgtgg ggcttcgacg gtgatgaaat agggcagaag    7320
cttaaccaac aagcggcccg cctgttcccc ggcaagtctt atatcattga gtaccctgcg    7380
ggctgcaagg atgctaacaa ggcattgatg gctggcaaat ccaaggagtt cgtagatgca    7440
tggttcaatg ccaagtcatc agatgaggtt ttcggtagcc agattaaatc catcgcctct    7500
caaagggaca agctgaaggc tgcacgccct gaaccgggat tatcttggcc ttggcctagg    7560
ctgaacaaga taacccttgg catccgtaag catcagctaa tcatcgtcgg cgctggttct    7620
ggtgtaggta agactgagtt cctccgcgaa gtagtgaagc acctcattga agaacatgga    7680
gagtcggtag gtattatctc cactgaagac cctatggtta aggtctcccg cgcattcatt    7740
ggtaaatgga ttgataagcg tattgaacta cctccaacca atgacccaag agaagatgga    7800
taccgtgagg tctttgatta taccgaagag gaagccaacg ctgccattga ctacgttgct    7860
gacactggta agcttttgt agctgacctt gaaggtgact attctatgga gaaggtagag    7920
cagacgtgcc ttgagtttga ggcaatgggt atttctaaca tcatcattga taacttaaca    7980
ggaattaaat tagatgaacg aaattttggt ggtaaagttg gtgcgcttga tgagtgcgtc    8040
aaaaggattg gcactatcaa agaccgacat ccggttacta tcttccttgt ctcgcacctt    8100
acacgtcctt caggacaacg tacctcacac gaagaaggtg gcgaggttat cctttctgac    8160
ttccgaggct caggggctat cggattctgg gcttcttacg ccttggggat tgagcgtaat    8220
acaagagctg aaacgcttga tgaaaggact accacgtaca tctcatgtgt caaagatcga    8280
gaccaaggca tctacactgg tactaaagtg atgctcaaag gggatgttag taccggcaga    8340
ttaatggaac cacaatcacg tactaaatca tttgatacag gtgctccaaa agagcaagct    8400
gtgcctgatg aattaggtga cactatagaa gagaacacac aggagtttaa tggatgattt    8460
aggttttggt tgttcgctac cgtactactt gttattaaca tagacaaggt tgctatgtta    8520
ttcaaatagt gtacttatca gggttttgtct aacatgttgg acaaactctt attaagtaca    8580
ttaactaact ggagattatt atgtgtaaat tgcacctcaa caaatcagat tgtgtgcgta    8640
acattaacaa gagatctatc cgctttcgct gggagggtgt agtgtttgat gtagatgaga    8700
gatactacca tgtagtgtat ggtaatggat tacgtcaaac ttatctgaag gctctggcgc    8760
atcattacct tgaaccgatt gaaccaacta agagtaactg cacctgtgta cacgatgatc    8820
tgtgtgatcg ctgtgctcgt caagttaata aggcattgac aatcatggag cgttacggtg    8880
caggccacaa ggcaatctct gaggctgcgt ggactgtact catgtttgaa cgccctaatg    8940
gtcgtaaggt gctgaatcgt gagcggcgta atgtaatcac aggtcaagac tttcgcatct    9000
tagaggaggc tatgtgtaat cctggtattg ctatacgtta tgaggatgta gaccatgcta    9060
tatctgaagg tatcggtaat cgtttggaat tgaataagca ttttgatcag gtattacgtg    9120
acactatagg tgggcgcaaa ggttttacct ttgagcgcgg gcatgttaca tttaacccta    9180
tcgttacgga ggaaacctat gtcacgcaat gacagtaagt acagcctgaa gttccttgag    9240
cagcatgaag aacttgcagc caaggtaact aaccaagcat tcctgtttgc acaactaacg    9300
ctggctgaag ctaagaagaa cagccttacg cgtgagcaga ttatcaagga aggaaccaag    9360
cgcagttaat aagtcgtgac ttgtctaaca tgttggacag gtcactctca tattaattgg    9420
agatacataa atgactaaag taactaagtt aaccgaacac ctgattaaac taagtgaaga    9480
actaaagaac agcgaagtta ggcttgagta ttacttcatt gacccaaggg aagatgatcg    9540
tgaaacacct gactacaagt ttgaaacgga gttaatgtat gaaaactatt aattgggcga    9600
```

```
aggaagcaga aggacgtatc ctagtaatgg atgcggaggc taaaggctta cttgatgcaa    9660
tccgatatgg aaaaggtaac gatgacgtgc atataatttg ctgcatggac ttgctcacca    9720
ctgaagagtt tctcttcttc aacccatatg accgtcgtga ccctaacgca agggagcacc    9780
tgaaggagtg ggatggtcat caggacggtg accttgaaga tggtgtgaga ttcctcaagc    9840
actgtgaagc tatcgtgtca cagaacttcc tcggctatga cggcttgctt tttgagaagg    9900
cattccccga tatatggaaa ggctataact cacggagaa gcgcggcaaa ggccgtctgc     9960
gggccgatct gtgcccggtt aaggtaatgg atacccttgt catgtcaagg ctcctgaacc    10020
cggataggcg actccctccg caggcatacg ctaagggtat gggtaacgtt gcacctcact    10080
ctattgaggc acacggtatc cgtataggtc gctataagcc tgagaacgag gactggtcta    10140
agctgacaga ccacatggtg caccgagtac gtgaggatgt ggcgatcggt cgtgacctgt    10200
tcctgtggct gtacaacggc gagtggatgg agcacaagcg gcgtggcgtc aatccaagga    10260
ctggtcttgg cattgagaca gccttccaca tggagtccat tgtagcactg gagatgtctc    10320
gtcaagcgga gcgcggcttc cggctggata tagacaaggc actggcacga tgcgaggagc    10380
ttgaccagaa gattgacgag actgttgcag ccttccggcc tcacatgcca atgcgcatca    10440
agtctaagcc tttcaaacct caagagaaac aggagcaagt agatgcggca aactcattta    10500
gtttacagaa tcatactggc gttacacttg gagccgatgc tttcattcat gccgagcggc    10560
gctccgatag aaagactgta tggtcagtca ctactaagtc aggtgattgg tcagctactg    10620
tcaagaaaga cttccctcac atccgaggaa acatcaatga tactccgagt attaaacaca    10680
tcgggccata tacacctgtc accttcgaag atatcccgct tggtaaccga gacacagtta    10740
agcaggttct gtatgacttt gggtggaggg gagttgagtt caacgacact gagcaatctt    10800
atctggacga gcatggagtg ttgcctaagc cgtggagtgg aaagataaat gagaagtccc    10860
ttactttatg gcaggaaagg gctgcacgtg aaggtaagtc agtacctgat tggtgcttgg    10920
gtatcgctgc atggtacata ctcgtatccc gtcgtggtca gatcctcaac cgtggtgatg    10980
ttgaaacctt cgattcaacg gggcgttggc cctcgcaagc tggtgtacga agtgtcgcg    11040 gcctcgtacc tgtagccttt aacaaggagc taggtatcaa tgcacaggca tactacgaaa    11100
catatggcta ctggcctacg tccgacaagg atgatggaga gtggcgtgtt cccgctgttg    11160
ctatttctat tggcacttct acgttccgta tgcgtcacag gaatgtggtt aacatccccg    11220
ctcgcggtct ttaccctctt cgtgatttat ttatagctgg taaaggtaag atgattcttg    11280
gttgtgatgg tgcaggactg gagttgcgtg tgttatcaca cttcatgaat gaccctgaat    11340
accaagagat tgtactgcat ggtgacatcc atacacacaa ccaacttaag gctggtttac    11400
ctaagcgtga catggcgaag acttttatct acgcattctt gtatggctct ggtattgcca    11460
accttgccgc tgtatgtggt gtaactgaag atgagatgaa ggaggttgtt gcacggttcg    11520
agatcgaact accatcactg gctcgtcttc gtgagaatgt catcgctgct ggtaataagt    11580 ttggataccct gcaagcacct gatggtcatt gggggcgcat ccgtatgagt ggtggtgagc    11640
ttaaagaaca caccatgctc aacgtattac ttcagatgac aggctccttg tgtatgaaat    11700
atgccttggt taaagccttt gcagtcatgc gccgtgaagg tgttgcactg gataacctgg    11760
ggaatccgtg tggcgtggct aacgtacacg atgaaatcca gatggaagtg ccagaagagg    11820
aggtgttata ccttgactat gaattaccttt cacgttgga aggtttcgaa tctgagaagc    11880
aagctatcaa agctgtgttc gaccctgaag agaagcgcgt acatgtggat tccgaagggc    11940
gcatgtggtc tgctgctaac ttggttgaag tggatactgc tgctggcgtg ctgcgttgtc    12000
```

```
agcgtcgcta ccacagggct ggtcatatta tcgctgacgc catgacatgg gctggtaagt   12060
acctgaatat gcgctgccct atggctggcg agtacaaaat aggtgcaagc tggaaggaga   12120
cacactaatg caaactgctc ttattattct tggagtcata ttatttatgg tagtgttctg   12180
ggccttctct ggtattgacc cagattacga tggtaactac gactgagtta tactcaaggt   12240
cacttacgag tggcctttat gaataactta actggagatt attatgatta aatattgctt   12300
atcaattaac taaagaccgt aagataggta ttgaggttaa agcctgggac gcgggacaca   12360
tctctgtagt tatagagtgc cgccaagaca atggtatgct gttaagaagc taccgttgct   12420
tcaccaaatt acgctgcaaa gatttaactg aagaattatt cttacgttgt attgttgaat   12480
ctattaaact tattagacct tacgctaagc aagttgtagg taatgtcaca gtggtaaatt   12540
gatttaggtg acactatagg aggaagacct aggtaatcta ggtttataat gtagtatagg   12600
taattaagta aatataggag atataaacat gtcaatggta actactctgg tattcgtggc   12660
tcaatacttt cgtggtctgg ctaataagtt caagtacaaa gctattgaag ctattgagga   12720
ccgcatcgaa gcagtacagg cagaacaagt tgaagttgaa gaacatcgta gttctcaaat   12780
gattgactgc cataatcgct attacgcatc tcgtgatgac cttaatgcac gacaagtcaa   12840
agaggtcgaa gagatgatgg cacgtcacca gcaagagcgt gacaacctga aggctgactt   12900
tgaagagcgc aaggcatcca ttgcccttgt acatcaagct gcatctgaca gcctgaagaa   12960
agagattgtt atgctggaag tggagttaga caatctgacc aaataattag gtgacactat   13020
agaacaatag gacgtgggtt tgtcggagac agtaaatcca aggtgctcag tgagcgtaaa   13080
gcctaagcac gtcctatgat tgtaaagtgt tgaacctctt gtgcatcttg cacacccga    13140
tacagtatcg ggcttttctag tgagtacatg cttgtgctca gtacaaagct aacaaacaac   13200
aggaggaata aattaatggc tcgtaatttt gattttggtg ctgaggttgc tgctgctact   13260
ggtggtgtgt ttaagaatcc agaagttggt gatcacgagg cagttatctc tggaatcatt   13320
cacgttggtt ccttccaaga catctttaag aaaggtaaca ctaccgaggt gaagaagcct   13380
gctaacttcg ttcttgttaa ggttatcctg atgggtgacg atgacaagaa cgaggatggt   13440
tctcgtatgg aacagtggat ggctgtgccg ctcaagtctg gtgacaaggc gacgctgacc   13500
aagttcctga atgcagttga ccctaaagaa ttactaggtg gtttcgatga cttcatcggc   13560
gagtgcatga ctgtgagcat ggttggcgat gagaaaggtg gcaagaatga tgacggcacc   13620
ttcaagtacg ttaactggaa aggcttcggt ggtatgccgg ataaattgaa gaagctggta   13680
ctggctcagg tagaggatga aggtctggaa atgactggtc acatcaccct tgacaagctg   13740
accaaagata tcatcgactc tattcctgca caccttgtac gtcagtacct gctgaacgag   13800
acgccgcgtg gtaagaacct gtcagtagtt ggttctcatg tagagggtat cattgccgaa   13860
gcacgcgcag cagaccctga gtggaagaag gccaagaaga agacaatga ggccacccct    13920
gaagaccgca gacgctggac cactggcgct gctgttccgc aggaagtacc ggaagcgcag   13980
aatgccccgg cacctgctat ggatgaagat gctgaatatt aatcaaggag gtttaatgaa   14040
agtagaagca gtaaccctac acttcaagcc cggcgtaacg tcgctgggcg gcacgcagtt   14100
catttctttt agcgagggca aggcctacca agacctgcac tatattaccc gtgagggca    14160
gcacgtcgtg aattacagcg accctgtgac aggcaaacgt cacggcattg gattccctat   14220
gacggacatc cgtcagacca atacgatttt gtaagtctaa cgcgttggac aaatctgtgt   14280
ctcttatttt aggggacacta tagaagagag aattttaatc ggcgataatg ccacaattaa   14340
```

```
cagaaggaga atttaaatat gttcactatc gaaactatcg taaaccgtgt tgttaaaggc    14400
gctaccttgg tatccgttga gtctttcatt atcgtcgatg aagctggctc gctggtagct    14460
ggcaccaaag catacgacac ccgcgaagaa gctcaagcta agattgacag catgggtaac    14520
tttgctactg gcctggagtt tgctcgtgct tgcttccctg agcaggctga caaagcacag    14580
attggtaagg ctaacattgt agctgaatat ctggattgga ttgctgctgg taagccagtg    14640
aaagaagtta agtctgctga agaagctgaa gctccggcag tggaagctgc accgaaagct    14700
ccggttagcg aagaagaaga gttttaattg atgccctgtc tgccttagtg taggcagggt    14760
cttttgcgta atagttattg gagaatgaat tatgccgact attagatctc gtttagtagc    14820
agattatgtg tatggtcgtg atgtcaaaat gatgaaagat tacctcaaag ttattatctt    14880
gcttgatggg gagttgtttc atactaaaac cttcaccctt cctgagttat ttgacttagg    14940
atattggggt tatacctatc aggccatagc aaataaggtg ctactcgatg tattaaagga    15000
gtggcctaca tgcgaccaaa cttcaacttc ggagctacag tatcggaaga caataatctc    15060
atcctgtggc cgactgaagg taagagaatc gctctcatag atggagatat gattccatac    15120
atcattggtt atactatcaa tgagatgaca cttgtccgag cgatgacccg cgttaagtca    15180
gggcaagtag agcgcatcga agatacacct gagtgtaagc aagcttgcga ccgtgtaaac    15240
tctatgctta actcttgggt gtatggtgct gaatgtgatg ccgcacgcat cttcctcacc    15300
aagtcagata ctaacttccg cctacgcttg gctttcacga aaccatacaa aggtacacga    15360
aaggcagaca agcctccttt cttctatgag atgcgacaac acctgataag tgtgcatggt    15420
gcagaactgg cagatgggga ggaagcagat gacttgatga gtatcgcaca atgggatagc    15480
cacaaccgat tcttgcaaga agtaggtaac gagttctcaa taggaagccc tgagcataag    15540
gtgttctccg ataccgttat tgtatctgcg gataaagacc tgatgatagt accggggtgg    15600
cacttgcagc cgggaagtga aatgaagtgg gttaaaccta tgggttggct tgaccttcgt    15660
cgtaagaata acgggcaggt caaagacctt aaaggtgcag gactaaagtt cttctatgca    15720
caaatgatta taggtgacga catagataac tatgcaggca tcccaggacg tggggccaag    15780
tacgcttatg acctccttga tagttgcaag actgagaagg aactctatat ggctgtgctt    15840
ggtgcctaca agtctaagtt tggagaaggg ccagtcaagc tcaagaacca tagaggaacc    15900
taccgcatcg gcaaggcttt tgatctgatg ttagaatgtg gccgcttggc tcatatggca    15960
caattcaaag gtgacatctg gcgtgcggat aagaatccaa ttgtgtgggg agatgatgat    16020
tcatggcaat cagattgaag gcttcggagg tagctgacta caagaaagag ctactagaga    16080
agcagaaatg gaagtgccct ttatgtggcg gcagcctcaa ggctgtcact gcaattaacc    16140
gtgtacttga ccatgaccat gagacaggct tctgtcgtgc agtggtttgt cgtggctgca    16200
atggtgcgga gggtaagatc ttaggtgtta tttctggtta tggtaaggca ggtaacaatc    16260
gctacttcca actgaagtgg ctggagaact tgtatacata ctggaagtta catcaaacac    16320
ctcagacgga taagttgtat cataagcata agactgaggc ggagaagcgc gaggctcgca    16380
atcgcaaggc tcgcttggca tacgcaagaa agaaggaggg taaagttggg taagctacgc    16440
tcactgtata aggactccga ggtacttgat gcaatagagc aggctaccga cgagaaaggt    16500
aatgttaatt ataacgagat ggctcgcgta ctttctgcgc atcctgtcgg caagaagatt    16560
acacggcagc ttgctcgtta ctggcatggt caattcatgc ataccaagaa gaacggtgac    16620
tactaccaga ctctttctca ggaggatagg cgactcaaag aagcacgtaa gctcaggact    16680
cctgaccgct atgaggatct ggctattgta ccattgcctg actcgcctca tagaagtgta    16740
```

```
ctggtgatcc ctgatacccca tgcaccttat gaacacccag ataccttgga gttcttggca   16800
gcagtggcgg cacgcttccg tcctgatacg gtggttcact taggagatga ggcagacaaa   16860
catgccttgt cattccacga tagtgaccct aaccttgact ccgctggtgt ggagttggag   16920
aaggcacgtg ccttcatgca caagctgcac cggatgttcc cggtcatgcg cctgtgccac   16980
tccaatcatg gttctatgca cttccgcaag gcaagcgcca agggcatccc tgtccaatat   17040
ctgcgcactt accgagaagt cttcttcccg catggtggcg cgaccaatg ggattggcaa    17100 cacactcatg tcctggagtt acctaacggg gagcaggttg cattcaagca tcaaccagca   17160
ggttctgtgt tagcagatgc ggcacatgag cgaatgaatc tggtgtgcgg ccacttgcat   17220
ggtaagatgt cagtggagta tgcacgtaac acacatgagc aatattgggc tgtgcatggt   17280
ggctgtctta ttgacgagtc gtctcgcgca tttgcttatg gccgtgagtc caagtataag   17340
ccagcattag gttgtgtggt gattgtagag ggtgtacctc agattgttcc aatgcagacc   17400
aatgcagaag gtcgttggat tggcaggatt taagtgacac tatagaacaa agggtcaggt   17460
aatacttatc ggctggcata tccaaatgat attgcactgg cccttgattg tatagtgaat   17520
ggaggaatta ttatgtcag aaattgtat tggtaagtac gttgtacgcc gtgcagctta    17580
tcgagatgcc ttctggaata aactgtgtga agcttaaac aagcaaccag atgggtgtt    17640 caaagtgtcc agtgtagaac ttaactacaa ctctatcatg ttagaaggtg tggagaaacg   17700
cgaatggtat gcaccttatt tccaggtcgt tgactccctg caaggcgaag agtccaacat   17760
gttggacaac aacatggtta ctaagcctaa gcactatgag ttcttcgagg gtgtcgaggc   17820
aatcactatc attgcccgta gcatgaccga gaagcaattt gctggttact gcatgggtaa   17880
tgcattgaag taccgtctgc gtgcaggtaa gaagttcaat actgaggaag acctgaagaa   17940
agcagactac tacaaagacc tgttccagaa gcatcgccat gaatgtattg atgaggatct   18000
ctaatgaata tcttccaatt cctaggtta cctgaagatc atcgttccaa acctgttatg    18060
ctggttaagc acagggatga agtgccagaa agcaaactta cattcccggt ttatgcacaa   18120
gtgaaaagag atgaatatt tagtgctaca gttgtgcgtt ctgatggtac tgtgggtatc    18180
tttggtcgca ctggcaaaaa gctggttaat gtagaacaac tggaagcgtc ttttataggg   18240
tggcctgctg gtgtctacct cggtgagttg caatctatgg ccgttgatat ctaccttgag   18300
gcgctttcgg gtgtggtgaa tccaaacagg actgagcctc ttgacttcat aggacagcag   18360
attaaagata acctgtacat tgacttcttt gatatgctga ctattaaggc attcatcgaa   18420
gggcagacgg aggttacatt cttaaagcga tatgaagctc tatgtcgcag attgaaaggt   18480
tgccttccac ctgagaatgc aatcctgact atcacaccatt gccacaccga gcaagaggta   18540
gaggcgtttg cacagaagca cattgatgcg ggcgagaag gtgcagtctt taagttagac    18600
tgtgactatg aagcgggcca caagggcttc cgacagacca agattgtacg catggtctca   18660
tacgacttaa cgtgtattgg ttgggaagag gggaaaggta aatacaaagg taaagtagct   18720
aatcttatat ttaaatggaa gggtggcaag acaatcaagg ctatgcttgg ccgtggctgg   18780
acacatgaag atgccacccg tatgtatcac gatattaaac acggtggtga actgaacgtc   18840
atcgggaaga tattcgctat caaggctctc caagaatcta gcaagggagt cctgcgactt   18900
cccaaggttg gagagttgcg ccatgacaag gaggagcctg atgtcttttg attcaatgaa   18960
agcgacaaag gcagttgagg tagcagaagc tatctttgat atgctgtctt gtgggattga   19020
agtcccttat acacttctgt ctgatgcaga agatttaggt ctgtctgtgg aagctatccg   19080
```

```
cgagaaagtg gaggagttgt atggcgacga ccaagaagcc gactatcaat attgaaggtt   19140
gggatatgct ggagaaaatt atacttgctc catcaagacc tcgaccggat aagtcacacg   19200
aagagttagt atgggatgaa gccaagcgct atatcctgtc ttgtatcaag cagcagtttg   19260
tggtgcagcc atgataaggc aggcttgctt cctagatatc cctgagataa ttaatctagg   19320
gaacaggtat gtagaagagg aagtcaaggt agttaagcat cattcagcta catgggatgc   19380
agatcaaagc gcacatcacc tttgtgcatc ccttaccagc aaggatttat ttctatgggt   19440
ggctgtggaa gatggtgtta tcataggttt cctgtgggcg gcggctcaca tcatggcacc   19500
ttggtctccg gcacttgtgg cttctgatct actattctac atcataccag aaaagcgagg   19560
gtctcttgct ggtgtgcgct tgctcaaagc ttacaagtct tgggccaagg agcgcggctg   19620
catagaggca aggttgtcta tcgcatctgg tatcaatgag gaacgtgtgg ggcggatgta   19680
tagtcgatta gggtttactc cgttcggtac agtgtataac ttgaagtttt aaggagataa   19740
catgggtgta gttaagaagg catttcaagc agtaggtctg gcacaaaagg cacctcgcat   19800
tgaggcagct aaggttccag cacaacaact tgagcggcag actgaggtta aatctgaaga   19860
catccagatt ggacaagagg atgatgctgc ggcatctgct aagggcaagc gtggccttgt   19920
gcgccctgta gcctctagct taggagtttg atatgcaaga cactatactt gagtatggtg   19980
gacagcgatc gaagataccct aaactatggg agaagttttc taagaaacgc agtccctacc   20040
ttgacagggc aaagcatttc gctaagttaa cactcccata cctgatgaac aacaaggag   20100
acaatgagac ctcgcagaat ggttggcagg gtgtaggtgc acaagctacc aatcacctag   20160
ctaacaagct ggcacaagtg ctattccctg cgcaacgatc attcttccgt gttgatttaa   20220
cagcaaaagg tgagaaggta ttagatgacc gagggctgaa gaaaactcag ctagcaacca   20280
tcttcgctcg cgtagaaacc actgcaatga aggcgctgga gcaaaggcaa ttccgcccag   20340
ctatagttga ggtgttcaag cacttaatcg tagcgggtaa ttgcctgttg tacaaaccaa   20400
gcaaaggtgc gatgagtgca gtaccaatgc accactacgt agtcaaccgt gacactaacg   20460
gcgacttgat ggatgtaatc cttctacaag agaaagcgct acgtacattc gacccagcaa   20520
ctcgcatggc aatagaggtt gggatgaaag gtaagaagtg caaagaggat gataacgtca   20580
aactgtacac tcatgcgcaa tatgcaggtg aaggtttctg gaagattaat caatctgctg   20640
acgcatcccc ggtaggcaag gagagccgca tcaagtccga gaagctacca ttcattccac   20700
ttacatggaa gcgcagttat ggcgaggatt ggggccgtcc cttggctgag gattattctg   20760
gtgacttgtt tgttatacag ttcttatctg aggccatggc ccgtggggct gcactgatgg   20820
cagatatcaa gtacctgatt cgacccggtt cacaaactga tgttgatcac tttgttaact   20880
caggtacagg tgaggtcatc acaggtgttg cggaagacat ccacattgtt cagttgggta   20940
agtatgcaga cctgacacct atcagcgctg tgctggaagt atacacccga cgcatcggtg   21000
tcatcttcat gatggagacc atgacacgcc gtgacgctga acgtgttact gccgtagaaa   21060
tacaacgtga cgcgcttgag attgagcaga atatgggtgg tgtatattcc ctgtttgcca   21120
tgaccatgca gacacctatt gccatgtggg gcttgcaaga ggcaggtgat tcattcacta   21180
gtgaactggt agaccctgtg attgtaacag gtattgaagc actaggccgc atggctgaat   21240
tggataagct ggctaacttt gcacagtata tgtccttacc tcaaacatgg cctgaacctg   21300
cacaacgtgc aatccgatgg ggtgattaca tggattgggt gcgtggtcag atatctgcgg   21360
aactcccatt cctcaagtct gaggaggaga tgcaacaaga aatggcacag caagcacagg   21420
cccagcaaga ggccatgctc aacgaaggtg tggctaaggc cgtaccgggt gttattcaac   21480
```

```
aagaaatgaa ggagggttaa ttagtggcct ttgaatttgt agaaccgacc aatgaaacta   21540
ccgctgctcc ggctgctgaa gagaacaagg aggtgactaa tgatgttgct ggtgttgacg   21600
ctggtaatac tggcattgac gtacagaatg gtgcagatga tcaaggcaat gaggacaccg   21660
gaggagaagc tgttggacag ccttcaggag agggagatgg tgaaccggat ggtaaaccta   21720
agccagatgg ttccacggat gaggaagcgc gatacttctt cggtgaacat gaagtaatca   21780
ttgaagtgcc tgatgatgtg accgaagctc tcaaagagaa gggcatcgac gctatgcagg   21840
tggctcgtga gttgtatggt gaaggtggta gatttgaact gtcagaagaa accaagcaga   21900
aactgtatga tgcatttggt aagttcgcag tagatgccta cctatctggc ctcaaggctc   21960
agaacgaaac ctttttcctc cgtgaagaaa ctgccgccaa ggaggcggaa gctgcaaacg   22020
cacagcgcta cacggatatt gccaaggagg ttggcggtga cgaaggctgg agccgtctgg   22080
aggagtgggc gcttgatact ctttctgatg aagaactgga agcatttaat gcagtgatgc   22140
agtctggcaa ccaatatcta cagcagtacg ctgtgcgcga gttagaaggt cgccgtaagg   22200
ctgcacaggg tgacgataaa cctaaccttattgaaccaac ggctaccgct gctgcatcgg   22260
aagataatgc acctctaagt cgggagcagt acatccgaga gattgcacag ttaggccaga   22320
agtatggacg tgaccgcaaa gggatggctg aagcacaggc acgtctggat gcacgtcgcc   22380
gcgcaggtat ggctcgcggt ctttaattgc ctatttaggt gacactatag aagggaggta   22440
gtcctcccta acctatcaac ttgatttata aggagattat aatacatgtc tacgccgaac   22500
aacttgacca acgttccgt ttccgcttcc ggggaagtag atagtcttct cattgagaag   22560
ttcaacggta aggtcaacga gcagtacctg aagggcgaaa acatcatgtc ctacttcgac   22620
gtgcagaccg tcacgggaac caacactgtg agcaacaaat acttgggtga accgagttg   22680 caggtattag caccgggtca gtctccggct gcgacctcta ctcaggccga taaaaaccag   22740
ttggtaatcg atgccactgt tattgcccgt aacacagttg cacacctgca cgatgtacag   22800
ggcgacattg atagcctgaa gccgaagctg gctaccaacc aagccaagca actgaagcgt   22860
atggaagatg agatgctgat tcagcagatg atgttgggcg gtattgccaa cactcaagct   22920
aaacgtacta acccgcgtgt taagggtcat ggcttctcta tcaacgtaga ggttgcagaa   22980
ggtgaagcgc tggtcaaccc tcagtacgta atggctgctg tagagttcgc gctggaacag   23040
cagttagagc aggaagtgga catctccgat gtggctatcc tgatgccgtg gcgctatttc   23100
aacgtactgc gtgatgcaga ccgtatcgtt gacaagacct acaccatcag tcagtctggt   23160
gcaaccattc agggcttcac cctgtccagc tacaactgcc cggtaattcc gtctaaccgt   23220
ttccctaaat attctcaagg tcaaactcat cacctgttgt ccaatgagga taacggctat   23280
cgttatgacc cgctcccggc aatgaatggt gctatcgctg tcttgtttac ggcggatgcg   23340
ctgctggttg gtcgctctat cgatgtgact ggtgacatct tctatgagaa gaaagagaag   23400
acctactaca ttgataccct tcatggctgaa ggtgcaatcc ctgaccgttg ggaggctgtg   23460
tctgttgtta caaccaagcg caacaccact actggagcag tagaaggcac tgatggtgcg   23520
cagcatacta tcgtcaagaa ccgagcacag cgtaaggctg tctatgtcaa gaatgcggca   23580
cctgtagctg ctgctgccgc tagcctgtct gctgaagatc tggttgctgc tgttcgtgct   23640
gtgatggcta atgacatcaa gccgactgca ctgaagccga ccgaggaata acctatgccc   23700
tatctacctt gcgtaggtag ggttcttttg tttaggagga ttcatgcctg taattcaaca   23760
atcaagtgat gtaggttaca tcatgtccga tgcaagcttt agcatcattg atagcaagct   23820
```

```
agaggccgtc aacctttgta tgcgggccat tggtcgtgag ggtgtggatt cccttgactc   23880
aggcgacctt gatgctgaag atgcaagtaa gatgttggac attgtgtcac agcgcttcca   23940
atataataaa ggtggaggtt ggtggtttaa tcgtgagcct aattggcgca tcgtgccgga   24000
cactaatggc gaagttaacc tgcctaataa ttgcctagct gtcttgcaat gttatgcatt   24060
aggtgagcgt aaagttccta tgacaatgcg tgcaggcaag ctgtactcca catggaatca   24120
tacgtttgat atgagaagtc atgtgaacaa agatggtgct attcgtctga cacttctgac   24180
atatctacct ttcgaacacc tacctactag cgtaatgcaa gcaatcgcat atcaggctgc   24240
ggtggagttc attgtatcta aggatgcaga taagaccaag ttgaccaccc atcagcagat   24300
tgcagcacag ctattcgttg atgttcaatc tgaacagatg tcccagaaga gactcaacat   24360
gttagtacac aaccctacac agcgtcagtt tggtatcatg gcaggtggat ctcagaacgt   24420
accagcttac tcgcattcac cttacgatgg tcatccactt aaaccttggg agagttatcg   24480
ctaatggaag ttcaaggttc tttaggtcgc cagattcaag gcataagcca gcaacctcca   24540
gcagtaagat tagatggaca gtgttcagaa atggttaaca tggtgcctga tgtagtggag   24600
ggaaccaaat cccgcatggg tacaacgcat attgccaaac tcttagaata tggtgaagat   24660
gacatggcag tgcatcatta ccgtagaggg ggtgaaggtg aggaggagta tttcttcata   24720
atgaagaagg gtcaagtacc tgaaatcttt gacaaacaag gacgtaagtg tatggtgcaa   24780
tcacaggatg cacctatgac ctatcttagt gaagtgacta cccctaggga agatgtgcaa   24840
tttatgacta ttgcagatgt gaccttcatg ttgaatcgca agaagatcgt caaggcccga   24900
cctgaacgct cccctcaagt aggtagcact gctattgtct ttatggccta tggtcaatac   24960
ggtacgcact acaagattat tattgatggc gtagtggctg ctggctataa gactagggat   25020
ggtgccgagc acaccatat tgaagacatc agaactgaaa gcatagctta caatctgtac   25080
cagtcactcc aaagttggga taagattgca gactatgaaa tccagttaga tggcacctca   25140
atctatatca caaggcggga tggctctact accttcgata taaccacaga agatgggca   25200 aaaggtaagg atttggtagc catcaagtac aaggtggcat ctacagacct cttaccatca   25260
cgtgcaccag aaggctacaa ggtgcaagtc tggcctactg gcagtaagcc tgaatctcgg   25320
tactggctgc aagctgagaa gcagaatggg aacattgtct cttggaagga gacactggcc   25380
gccgatgtgt tgatagggtt tgataagtca accatgcctt acattataga acgtacaggg   25440
tttgttaatg gaattgcgca gtttaaaatt agacaaggcg actgggaaga tcgcaaagta   25500
ggcgatgacc tgactaaccc tatgccttca ttcattgatg aggaagtgcc tcagacatta   25560
ggtggtatgt ttatggtgca gaatcgtcta tgtgttactg ctggcgaggc tgtaattgca   25620
actcgcacat cttacttctt tgacttcttc cgatatctcg ccgtatctgc tgtagccact   25680
gacccatttg atgtattctc agatgcgagt gaggtttatc agcttaaaca cgcggttaca   25740
ttggacgggt ctactgtctt gtttgcagat aaatctcagt tcatccttcc tggagataag   25800
cctcttgaga agtcaaacgt attgctcaag cctgtaacca catttgaagt taacaataat   25860
gtcaagcctg tagctacagg tgagtccgta atgtttgcta caagtgaagg tgcttactca   25920
ggcataaggg agttctacac agactcttat agtgatacca agaaggcaca agcaataact   25980
agtcatgtca ataagttgct agaaggtaat gttattatga tgtcagccag tactaatgtg   26040
aacaggctgc ttgtcttgac cgacaagtac cgaaacatta tctactgcta tgactggttg   26100
tggcaaggaa ccgaacgtgt acaagctgca tggcataaat gggagtggcc tttgggtacg   26160
tttatccgtg gcatgttcta ttcaggtgag cacctatatt tgctcatga aagaggcagt   26220
```

```
actggtgtgt atcttgagcg catggacatg ggtgatgcgc ttgtatataa cctgaatgac    26280
cgcatccgta tggataggca agctgaactt atctttagac atatcaaggc agaagatgtg    26340
tgggtgtctg agccgttacc ttggcaacca accgatgtaa cattgcttga ctgtgtactg    26400
atagatgggt gggactctta cataggcggg tctttcttgt ttagctataa cccaggcgat    26460
aacaccttaa ctacaacctt tgatatgcac gatgatgacc atgtgaaggc taaggtagta    26520
gtcggccagt tatacccaca agagtttgaa cctacacagg tagtaatacg tgataaccaa    26580
gagagggtgt cttatataga tgtgccaacg gtggggcttg ttcacctaaa cctagacaaa    26640
taccctgact tcaaggttga ggtcaagaat ttgaagagtg caaagtacg taatgtgctg     26700
gcctctaaca gggtgggtgg tgccataaat aatattgttg gctatgtaga gccgagagaa    26760
ggtgtgttca aattcccact aaggtctctt agcaccgaca cagtttatcg tgtgatggta    26820
gaatcgcctc ataccttcca gcttagggat attgagtggg aaggttcgta caaccctact    26880
aagaggagag tgtaaatggc aataggtact gctcttacag caggattgtc cagtgtagca    26940
ggtagtgctg catctggtgg tttcctgtct tcgttgggtg gtgctatagg tgcagaaggg    27000
gtaatgggtt ctgccatgag tttcttaggc ggaaccactg gaggcttctc taatgctggc    27060
ctcctgtcgg caggtatgca aatgcttaac ccgataggag actacttcac gcagaaagaa    27120
acagcgaagg cgatgaagaa ggcgcaagat gagcaatggc gtcagcagtt gatagccaca    27180
agggaggctt atgcttccgt ggctaatgct gaaaggtctg cctctaagca ataccattct    27240
gaactaatag acaatcaggt atccttatta cagcaacgag cacaagttgc cttgcttgca    27300
ggtgcgagcg gcacaggtgg taactctatc acctctatgc tgaatgacct tacaggtgaa    27360
gctggtagga accaagccac cattattgac aactatgaaa cacagcagat taactttgct    27420
aaccagctca agtctatcca gaaaggtggt cagatgatga tgcgctcctt tgagaagcca    27480
tctgcattca gtgccatagc caaggtgtg tctggtatag gtgaggctta cctgtctggt    27540
catcagaagg gtacagcact tagcaaggct tggtctgact ctaggacata ttcatcagga    27600
acaagaggag tttaaatggc aattgaacgt caagctgtac agggcttacg ccgagtgcag    27660
tctactggtg ggccaagtgc tgctagtttt gcgactcgtc aggttggggt gcaagagact    27720
agtgcatctg gtagccgctt tcttgaagac cttgtaaatg ctgctggcag tttggcgact    27780
gtcactactt ctattctgaa ccaaagagtg gaagatgata aggtaagaca atataatagg    27840
gcgcttactg gcctaatgcc aactgaagat gcaacggtag gcggcgcacg cgcacacatg    27900
cttgttagtc tacaaaatga catcatcgcg caaactatgc aactgtccga tgatgcacaa    27960
cgctttgatg gcgatgacag tcaatgggaa gatcacgtca ttaatgcccg catggctgtg    28020
caagaccgcc tatgggatac ctaccctgaa cttcgtggtg ataaggagtc catgcgggta    28080
gttactaatg ccttcatgga gcagcaacct aaaatatttg cagcaaggga gaccgccaag    28140
ctgaagcagg aggcggaagc ccgcatcaag tctatggagt cacgcattct gctggctacc    28200
cgtgatgttc ctggcgaagc tatgggtgat gccttgaatc agttgcagaa agaagctatg    28260
gctatgcaaa tcaccaagca ggagtttgat gcactggttt ctcaattggc agctaatcgt    28320
gcagctattg tgatgattc tatgattcaa ggaaccaagt ctcttaagga tgagaatgga    28380
gtatcactct atgaccgagt aggtcagtta cagacaggag agattcaggc caaccgcaca    28440
tgggcggcgc agaaccaagt ggcactcttt gagaagaagg atgctgcaat caaagccttt    28500
gaagctggac agcttaaccg cgaacagcta cttcaggtca tgcagaacca caatgaaatc    28560
```

```
tcaggaggca ccgcttggtc tgatagcgag atcaaatctt tatttgatag acaggctaag    28620
gctcgtgcta cgtctgccaa gctggaagat ttggtggccc gtggtgaaca tggctcaccc    28680
ctaggcttgc aagatatcag taaggaagac cgcaaagcgt atgctggtgc attggttgat    28740
gcctacacca agttagccaa tgacgagata acccgtacag gagctactgg tgaagaagct    28800
gaagctatcc gtggccgcta tgagcagatg cgatatgcca agctgggcca gcagttgatt    28860
gaagacccta tcattaaaga acggtacggc tcgctgatgc aactctcttc tgccaacctc    28920
aaagatatga agattgaacc tgaagcattg cagactatta tgcgcgcccg cgattctatc    28980
ccggaagatg cccgccggge ggtgatgggt gacaaggagt acgcctttgc ggagaattat    29040
gatttggcga cacgcatggg ttacactcct ggacaggcta tagagtttgc acagaatgca    29100
tcgcgtgggg acaagcttcc cggttctgtt atgaaagaat tgaatgatga agtagatggt    29160
gtggttagtg atgttgcgag cggtagctgg cttacgcgtg gcgacaacat gagtgacatg    29220
ggtcgtgacc ttatgctaga agaggcaaac cagattgctc gctctatgaa ggttgcaggt    29280
cataacaatg acaccattaa gcgtcatctc aaatctttcc tacagaatca gtacactcag    29340
ctatctgaag gtttcttcac tcaaggtgtt ctggtcaaag gtgatgtgag gacgctaggt    29400
gacactatag gtgccaacca aaaagacgta cctacggtat tacgtcagta ccttgacaat    29460
cataagcaag cattgctgga tgcatctggc ggtatggaag aaggagactt atactttgat    29520
gtagactcta agcgcggtat gtttacaata cgtgctggtt ctgggcgtgt gccagttact    29580
ccagctatgc ctttgtctga aatcaaggga caggacttac tgaaggagca ctacgagaag    29640
gcagttaaag agcgcgatga agcgaagaag aactttgaag ctaatcagat gcgtatgtgg    29700
ggtgctggtg gttaccaatc tcctgcacca gaaaagacta cagctaagac tgtaggttcc    29760
cgtggcatcg ctgacttcct catgtcgcct gcctttgcat ccggtgagaa tctaccttcc    29820
aactttgaat tcaactacaa gaggaataat atggacttct acaattatgt agctaagacc    29880
gagaatgggg ccaacgtagg gtttgaccga gtagctggcg tgtacactcc gtacaaagat    29940
gcacacggtc agtctgtagg ttatggtcac ttcctcacgg aggaggagaa gaagaatgga    30000
tacatcacta ttggcgaaga taaagtacca tttgcaccgg acaatctcca gttaacacct    30060
gagcgggcaa tgcgtctgct tgagcaggac atgaagagcc acgtacctag cacaaaggat    30120
tgggctgtac cttttgatgc aatgcatccg ggagtgcaac gtggcctcat ggatttatct    30180
tacaacttag gaaaggatgg catcaagaat gcaccgaaag cctatgcagc cttcaaggct    30240
ggcaagttca ccgatggggtt tatcgagatg ctgtctactg catctactga aggtaagcgt    30300
agctccggcc tgctagttcg cagggcggaa gcttataacc ttgcacaaag cggagggtct    30360
gtacctaaga ttagcgaagt tgagacaagg gaagatggtt ccatgtacgt taagttctca    30420
ggtagcatgt cagaagcatt tgtgagcaag tctatccttg gtaagatagg taaagatggg    30480
tggatggaag tctaccctcc taaagcagga gcacttgcaa gcggcaccaa agtgggtcgt    30540
attaaactgt agtgtcatac tcaaggttgt ctaacatgtt ggacagcctt tatgaatgac    30600
attaactaag gaggtaacat ggctgacgat attagccaaa gctgggtgac ggtatctcaa    30660
cgcaggttgc cgcctacctt tgcacaagtg gcagaagccg agcgtaagct tgaagaacaa    30720
agagctagcg ataaggttat gcagactgca ctggaaagcg aatgggcgct atacggtggt    30780
cagcgtgcta ttgagcggca tacaactgag tttgccgaac aagaaggcta cacggttcct    30840
gagtcaacaa aagatgaact atcaaagatt catggttttg aaattgcaca ggatattgtg    30900
aaggatgtta agtcaccaga agagttgcag tttcgtatgt ccaatgctat ggcggataag    30960
```

```
gagcgatcgg agatccttgc acgtaatggg tttacagggt ttagcgctca gttagctgct   31020
ggtatcttcg acccagttgg ttgggctgcc tctatggttg ccgcccctgt agctggtgca   31080
gtaaaggttg cccgtgtcgg tcgtatcata aagacggcag cagtggctgg tgccgagaac   31140
gcagcattgg aagccatcct agccagcggt gattaccaga agggcgcaga tgatgtgctg   31200
gctgctgctg gctttggtat gataatgggc ggcaccattg gcgcagctac acgcgaacgc   31260
atcgccagaa agccaggagt acaaggagtg aatgacggtg ctgagaccgt agtggatgac   31320
ttagatacgg tcgtaaaggg agcagatgag tttgatgcat ctgcggctaa ggctgtacga   31380
gaggctatga gtatgacgc gtacatggct gtgcgttcct atgaaccact gagggctaag   31440
gaagtggata tggatgtagc aatcctgtct cacttagatg acctgaaggc taactctagc   31500
gtgcgtatga gtgcctccga gaaaggtaaa ctgaaggagc agatacgcca gcttgaaaca   31560
gaagccgcca ccattaaagg caagaaggta gatgccgtgg cagaagctgc tgctgctaag   31620
ggtgcgccta gtctgctgc tgataggcta gacttggatg ttaagaagaa ggcactggca   31680
cgtcgctttg atgagccgct tgccgacatc caaacaagac tcgacgaact taatgctaaa   31740
ctggcccgcg tggagaacgt aggtaagtca aaggaggagt tgaagagatt ctctaatcta   31800
actgggagc agcaaatcaa ggagctaggg ttagatgctc cggctcgtaa agttgagatg   31860
acaagtgcgg tacgggaggc tcttgcagct atacgtgctg agaagaagaa gacacccact   31920
cagactcatg ccgaagccaa agcacaggca gaagaggaag tgcggcagaa gcgagatgac   31980
tctatcggcg ctaagcgtgt agaggattct gaaattgcag gtgaacaatt tgacctgtct   32040
gatagcatgg aagatcttat ggatgacctt gcacgtgaag catatcagtc tgaagttaga   32100
cctgtaaacc tcaagggact tggttctgta tcttccgtga ttctgaactc aaagaaccct   32160
gtgtttcggg gtcttggttt gcgactgctg gagaatgcac aaggtggtgc ctaccaaggt   32220
aagaccgctt ctatcttgtc taacgtgtat ggtaacttga ttcgctttgc tgagaagaat   32280
cgatacaatg atggcttctc tcaattcatc aaggataaca atttacgtgc tgttgattac   32340
ctgaaccctg ctgttacgag ggattttaat aaccagattt atactgctat tgtcaaagga   32400
atacctgatg acacgccacg tggtgttaag cttgctgctg aaggcatcgc agataagctg   32460
gctaagtctc ttgaaatcag aaaggctgct ggtgagaaag gcttcgaaga tgtcaagtcg   32520
gcacgtgatt atatccctgt gatatatgat ggtatcaagg tgactgaagc agtcaataga   32580
cttggtagta gcgaggctgt tattgccctg ctgtccaaag ttatcagac tggtaagtat   32640
aagatgggta agaaggcagc ggatgcactg gctaaggtgc agtatattcg cgcctccgat   32700
tctaccttat caagccgtgt agcctttgac agggtagttt ctcagcagca acaagcacag   32760
cttattgaag acctgaagag agcaggtgtg cctgataata tcatagataa cttcatcgaa   32820
ggcactgagt tgcaagagat ggcggaatca gtgtctaacc gagctaaggc aagcatgggt   32880
atcaacactc aggctgaata tggcgggatg aaggttcagg acttgctcaa cactaacgta   32940
ggtgagttgg cggagaacta cggcaaggag gcagcaggtg gtgcagcttt ggcggctatg   33000
gggttcccga cccggcagtc tgtactgaat gcaattgacg cagcagaacg cgcagggcgc   33060
aatatggcgg gcgctgacgc caaggcaatc aaacagctta gggcggaatc agaaatgctc   33120
agggactccg tgaagctcat atacggcaac accattgacg caaatccaaa tgcgggtatc   33180
gtccgaggga ctcgccgtgt acgtgagatc actggccttc tgcgtttggg tcagatgggc   33240
tttgcgcagg tgccggagtt ggcccgcgcc attaccaaga tgggagtagg tacagtgctg   33300
```

```
aagtctatcc ctgccactaa gttcttacgc tcccgcgccg ggcgtaaggg cgggacagca   33360
caaggtgagc tacttgagcc ggaactgcga gagatggaag aactcatagg ttatatcggg   33420
gaagataact ggctatcagg ttggaacgta aggcacgatg agttcggaga gaccgctgac   33480
aacatgggac gtctgtctgc catcatcgac aatgggttgg ctatgggtag ccgtattaac   33540
acatggctgt ctggcttcaa ggcgatacag ggtggttctg agaagatcgt agcacgctct   33600
atcaataagc gactcaagca acatttgatg ggcgagcgag agctacctaa gcgtgacctt   33660
gaagaggttg gcttggatga ggctaccatg aagcgactca agcgccactt tgatgagaac   33720
ccgatgtatg ccgactataa cggcgagaag gttcgaatga tgaactttga cgccatggag   33780
ccagacttac gagaaatcgt aggtgtggca gtgcgccgta tgtctggtcg tcttattcag   33840
cgtaacttca ttggtgatga aggtatctgg atgaacaagt ggtggggcaa ggctctcact   33900
cagtttaaat cattctctat tgtgtctatt gagaaacagc ttattcacga cttgcgtggt   33960
gataagattc aggcagcaca gattatggca tggtcttcct tgctaggttt tgcatcatac   34020
gctacacaga tgcagatgca ggcgattgga cgagaagacc gagacaagtt cttacgggag   34080
aagtttgata ctcagaacat agctatgggt gtattcaata aactaccaca agtggctggc   34140
tttggcttag ctggggatac cttttgcaaca ttcggcctta tgccggactc catgatgcag   34200
gcaccgggtc gtatgggctt ccgtcagcaa ggatttggcg acttagtggc tggtgctggt   34260
gtcataagtg atgctgtgaa cttgtcacag gctttagtga agtatgccaa tggagatgat   34320
gatgtctcca ctaggcagtt agtagataag gtacgacgtc ttgtgccttt ggcaaatacg   34380
attggtgtag tcagatgac caaggccagc gtagacttat tggaggattg atgagttata   34440
ctttcacaga acacacagcg gtaggttctc agacgactta tccgtttagc tttgctgggc   34500
gcgacaaggg ttacattcgc gcatcagata ttattgtgga agtgtttcat gaaggcgagt   34560
ggagtattac acaaggttgg gtgctatctg gcactcacca gattaccttc aatgtagcac   34620
taccagcagg gactaagttc cgcatacgta gagatgtaga caaagagtac ccttacgcgg   34680
agtttgatag aggtgtggct cttgatatga aatcattgaa caactcattc attcatatct   34740
tgcagattac acaggagatt cttgatggct tctacccaga aggttacttc gtcaaacaga   34800
atgtgtcttg gggtgggtat aaaattactg acctagctga tggcacaaac cctcacgatg   34860
cagtgaataa ggggcagctt gacgcaatcg acaggaagca tactgagtgg aatgaacagc   34920
aagatattgc aattgctgga ctcaaggcag ggatgacatc aggtctctct catcggacag   34980
taccttgggt tacagtagcc gccgggggag agcaagttat taggcctcct tacatctttg   35040
aatccgcctt ggttttcctt gatggggtct tgcagcacga actgtcaggt gcagttacta   35100
tagctaacag caccctcacc ttctccgagc ctctacgtcg tggcacagaa gtgtatgtat   35160
tgataggtag tcgtattgca acctcttcac cgggcctgca tatggagttt aataaagact   35220
taggtgcagg gactacggag gttaggattg gtatggcttt ctctcatatt gatatctacc   35280
ttgatggctt gttccaacct aagtcaacat atcaaataaa cggcgatctt gttacattct   35340
ctgagggtgt accagcttgc catatgtcag cggatgtagt cactttatag gaggtaagat   35400
ggttgattcc gaactggtta gcggcgggat gaagttagcg ccatctgcct tagtatcagg   35460
tgggtacttc ctcggcatca gttgggacaa ttgggtactg attgcgacat tcatttatac   35520
tgtgttgcag atcggcgatt ggttctacag taaatattca ttatggaagg agaagaagcg   35580
tggcaaaaca caataaacac gcagctactg aagacgaggt aggtaagtta catagtgcta   35640
tcactaatct tttcaataag aaagctgctg caatcctagc tgcggtagaa gaagatcctg   35700
```

```
atgcagcaat tgcactggtt tccggcaagg acatgggtgc catgtgtaag tgggtattgg    35760
ataatggtat tatggctaca cctgctgcac agcaagaaga gtctgcacta tctaagcgcc    35820
ttgctaagat caaagcagca tctcaaggta agtaatccaa atttgctaag gaggcttaat    35880
ggctagagca agggagtcac aagctgaagc ccttgcccgt tgggaagccc tgcatgagtt    35940
acagcaaact tttccgtaca ctgtagcagg gctactctca tttgctcagg ttgtaatcaa    36000
taatttaatc actggcaatc cagacctgaa ccgggtacaa gcggatattc tgaaatttct    36060
ctttggaggt aacaagtatc gaatggtaga agcacagcgt ggtcaggcta agacgaccat    36120
tgcagctatc tacgctgtgt tccgtatcat ccacgagcca cataaacgta tcatgattgt    36180
gtctcagaca gcgaagcgag cagaagaaat cgctgggtgg gttatcaaaa tcttccgtgg    36240
tctggacttc ttggagttca tgttgcctga tatctacgca ggtgacaagg ctagtataaa    36300
aggttttgaa atccactaca ccttgcgtgg tagcgacaag tctccatcag tggcttgcta    36360
ctccatcgaa gcaggtatgc agggtgcgcg tgcagatatc atcttggcgg atgacgtaga    36420
gtcgttgcag aactctcgta ctgccgcagg tcgtgcttta cttgaagacc ttaccaagga    36480
gtttgaatcg atcaaccagt ttggtgatat catctacttg ggtactcctc aaagcgtaaa    36540
ctccatctac aacaacctcc ctgcgcgtgg gtatcagatt cgcatctggc caggtcgcta    36600
ccctacactg gagcaggagg cttgctatgg ggacttccta gcgccgatga ttcgtcagga    36660
catgattgat gacccaagtc tgcgctcagg ctatggcata gacggtacac aaggcgcgcc    36720
gacttgtcct gaaatgtatg atgacgagaa gctcattgag aaggaaatct ctcaaggtac    36780
agctaagttc cagttgcagt tcatgctgaa cacgcgcttg atggatgccg accgctaccc    36840
tcttcgtctt aatcagctta tcttaatgag ctttggcact gacgtagtgc cggagatgcc    36900
gacttggagt aatgattcgg taaaccttat cagtgatgcg ccacgcttcg ggaacaagcc    36960
cacagactac ctgtatcggc ctgtgccgcg tccgtatgag tggcggccta ttcagcgtag    37020
gttgatgtat atcgacccgg caggtggagg taagaacggc gacgagacgg gtgtagccat    37080
tgtgttcttg cttggaacct ttatctacgt ctacaaagtc ttcggcgtac cgggcggata    37140
ctcagaatcg gccctcagtc gcattgtgag agaggcaaag caggcggagg taaagaggt    37200 cttcatagag aagaactttg gtcatggtgc gtttgaggcg gtaattaagc catacttcga    37260
acgcgaatgg cctgccgagt tgaaagagga ttacgccact ggtcagaaag aggcccgcat    37320
cattgagaca cttgagcctc ttatgtccgc acaccgcatc atctttaacg ctgagatgat    37380
caagcaggac atcgatagcg ttcagcacta ccctcttgag gttcgcatga gctacagtct    37440
atttgctcag atgtcgaaca tcacccttga gaaaggatgc ctgcggcacg atgaccgctt    37500
agacgcgctg tatggcgcta tacggcaact gacctctcag atagactatg acgaggccaa    37560
ccggataaat cgtctcaggg cgaaggagat gcgcgaatat ctggagatga tgaccgaccc    37620
tctacgtcgc cgggagttct tcactggaca agacacgggg tatcgcaaat caactaacgt    37680
gtccaatgcg atgcagtcta gggtgtttgg tggtagccgt gttaaagtga atccagaaa    37740 taccatttct tcaagaattt caaggacttg gtaattaggg gacactatag aaggaggccg    37800
aggaataaca ggaagttata ggaggtcata ggtattccta ggtagtatag gtacgcctta    37860
gtgggaggta tcctacctcc ctattccttc ctttatatta actatagata aggagtaata    37920
atgcctaatc gtcctaataa ttatggtaat atgggtctga caggtaaacc tcgtcgtaaa    37980
caagagaagc ctattgccac tgcactgatg gttccttttg cagaagatga agcccatgag    38040
```

```
catggtgaga acatcgaagt acgtgagaac cgcattaatg accagaccaa atcaggtaag    38100
cgccgtggtg ctatgctgct gacagacaag catggccttg tggttgcatc tggcagccgc    38160
ttcaatgaca tctggtatag ctttaaattc gaagaaattg gtacaattca acctgcataa    38220
gaaggagata acatatggca actatcaaat acggtgatgc tggtactgca actggtaagg    38280
ctttcctgaa acagcaactg gaaaccacag cgactgcact gccacttcca atcgtgtcca    38340
agtcagactt gggtcgtgca ctggcaccta tcaatcaggc tcgcctgtct ggtaagcaga    38400
agggtgctat ggtaatcatg gaagatgacg gtacgcatga actgcacatt gcggtggctg    38460
atggcccgct tccgactgac gcatggaaca tttgcagcct tgacggtgaa gtaactccgg    38520
cacagggccg ctaaggaggc tagatgctac gacatcagat taacgggaat cacaacccgt    38580
tacatgtaac aggccaacgc tcacggagta ataagagtat tgccatccag gagggtgtgc    38640
ctattgtacg tgcttctgtt ctagcatctc cgacatctta catcaatgac cctcacctgt    38700
caggtaagcg tgaaggtatg atggtggctg tactggcacc tgaagatgga gacaaggcag    38760
gtctatatct ctacaggtgg gccagataaa cataacatca ttgaccatgc ggtgttcaaa    38820
cattttgtaa ctaacggctt ggttgtaggc gctattgaga cgcacactgc caccactaac    38880
aacatccatg tacgtatgca catcacgaaa ggttctacgg gtgcatacac ctttagcttt    38940
tcctttgagt ggacatctga cttcgactta ctggagtgat aatgttgaac aaatacttca    39000
agcgtaacga gttcgcttgc cgttgtgggt gcggtacatc cactgttgac gcggaactgt    39060
tgcaggttgt cacagatgtc cgtgaatact tcgggttacc tgtagttatt acatcgggtc    39120
atcggtgcat tgaccataac cgccgcgtag gtggtgctgc atcttccatg cacatgactg    39180
gcaaggctgc tgatattaaa gtgaaaggga aggacgcgag tgctatcgca tcctacttgg    39240
aacacaagta ccctgataaa tatggtatcg gtcgatacaa ctccttcact cacattgacg    39300
tgcgtgatgg taaggctcgc tggcgtggat aactgcattg catggtgtga aagatggtt    39360 gctaaggcat ctgctgaagg taactatgtt gactggcaga attacaccaa tctgcttaac    39420
gaatggaaat ggagagcatt acgatgaaga aactattcaa gagcaagaag gtgatcggcg    39480
cactagttac actgatcgtt gcgccttgtat cggtatggct tggtgttgac ctaggctcag    39540
gtgcggagtc ttctgttacc gatgtggtct gccaagtaat tacctgtgag taggttactt    39600
gaagtagtgg caggacttct tggcctgctg cttgcctata agaagaagca agaccagaag    39660
gaggcgcaac atgaagcaga tctggctagc gatgaccctg ctgattggtt cgctgaccat    39720
ttccgggtgc gggacggcgt taccagaaac tcagaaggtt cgtccaacca aaccgactct    39780
gacggcagtt tacgagagag atgatagggt ctgcttcagt aagccagatg ctacacaatt    39840
aggcttgtac atattgtcgt tagaacgcgg ctacaattaa tacataaccct tatgtatcat    39900 acacatacga tttaggtgac actatagaat agaagtatag tgccgttctt ttgagcggcc    39960
tattactcac cagtcttcac ggggagggct ggatagtaat aggaggttta atgtcattaa    40020
ctaaaccacg ttgcttcagg aaggcaagtt atctaagcca gttaggcact ttgcagaatc    40080
tggctaacac tggagatgac gtacttgtta tcgatgttga ctacaagttc accaatggag    40140
agactgtaga cttcaaaggt cgattggttc gtatagaatg cgaagctaga ttcataggcg    40200
atggagcttt aatttttcact aatatggcta gtggttctgt agtagaaaag cctttcatgg    40260
agagcaagtc cacaccttgg gttatctacc cttggacaga agatggcaag tggattacag    40320
atgcacaagc tgttgctgct acgcttaaac aatctaagac cgaaggatat caacctggag    40380
tcaatgattg ggtcaagttc ccaggacttg aagcattgat accgcaagag gtgaaagacc    40440
```

```
agtatgtagt atcaacactg gacatccgtg attgtgtagg tgttgaggtt agacgtgctg    40500
gtgggcttat ggcagcttac ttgttccgca actgtcatca ttgtaaggta attgattctg    40560
acaccatcat tggtggtaaa gacggcatca taacctttga aaacttaggt ggtgaatggg    40620
gtatcggcaa ctatgccata ggtggtcgtg tacattatgg ctcatgtagt ggtgtgcagt    40680
ttcttcggaa caatggaggt gcatcacata atggtggagt tattggtgtg acctcatggc    40740
gcgcaggtga gtctgggttt aaaacatggc aaggttctgt aggtgcaggt acatctcgta    40800
actataacct tcagttccgt gactcagttg cattatctcc agtatgggac ggctttgact    40860
taggctcaga ccctggaatg gcaccagaag aggatagacc gggagattta cctgtatctc    40920 aatacccat gcaccagtta cctaataacc acatggttga taacatactt gttatgaact    40980
cattaggtgt aggtttaggt atggacggta gaggtggtta tgtgtcgaat gttaccgtgc    41040
aggattgtgc aggcgcaggt atacttgctc atgcattcaa ccgtaccttc tctaacatta    41100
cggtgattga ctgcaactac atgaacttcg attcagacca gataatcatc attggtgact    41160
gcatcgtgaa tggcatccga gcagcgggta ttaagcctca gccatccaaa ggcatgatca    41220
tcagtgcacc tcactcaacc ttgagcggta ttgtgggtaa tgtgccgcca gaccgtattc    41280
ttgcaggtaa catccttgac cctgtgttgg gtcatacaag gattaatggg tttaatagtg    41340
actcggcgga actgagcttc agaatccaca agcttaccaa gaccttggat agtggtgcta    41400
ttcgctctac gctgaacggt gggccgggta ctggttctgc atggactgag atgactgcaa    41460
tttcagggtc agctccaaat gctgtctcgt tgaagattaa ccgaggagac ttcaaggcaa    41520
ctgagatacc agtagcacct actgtgcttc cagatgaagc ggtaagagac cacagctcta    41580
tcgcacttta ttttgatcag gaagctcttt gggctttagt taagaagccg aacggaagcc    41640
tcacacgaat gaagcttgct taatgtaggc agcgcgttag cgctgctttc acgcgaactt    41700
ttcttaaagg ttatcatagt ggtagccttt cagaaaagga ggtgacatga tacaaagatt    41760
aggttcttcc ttagtgaaga tgccaaatgg tattacattg acacagtggt tgcaacctgc    41820
aaacatcatc aaggtagatg atgcaccata caatggagac cttattgctg catataatgc    41880
tattcccgtt ataggtaatt atgctttggt tcttaccaac cacacttaca atgcagttgg    41940
tttgtttgat gcaggtcgta acatgaagcc taacatcacc atcattggtg ctggtatgcc    42000
tcaacttgca gatgataggt cgtccttttgt tgaaggttct ggcactatca ttaaaggcgc    42060
agtcaagaac tccgccaagg gcttccagat tggtaaccta ggtattgatt gtggtaacac    42120
agttagtcgt acagactacc aacctgcacg cttcgaagac ccactacaga tatacggggtg    42180 tggcgctaat gctaacatct ttatcgataa cgtgaagtgc cttagtgcag tttctgtaga    42240
cgagagaccg ggaacacaca gcattctgct tgagcaaact gaaggtgtta ctctcggata    42300
tgtagagtgc attggtggct ccacggact taccatcaag tgccgtaacc tacgtggcgg    42360
gattgcacat tgctatggcc agtatggtga tggcttcatc atcaaatctg acgctggtgg    42420
tgcagcgagt catatctaca tggagcggat tcaagtgggg catccagatc aatctatgtg    42480
gcctgatgta cacttaggtg gtatctacga tgctcatgat ggagtgacaa ttgacagtgt    42540
tagtattggc gagttcatg ttgtacgagg gtcttggggc ctgatacctg cggataacgc    42600
cacgggtagt atcaccaact tccatattgg acattatgag tgtcacctta cttatggcaa    42660
ctactactcc cttgttatca acgacaaggt tgtaggttgg actatgggta ctcacaacat    42720
cacgacctgc tcaggtggca tcaaggtaga ccctgcatcg gtgtatgtaa acatcggaac    42780
```

| | |
|---|---|
| tggacgctcc accaacaaca ctgagagtgg gtactctctt ggtggacaca ccctgattca | 42840 |
| tggtgaactg attgcagatg ctaatggtaa gtacggtgta gagtatacag gtggcctagg | 42900 |
| tcttgatgta agtaagattc atgggttcca gaaccatctt ggtacttact caggctactc | 42960 |
| ttctgctatc caatctctac tgtggcctga cgctgggttt gaagcgatgg ttacagggcg | 43020 |
| cactgtgaca ttgcgtgggt ctctcacgaa aggtacgact gcatggtgtg gtcaggtact | 43080 |
| cgatgctgtt aagcctacac gagacattcg tatatacgca tgggctgttg gtcttggtgg | 43140 |
| ttctatggtt ccagtggaag catggattcg ttctgctaat ggagctatag acgtagtagg | 43200 |
| aaaggactcg gtgggcgaag ggcagattgt tagcttcact ggcagctaca tattcaagtg | 43260 |
| aggtctgtat gccattagtg aagtctatca aggagaaggc tgtacgccag aacacagaag | 43320 |
| aactcatcaa gtcaggtcgt gaccctaagc aggcttatgc aattgctaag gatgtacaac | 43380 |
| gtcgtgccat gaagaaacct tctgcatctt agtgtaacca aagggttggc ttaggttgac | 43440 |
| ccttagtgta atcaaaggag ataacatgta tattccaatg gaagcagtag taggtatcgc | 43500 |
| ttgtttgcta gtagggtttg tcataggttt gatagcacaa taatggtggt cacaaagtag | 43560 |
| ccaaagtcaa aattttgata taggcgtgtg tcagctctct cggcctcggc ctcgccggga | 43620 |
| tgtccccata gggtgcctgt gggcgctagg gcggcctgtg gaggcctgag agaagctctt | 43680 |
| agtgtgggcc aaagggtaac ctgaggcctg ccggagcgag cgatagggac gcgtgtaggc | 43740 |
| cgcttgacag cgtgtgtggg cgtgggcta | 43769 |

<210> SEQ ID NO 3
<211> LENGTH: 44385
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| tcgccctcgc cctcgccggg ttgtcccat agggtggcct gagggaatcc gtcttcgacg | 60 |
| ggcagggctg atgtactcct tgtctagtac aagggaggcg gagggaacgc ctagggaggc | 120 |
| ctaggaatgg cttagtggtg gacaaggtga ttaccttagt gaagcctctt agtgcattcc | 180 |
| tgaggccatt cagggcgttt atgagggatt gacagggtgt gagggcgtgg gctatctgtt | 240 |
| cctttgctcc tcacttcgtt cgtcgctgcg gtagcctgat gtgtacccta ggttattcct | 300 |
| tgatggatag cttaggttag ccttagtgga ttaccttagt taaagcctta gtgcttcact | 360 |
| tagtatcagc ttagtagtgt accttagtaa gtcttagtgt cttctcttag tgattgcaca | 420 |
| tgcaagcatg taagatgcta ataggtcgcg gtcggcagac cgctaaagaa agagaatggt | 480 |
| aataagatgc agtaggagga acaccagaag cctagccaac ctaagctatc ctagctctat | 540 |
| atctattgct tttccttagt ctaacacgtt agacaaccta tcttattctt agtgatggta | 600 |
| acttagtgtt gacaagataa tcttagtgta atactatgca tcacgtaggc ggtgctgagg | 660 |
| cacctagtag ccagctagta aggcatacga agagactagc gcttacattg ctctttaaca | 720 |
| atttgcttag tgtaacctat gtatgccgtg gttaactact tattgaatga ggtattaact | 780 |
| atgcacattaa ataaccgtga actgtccgtt ctcttcactc tgttgtgcta catgattcgt | 840 |
| aacaacgaat tacttacaga tgatgagtta gccttgtatc accgctttct taacgaaggt | 900 |
| tggaccgata cagttaatca ataccgtaac atgatagatg agttgaggga gggtaaataa | 960 |
| tgtatcaaca tgaggtattc tttgaatcag ctagcgaagc tattcgcttc cgtgatgata | 1020 |
| tgatgcaagc tggtgtaggc gttgatgtgt atcactattt gatagattac gacactgaat | 1080 |

```
atcaccgagt taccttagta tctgagtatg acaaccaagt cattactgag tatctaggca    1140
gtgaagatta cgattacgat gaagtaatca cgacaaatct ctaaattaac tgttgacagc    1200
cacggcatac aaggttacat taagcatcaa gacggcgacg tctttaaaca tcccgctctt    1260
taacaatacg gtttgtgtct tgataggcta actaactaac taaggtaatt atcatgaaag    1320
ggttaatttg tgtagaacgt atggtcaatg gtaaacttga atattacca ctggaaaacc     1380 aatctagctt caaagagtgg tatggctgtt tctcactgat ttaaggtaaa ggctggcact    1440
agtcagccta tcaaggcgca aaccaagctc tttaacaatt tggatggtag cttcttagtc    1500
tggataggtt aaacctagga gattctcttg agtctcctat aatgtaacct aactaactaa    1560
atgaggatta aatcatggaa cgcaatgcta acgcttacta caaccttctg gctgcaactg    1620
ttgaagcatt caacgagcgt attcagtttg atgagattcg cgaaggtgat gattactctg    1680
atgcactaca tgaggttgta gacagcaatg ttccagttta ttacagcgaa atctttacag    1740
tgatggctgc tgatggtatt gatgttgatt ttgaggatgc tggtttgatt cctgacacga    1800
aggatgtaac caagattcta caagctcgca tctatgaagc tctttataat gatgtaccaa    1860 atgcacagcga tgtagtttgg tgtgaaggcg aagaagagga agaataagga tggaaaagca    1920
atataacttt atcttttcag acggtgtaac cctgaagtgt tccctacgat tcgcacaaat    1980
tcgtgaggaa gtactaggca ctacatacaa actatttagc tgacactata agagaaggct    2040
taacaaggcg ttactaaggt agcgcctgat taaactttca cttactagga gttgagatta    2100
tgaaaacctt gattggatgc ttcttgttgg cttctcttgc tctggcattt accgctaaag    2160
ctggttatga cgcttataaa gtagaacaag cccagcaaga ctgggccaaa aaaagttca    2220 acttgtgcag caagagcaac acctacgagt actgcaacaa acactaaga cacttatgga    2280 aagagtaact agcctatagc ccacctgagt gggctatgtg atatttactt aacactatat    2340
aaggtgatta ctatgactac tgaaaacacc ctcgtgtctg tccgtgaagc tgcaaccgct    2400
gaaatcaagc aacatttaga caatatcggc acttcttaca tcaaagtagg ggcttgtctg    2460
aatgagttac gcggagactt tgaaggtcaa aaagagtttt tagcctatgt tgaagcagag    2520
tttgccatta agaaggcaca atgttacaag ctgatgagtg tagcccgtgt ctttgaaggc    2580
gatgatcgct ttaaaggcgt ggcgatgcgt gtaatgctgg cgcttgttcc tttcgctgat    2640
gaaaatataa tcatggagaa ggccgcagaa ctcgccgcaa atggcaagct ggacactaat    2700
gccgtaaacg ccctgattga acctaagaaa gagtcaaagg ccgaaacggt acaatctaag    2760
gctgagacag taaaaccgca ggagaacgcg actgagtccg cagaatcaca tgaaatgcaa    2820
gcgccgcagg tagtgccacc cgcgagcgag caggagtccg acgaatcagc accttgggaa    2880
gaggaaagca aaccggaagc gccaaaggca gctccgatgg ataacacggc taatactgag    2940
aatgccgcta ttgctggtct gctggcacaa attaaagcac tgactgagca attacaggca    3000
gccaatgacc gcatcgcctc cttaagtagc gcacgcgaaa gcaagaaggc atccgcacct    3060
atgctgccgc agttcaaatc ttcctgcttc tacgctcgct taggcttgag cgcggaggag    3120
gcaacgaaga aaacagcagt taacaaggca cgccgcgaac tggttaagct gggatacggt    3180
gaaggccatg aggcatggcc cttaatctct gaggcagtag aagagttgac taagtaacct    3240
tatcggtggc atcttcttag gtgtcaccta ttaaggtttc tttcactagg agtaaacaag    3300
atgcaaggcc tacacgctat tcaacttcaa cttgaagaag aaatgtttaa cggcggtatc    3360
cgtcgctttg aagcggacca acaacgccag attgcatccg gtaatgaatc agacacggca    3420
```

```
tggaatcgcc gcttattgtc cgagttaatc gcgccaatgg ctgaaggtat tcaggcatac    3480
aaggaagagt atgaaggtaa aagaggccgt gcaccgcgtg cattagcttt cattaactgc    3540
gtagaaaacg aagtggcagc atatatcacg atgaaaatcg ttatggatat gctgaacacg    3600
gatgtaacct tgcaggctat agccatgaat gtagctgacc gcattgagga ccaagtacgt    3660
tttagcaagc tggaaggtca cgccgccaaa tactttgaaa aagttaagaa gtcacttaag    3720
gcaagtaaga ctaaatcata tcgccatgcg cacaacgtag cggtagtggc tgagaagtca    3780
gtagctgacc gtgacgctga tttctcccgc tgggaggcat ggcctaaaga caccttgctg    3840
caaattggga tgaccttgct tgaaatctta gagaatagcg tattcttcaa cgggcaacct    3900
gtcttcctcc gcaccttgcg cactaatggc ggcaaacatg gtgtttacta cctacagact    3960
agtgaacacg taggtgagtg gataactgca ttcaaagagc acgtagcgca actgagtcct    4020
gcctatgctc cttgcgtcat ccctccgcgt ccgtgggtat cacctttaa cggcggtttc    4080 cacactgaga aagtagcaag ccgtattcgt ctggtaaaag gaaaccgcga acacgtccgc    4140
aagctgacca aaaagcaaat gccagaggtt tacaaggctg ttaacgcgtt gcaggcgact    4200
aaatggcagg ttaacaagga agttttacag gttgtggaag acgtcatccg tctagaccta    4260
ggttatggtg taccttcctt taaaccactc attgaccgcg agaacaagcc agctaatcca    4320
gtgccgctag aatttcagca cctacggggc cgtgaactga agaaatgct tacgccggaa    4380 caatggcaag cctttatcaa ctggaaaggt gaatgtacta agctgtacac cgctgaaact    4440
aagcgcggaa gcaaatcggc ggcaaccgtt cgcatggttg gtcaggcccg taaatatagc    4500
cagttcgacg caatctactt cgtgtatgca ctggacagcc gcagccgcgt ctacgcgcaa    4560
tctagcacac tctcaccgca atcaaatgac ttgggcaagg ccttgctccg ttttaccgaa    4620
gggcagcgtc ttgatagcgc tgaggcgctt aagtggtttt tggtgaacgg ggctaataac    4680
tggggttggg ataagaaaac ttttgacgtg cgcaccgcta acgtgctgga tagtgaattt    4740
caagacatgt gccgcgacat tgcagcggat ccgctgacct tcactcaatg ggtaaatgcc    4800 gactccccctt acggcttcct tgcatggtgc tttgaatatg cgcgttatct ggatgcactg    4860
gatgaaggca cgcaagacca attcatgacg cacctcccag tccatcaaga tggtagttgt    4920
tctggtatcc agcactacag tgctatgcta cgcgatgcag taggtgcgaa agcagtaaac    4980 cttaagcccct ctgactctcc tcaagatatt tatggtgccg ttgcgcaggt agtaattcag    5040
aagaattatg catacatgaa tgcagaggat gcggaaacct tcacttctgg cagcgtgact    5100
ttaacaggtg cggagctgcg tagtatggct agtgcgtggg atatgatagg aatcactcgc    5160
ggcctgacca aaaagcccgt aatgacacta ccttatggca gcacacgtct aacctgccgt    5220
gagtcagtga ttgattatat cgttgattta gaagaaaaag aggcccaacg ggctattgcg    5280
gaagggcgta ccgccaatcc tgtacaccct tttgataatg accgtaaaga cagcctgaca    5340
cctagcgcag cttataacta tatgacagct ttaatctggc cttctatttc ggaagtggtt    5400
aaagccccta tagtggcaat gaaaatgatt cgtcagcttg cccgtttcgc agctaaaagg    5460
aatgaaggct tagagtatac cctgcctact ggcttcatct tgcaacaaaa gattatggct    5520
actgatatgc tccgcgtatc tacttgcttg atgggagaaa tcaagatgag tctacagatt    5580
gaaacagacg tagtggatga acggcaatg atgggcgctg ctgctcctaa cttttgtgcat    5640 ggtcatgatg ccagccacct tatcttaaca gtctgcgacc ttgttgataa agggattaca    5700
tctatcgcag ttattcatga ctcttttggc actcatgcag gccgtacagc cgaccttcgt    5760
gatagcttaa gggcagaaat ggtgaagatg tatcaaggcc gtaatgcact gcaaagcctg    5820
```

```
ctagatgagc acgaagaacg ctggttagtt gataccggaa tacaagtacc agagcaaggg    5880
gagtttgacc ttaacgaaat cttagtttca gactattgct tcgcataata ttaataggcc    5940
attccttcgg gagtggcctt tcttttacct actacctgta acatttcatt aacataaaag    6000
tgtctcacat gtgagactta tttaccggac actataggag agccgtcgga gacgggaaag    6060
aaagggaaga taaaggatat aaaggaagta ataggtatta aaggttatat aggttatcta    6120
ggaataccta ttaccttctt ccttcctctt attaccactc agaggaaggg cagacctagg    6180
ttgtctcaca tgtgagactt cgtatttacc ggacagtata gataagatta actcactttg    6240
gagatttaac catgcgcaac tttgagaaga tggcccgtaa agctaaccgt tttgacatgg    6300
aagaggggca gaagaaaggc aagaagctga ataagcctgt ccgtgaccgt gcatctaaac    6360
gcgctgcgtg ggagttctaa gttatggcta ttattcagaa tgtaccgtgt cctgcctgtc    6420
aaaagaatgg acatgatatt actggcaacc atctcatgat atttgatgat ggtgccggct    6480
actgtaatcg tggacacttt catgataatg gtagaccttg ctatcacaag ccggaaggtg    6540
gcatcgagat aaccgagtta tctattactg gcaatatcaa atatacacct tctcaattca    6600
aagaaatgga gaaggaaggg aagataagcg accctaaatt acgtgccatc gcacttggtg    6660
gtatgcgtat gaaagaccgt tgggaggtca tgaatgaaca agaaagggca gagcaagaag    6720
cagagtggaa acttgatgtt gaatggttcc tcacgcttaa gcgtaagaac cttgtttcca    6780
ggcacattcg cggcgacatt tgcgcattgt atgatgtacg tgttgggcac gatgaagagg    6840
gtagagtctc acggcattac tatccgcgct tcgaaaaagg tgagctagta ggcgctaagt    6900
gtcgcacatt acctaaagat tttaagtttg gtcatttagg taaactcttt ggtatgcaag    6960
atcttttcgg tatgaatact ttgtctcacg tgttagacaa gggaagacga aaggattgct    7020
tgctcattgt cggcggcgaa ctggatgcac tagcagcgca gcagatgctc cttgattctg    7080
ccaagggtac taagtgggaa ggccagccat accatgtatg gtctgtcaac aaaggcgagt    7140
cttgccttga agagatagtg cagaaccgtg agcatatcgc ccaattcaag aagattatat    7200
ggggttttga tggagatgag gtagggcaga agcagaatca gcaagcggct cgcctgtttc    7260
ctggtaaatc ctatatcctt gaatacccct ctggttgcaa agatgctaac aaggcattga    7320
tggctggcaa ggctaaagaa tttgtagatg catggtttaa tgccaagtca tctgatgaag    7380
tctttggtag ccagattaaa tctatcgcat ctcaaaggga taagctcaag gctgcacgtc    7440
cagagcaagg actgtcatgg ccttggccta agctgaacaa ggtaacgcta ggtattcgta    7500
agaaccagct tatcattgta ggtgcagggt ctggtgtagg taagactgag ttccttcgtg    7560
aagtagttaa gcacctcatt gaagaacacg gtgaatctgt aggcatcatt tctacagaag    7620
acccgatggt caaggtgtcc cgtgctttta tcggcaagtg gattgataag cgtattgagt    7680
tacctccaac caacgacccg aaagaagacg gataccgtga ggtgttcgac tataccgagg    7740
aagaagctaa cgccgccatt gattatgtag ctgatacagg taagctgttt gtagctgacc    7800
tagagggtga ctattcgatg gaaaaggtag agcaaacttg cctagagttt gaggctatgg    7860
gtatttctaa tatcatcatt gataacttaa cggggattaa attagatgag cgtgcttttg    7920
gtgggaaggt tggtgcactt gatgaatgcg tcaagcggat tggtactatc aaagaccgac    7980
acccggttac tatattcctt gtatcacacc ttacgtcc tccggcaaac cgtacccaac    8040
acgaagaagg tggcgaagtt atcctttctg acttccgagg ctcaggcgct atcggattct    8100
gggcatctta cgccttgggg attgagcgta atacaagagc tgaaacgctt gacgaaagga    8160
```

```
ctaccacgta catctcatgt gtcaaagacc gcgaccaagg tatctacact ggaaccaagg    8220
tcatgcttaa gggtgacatt caaaccggac gtttaatgga accacaagcc cgtactaagt    8280
catttgatac aggtgaagca aggcaacaag aagtaccaga tttaccggat actatagaag    8340
agactacctt cgatgaagaa agtgagttct gattagtgta tttatcaggc ttgtctcaca    8400
tgtgagacag gctcttatta agtacattaa ataactggag attgattatg tataacttag    8460
tgttgaatgt aggtgacttt gtacgcaaca tcaagaaaga ttcaagtcgc tatctttgcc    8520
gtggtgttgt aacctttgta ggtgagaacc tgtattatgt agaatatcgc agtggtgtta    8580
agcaatatta ccacaagaag acagcacata aatatcttga aaagattgta gagataaaca    8640
atcaatgtaa gtgcatacat gatgaggttt gcgataaatg tgctcgccag atgcttaaga    8700
atttcctagc tcctctttat tatggtgctg gtcctcaaac actagcagag tgcatggcag    8760
aaaagaaaac cacactcaag aaagagcgtc gcaatgtaat cactggtaag actcaaagtg    8820
agatgattaa gcaatgtggc actgcattag gtgttacaca gtttaatact cgtgcattgg    8880
gtaaatccac aggacaagct atggtaaaga ttggagaagc catgatgcat ccaaatgtac    8940
ctgtgcgaat catggatgtt gaccatgcaa tcacagaaca aggtacgcaa cgacgtgtaa    9000
ttaataagca ttttgccgac actatagaag gcattattcg taagcaaggg ttgaaaggtc    9060
ttcacatctt aaatggtgaa gaattactgt acctacctat cgttactgaa gaaacatacg    9120
tgaatatcta aggagttaat catgactaag gtattaattt atatgcgtgg acctcataaa    9180
tgctatgcag ttgtagcacc aaatggtgtt aagccttatc gtacttcaaa aagattggca    9240
ttaataggtc tagtagtag tgcaagtttc caaatggaac tttttggtca ttggactgaa    9300
aggcaattcc gtgaggattt taaagtcatt ggcagcttca tggtgaaata tgcagaataa    9360
acatagtctt agaatgttcg atggtcatga aaacctgcaa gccaagatta ctaaccaagc    9420
cttcctgttc gcacagttaa ctatggctga ggctaagaag aatagtctca ctcgtgaaca    9480
ggttatcaag gaggccactt gggaaccaca ccaaggtaaa tatatgggcc acaaattaac    9540
tgtaacacgc agtcgataag tcaagggttg tccaacgtgt tggacagcct ttcatcatat    9600
tgattgggag gtattaaatg actaagtttt actatgcaaga cctcattaaa ttacgtgatg    9660
aaatagaatc accggaagtt aatacagagt ttcactacat tgatccacga gataaacgag    9720
agattcctga ttatcagatt gagacggagt taatgtatga agattattga ttggaagaag    9780
gaagcagaag gccgtatcct agtgatggat gcggaggcta aaggcctgct gggtgctatc    9840
cgctacggtc atcgtgaaga tgtacacatt atttgctgca tggacttgct caccactgag    9900
gagttcctct tcttcgaccc atatgagatg cgtgaccctg aagcaaggga cacttgaaa    9960 gagtgggaag gccatcaaga tgggaccttg gttgatggtg ttaacttcct aaagcactgt   10020
gaagccatcg tctcacagaa cttcctaggc tatgacgggc ttctctttga gaaagccttc   10080
cctgacatct ggaagggatt taactacacc gagaggcgcg gcaagggcag actacgtgct   10140
gacttgtgtc cggtacgcgt catggatacg ctggtcatga gtcgcctgtt aaacccagat   10200
agacgccttc ctccgcaagc atatgccaaa ggtatgggta acgttgcccc tcactcaatt   10260
gaggcgcacg gcattcgtat aggccgttat aagccggaga acgaggattg gtctaaacta   10320
actgaccaca tggtacatcg tgtacgcgag gacgtggcga taggccgtga cctattcctc   10380 tggctatttta acggagaatg gacggagcac aaacgccgtg gcgtgaataa acgcactggc   10440
ctaggtattg agacagcctt ccacatggag tccattgtga cgctggagat gagccgtcag   10500
gccgagcgtg gattccgtct ggatatagat aaagcattag cacgatgcga ggaattggac   10560
```

```
gctaagattg atgagacagt cgcagcgttc cgtccgcaca tgcctatgcg tatcaagtct   10620 aaaccttta aaccggaaga aaagaatgaa gtatgccaac gcgcaaatga gtatggagct   10680
agcaacaata tacctactgt ccttgacccc tctcactttc ttcacgcaga gagacgagga   10740
gatcgcaaga cagtatggag tgtcactact aagtctggtg attggtcggc tagcgtcaag   10800
aaagactttc ctcaccttag aggaaaccgt aatgacacgc caagtgtcaa gtggattggc   10860
gcttactcgc ctgttacttt cgaagagatt cccttgggta cagggatac agttaagcaa    10920 gtgctctatg attatggatg gaaaggtgtt gaatttaacg ataccgagca agcgcatctc   10980
gatgagcatg gcgtattacc caagccttgg agtgggaaga taaatgaaaa gtcccttact   11040
ttatggcaag agagagccgc acgtgaaggt aaaacagtcc ctgattggtg cttgggtatc   11100
gctgcatggt acatactcgt atcccgtcgt ggtcagatcc tcaaccgtgg tgacgttgaa   11160
gccttcgacc agaaggggt gtggccttcg caagctggta tacgaaagtg tcgcggcctt   11220
gtacctgtag catttaacaa ggagttagga atcaatgcgc agcaatacta cgaaaggtac   11280
ggatgctggc ctacgtcaga caaggatgac ggagaatggc gtgtgccagc tattgctatt   11340
agtattggaa cttctacgtt ccgtatgcgt catcgtaacg tggttaatat tcctgcccgt   11400
ggcttgtatc ctttacgtga tttattcata gcagggaaag gcaagctaat ccttggttgt   11460
gacggtgcag tcttgaact gcgtgtcctg tctcacttca tgaatgaccc tgagtaccaa    11520
gagattgtac tgcacggtga tattcatacg cataaccaga tgaaggctgg tcttcctaag   11580
cgtgatatgg cgaagacatt tatatatgcc ttcctatatg ggtctggtat agctaacctt   11640
gcagcagtat gtggtgttac tgaggaagaa atggaggaag ttgtggcaag atttgaggtt   11700
gaactaccat ctcttgcacg tcttcgtgag aatgttatcg cacaaggtaa caagtttggc   11760
tacctacaag cacctgatgg tcattggggt cgcatccgta tgtctggtgg tgaacttaaa   11820
gaacacacta tgcttaacgt actactccag atgactggtt ctctgtgtat gaaatacgca   11880
ttggtcagag cgtttgcagt gatgcgcaag gaaggtgtgg ccttagatag catgggaaac   11940
ccttgcggta tagctaacgt gcacgatgaa atccagatgg aagtccctga agatgaggtc   12000
ttgtatctca actacgactt gcctttcacc ttagaagggt tcgaaacaga gaaggctgct   12060
gtgaaagcag tgttcgatgc agaggagaaa cgtgttcatg tggattctga aggacgtatg   12120
tggtctgctg caaatctcgt tagtgttgat gctggtgtac ttcattgcca gcgtcgttat   12180
caccgtgcag gcatatcat tgccgacgca atgacctggg cgggtcagta cctgaagatg   12240
cgttgtccga tggcaggtga gtataagatt ggtgcaagtt ggaaggaaac acactgatgg   12300
acaggtttga tattgtttgc ctattctcta ccttctttct tatattcctt atgcttgctt   12360
gctatggaag tatgcgatta gatatacctg atgaagagga gggttacgat tgatgcaggc   12420 atctttatt attcttggag tcatattatt tatggtagta ttctgggctt tctctggcat   12480
tgacccagat tgtgatggta actacgactg agttatactc aagtcacttt acgagtggcc   12540
tttatgaata acttattcct acttattttg tctaacatga tttactggac actatagaag   12600
gaaagcatag gtaatctagg tttataaggt agtataggta attaagtaaa tataggagat   12660
ataaatatgt ctatggtaac tactctggta ttcgtggctc aatactttcg tggtcttgct   12720
aataagttca agtccaaggc tatcaaagct attgaggctc gcatcgaagc agtacaggca   12780
gagcaagtta agttgaaga acatcgtagt tctcaaatga ttgactgtca taaccgctac   12840
tatgcatctc gtgatgaact aaatgcacgt caagtcaaag aggtagaaga tatgctggca   12900
```

```
cgtcaccagc aagagcgtga cagcctgaaa gctgaatttg aagagaacaa ggcatcaatt    12960
gctcttgtac atcaagctgc atctgacagt ctgaagaaag agattgttat gctggaaatc    13020
gaactggata acctgaccaa ataaggggg gttatgatgg aagaagtaat tcaagctaaa    13080
catgtaggta ttatctttcg cgatctagag cagcgtaaag ttgcaggtca tactcgtctg    13140
gctaaagagg aagacaccgc aatcactact gtagaacaag cagatgccta tcgtggacca    13200
gagttcactc aaggtgaaac ttgtcaccaa ttgagcctat caatttgtga cactatggct    13260
attgtaaatg tgcaagaagt cgaagagggt gagtgtgtca gttacatcta ccctttagat    13320
actattgcac gcattaaggt aatccataag taattactag acactataga acaataggtc    13380
ggcttagttc ggcctatgat tgtaaagtgt tgttgatgtt gaaccattgt gcatcttgca    13440
caacccgata ccgtataggg ctttctagtg agtacatgct tgtgctcagt acaaagctaa    13500
ctgacaatag gagactaaat aaatggcacg tggtgatttt gattttggtg ctcaggttac    13560
taaatctgaa ggtaaagtct ttaagaatcc agaagtaggt gatcatgaag cagtaatctc    13620
tggcatcatt catgttggtt ccttccaaga catctttaag aaaggtaata ccactgaagt    13680
taagaagcca gcaaactttg ttctggttaa gattgtcctg atgggtgacg atgacaagaa    13740
cgaagatggt tctcgcatgg aacaatggat ggctgtgcct ctgaagtctg gtgataaggc    13800
aacactgact aagttcctga atgcagttga ccctaaagag ttgctgggtg cttcgatga    13860 tttcattggt gaatgcctga ctgcaacgat ggtcggttct ggtgataaga atgacgatgg    13920
ctcattcaag tatgttaact ggaagggatt tggtggtatg ccggacaagc tgaagaaact    13980
ggtcattgct caggttgaag aggaaggtct gtctatgaca ggtcacatta ccttcgacaa    14040
gctgaccaaa gaaatccttg atgacatccc agccaacttg gtgcgtcaat acttcctgaa    14100
cgagacgcct cgtggtaaga acctgtctgt tgctggttct cacgtagaag caatcattaa    14160
agctgctcgt gaagaagacc cagaatggaa gaaggctaag aagaaagacg aggaagatgc    14220
taccccagct aatcgtaaat ctctggatac tggtgagtct gttccacagg aagtacctga    14280
agcagaagat actcctgcac cggagatgga tgaggacgcg gaatattaag gagaaaggat    14340
gaaagtacaa atcgtaaccc tgcactgcaa gaaaggaatt acaactcttg gcggcaacac    14400
ttttcactcc ttctctgaag gggacacata tgccgacctg cactacatct ggcgcgacgg    14460
acagcacgtg gtgaactaca gcgacccagc tacggggaaa cgccacggcg tatcgcttcc    14520
ggcgcatgac attgctcagg tgaacacagt tttataaagt ctcacgtgtg agacaaatcg    14580
gtgtccggta tttactggac actatagaag agaagaattt taatcggcga taatgccata    14640
accaacaaaa ggagaattta atatgttcaa gattgaaact atcgtaaacc gtgttgttaa    14700
aggtgctgct ctggtatccg ttgagtcttt cattatcgtc gatgaaactg atcaactggt    14760
agctggtact aaggcttacg ataccgtgta agaagctcag gctaagattg acagcatggg    14820
taacttcgct gctggtctgg agttcgctcg tgcttgcttc cctgagcagg ctgacaaagc    14880
tcagattggt aaggctaata tcgtagctga atatctggat tgggttgctg ctggtaaacc    14940
agtgaaagaa gttaaggctg ctgaagaagc tgaagctcca gcagaagaag tagctgcacc    15000
ggaaactccg gtaagtgaag aggaagaatt ttgataatag caggtgttgc ctctgttagt    15060
cctagctgac tatcacgctc acctcatcta atgccctgtc tgccttagtg taggcagggt    15120
cttttgcgta atagttattg gagaatgaat tatgccgact attgaatctc gaattgaact    15180
ggacattagc tacaatgcaa tcaccagaca gtatattggg gttgcctatg attacaaaac    15240
tggtgagaag ctagtggagg tgagacaatg ggatgactat tggttaagac agaacctcca    15300
```

```
tgatgcggtg tcctccttcc tgaaggagtg gcctacatgc gaccaaactt cgacttcgga    15360
gctacagtat cggaagacaa taacctgttg ctgtggccaa ctgaaggtaa tcgaatcgct    15420
ttaatagatg ctgatatgtt accttacatc atagggtata caatcagtga tatgacttat    15480
gtacgagcca caactcgtgt taagtcaggg caagtcccct caatcaaaga tacacctgag    15540
tgtaagcaag cgtgtgaccg tgtgaactcc ttgcttaact cttgggtgta tgcagcagaa    15600
tgtgatgcag ctaagttgtt catgacgaaa tcagaagcta acttccgtgt ccgcctagca    15660
ttcaccaagc cttataaagg tcaacgtaag accgagaagc ctccattctt ctatgaattg    15720
cgagagcatc tcttagaggt tcacggtgca atcttggcag atggagagga agcagatgac    15780
ctcatgagta tcgcacaatg ggacagccac cgccgcttcc agcaagatac aggtaacgag    15840
ttccctatcg gtagtccaga gcataaagca ttctctgata cttgcatcgt ttccttggat    15900
aaggatttga tgattgttcc cggttggcat ctacagccgg tcaagagaa gaaatgggta     15960
gagcctatgg gttggcttga gctacgccgt aaggctaatg gcaagtcaa agatctaaaa      16020
ggtgctggcc tcatgttcca ctatgcacag atgattatcg gtgatgatat tgataactat    16080
gctggcatac caggtcgtgg tgctaaatat gcctatgatc ttctcaaaga ttgtaagaca    16140
gagaaagagt tgtacatggc agtgctgggt gcttacaagg ctaagttcgg gcatggacaa    16200
gttaaaatta agaattaccg aggtggttat cgtatcggca aagcctttga cctaatgctt    16260
gagtgtggtc gcttatctca catggcaaga ttcaagggtg atatatggcg agccgataag    16320
aacccaatct tgtggggaga tgatgcggaa tggttagcaa attaaaatca tcggaggtgg    16380
cagcttataa gaaggaattg ctagataagc aaggatggaa atgccctctg tgtggcggca    16440
gtctcaaagc tgtcacacct gtaaaccgtg tacttgacca tgaccatgag acaggattct    16500
gccgcgctgt tgtatgccga ggctgcaatg gtgcggaagg gaagattaag ggtgttatct    16560
ctggttatgg taaggctggt aacaaccgtt acttccagct tcaatggtta gagcgactat    16620
atgaatactg gaagttacat agtacgcctc agacagataa gttatatcac aaacatcaaa    16680
cggaggcaga gaagcgcgag gctaagaacc gtaaggcacg ccttgcttat gcaagaaaga    16740
aggaggttaa agttgggtaa gctgcgcagc ttgtacaaag actccgaggt acttgatgca    16800
atcgagcaag ctaccgacga gaaaggtaat gttaactaca atgagatggc acgtgtatta    16860
tcgtgtcata ctgtgggtaa gaagattacc cgccagttgg ctcgatactg gcatggtcaa    16920
ttcaagaaga ccaagaagaa tggtgattac taccagaccc ttctgcaaga agataagcgt    16980
atcaaagaag agcgtaagct caggactcct gaccgctacg aggatttggc tattgtgcca    17040
ttgcctgact cgcctcatcg aagtgtactg gtgatccctg atactcatgc accttatgag    17100
cacccagata ccctagagtt ccttgcagcc gtggcagcac gttaccgtcc agacacagtg    17160
gtacacctag agatgaggc agacaaacat gccctgtcat tccacgattc ggacccaaat    17220
ctggatagtg ctggcatgga gttagagaag gctcgtatct tcatgcacaa attgcacaag    17280
atgttccctg tgatgcgcct gtgtcactct aaccacggct ctatgcactt ccgtaaggca    17340
agcgccaaag gcatccctgt gcaatacctg cgcacctatc gtgaagtctt cttcccgcag    17400
ggaggtggcg accagtggga ttggcaacat acgcacgtcc ttgagttgcc gaatggtgaa    17460
caagtggcat tcaagcatca acctgctggc tctgtcctag cagatgcagc gcatgagcgt    17520
atgaaccttg tgtgtggtca cttgcacggt aagatgtctg tggagtacgc acgtaataca    17580
catgaacagt attgggctgt gcaaggtggc tgcttaattg atgagtcatc ccgtgcattt    17640
```

```
gcctatggtc gtgagtctaa atacaagcca gcattaggtt gtgtggtcat tctggagggt   17700
gtgcctcaca ttgtcccgat gcaaaccaat agcgacaacc gttggattgg caagatttag   17760
ttgacactat agaacaaagg gctaggtaag actttatcgg ctggcgtatc caaatgatat   17820
tgcactagcc cttgattgta tagtgaatgg aggattcaat atgtcacact atgaatgtaa   17880
gaagtgtcat aagcgttatg attactgtac ttgtggtcaa gagaaaacat cttttaaagt   17940
tggagacaag gtatttcgta atgaaaaaga ttcgattcct tggaatcaat actgcaaaga   18000
agctggtatt gaccctgata gccctgtaac catagatgat attgatggca ttaacttgtg   18060
ctttcgtgag gtgaggggta caggttggga ttccaaaaaa ttcaaacttg catctgataa   18120
gttagacaac aatatggtaa ttaagcctaa gcactacgag ttctttgatg gcgtagaggc   18180
aatcactatc attgcccgca gtatgaccga gaagcaattc gctggctatt gcatgggtaa   18240
tgctttgaag taccgtctac gtgcaggtaa gaagttcaac actgaagaag acctgaagaa   18300
agcagattac tacaaagagt tattccagaa gcatcgtcac gaatgtattg atgaggatat   18360
ttgatatgaa tatctttgag ttcctaggtc ttccagaaga ccaccgcaat cacccattca   18420
tgctggtgaa gcatcgcggt gaagttcctg agaagaaatt aacttttcca tgttatgcac   18480
aggtgaaacg agatggtatc ttttctgctg ttgttgttcg cactgatggt gtcgttggca   18540
tttttggtcg cactggtaag aaattggcaa acactgaagg actcgaacaa gcctttgcta   18600
cctttccggt tggcatttat cttggtgagc ttcagtctat ggccattgat atctaccttg   18660
aggcaatctc tggggttgtg aaccccaatc gcactgagcc acttgatttc ataggccagc   18720
agattaaaga caacctgtat atcgacttct tcgatatgtt aactattaag gcattccatg   18780
atggattcac tgatgtttct tatctcaaac gttacgatgc tttacatcgt cgtatcggcg   18840
ctcatcttag cgggtgcaac gctatccttc ctatcactcc ttgccataat gagcgagaag   18900
ttgaagcgtt tgcgcaagag caaatagatg caggacgtga gggtgctgta ttcaaactgg   18960
actgcgatta tgaagcagga cacaaaggtt atcgtcagac taaagaagtc cgtaaggtaa   19020
cctatgacct tacttgtatt ggctttgaag aaggtaaagg caaatacaaa ggtaaggtag   19080
ctaacctcat tttcaaatgg aaaggaggca agacaatcaa agctatgtta ggtaagggt    19140
ggactcatgc agatgcagag cagatgttcc acgacattaa acatggtgga cgattgaatg   19200
tcattggtaa aatctttgaa gtcaaaggtc ttcaggattc aagcaagggc aacattcgtc   19260
tgcccaaagc gggagaatta agacatgaca aagatgaacc agatttctttt gatagcatg   19320
aaggcaactc gtgcagttga ggtagcagaa gctatcttcg aaactttatc ctgtggcatg   19380
gaagtgccat atactttact tgctgatgca gaagaacttg gtctttctgt agaagctatc   19440
caagagaagg ttgacgaatt atatggtaca gacgaagaag aaaccgacga tttcatttga   19500
aggaatggag atgcttgaga tgattctcaa gccttcttct cctaaggtga ctaagactca   19560
tgaagagtta atcgttgatg aagttaagcg ttacatcatg gattgtgtca gagcacaact   19620
ggtggtccaa tgatacgtcc agcctccttc ctagatattc ctgagattat aaaccttggg   19680
aataaatatg tggaagagga agtcaaggtt gtagcccacc actcagcctc atggaatgca   19740
gaacaaagtg ccataacctt tgtgcatctc ttaatagaga cccaccactc agcctcatgg   19800
aatgcagaac aaagtgcaca taacctttgt gcatctctta gtagagaaga tttatcccta   19860
tgggttgctg tagatgaagg gcagattgta gggttcctgt gggctggcta tcacgagttg   19920
gccccttgga cacctgtaag agttgcctct gacattctct tttatattat accagagagg   19980
cgaggaacac tacttggtat gcgtctcatc aaagccctaa agcaatgggc tagtgataat   20040
```

```
gaatgctctg aggttcgcct gtctatcgcc tctggtatta atgaagaacg tgtcggacgt  20100
atgtataagc gacttggctt tgaaccgttt ggcactgtgt ataacctgaa gttctaagga  20160
gataacatgg gtgttgtaaa gaaagcattt aaggctatcg gtcttgctca agatgcacca  20220
cgtattgaag ccaaagtccc agcacagcag cttgagcgta agcctgagac tgaagctgaa  20280
gatattcaaa ttggtgcagg ggatgatgct actgcatctg caaaaggtaa gcgtggcctt  20340
gtccgtccgg tagcttctag cttgaaggtg taatatgaaa cagagcatag atttggagta  20400
tggaggtaag cggtctaaga tacctaagct atgggagaag ttctccaata acgtagctc   20460
tttccttgat agggcgaagc attactccaa attaaccttg ccctatctga tgaatgacaa  20520
aggtgataac gagacttcgc agaatggatg gcaaggtgta ggtgctcagg caaccaacca  20580
tctagccaac aagctagcgc aagtactatt ccctgcacag cgttccttct tccgtgtaga  20640
cttaactgca caaggtgaga aggttcttaa tcagcgtggc ctgaagaaga cagagctagc  20700
taccatcttc gctcaagtgg aaacacgggc aatgaaagag ttagagcaac gtcaattccg  20760
gcctgctgta gtagaagcat ttaagcatct tattgttgct ggcagctgta tgctatacaa  20820
gccgagcaaa ggtgcaatca gtgctatccc aatgcatcac tacgtagtta accgtgatac  20880
caatggcgac ctgttagaca ttatcttgct acaagagaaa gccttacgta cctttgaccc  20940
agctacacgt gcggtagtag aggttggcct gaaaggtaag aagtgcaagg aagatgacag  21000
cgttaagctg tacacacatg ctaagtatct tggtgatgga ttttgggaac tcaagcaatc  21060
tgctgatgat atccctgtgg gtaaggtgag taaaatcaaa tcagaaaagc tacctttcat  21120
cccattaact tggaagcgaa gctatggtga ggattggggt cgacctcttg cagaggatta  21180
ctccggtgat ttattcgtta tccaattctt atctgaagcg gttgcccgtg gtgctgcgct  21240
gatggcagat atcaagtacc tgattcgtcc tggtgctcaa actgatgttg accactttgt  21300
taactctggc actggtgagg ttgtcactgg tgtagaagaa gacatccata ttgtacagtt  21360
aggtaagtac gcagacctca cacctattag cgcggttcta gaggtataca ctcgccgtat  21420
cggtgttgtc ttcatgatgg agacaatgac acgccgtgac gccgaacgtg ttactgctgt  21480
agaaatccag cgagatgcgt tagagattga gcagaacatg ggtggtgtat actccctctt  21540
tgctactact atgcaatcgc cagtagcgat gtggggtctg ctggaggcag gggagtcctt  21600
cactagtgac ttagtggacc ctgtgattat cacaggtatt gaagctttag gacgcatggc  21660
tgagttggat aaactggcta actttgctca gtatatgtca ctgccattac aatggcctga  21720
gcctgtccta gctgctgtga atggcctga ctatatggat tgggtgcgtg gtcaaatctc  21780
tgctgaactg ccgttcctta aatcggctga gagatggca caagaacagg aagcacagat  21840
gcaagcacag caagcacaga tgcttgaaga aggtgtggct aaggccgtgc cgggtgtaat  21900
tcaacaagaa cttaaggagg cgtaatgtct ttctcattta ctgaaccgtc aaccactcac  21960
cctactgcta agagggtcc ggtagaaacc aaggaggtaa caactgatgc tgctactact  22020
gatgctcctg ctgacgctgg cacttctgta caagatgaca atgctggtgc acaacctact  22080
gaagacaccg gaggagaagc ttctggacag ccttcagaaa aaggagacaa tggcggagag  22140
aatggtgaac ctaagccaga tgataccgcg accgacactg aggaagtgca atacttcttc  22200
ggagaacatg aagtaacagt agacatccca caggatgtaa ctgacagcct taagagaaa  22260
ggcattgatg ccaagcaggt tgccaaggaa ctctattcca aggtggcaa gtttgaactg  22320
tcagatgcaa ccaagcagaa attgtatgat gcttttggca gtttgcggt agatgcttac  22380
```

```
ctatcaggtc taaaggctca aaatgaagcc ttcttcctga agaagccaa cgcagctaaa    22440 gagttggaag cagctaacac ccaacgcttc tctgatgttt ctaaggaaat tggtggcgaa    22500
gaaggttggt cccgtcttga ggagtgggca cttgaagcgc tgtctgatga cgaactaatg    22560
gcattcaatg cggtgatgga atctggcaac cagtacctgc aacaatatgc tgttcgtgaa    22620
ctggagggtc gtcgtaagca ggcacagggg gatgataagc catccctgat tgagccatca    22680
gcacctgcta aggctaatga agagaatggc ccactgacgc gagatcagta cgttcaagca    22740
atcgcaactc ttagccagaa gtacggcaat gaccgtaaag ctatggcaga agctcaggct    22800
aaactggacg cccgtcgccg tgctggcatg gctcgcggta tctaattcag tatttactgg    22860
acactataga agggagaaaa gttctcccta gttatcaatt tgatttataa ggagattata    22920
atacatgtct acaccgaata ctctgactaa cgttgctgta tctgcgtccg gtgaggttga    22980
cagccttctc attgagaagt ttaatggtaa ggtcaatgag cagtacctga aggtgagaa     23040 cattctgtcc tactttgatg tacaaactgt tactggcact aacacagtga gcaacaaata    23100
tttgggcgaa actgagttgc aggtgctagc accgggtcag tcccctaatg ccaccccta    23160 tcaggcggat aaaaaccagt tggtaattga taccactgtc attgctcgta acactgtggc    23220
tcacatccac gatgtacaag gtgacatcga tagcctgaaa ccaaaactgg ctatgaacca    23280
agccaagcaa ctgaaacgtc tggaagacca gatggcaatt cagcagatgc tgttaggcgg    23340
tattgctaac accaaggccg aacgtaacaa gccgcgtgtt aaagggcatg gcttctctat    23400
caacgttaac gtaactgaga gtgaagcact ggctaaccct cagtatgtta tggctgcggt    23460
agagtatgct ctggagcaac agcttgagca ggaagtggac atctctgatg tagctatcat    23520
gatgccgtgg aagttcttca atgctttgcg tgatgcagac cgaattgtag ataagactta    23580
cactatcagc cagtctggtg caaccattaa tggcttcgtt ctctcttctt ataactgccc    23640
tgtgatcccg tctaaccgat tccctacctt cgctcaggat caggctcacc acctgttgtc    23700
taatgaagat aacggctatc gttatgaccc tatcgcagag atgaatggtg cagttgctgt    23760
tctgttcact tccgacgcac tgctggtggg tcgtaccatt gaagtgactg gtgacatctt    23820
ctatgagaag aaagagaaga cttattacat tgacaccttc atggctgagg gtgcaatccc    23880
tgaccgttgg gaagcagtgt ctgtagttac cactaaacgt gatgcaacta ctggtgatgc    23940
tggaggtcct ggtgatgatc acgcaaccgt actggctcgt gcacagcgta aggctgtata    24000
tgtcaaaacc gaaggtgctg cggctgcatt ctctgctgcc ccagcaggta tccaagcgga    24060
agaccttgta gcggcggtac gtgctgtaat ggcaaatgac attaagccga ctgcaatgaa    24120
acctactgag taacacctat gccctatcta ccttgcgtag gtagggttct ttttgttagg    24180
aggattcatg cctgtaatta gacaaaccag taaattagga catatgatgg aagatgtggc    24240
cttccagatt attgatagta agctggaagc ggtaaacttg tgtatgcgag ctattggtcg    24300
tgagggtgtg gattccctcg actcagggga cttggacgca aagatgcaa gcaaaatgat     24360 cgacatcgta tcccagcggt tccagtacaa caaaggaggt ggctggtggt tcaatcgtga    24420
accaaactgg caacttgcac cagacactaa cggtgaagtt aatttaccta caactgcct     24480 agcagtattg cagtgttatg ctttaggtga aaagaaagta cctatgacta tgcgagcagg    24540
taagctctac tctacttgga gtcacacctt tgatatgcgt aagcatgtta atgctaatgg    24600
tatgattcgt cttaccttac tcaccttact accctacgag catctaccta caagtgtaat    24660
gcaggctatt gcctatcaag ctgctgtaga gtttattgtg tctaaggatg cagatcagac    24720
taagctagcc actgcgcagc agatagccac tcagcttctt atggatgtac aatctgagca    24780
```

```
aatgtcacag aagcgattaa acatgctggt acataaccct actcagcgtc agtttggtat   24840
catggctggt ggctctcaga atgtacctgc ttactctcat tcaccttatg agagttgggc   24900
gctccgtccg tgggaggatc gttaatggaa gtacaaggtt cattaggtag acaaatccaa   24960
gggattagcc agcagccgcc agcggtacgc ttgatggtc agtgcacagc tatggttaat    25020
atgatacctg atgtagtgaa tggtactcaa tcacgcatgg gtacaactca tattgcaaag   25080
atacttgatg cggggactga tgacatggct actcatcatt atcgcagagg tgatggtgat   25140
gaagagtatt tcttcacgtt gaagaaagga caagttcctg agatatttga taagtatggg   25200
cgcaaatgta atgtgacttc acaagatgca cctatgacct acctctctga ggttgttaat   25260
ccaagggaag atgtgcaatt catgacgata gctgatgtta ctttcatgct taatcgtagg   25320
aaagtagtta aagctagtag caggaagtca cctaaagttg aaacaaagc cattgtgttt    25380
tgtgcgtatg gtcaatatgg tacatcttat tccattgtaa ttaatggggc caacgctgct   25440
agttttaaaa caccggatgg tggaagtgca gaccatgttg aacaaattcg aactgaacgt   25500
atcacttctg aattgtactc taagttgcag caatggagcg gtgtgagtga ctatgaaata   25560
caaagagacg gtactagtat atttatcgag agacgggatg gtgctagctt tacaataaca   25620
accaccgatg gtgcaaaagg taaggactta gtggctatca agaataaagt tagctctact   25680
gacctactcc cttctcgtgc gcctgctggt tataaagtac aagtgtggcc tactggcagc   25740
aaacctgagt ctcgttactg gctgcaagct gagcctaaag agggaaccct tgtgtcttgg   25800
aaagaaacaa tagctgctga tgtattactt gggtttgata aaggcacaat gccttacatt   25860
attgaacgta cagatatcat caacggcata gctcaattca agataagaca aggtgattgg   25920
gaagatcgta aagtagggga tgacttgact aaccctatgc cctcttttat tgatgaggaa   25980
gtaccccaga caataggtgg aatgttcatg gtgcagaacc gcctatgctt tacagcaggt   26040
gaagcggtta ttgcttctcg tacatcatac ttcttcgatt tctttcgtta tcggttatc    26100
tctgcattgg caactgaccc ctttgatatt ttctcagatg ctagtgaagt ctaccagcta   26160
aaacatgcag tgaccttaga tggcgctacc gtgttgttct ctgataagtc acaattcata   26220
ctgccaggcg ataagccttt agagaagtca atgcactgc ttaagcctgt tacaacattt     26280
gaagtgaaca ataaagtgaa gccagtagta actggtgaat cggtaatgtt tgccactaat   26340
gatggttctt actctggtgt acgagagttc tatacagact cttatagtga cactaagaag   26400
gcacaagcaa tcacaagtca tgtgaataaa ctcatcgaag gtaacattac caacatggca   26460
gcaagccacca atgtcaacag gttacttgtc actaccgata gtatcgtaa cataatctac    26520
tgctacgatt ggttatggca aggaacagac cgtgtacaat cagcatggca tgtatggaag   26580
tggcctatag gtacaaaggt gcgaggtatg ttttattctg gtgaattact ttacctgctc   26640
cttgagcgag gagatggcgt gtatctggag aagatggaca tgggtgatgc actaacctac   26700
ggtttgaatg accgcatcag aatggatagg caagcagagt tagtcttcaa gcatttcaaa   26760
gcagaagatg aatgggtatc tgagccgctc ccttgggttc ctactaaccc agaactttta   26820
gattgcatct taatcgaggg ttgggattca tatattggcg gctctttctt attcaagtac   26880
aaccctagtg acaatacttt gtctacaacc tttgatatgt atgatgacag ccatgtaaaa   26940
gcgaaggtta ttgttggtca gatttaccct caagagtttg aacctacgcc tgtggttatc   27000
agagacaatc aagaccgtgt atcctacatt gatgtaccag ttgtaggatt ggttcacctt   27060
aatcttgaca tgtaccccga tttctccgta gaagttaaga atgtgaagag tggtaaagta   27120
```

-continued

```
cgtagagtat tagcgtcaaa ccgtataggt ggtgctctca ataatacagt aggctatgtt   27180
gaaccgagag aaggtgtctt cagatttcca ctgagagcta agagcacgga tgttgtttat   27240
cgtattattg tagagtcacc tcacacattc cagcttcgtg atattgagtg ggaagggagc   27300
tacaatccaa ccaaaaggag ggtctaatgg ctataggttc agccgttatg ctggtatgt    27360 cttctattgg tagcatgttt gcaggcagtg gtgcagcagc cgctgctgga ggtgctgccg   27420
caggtggcgg aggtttgcta ggttcactag gtggattcct aagtggctct actgctggtt   27480
tctctaatgc tggccttctt ggtgctggcc ttcaagggtt aggcttgatt ggtgatctat   27540
ttggtggaag tgatgaagcc aaggcgatga agaaagcaca agaagagcaa tggcggcagc   27600
agcttattgc tacacaagag gcgtacaaga cagtggcaga cgcagaacgt tctgctgcta   27660
aacaatatca tgcagatgca atcagtaatc aggcttcact gctacagcag cgagcacagg   27720
ttgcattact tgctggggct actggtactg gtggtaattc tgtgtcctct atgcttaatg   27780
acttagcagc agatggcggc aggaaccaga gtactatcat tgataactat gagaatcaga   27840
agattaattt caccaaccag cttaagtcta tccaacgtgg tggtcagatg cagatgcgtg   27900
agtttaagaa gccttctgct atgaatacct tggttaaagg tattccaagt ctggcatctg   27960
cctatgtaac tggtagtaag tctggcaagg cattgggtaa agccttaact gattctcgca   28020
catattcatc tggaacaaga ggtatttaat ggcaattgag cgacaagcag tacaaggtct   28080
gccacaagtg caggccactt ctcctaatgt catgaccttt gcacctcaac aagtgggagg   28140
tgtggaggct ggcgtggctt ctacctccgg tagtaggttt atcgaagacc ttattcgtgc   28200
agcaagcagc gtggctgatg ttaccactgg tatccttaat cagaagattg aggaagataa   28260
ggttgttcaa atggaacggg catataacgg attaatgcct tctgaggatg caactcgtgg   28320
tggcgctcgt gctaacatgc ttgtcaaagc tcaactgcta gctaatgatg aagcagcacg   28380
aatgaaagac atggctactc gtttccaagg aacggatgac gaatggacac aacttatggt   28440
tgactctcgt aatgagatgc agaataagct gttccagcaa tacccgtgagt tgcaaggtga   28500 caaagatact atgcgtatgg tcactaatgt cttccaagaa cagcagcctc agatttgggc   28560
tacacgaacc cagcataaac ttgaccgtga acaagcagac cgtgaggata cctttgacgg   28620
gcgagtggct tctacttggg attctaatat tgaccctgaa gcctctggct atgctttaca   28680
ggaacgaatc cgcgaaggtc ttactcaagg attactacct gaacagatgt acaagaagtt   28740
agtccagcga gcaatttcac ttgcacaagg cggtgatgtt agcatggctg aagccctgaa   28800
gtatgtgaag gacgataagg gtgtttctgt ttatgctaag aatccacagc ttatcacagc   28860
catcactagt ggtaatgcag tttgggctag gaataatgta gctgatgtaa ctcgtatgtc   28920
tttcgaagtt aaagaatcct accttgcagg tgatttaact gatgaagaat tgttggaacg   28980
agcacagcac attaataatc tgacaggtaa ctctgtcttc tctaatccag aactagaggc   29040
actgatgcgc caacgggcta agcagaatgc agagctaggt caatgcagg atatgcgacg   29100 tgagctttac tccgaccgcc tgactggctt ccaaggtaag actgataaag agaagaaggc   29160
ttacattgat gttatcaaac aggatagcca actttatgca gaccagcaaa tcaaacaacg   29220
tggcttggac ccttacagtc aagaggctga agctattcgt gtggcagtgg aagtgcagcg   29280
cctgcaattc atgaactcca aaggcttagt ggatgatacc tttgagtctc gtatcaaagc   29340
catggaatct atgctatcgc ctgagcactt tgccaagggc gaaccacagg agttgatgac   29400
tattcgccag ttgtgggaac agttaccaga agagagccga ggtgtctttg gtgacacggt   29460
gaatggctac atggataact acaacactgc actacaaatg ggagagacac ctttgcaggc   29520
```

```
tgcaaggttt gcgcgtaaag cacagcagaa attctctcgt actgagaagg aaaccaagaa   29580
gttcaactca gctattggag atgcactgga tgaggtatct ggtgctggct ggtttgatgg   29640
taaaaccgaa gtgtcagact taggtaaagc tattgcggaa gaagagttac gagctaaggc   29700
caatatgttg tggtctagtg gtatgcgtaa catggattcc atcaagaagg ctttaattac   29760
ttggggcaat aaacgctaca ctcaatcaga ggatgcaaag acttccggtg gctatttcat   29820
taaaggtgat tacacttctg catctgatat gcttatgtca gttgggaaag gcgtaaaccc   29880
taccgatgta cctctggcgc ttggtaggta tgtagaaaca cagatgccag aattgaagaa   29940
ggagcttcaa gagggggaaa ctaaagatga tatatacatt gattacaatg aacagaaagg   30000
tactttcgtg attcgtgctg gtgcagcagg tcgccctctt tctggagtaa tccctgtaac   30060
ctctttagat accacttcac tactagattc tgcctatcag aagaaagtag aggaacgaga   30120
taaaggcgag tatgttcacc cgtatcgtac agatattggt gcacaagagc ctatgccagc   30180
taaaccaact gccaaagata ttggtaaatt tggactagct aacttcctca tgtcttctgc   30240
ttttgcttct ggtgagaatc tgccttctaa cttcgagatt aactatcgag gtaatatgca   30300
acaattctat gacaagctag ctatggatga gaataaagat aaagttggct ttaataaggc   30360
aactggaacc tttactccat ataaagacgc tcacggtgag tctatcggtt acggtcattt   30420
cttaacggaa gaagagaagc gaaacgggta tattaagatt ggcgatgaac tagttcccta   30480
tcgagggtct atgtctcagc ttacagagag caaggctcgc gctcttatgg agcaagatgc   30540
taagaagcat gtgcctccta ctcgtgactg gaagattccg tttgaccaga tgcaccctgc   30600
acagcaacgt ggcttgatgg atttaagcta caatttaggt aaaggtggaa tccagaactc   30660
accgcgtgct cttgctgcat tcaaagctgg taagcttacg gagggctttta tcgaaatgct   30720 gggcactgca tcaagtgaag gtaagcgtat tcctggccta ctgaagcgac gcgctgaggc   30780
atacaatatg gcatctgctg gtggtgtgcc taagattacc gaagtggaga ctcgtgaaga   30840
tggctccatg tgggttaggt ttggtggacc tatgccagca ggttctgtct cggcatggac   30900
tcataaacgt attggcgcgg atggttggta tcaggtttat gaggctgcac ctaccaagtt   30960
agctaaagat tctaaggtag gtaaagttaa gttgtagtac ctaactcaag gcttgtctca   31020
catgtgagac aggtctttat gataggcact atggaggaat tatggaacaa gacattaaga   31080
ctaattgggc tggatatgtc cagtctactc ctgagccgtt ttctattgag gcggctccgg   31140
tatcggctcc tacgatacgc cagcgtaatg agttacaaga gcaagttctt gaagctaaag   31200
ctgacgctga tatcttaggt gctgtaggtg ctgccttcca gaatgagtgg ttggcattcg   31260
gaggcaagcg gtggtatgac cgtgccactg ctgatttcac acctcaacca gactttgaga   31320
tacaacctga gcaacgtgaa gcactacgtt tcaaatatgg tacggatatg atgcagacaa   31380
tcactgaggg tgttcgttct gaggatgaat tgaacttccg tattcagaat gcggatgaag   31440
accttgagcg caataagcgc attgctcagg ctggctgggt tggctctgtg gcgacgattg   31500
gcgctgctgt gcttgaccct gtgggatggg ttgcctctat tccaaccggt ggtgccgcta   31560
aagttggact cgtaggccgt gctgtgcgtg gcgctatcgc cgctggcgtg agtaatgccg   31620
ctattgaatc cgtattggtc caaggtgaca tgactcgtga tttagatgac attatggtag   31680
cactgggttc cggtatggct atgggtggcg ttattggcgc tgtagcgcgt ggtagggcca   31740
ctaagctcag tgagcaaggt gatgacaggg ctgctagcat tgtgcgcagt gcagacgcag   31800
gggaccgcta tgttcgtgct gttgccgatg acagtatcgg tgcgatgcgt gttaagggcg   31860
```

```
cagaggttct cactgagggt gtattcgata tctccagtaa gagtgaagac ctactgaaaa   31920
ccttgcaacg agaaggtaat gcgattgata tgacacctcg ccgttgggct ggaactatgt   31980
ctgccctcgg tactgtcgtg cactcatcta aagatgcaag tatccgaggc cttggtgctc   32040
gtctgtttga atccccacaa ggtctaggta tgcagaaggc atctgctagt cttatgcaga   32100
atactaactt aaatcgcctg aaatctgctg atatgaaccg cttcaatgat gggtttgatt   32160
tgtggcttaa agagaataat atcaatccag tagcagggca taccaactct cattatgtac   32220
agcaatacaa tgaaaaggtg tgggaggcag tgcgtattgg catggatgag tctacaccta   32280
aatctatccg catggctgct gagggacaac aggctatgta cagagaggcg ctggctttac   32340
gtcaacgttc tggtgaagcg ggatttgaaa aggtaaaagc cgacaacaaa tatatgcctg   32400
atatctttga tagtatgaaa gccagacgtc aattcgatat gcacgataaa gaagacatca   32460
tcgaactttt ctctcgtgcc taccagaatg gcgctcgtaa gattccaaag gaagcagcag   32520
atgagattgc acgagcacag gtaaatcgcg ttgctgatgc taccttaact ggaaagctta   32580
gttttgaaaa ggcaatgtca ggtcagacta aggcagagta tgaagctatc atgcgtaagg   32640
caggcttcag tgatgaagaa attgaaaaga tgatagaagc tctggataac aaagaaacca   32700
gagataacat ctctaaccga gctaaaatga gtttaggatt agatgttact caagaataca   32760
atggcattcg tatgcgtgac ttcatgaata ccaacgtgga agagctaaca gataactata   32820
tgaaggaagc agcaggtggc gctgcattgg ctcgccaagg cttctctacc tatcaggctg   32880
cacttaatgc aattgacctt gtagagcgaa atgcacgaaa cgcggctaag gatagcaagg   32940
ctagtttggc attagatgaa gagattcgtc agatgcgaga aggtcttcgc ctgattatgg   33000
gcaagtcgat tgatgcagac ccacaggcta tatctactaa gatgatgcgt cgtggtcgtg   33060
atatcacagg tgtgcttcgc ttaggtcaaa tgggcttcgc acagctaggt gaacttgcca   33120
actttatggg tgaatttggt attgctgcaa ctactatggc tttagtaag caattccgct   33180 tcacctctaa ggcgttgcgt aatggcgatg gcttcttccg agataagaac ttagctgagg   33240
ttgagagaat ggtggggtac attggtgagg ataactggct aacaactaag ggtgcacgtc   33300
ctgatgaatt tggtgatgta accacagtaa gagggatgat ggctcacttt gaccaatcca   33360
tgaactcaat acgtcgtgct caaaccaacc tatcactctt ccgcatggca cagggttctc   33420
tggagcgaat gactaatagg caaatagctt tgtctttcat tgaccacctt gaaggcaaga   33480
agattattcc tcagaagaaa ctggaggaac ttggtcttac tcaggagttc atgactaacc   33540
tacagaagca ctatgatgct aactctaaag gttctggctt gcttggcttt gatacaatgc   33600
cttatgccat gggtgaaact ttagctaatg ctattcgtcg taagtcaggt ctaatcatcc   33660
aacgtaactt cattggtgat gaaggtatct ggatgaacaa agcactaggt aagacatttg   33720
cacagcttaa gtcattctct cttgtatctg gtgagaagca atttggtcga gggattcgcc   33780
acgataaaat tggtcttgct aagaagacag cttacgggtt tgctttgggt tcaatagtgt   33840
atgcggcaaa agcctatgtg aactctattg gcgagaagaa ccaagatgaa tatttggaag   33900
agaagttatc gcctaagggg ttggcctttg gtgcaatggg tatgatgagt acaactgctg   33960
tatttagtct aggtggagat ttcttaggtg gcctaggtgt tctaccttcc gaactcattc   34020
aatcacgcta tgaagcaggt ttccaaagta agggtctgat tgaccaaata cctctggttg   34080
gcgttggtgc agatgcagta aatctggcta actcaatcaa gaagtatgca gaaggtgaca   34140
cagaaggtgt agatatcgct aagcgagcac tccgtcttgt gccacttacc aatataatag   34200
gtgtccaaaa cgcattgcgt tatggcttag atgaactgga ggattgatga gttatacttt   34260
```

```
cacagaacat acagccaatg gtacgcaagt cacctatcct tttagctttg ctggtaggga   34320
taaaggttat cttcgtgcct cagatgtgat agtggagtct cttcaaggta acacttggat   34380
tgaagttaca tctggctggc aactaactgg cacgcaccag attacttttg atgtagcacc   34440
agttgcaggt ttgaagttcc gtattcgaag ggaagtacaa aaagaatatc catacgctga   34500
gtttgaccgt ggtgttacct tggatatgaa gtctttaaat ggttctttca ttcatatact   34560
ggagattaca caggagttac ttgacgggtt ttatccagaa ggatacttca ttaaacagaa   34620
tgtaagctgg ggcggcaata agattactga tttggctgat ggcacaaatc cgggagatgc   34680
agtaaataaa gggcagcttg atgccatcga caagaagcat acagattgga acgccaaaca   34740
ggacattgag attgctggcc ttaaggctgg tatgacttct ggtattgcgc acagaactgt   34800
tccttggtac acgatagccc aaggtggtga gatttccgta aaaccacctt atgaatttca   34860
agatgcacta gttttcctta atggggtatt gcagcaccaa attgtaggcg catactctat   34920
aagcaacaac actatcactt tcgcagagcc gcttgtggct ggtacagagg tgtatgtgct   34980
gattggtagt cgtgtggcta catctgaacc taatattcag ttggagttga actttgactt   35040
agtagaaggc caacaagtag tacagattgg ctctgcattt aagtacattg aggtctacct   35100
tgatggatta ttcaacccta aacttgctta tcaggtagac ggtgacattg ttactttctc   35160
agaaagagta ccagaatgcc ggatgactgc taagattatc acagcataag gaggtgggat   35220
gattaactcc gaactggtag atagtggtgt gaagcttgcg ccacctgcac tcatatcagg   35280
tgggtacttc ctcggtatca gttgggataa ttgggtgtta atagcaacat tcatttatac   35340
cgtgttgcaa attggggact ggttttataa taagttcaag atttggaggg agaagcgtga   35400
gcgtacacaa taaacatgca gctacagagg acgaggttgg cattctgcat ggtgctatta   35460
ccaaaatctt caataagaaa gcacaggcaa tactggacac tatagaagaa gaccctgatg   35520
cagcattaca tttagtgtct ggtaaggata ttggtgcgat gtgtaagtgg gttcttgata   35580
acggcattac cgccacacct gctgcacagc aggaagagtc caagttatct aagcgcctca   35640
aggctatccg agaggcatcc agtggtaaga taattcaatt cactaaggag gattgatggc   35700
taaggcaaga gaatcacaag cggaggctct tgccagatgg gagatgctac aggagttaca   35760
gcagaccttt ccttacaccg cggaaggttt gcttctcttt gcagatacag ttattcataa   35820
cttaattgca ggcaacccte atctgattcg tatgcaggcg gatatcttga agttcctatt   35880
ttacggacac aagtaccgcc tcatcgaagc gcctcgtggt atcgctaaga caacactatc   35940
agcaatctat acggtattcc gtattattca tgaaccgcat aagcgtatca tggttgtgtc   36000
ccaaaacgcc aagcgagcag aggaaatcgc aggttgggta gttaaaatct tccgtggctt   36060
agactttctt gagtttatgc tgccggatat ctacgctggg gaccgtgcat ccgttaaggc   36120
gtttgagatt cattacaccc tacgtggtag tgataagtct ccttctgtat cctgttactc   36180
aatcgaagca ggtatgcagg gtgctcgtgc tgatattatt ctagcggatg acgtagagtc   36240
gatgcagaat gctcgtacgg cagcgggccg tgccttgctt gaggagctga ctaaggagtt   36300
tgaatctatc aaccagtttg gggatatcat ttaccttggt acacctcaga acgtaaactc   36360
tatctacaac aacctacctg ctcgtggtta ctctgttcgt atctggactg cgcgttaccc   36420
ttcagtagag caagagcaat gttatggcga cttccttgca cctatgattg ttcaagatat   36480
gaaggacaac ccagcacttc gctcagggta cgggttggat ggtaatagtg gtgcaccttg   36540
tgcccctgaa atgtatgatg atgaagtcct gattgagaag gaaatctctc agggtgctgc   36600
```

```
taagttccag cttcagttca tgcttaacac tcgcatgatg gatgctgaca gatacccatt   36660
acgcctgaac aatctaatct tcacctcgtt tggtacagag gaagtccctg tgatgcctac   36720
gtggagtaat gattccataa acatcattgg tgatgcacct aagtatggta acaagcctac   36780
ggatttcatg tacagacctg tagctcgccc atatgaatgg ggtgctgtct cccgcaagat   36840
tatgtatatt gaccctgcgg gtggtggtaa gaacggagat gagacgggtg tagccatcgt   36900
attcctgcac ggcacattca tttatgtgta tcagtgcttt ggtgtacctg gcggataccg   36960
agagtcgtcc ctgaatcgca ttgtgcaggc cgcaaagcag gcgggtgtta aagaggtatt   37020
cattgagaag aactttggtc atggcgcgtt tgaggcggta attaagccgt actttgaacg   37080
agagtggcct gtaactctgg aagaggatta cgccaccgga cagaaagagt tgcgtatcat   37140
tgagacgctg gagccgctca tggcagccca taggcttatc ttcaatgcag agatggtgaa   37200
gtcagacttt gagtcggtac agcactatcc gcttgaacta cgcatgtcct acagtctttt   37260
caatcaaatg tcgaacataa cgattgagaa gaacagcctc cggcacgatg accgcctaga   37320
cgccctgtat ggcgctatac ggcaattaac ttctcagata gactatgacg aggttacacg   37380
gattaatcgc ctcagagcgc aggagatgcg cgattacatc catgctatga acacacctca   37440
tctacgcagg gcaatgctat atggagatta cggtactgag cgaagagtga ccaacacttc   37500
cgtagcgatg cagcagcgag tttacgggca gaactaccga aataaatcgg caagcagaaa   37560
tacactttct gcaaggattt caaggactta ttaattactg gacactatag aaggaaggcc   37620
cagataataa gagaaaataa taggtaatat atatataggt taacctaggt tatataggta   37680
tgccttagta tgggtgtact cctgtacacc ctattcctta ctaccttact atatttacat   37740
aataggagag agacaatggc taatgattat agtagtcaac cattaacagg taagtctaag   37800
agaaagcagg tacaacctgt aagtgaagaa ctaatgcttc cggtgctcaa aaagaggaa    37860 gttagtaaga aaagcaatgt tattaatgat gccaccaaat caggtaaaca gaaaggggcc   37920
atggtgtgcc ttgaagtgaa aggtggtgta ttgaagattg ctatcgcggt tgatggcaaa   37980
gaagattcag agtggaagtt agtaacagtg gaaccaactg ttaacccagt ttaagataag   38040
gaggaagatt acatggctaa atatggtact acaggttctg ttactggtca ggcttttcga   38100
gtaaaagcag tacaaactat tgcaacggca atcccgatgc ctgttgttaa agaagaagac   38160
cttaagagta aagaccaccc tatcaacatc aaacatttat caggtaaaca gaaaggtgca   38220
atggttgctc ttgagaaagg tgacacaacc ttacatattg ctgttgcacg tggtagtgaa   38280
cccacagacc cttgggatgt aactggtatg gaaaaggacg ctgttactcc agcagggta   38340 taataatgct taataaatac ttcaagcgta aagagtttgc ttgccgttgt gggtgcggta   38400
catccactgt tgatgctgaa ttactacagg tagtcacaga tgtgcgtgag cactttggtt   38460
ctcctgtagt tatcacttcg ggtcatcgct gtgctaagca caatgccaat gtaggtggcg   38520
ctaagaactc catgcatctt actggtaagg ctgctgacat taagtgtct ggcatattac   38580 cttctgaagt gcataagtat cttactagca aataccaagg caagtatggt ataggtaagt   38640
ataactcctt cactcacatc gatgtacggg atggttgtgc gcgatggtaa gatgtgttga   38700
atggtgtgag cgtatggttg cccaagctgc cgaggatggc aactatgatg actgaagaa    38760 ctactctgac ttgttagctc aatggaaagg gagatgcaat gaaaaagctg tttaagtcta   38820
agaaggttgt aggtgcactg gttgcacttg ttattgctct tgtttctgta ggtcttggtg   38880 tagacccttgg ctctggcacg gaatcctctg tgacagatgt ggtctgccaa gtgatcacct   38940
gtgaataagt ttctagaagt tctggcaggt cttattggcc tgcttgtctc tgctaagaag   39000
```

```
aaacaagaag agaaggaggc acaaagtgaa gcgaatcatg ttagtgacaa cccttctgat    39060
tggttcgctg accacttccg ggtgtcagca ggcgttacca gagaaagcaa tggtgaaacc    39120
tctgaggccg acgctgacgg cagtttacga ggtagacgat aaggtctgct ttagtaagcc    39180
tgacgctaca aaacttggtt tgtacattct ctcgctagaa cgcggataca attaatacat    39240
agctttatgt atcagtgtct tacgatttac tggacactat agaagaggta agatagcgcc    39300
gttcttttga gcggcctatt actagccaat cttcataggg agggttggaa agtaatagga    39360
gatagcatgg ctaaattaac caaacctaat actgaaggaa tcttgcataa aggacaatct    39420
ttgtatgagt accttgatgc gagagtttta acatcaaagc cgtttggtgc tgcaggtgac    39480
gccactactg atgatacgga ggttatagct gcttcattaa actctcagaa agctgtcaca    39540
gtctcagatg gtgtattctc tagctctggt attaacagta attactgtaa cttagacggc    39600
aggggtagtg gcgtgctaag tcaccgttca agtacaggta actcttagt atttaacaat     39660 ctacgtgcag gtcgcttaag taatattacg gtagaaagta ataaggcgac tgatacaact    39720 caggacagc aggtatccct tgctggtgga agtgatgtta ctgtaagtga cgttaacttc     39780
tcaaacgtta aaggtactgg tttcagttta atcgcatacc ctaatgatgc gccacctgat    39840
ggacttatga ttaaaggcat tcgaggtagc tattccggct atgctactaa taaggcagcc    39900
ggatgcgtac ttgctgattc ctcagttaac tccctcatag ataacgtcat tgctaagaac    39960
taccctcagt tcggagcagt agagttgaaa ggtacagcca gttacaacat agtcagtaat    40020
gttataggga cagattgcca gcatgtaact tacaacggca ctgaagggcc aatagctcct    40080
tctaataacc ttatcaaggg ggtgatggct aataacccta gtatgcagc ggttgttgca     40140 ggcaaaggaa gtacgaactt aatctcagac gtgctcgtag attactcaac ttctgatgct    40200
aggcaggctc atggtgttac agtagagggt tctgataacg tcataaataa tgtgcttatg    40260
tcaggatgtg atggtactaa ctcttttagga caagggcaga ctgctacaat tgcacgcttt    40320
ataggtacag ctaataacaa ctatgcgtct gtatttccta gctacagtgc tacaggtgtt    40380
attactttcg aatccggctc tacccgtaac ttcgtagagg taaagcaccc tggcaggaga    40440
aacgaccttc tcagttctgc tagtactatt gacggtgcag ctactattga cggcactagt    40500
aatagtaacg tagtgcacgc acctgcctta gggcagtaca taggtagtat gtcaggtagg    40560
ttcgaatggc ggattaagtc catgtcactc ccttcaggcg ttcttacttc tgctgataag    40620
tacagaatgc ttgagatgg tgctgtgtca ttagctgtag gtgggggcac ttcttctcaa    40680
gttcgcctat ttacttctga tggtacttct cggacagtgt ccctcaccaa cggtaacgtg    40740
cgtctttcta ccagtagcac aggcttttg cagttaggtg ctgatgcaat gaccccagac     40800
agtactggta catacgcatt aggttccgcc agccgagcat ggtctggcgg ttttactcaa    40860
gcagcattca ctgttaccctc agatgctcgg tgtaaaacag aacctcttac tatctcagat    40920
gccttactgg atgcttggtc tgaagttgac tttgtgcagt ttcagtatt ggatcgtgtt      40980 gaggagaagg gtgcagactc agctagatgg cacttcggta tcatcgctca gcgagctaag    41040
gaggctttcg aacgtcacgg tatagatgca catcgctatg gcttcttgtg cttcgacagt    41100
tgggatgatg tatacgagga agatgccaat ggctctcgta aactgattac accagcaggt    41160
tcccgctacg gtattcgtta cgaggaagta ctgatattag aggctgcgtt gatgcggcgg    41220
actattaagc gtatgcagga agcactagct tccctgccta gtaagcaac aggcagtgcg     41280 taagcactgc ttttagcgca acttttctta aaggttatca cggtggtagc ctttcagaaa    41340
```

```
aggaggttac atgattcaaa gactaggttc ttcattagtt aaattcaaga gtaaaatagc    41400
aggtgcaatc tggcgtaact tggatgacaa gctcaccgag gttgtatcgc ttaaagattt    41460
tggagccaaa ggtgatggta agacaaacga ccaagatgca gtaaatgcag cgatggcttc    41520
aggtaagaga attgacggtg ctggtgctac ttacaaagta tcatctttac ctgatatgga    41580
gcgattctat aacacccgct tcgtatggga acgtttagca ggtcaacctc tttactatgt    41640
gagtaaaggt tttatcaatg gtgaactata taaaatcacg ataacccctt attacaatgc    41700
ttggcctcaa gacaaagcgt tgtatatga gaacgtgata tatgcacctt acatgggtag     41760
tgaccgtcat ggtgttagtc gtctgcatgt atcatgggtt aagtctggtg acgatggtca    41820
aacatggtct actccagagt ggttaactga tctgcatcca gattacccta cagtgaacta    41880
tcattgtatg agtatgggtg tatgtcgcaa ccgtctgttt gccatgattg aaacacgtac    41940
tttagccaag aacaaactaa ccaattgtgc attgtgggat cgccctatgt ctcgtagtct    42000
gcatcttact ggtggtatca ctaaggctgc aaatcagcaa tatgcaacaa tacatgtacc    42060
agatcacgga ctattcgtgg gcgattttgt taacttctct aattctgcgg taacaggtgt    42120
atcaggtgat atgactgttg caacggtaat agataaggac aacttcacgg ttcttacacc    42180
taaccagcag acttcagatt tgaataacgc tggaaagagt tggcacatgg gtacttcttt    42240
ccataagtct ccatggcgta agacagatct tggtctaatc cctagtgtca cagaggtgca    42300
tagctttgct actattgata acaatggctt tgttatgggc tatcatcaag gtgatgtagc    42360
tccacgagaa gttggtcttt tctacttccc tgatgctttc aatagcccat ctaattatgt    42420
tcgtcgtcag ataccatctg agtatgaacc agatgcgtca gagccatgca tcaagtacta    42480
tgacggtgta ttatacctta tcactcgtgg cactcttggt gacagacttg gaagctcttt    42540
gcatcgtagt agagatatag gtcagacttg ggagtcactg agatttccac ataatgttca    42600
tcatactacc ctaccttttg ctaaagtagg agatgacctt attatgtttg gttcagaacg    42660
tgcagaaaat gaatgggaag caggtgcacc agatgatcgt tacaaggcat cttatcctcg    42720
taccttctat gcacgattga atgtaaacaa ttggaatgca gatgatattg aatgggttaa    42780
catcacagac caaatctatc aaggtgacat tgtgaactct agtgtaggtg taggttcggt    42840
agtagttaaa gacagctaca tttactatat cttttggtggc gaaaaccatt tcaacccaat    42900
gacttatggt gacaacaaag gtaaagaccc atttaaaggt catggacacc ctactgatat    42960
atactgctat aagatgcaga ttgcaaatga caatcgtgta tctcgtaagt ttacatatgg    43020
tgcaactccg ggtcaagcta tacctacttt catgggtact gatggaatac gaaatatccc    43080
tgcacctttg tatttctcag ataacattgt tacagaggat actaaagttg gacacttaac    43140
acttaaagca agcacaagtt ccaatatacg atctgaagtg cagatggaag gtgaatatgg    43200
ctttattggc aagtctgttc caaaggacaa cccaactggt caacgtttga ttatttgtgg    43260
tggagaagag acttcgtcct cttcaggtgc acagataact ttgcacggct ctaattcaag    43320
taaggctaat cgtatcactt ataacggaaa tgagcaccta ttccaaggtg caccaatcat    43380
gcctgctgta gataaccagt ttgctgctgg tggacctagt aaccgattca ctaccatcta    43440
cctaggtagt gaccctgtta caacttcaga tgctgaccac aagtacagta tctctagtat    43500
taataccaag gtgttaaagg cttggagcag ggttggtttt aaacagtatg gtttgaatag    43560
tgaagcagag agggaccttg atagcataca cttcggtgtc ttggctcagg atattgtagc    43620
tgcttttgaa gctgaaggt tggatgccat taagtatgga attgtgtcct tcgaagaagg    43680
taggtacggt gtgaggtata gtgaagttct aatactagag gctgcttata ctcgttatcg    43740
```

-continued

```
tttagacaag ttagaggaga tgtatgccac taataaaatc agttaagcaa gctgctgtac    43800
tccagaacac agaagagctt attcaatcag gacgtgaccc taagcaggct tatgccattg    43860
ccaaggatgt tcaacgtcgt gccatgaaga aaccttctgc atcttctgcg taagcaggtt    43920
aatatcttag tataaacaag ggcagactta ggtttgtcct tagtgtattc caaaggaggt    43980
aacatgctga agatggttg ggtttcatat gaccctacag accctaagaa ttggctacag     44040
gttatcgcta tagcttgtgc aggtagccta ttggctgccc tgatgtattc attatggatg    44100
tacacaaagt aaccaaagtc aaaattttga tgtaggcgtg tgtcagctct ctcgccctcg    44160
ccctcgccgg gttgtcccca tagggtggcc tgagggaatc cgtcttcgac gggcagggct    44220
gatgtactcc ttgtctagta caagggaggc ggagggaacg cctagggagg cctaggaatg    44280
gcttagtggt ggacaaggtg attaccttag tgaagcctct tagtgcattc ctgaggccat    44340
tcagggcgtt tatgagggat tgacagggtg tgagggcgtg ggcta                    44385
```

<210> SEQ ID NO 4
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 4

```
gtttttgaac acacatgaac aaggaagtac aggtctcaca gtgtacggac ctaaagttcc    60
```

<210> SEQ ID NO 5
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 5

```
ttacgcgaac gcgaagtccg actctaagat                                     30
```

<210> SEQ ID NO 6
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 6

```
ccagttgcac gagtctcaat tggacaaaat                                     30
```

<210> SEQ ID NO 7
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 7

```
tcagtggcaa atcgcccaat taggacccat                                     30
```

<210> SEQ ID NO 8
<211> LENGTH: 24
<212> TYPE: DNA
<213> ORGANISM: Artificial Sequence
<220> FEATURE:
<223> OTHER INFORMATION: Synthetic Polynucleotide

```
<400> SEQUENCE: 8
ccgaaggtaa gatgggtcct aatt                                      24

<210> SEQ ID NO 9
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 9
ttaaataccg gaacttctcc gtaagtagtt                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 10
gttcaacact gtatacatct tgtcagatga                                30

<210> SEQ ID NO 11
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 11
gaaatgtgcg cggaacccct atttgtttat agggacacag agagacactc aagtaacac  60

<210> SEQ ID NO 12
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 12
cagtatgata gtacatctct atgtgtccct tgtctcatga gcggatacat atttgaatgt  60

<210> SEQ ID NO 13
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 13
gggggtactt tgggttcttg aactatgaga ccttgttcat gtgtgttcaa aaacgttata  60

<210> SEQ ID NO 14
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 14
gtgttacctt gagtgtctct ctgtgtccct tgtctcatga gcggatacat atttgaatgt  60

<210> SEQ ID NO 15
<211> LENGTH: 60
```

```
<212> TYPE: DNA
<213> ORGANISM: Artificial Sequence
<220> FEATURE:
<223> OTHER INFORMATION: Synthetic Polynucleotide

<400> SEQUENCE: 15
gggggaactt taggtccgta cactgtgaga ccttgttcat gtgtgttcaa aaacgttata    60

<210> SEQ ID NO 16
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 16
tcctgtcggg tggtggtgcg ggagtggcta tgtctcatga gcggatacat atttgaatgt    60

<210> SEQ ID NO 17
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 17
ggaagggtgg gctgatcaga gtcgggaggg ccttgttcat gtgtgttcaa aaacgttata    60

<210> SEQ ID NO 18
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 18
tgtctcatga gcggatacat atttgaatgt                                     30

<210> SEQ ID NO 19
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 19
ccttgttcat gtgtgttcaa aaacgttata                                     30

<210> SEQ ID NO 20
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 20
cctgtacttc cttgttcatg tgtgttcaaa                                     30

<210> SEQ ID NO 21
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 21
```
ataaacaaat aggggttccg cgcacatttc                                30

<210> SEQ ID NO 22
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 22
tataacgttt ttgaacacac atgaacaagg tctcatagtt caagaaccca aagtaccccc    60

<210> SEQ ID NO 23
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 23
acggaacctc cttcttgggt tctttgacgc                                30

<210> SEQ ID NO 24
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 24
ccagtggctg gcgtcaaaga acccaagaag                                30

<210> SEQ ID NO 25
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 25
ggaagtcggt tcatcgctaa gcacgattgc                                30

<210> SEQ ID NO 26
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 26
tggcgatgat gcaatcgtgc ttagcgatga                                30

<210> SEQ ID NO 27
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 27
gatgcaacgt tcagcgcagc actttcggca                                30

<210> SEQ ID NO 28
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 28
ttgtagttgg tgccgaaagt gctgcgctga                              30

<210> SEQ ID NO 29
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 29
acattcaaat atgtatccgc tcatgagaca agggacacat agagatgtac tatcatactg    60

<210> SEQ ID NO 30
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 30
aacagcgtcg cggtcatcca cagcgttcgc                              30

<210> SEQ ID NO 31
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 31
gcgaacgctg tggatgaccg cgacgctgtt ccgtttggtc aactaaagac catgaaccag    60

<210> SEQ ID NO 32
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 32
gtggacttaa agtagttcct ttgatgctta ttactcgttc tccaccatga ttgcattagg    60

<210> SEQ ID NO 33
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 33
cctaatgcaa tcatggtgga gaacgagtaa taagcatcaa aggaactact ttaagtccac    60

<210> SEQ ID NO 34
<211> LENGTH: 6021
<212> TYPE: DNA
<213> ORGANISM: Artificial Sequence
<220> FEATURE:
<223> OTHER INFORMATION: Synthetic Polynucleotide

<400> SEQUENCE: 34
tgaggtaact cacattaatt gcgttgcgct cactgcccgc tttccagtcg ggaaacctgt    60

```
cgtgccagct gcattaatga atcggccaac gcgcggggag aggcggtttg cgtattgggc    120
gctcttccgc ttcctcgctc actgactcgc tgcgctcggt cgttcggctg cggcgagcgg    180
tatcagctca ctcaaaggcg gtaatacggt tatccacaga atcaggggat aacgcaggaa    240
agaacatgtg agcaaaaggc cagcaaaagg ccaggaaccg taaaaaggcc gcgttgctgg    300 cgttttttcca taggctccgc cccctgacg agcatcacaa aaatcgacgc tcaagtcaga    360
ggtggcgaaa cccgacagga ctataaagat accaggcgtt tccccctgga agctccctcg    420
tgcgctctcc tgttccgacc ctgccgctta ccggatacct gtccgccttt ctcccttcgg    480
gaagcgtggc gctttctcat agctcacgct gtaggtatct cagttcggtg taggtcgttc    540
gctccaagct gggctgtgtg cacgaacccc ccgttcagcc cgaccgctgc gccttatccg    600
gtaactatcg tcttgagtcc aacccggtaa gacacgactt atcgccactg gcagcagcca    660
ctggtaacag gattagcaga gcgaggtatg taggcggtgc tacagagttc ttgaagtggt    720
ggcctaacta cggctacact agaaggacag tatttggtat ctgcgctctg ctgaagccag    780
ttaccttcgg aaaaagagtt ggtagctctt gatccggcaa acaaaccacc gctggtagcg    840
gtggtttttt tgtttgcaag cagcagatta cgcgcagaaa aaaggatctc aagaagatc     900 ctttgatctt ttctacgggg tctgacgctc agtggaacga aaactcacgt taagggattt    960
tggtcatgag attatcaaaa aggatcttca cctagatcct tttaaattaa aaatgaagtt   1020
ttaaatcaat ctaagtata tatgagtaaa cttggtctga cagttaccaa tgcttaatca    1080
gtgaggcacc tatctcagcg atctgtctat ttcgttcatc catagttgcc tgactccccg   1140
tcgtgtagat aactacgata cgggagggct taccatctgg ccccagtgct gcaatgatac    1200
cgcgagaccc acgctcaccg gctccagatt tatcagcaat aaaccagcca gccggaaggg    1260
ccgagcgcag aagtggtcct gcaactttat ccgcctccat ccagtctatt aattgttgcc    1320
gggaagctag agtaagtagt tcgccagtta atagtttgcg caacgttgtt gccattgcta    1380
caggcatcgt ggtgtcacgc tcgtcgtttg gtatggcttc attcagctcc ggttcccaac    1440
gatcaaggcg agttacatga tcccccatgt tgtgcaaaaa agcggttagc tccttcggtc    1500
ctccgatcgt tgtcagaagt aagttggccg cagtgttatc actcatggtt atggcagcac    1560
tgcataattc tcttactgtc atgccatccg taagatgctt ttctgtgact ggtgagtact    1620
caaccaagtc attctgagaa tagtgtatgc ggcgaccgag ttgctcttgc ccggcgtcaa    1680
tacgggataa taccgcgcca catagcagaa ctttaaaagt gctcatcatt ggaaaacgtt    1740
cttcggggcg aaaactctca aggatcttac cgctgttgag atccagttcg atgtaaccca    1800
ctcgtgcacc caactgatct tcagcatctt ttactttcac cagcgtttct gggtgagcaa    1860
aaacaggaag gcaaaatgcc gcaaaaaagg aataagggc gacacggaaa tgttgaatac    1920
tcatactctt cctttttcaa tattattgaa gcatttatca gggttattgt ctcatgagcg    1980
gatacatatt tgaatgtatt tagaaaaata aacaaatagg ggttccgcgc acatttcccc    2040
gaaaagtgcc acctgggtcc ttttcatcac gtgctataaa aataattata atttaaattt    2100
tttaatataa atatataaat taaaaataga aagtaaaaaa agaaattaaa gaaaaaatag    2160
tttttgtttt ccgaagatgt aaaagactct aggggatcg ccaacaaata ctacctttta    2220
tcttgctctt cctgctctca ggtattaatg ccgaattgtt tcatcttgtc gtgtagaag    2280 accacacacg aaaatcctgt gattttacat tttacttatc gttaatcgaa tgtatatcta    2340
tttaatctgc ttttcttgtc taataaatat atatgtaaag tacgcttttt gttgaaattt    2400
tttaaacctt tgtttatttt tttttcttca ttccgtaact cttctacctt ctttatttac    2460
```

```
tttctaaaat ccaaatacaa aacataaaaa taaataaaca cagagtaaat tcccaaatta     2520
ttccatcatt aaaagatacg aggcgcgtgt aagttacagg caagcgatcc gtcctaagaa     2580
accattatta tcatgacatt aacctataaa aataggcgta tcacgaggcc ctttcgtctc     2640
gcgcgtttcg gtgatgacgg tgaaaacctc tgacacatgc agctcccgga dacggtcaca     2700
gcttgtctgt aagcggatgc cgggagcaga caagcccgtc agggcgcgtc agcgggtgtt     2760
ggcgggtgtc ggggctggct taactatgcg gcatcagagc agattgtact gagagtgcac     2820
catatcgact acgtcgtaag gccgtttctg acagagtaaa attcttgagg gaactttcac     2880
cattatggga aatggttcaa gaaggtattg acttaaactc catcaaatgg tcaggtcatt     2940
gagtgttttt tatttgttgt atttttttt ttttagagaa aatcctccaa tatcaaatta     3000
ggaatcgtag tttcatgatt ttctgttaca cctaactttt tgtgtggtgc cctcctcctt     3060
gtcaatatta atgttaaagt gcaattcttt ttccttatca cgttgagcca ttagtatcaa     3120
tttgcttacc tgtattcctt tactatcctc cttttctcc ttcttgataa atgtatgtag     3180
attgcgtata tagtttcgtc taccctatga acatattcca ttttgtaatt tcgtgtcgtt     3240
tctattatga atttcattta taaagtttat gtacaaatat cataaaaaaa gagaatcttt     3300
ttaagcaagg atttttcttaa cttcttcggc gacagcatca ccgacttcgg tggtactgtt     3360
ggaaccacct aaatcaccag ttctgatacc tgcatccaaa acctttttaa ctgcatcttc     3420
aatggcctta ccttcttcag gcaagttcaa tgacaatttc aacatcattg cagcagacaa     3480
gatagtggcg atagggtcaa ccttattctt tggcaaatct ggagcagaac cgtggcatgg     3540
ttcgtacaaa ccaaatgcgg tgttcttgtc tggcaaagag gccaaggacg cagatggcaa     3600
caaacccaag gaacctggga taacggaggc ttcatcggag atgatatcac caaacatgtt     3660
gctggtgatt ataataccat ttaggtgggt tgggttctta actaggatca tggcggcaga     3720
atcaatcaat tgatgttgaa ccttcaatgt agggaattcg ttcttgatgg tttcctccac     3780 agttttctc cataatcttg aagaggccaa aacattagct ttatccaagg accaaatagg     3840
caatggtggc tcatgttgta gggccatgaa agcggccatt cttgtgattc tttgcacttc     3900
tggaacggtg tattgttcac tatcccaagc gacaccatca ccatcgtctt cctttctctt     3960
accaaagtaa atacctccca ctaattctct gacaacaacg aagtcagtac ctttagcaaa     4020
ttgtggcttg attggagata agtctaaaag agagtcggat gcaaagttac atggtcttaa     4080
gttggcgtac aattgaagtt ctttacggat ttttagtaaa ccttgttcag gtctaacact     4140
accggtaccc catttaggac cacccacagc acctaacaaa acggcatcaa ccttcttgga     4200
ggcttccagc gcctcatctg gaagtgggac acctgtagca tcgatagcag caccaccaat     4260
taaatgattt tcgaaatcga acttgacatt ggaacgaaca tcagaaatag ctttaagaac     4320
cttaatggct tcggctgtga tttcttgacc aacgtggtca cctggcaaaa cgacgatctt     4380
cttaggggca gacataggg cagacattag aatggtatat ccttgaaata tatatatata     4440
ttgctgaaat gtaaaggta agaaaagtta gaaagtaaga cgattgctaa ccacctattg     4500
gaaaaaacaa taggtcctta aataatattg tcaacttcaa gtattgtgat gcaagcattt     4560
agtcatgaac gcttctctat tctatatgaa aagccggttc cggcctctca cctttccttt     4620
ttctcccaat ttttcagttg aaaaaggtat atgcgtcagg cgacctctga aattaacaaa     4680
aaatttccag tcatcgaatt tgattctgtg cgatagcgcc cctgtgtgtt ctcgttatgt     4740
tgaggaaaaa aataatggtt gctaagagat tcgaactctt gcatcttacg atacctgagt     4800
```

```
attcccacag ttaactgcgg tcaagatatt tcttgaatca ggcgccttag accgctcggc    4860
caaacaacca attacttgtt gagaaataga gtataattat cctataaata taacgttttt    4920
gaacacacat gaacaaggaa gtacaggaca attgattttg aagagaatgt ggattttgat    4980
gtaattgttg ggattccatt tttaataagg caataatatt aggtatgtgg atatactaga    5040
agttctcctc gaccgtcgat atgcggtgtg aaataccgca cagatgcgta aggagaaaat    5100
accgcatcag gaaattgtaa acgttaatat tttgttaaaa ttcgcgttaa attttttgtta   5160 aatcagctca ttttttaacc aataggccga aatcggcaaa atcccttata aatcaaaaga    5220
atagaccgag atagggttga gtgttgttcc agtttggaac aagagtccac tattaaagaa    5280
cgtggactcc aacgtcaaag ggcgaaaaac cgtctatcag ggcgatggcc cactacgtga    5340
accatcaccc taatcaagtt ttttggggtc gaggtgccgt aaagcactaa atcggaaccc    5400
taaagggagc ccccgattta gagcttgacg gggaaagccg gcgaacgtgg cgagaaagga    5460
agggaagaaa gcgaaaggag cgggcgctag ggcgctggca agtgtagcgg tcacgctgcg    5520
cgtaaccacc acacccgccg cgcttaatgc gccgctacag ggcgcgtcgc gccattcgcc    5580
attcaggctg cgcaactgtt gggaagggcg atcggtgcgg gcctcttcgc tattacgcca    5640
gctggcgaaa gggggatgtg ctgcaaggcg attaagttgg gtaacgccag gttttccca     5700 gtcacgacgt tgtaaaacga cggccagtga gcgcgcgtaa tacgactcac tatagggcga    5760
attgggtacc gggccccccc tcgaggtcga cggtatcgat aagcttgata tcgaattcct    5820
gcagcccggg ggatccacta gttctagagc ggccgccacc gcggtggagc tccagctttt    5880
gttcccttta gtgagggtta attgcgcgct tggcgtaatc atggtcatag ctgtttcctg    5940
tgtgaaattg ttatccgctc acaattccac acaacatagg agccggaagc ataaagtgta    6000
aagcctgggg tgcctaatga g                                              6021

<210> SEQ ID NO 35
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 35
tataacgttt ttgaacacac atgaacaagg tctcacagtg tacggaccta aagttccccc    60

<210> SEQ ID NO 36
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 36
attacgcgat gacagtagac aacctttccg                                     30

<210> SEQ ID NO 37
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 37
tgcagcaata ccggaaaggt tgtctactgt                                     30
```

```
<210> SEQ ID NO 38
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 38
atatgtctcc tcatagatgt gcctatgtgg                              30

<210> SEQ ID NO 39
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 39
acttgtgact ccacataggc acatctatga                              30

<210> SEQ ID NO 40
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 40
gaataacctg agggtcaata ccctgcttgt                              30

<210> SEQ ID NO 41
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 41
gacatgatgg acaagcaggg tattgaccct                              30

<210> SEQ ID NO 42
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 42
acattcaaat atgtatccgc tcatgagaca agggacacag agagacactc aaggtaacac    60

<210> SEQ ID NO 43
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 43
aacagcatcg cggtcatcca cggcgttcgc                              30

<210> SEQ ID NO 44
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 44
gcgaacgccg tggatgaccg cgatgctgtt ccgtttggtc aacttaagac catgaaccag    60

<210> SEQ ID NO 45
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 45
gactacacgt ctttccttgt gatttaccaa ttacacgtcc tctacggcta ttgctgttgg    60

<210> SEQ ID NO 46
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 46
ccaacagcaa tagccgtaga ggacgtgtaa ttggtaaatc acaaggaaag acgtgtagtc    60

<210> SEQ ID NO 47
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 47
tttgaacaca catgaacaag gaagtacagg tctctcggcc tcggcctcgc cgggatgtcc    60

<210> SEQ ID NO 48
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 48
cgtcctgatg tactggtagg tgagtgcgga                                     30

<210> SEQ ID NO 49
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 49
atttggtgga tgaaggaagg gccgacgaat                                     30

<210> SEQ ID NO 50
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 50
ttctccgtgt agttatagcc tttccatata                                     30

<210> SEQ ID NO 51
<211> LENGTH: 30

```
<212> TYPE: DNA
<213> ORGANISM: Artificial Sequence
<220> FEATURE:
<223> OTHER INFORMATION: Synthetic Polynucleotide

<400> SEQUENCE: 51
cggcttgctt tttgagaagg cattccccga                                            30

<210> SEQ ID NO 52
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 52
aagataataa ctttgaggta atctttcatc                                            30

<210> SEQ ID NO 53
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 53
agattatgtg tatggtcgtg atgtcaaaat                                            30

<210> SEQ ID NO 54
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 54
ctggaacctt agctgcctca atgcgaggtg                                            30

<210> SEQ ID NO 55
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 55
catttcaagc agtaggtctg gcacaaaagg                                            30

<210> SEQ ID NO 56
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 56
cttgtttgtc aaagatttca ggtacttgac                                            30

<210> SEQ ID NO 57
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 57
```
aggaggagta tttcttcata atgaagaagg               30

<210> SEQ ID NO 58
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 58
ccacatacgc atctgattag cttcaaagtt               30

<210> SEQ ID NO 59
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 59
gcagttaaag agcgcgatga agcgaagaag               30

<210> SEQ ID NO 60
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 60
tcaatcctcc aataagtcta cgctggcctt               30

<210> SEQ ID NO 61
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 61
gcaaatacga ttggtgtagg tcagatgacc               30

<210> SEQ ID NO 62
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 62
taaacctcct attactatcc agccctcccc               30

<210> SEQ ID NO 63
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 63
ttgagcggcc tattactcac cagtcttcac               30

<210> SEQ ID NO 64
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 64
gaaatgtgcg cggaacccct atttgtttat tagcccacgc ccacacacgc tgtcaagcgg      60

<210> SEQ ID NO 65
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 65 gttttttgaac acacatgaac aaggaagtac aggtcgccct cgccctcgcc gggttgt        57

<210> SEQ ID NO 66
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 66
ggagagtcag agggcttaag gtttactgct                                       30

<210> SEQ ID NO 67
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 67
tgctatgcta cgcgatgcag taggtgcgaa                                       30

<210> SEQ ID NO 68
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 68
cagggtcacg catctcatat gggtcgaaga                                       30

<210> SEQ ID NO 69
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 69
tggacttgct caccactgag gagttcctct                                       30

<210> SEQ ID NO 70
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 70
gctttgtcag cctgctcagg gaagcaagca                                       30

<210> SEQ ID NO 71
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 71
taacttcgct gctggtctgg agttcgctcg                                    30

<210> SEQ ID NO 72
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 72
tgtgcacttt gttctgcatt ccatgaggct                                    30

<210> SEQ ID NO 73
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 73
tgtgcatctc ttaatagaga cccaccactc                                    30

<210> SEQ ID NO 74
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 74
aagaagctga gtggctatct gctgcgcagt                                    30

<210> SEQ ID NO 75
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 75
tctaaggatg cagatcagac taagctagcc                                    30

<210> SEQ ID NO 76
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 76
gccttagctc gtaactcttc ttccgcaata                                    30

<210> SEQ ID NO 77
<211> LENGTH: 30
<212> TYPE: DNA
<213> ORGANISM: Artificial Sequence
<220> FEATURE:
<223> OTHER INFORMATION: Synthetic Polynucleotide

```
<400> SEQUENCE: 77
taaaaccgaa gtgtcagact taggtaaagc                                    30

<210> SEQ ID NO 78
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 78
tattgccgcc ccagcttaca ttctgtttaa                                    30

<210> SEQ ID NO 79
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 79
ttgacgggtt ttatccagaa ggatacttca                                    30

<210> SEQ ID NO 80
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 80
gctatctcct attactttcc aaccctccct                                    30

<210> SEQ ID NO 81
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 81
ttgagcggcc tattactagc caatcttcat                                    30

<210> SEQ ID NO 82
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 82
gaaatgtgcg cggaacccct atttgtttat tagcccacgc cctcacaccc tgtcaatccc   60

<210> SEQ ID NO 83
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 83
tataacgttt ttgaacacac atgaacaagg tctcacagtt tacacttttg gttatccccc   60

<210> SEQ ID NO 84
```

```
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 84
attagaagtc atcgtcttct tcggcttcgc                                      30

<210> SEQ ID NO 85
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 85
agcggacgaa tctcgcagcc gtaaacctca                                      30

<210> SEQ ID NO 86
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 86
tcatcacctt cgagggcctt aagggctgac                                      30

<210> SEQ ID NO 87
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 87
attgccgcat ggtcagccct taaggccctc                                      30

<210> SEQ ID NO 88
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 88
catcgtgtcc ttgaacacat cgtacccatc                                      30

<210> SEQ ID NO 89
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 89
cggggacgct gctgaggctc agattcagaa                                      30

<210> SEQ ID NO 90
<211> LENGTH: 60
<212> TYPE: DNA
<213> ORGANISM: Artificial Sequence
<220> FEATURE:
<223> OTHER INFORMATION: Synthetic Polynucleotide
```

```
<400> SEQUENCE: 90
acattcaaat atgtatccgc tcatgagaca agggacacag agacatcaac atatagtgtc     60
```

TUNING BACTERIOPHAGE HOST RANGE

RELATED APPLICATION

This application is a continuation of U.S. application Ser. No. 15/445,700, filed Feb. 28, 2017, now abandoned, which is a continuation of U.S. application Ser. No. 14/478,657, filed Sep. 5, 2014, now U.S. Pat. No. 9,617,522, which claims the benefit under 35 U.S.C. § 119(e) of U.S. provisional application No. 61/873,901, filed Sep. 5, 2013, each of which is incorporated by reference herein in its entirety.

FEDERALLY SPONSORED RESEARCH

This invention was made with Government support under Contract Nos. W911NF-07-D-0004 and W911NF-13-D-0001 awarded by the Army Research Office and under Grant No. OD008435 awarded by the National Institutes of Health. The Government has certain rights in the invention.

BACKGROUND OF THE INVENTION

A bacteriophage ("phage") is a virus that can specifically infect host bacteria and reproduces at the expense of the host bacteria. Shortly after their discovery, phages were proposed as a means to control pathogenic bacteria (d'Herelle, F., *Bulletin of the New York Academy of Medicine* 7, 329 (1931)); however, a poor understanding of the relationship between bacteria and phages led to frequent treatment failures, and the emergence of readily-available chemical antibiotics made phage therapy obsolete (Carlton, R. M., *Archivum immunologiae et therapiae experimentalis* 47, 267 (1999)). Presently, with the rise of drug-resistant bacteria and the sharp decline in antibiotic discovery (Fischbach, M. A. et al. *Science* 325, 1089 (2009)), phage therapy is regaining attention.

The limited range of bacterial cell hosts for a single type of phage has been a major challenge to the development and approval of clinical phage-based products. Traditionally, a phage "cocktail" was used to address this challenge (Sulakvelidze, A., et al. *Antimicrobial agents and chemotherapy* 45, 649 (2001)). Still, the desire to broaden the host range by adding different types of phages to a phage cocktail must be balanced with another challenge of producing and testing well-defined multi-component combinations for government regulatory approval.

Further still, creating phage-based therapeutics and diagnostics is limited by the difficulty of engineering phages. Phage genomes are often too large to be handled efficiently in vitro and reside for short periods of time in bacteria, which makes it difficult to modify the genomes during the phage reproductive cycle. Thus, phage genome engineering is classically performed with allele replacement methods whereby a piece of the phage genome is cloned into an appropriate bacterial vector, remodeled using classical molecular biology, and the bacterium containing the resulting construct is infected with the phage. The phage then recombines with the plasmid to acquire the desired mutations. This process, though, is inefficient because many phages degrade resident DNA upon entry and because the lack of phage selectable markers often make screening for acquired characteristics labor intensive. Moreover, there are very large stretches of phage DNA that harbor toxic functions and thus prevent their manipulation within bacteria.

SUMMARY OF THE INVENTION

The present disclosure addresses the above challenges by providing, inter alia, recombinant bacteriophages with tunable host ranges for controlling phage host cell specificity and high-throughput bacteriophage engineering methods. Artificially controlling phage specificity contributes to practical applications such as, for example, bacteriophage therapy and bacterial identification by altering and/or expanding the range of host cell strains recognized and/or infected by particular types of bacteriophages. This is achieved, in some embodiments, by altering host recognition elements such as, for example, tail fibers of a particular type of bacteriophage. A bacteriophage, using its tail fibers, recognizes and adsorbs to the outer membrane of its host bacterial cell(s) (Weidel, W. *Annu Rev Microbiol* 12, 27-48 (1958)). Altering (e.g., swapping, mutating) the tail fibers of a bacteriophage can alter the range of host bacterial cells recognized by the bacteriophage. For example, a T3 bacteriophage may be modified to have tail fibers from one or more different types of bacteriophages (e.g., T7, SP6, yppR, K1-5, K11), thereby expanding the bacterial cell host range of the T3 bacteriophage to that of the one or more different types of bacteriophages. Thus, instead of using a cocktail of different types of bacteriophage to try to target multiple different strains of pathogenic bacteria, the present disclosure contemplates, in some embodiments, the use of a cocktail of one type of recombinant bacteriophage with heterologous host recognition elements (e.g., heterologous tail fibers). Accordingly, various aspects of the present disclosure provide compositions that comprise recombinant bacteriophages with heterologous host recognition elements.

Methods of the present disclosure for altering bacteriophage host range overcome some of the difficulties of phage engineering, particularly those associated with the large size of a phage genome, by using, for example, copies of a linearized capture vector (e.g., yeast artificial chromosome) and a set of linear bacteriophage genomic fragments with homologous "arms" that facilitate recombination.

Thus, various aspects of the invention provide methods that comprise introducing into yeast cells (a) copies of a linearized yeast artificial chromosome (YAC) and (b) a set of linear bacteriophage genomic fragments of defined sequence from at least two different types of bacteriophages, each genomic fragment comprising at each end a sequence of at least 20 contiguous nucleotides, wherein one of the two end sequences of each bacteriophage genomic fragment is homologous to only one other end sequence of an adjacent genomic fragment, and wherein the set of bacteriophage genomic fragments of defined sequence, when recombined, forms a nucleic acid encoding a viable recombinant bacteriophage with heterologous host recognition elements; and culturing the yeast cells to permit homologous recombination of the end sequences of the bacteriophage genomic fragments and the end sequences of the YAC, thereby producing a recombined YAC::phage construct that encodes a viable recombinant bacteriophage with heterologous host recognition elements.

In some embodiments, the methods comprise introducing into yeast cells (a) copies of a linearized yeast artificial chromosome (YAC) and (b) a set of linear bacteriophage genomic fragments of defined sequence from at least two different types of bacteriophages, each genomic fragment comprising at each end a sequence of at least 20 contiguous nucleotides, wherein one of the two end sequences of each bacteriophage genomic fragment is homologous to only one other end sequence of an adjacent genomic fragment, and wherein the set of bacteriophage genomic fragments of defined sequence, when recombined, forms a nucleic acid encoding a viable recombinant bacteriophage with heterologous tail fibers; and culturing the yeast cells to permit homologous recombination of the end sequences of the bacteriophage genomic fragments and the end sequences of the YAC, thereby producing a recombed YAC::phage construct that encodes a viable recombinant bacteriophage with heterologous tail fibers.

In some embodiments, the methods further comprise isolating and/or purifying the recombined YAC::phage construct.

In some embodiments, the copies of a linearized YAC comprise at each end a sequence of at least 20 contiguous nucleotides.

In some embodiments, the nucleic acids that encode a viable recombinant bacteriophage are formed by (i) a first subset of the genomic fragments of defined sequence that, when recombined, encode tail fibers from one type of bacteriophage and (ii) a second subset of the genomic fragments of defined sequence that, when recombined, encode a structure (e.g., capsid head, tail sheath) from a different type of bacteriophage.

In some embodiments, the methods further comprise expressing the YAC::phage construct to produce the viable recombinant bacteriophage.

In some embodiments, the set of bacteriophage genomic fragments of defined sequence is from at least one bacteriophage selected from the group consisting of: Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, Ampullaviridae, Bicaudaviridae, Clavaviridae, Globuloviridae and Guttavirus.

Various other aspects of the invention provide methods that comprise (a) introducing into yeast cells (i) copies of a linearized yeast artificial chromosome (YAC) comprising at one end a first end sequence of at least 20 contiguous nucleotides and at the other end a second end sequence of at least 20 contiguous nucleotides, and (ii) a first bacteriophage genomic fragment of defined sequence comprising at one end a third end sequence of at least 20 contiguous nucleotides and at the other end a fourth end sequence of at least 20 contiguous nucleotides, wherein the third end sequence is homologous to the first end sequence of the YAC, (iii) a second bacteriophage genomic fragment of defined sequence comprising at one end a fifth end sequence of at least 20 contiguous nucleotides and at the other end a sixth end sequence of at least 20 contiguous nucleotides, wherein the fifth end sequence is homologous to the end nucleotide sequence of the YAC, (iv) a third bacteriophage genomic fragment of defined sequence comprising at one end a seventh end sequence of at least 20 contiguous nucleotides and at the other end an eighth end sequence of at least 20 contiguous nucleotides, wherein the seventh end sequence is homologous to the fourth end sequence of the first bacteriophage genomic element, and the eighth end sequence is homologous to the sixth end sequence of the second bacteriophage genomic element, wherein the third bacteriophage genomic fragment comprises one bacteriophage genomic fragment or more than one bacteriophage genomic fragments that overlap by at least 20 contiguous nucleotides, wherein the first, second and third bacteriophage genomic fragments, when recombined, produce a nucleic acid encoding a viable recombinant bacteriophage with heterologous tail fibers, and wherein at least one of the bacteriophage genomic fragments is from one type of bacteriophage and at least one of the bacteriophage genomic fragments is from at least one different type of bacteriophage; and (b) culturing the yeast cells to permit homologous recombination of the end sequences of the bacteriophage genomic fragments and the end sequences of the YAC, thereby producing a recombined YAC::phage construct that encodes a viable recombinant bacteriophage with heterologous tail fibers.

In some embodiments, the methods further comprise isolating and/or purifying the recombined YAC::phage construct.

In some embodiments, at least one bacteriophage genomic fragment is from one type of bacteriophage and at least one bacteriophage genomic fragment is from a different type of bacteriophage.

In some embodiments, the bacteriophage genomic fragments, when recombined, produce a nucleic acid encoding tail fibers from one type of bacteriophage and a structure from a different type of bacteriophage.

In some embodiments, the methods further comprise expressing the YAC::phage construct to produce the viable recombinant bacteriophage.

In some embodiments, the first, second and/or third bacteriophage genome fragment of defined sequence is/are from at least one bacteriophage selected from the group consisting of: Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, Ampullaviridae, Bicaudaviridae, Clavaviridae, Globuloviridae, and Guttavirus.

Still other aspects of the invention provide yeast artificial chromosomes (YACs) that comprise a bacteriophage genome that encodes a viable bacteriophage with heterologous tail fibers.

In some embodiments, the bacteriophage genome comprises a set of overlapping bacteriophage genomic fragments of defined sequence from at least two different types of bacteriophages.

In some embodiments, the set of overlapping bacteriophage genomic fragments of defined sequence is from at least one bacteriophage selected from the group consisting of: Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, Ampullaviridae, Bicaudaviridae, Clavaviridae, Globuloviridae and Guttavirus.

Various aspects of the invention also provide compositions that comprise recombinant bacteriophages with heterologous tail fibers from at least two different types of bacteriophages.

In some embodiments, the heterologous tail fibers are from at least two bacteriophages selected from the group consisting of: Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, Ampullaviridae, Bicaudaviridae, Clavaviridae, Globuloviridae and Guttavirus.

The invention also provides, in some aspects, methods that comprise providing phagemids, each phagemid containing a nucleic acid that encodes a bacteriophage host recognition element, mutagenizing the nucleic acids that encode the bacteriophage host recognition elements to produce a phagemid library comprising a plurality of nucleic acids that encode a plurality of mutagenized bacteriophage host recognition elements, transforming bacterial cells with (a) lysogenic bacteriophages that are defective in the host recognition element and (b) the phagemid library, and isolating packaged phagemid particles.

In some embodiments, the methods further comprise infecting bacterial cells with the packaged phagemid particles.

In some embodiments, the methods further comprise culturing the bacterial cells infected with the phagemid particles.

In some embodiments, the methods further comprise isolating a nucleic acid that encodes a mutagenized bacteriophage host recognition element from the bacterial cells infected with the phagemid particles.

In some embodiments, the methods further comprise characterizing the nucleic acid that encodes the mutagenized bacteriophage host recognition element.

In some embodiments, the characterizing comprises amplifying from the bacterial cells infected with the phagemid particles a nucleic acid that encodes the mutagenized bacteriophage host recognition element and a nucleic acid that encodes a bacterial 16S sequence to produce a first amplified nucleic acid fragment and a second amplified nucleic acid fragment, respectively.

In some embodiments, the methods further comprise fusing the first amplified nucleic acid fragment and the second amplified nucleic acid fragment to produce a single amplicon.

In some embodiments, the methods further comprise sequencing the amplicon to identify bacterial cell host ranges of the mutagenized bacteriophage host recognition element.

In some embodiments, at least one of the bacteriophage host recognition element is from at least one bacteriophage selected from the group consisting of: Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, Ampullaviridae, Bicaudaviridae, Clavaviridae, Globuloviridae and Guttavirus.

In some embodiments, at least one of the bacteriophage host recognition elements is a tail fiber.

BRIEF DESCRIPTION OF THE DRAWINGS

The accompanying drawings are not intended to be drawn to scale. In the drawings, each identical or nearly identical component illustrated in various figures is represented by a like numeral. For purposes of clarity, not every component may be labeled in every drawing.

FIG. 12A also shows that synthetic T7 with K11 tail fibers ($T7_{K11gp11\text{-}12\text{-}17}$) is capable of infecting *Klebsiella* and that synthetic K11 with T7 tail fibers ($K11_{T7gp\text{-}11\text{-}12\text{-}17}$) is capable of infecting BL21.

DETAILED DESCRIPTION OF THE INVENTION

Figure 1:
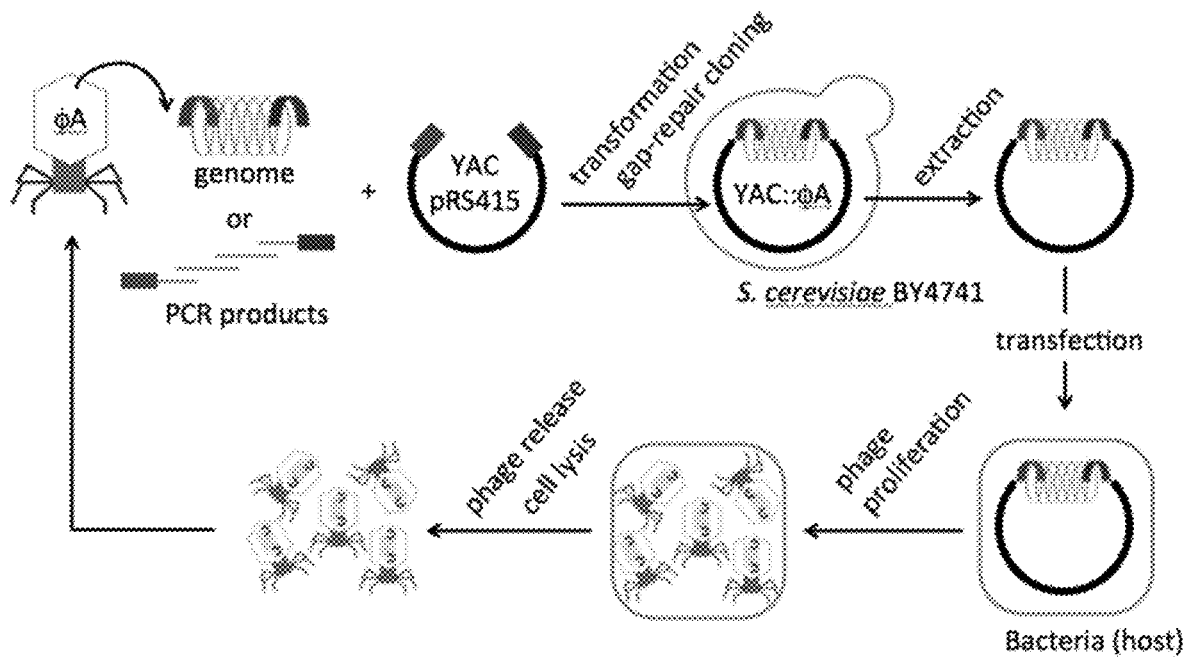
FIG. 1 depicts a yeast-based platform of the present disclosure for engineering recombinant bacteriophages with heterologous host recognition elements.

Bacteriophages are composed of proteins that encapsulate a DNA or RNA genome and may have relatively simple or elaborate structures. As used herein, the term "bacteriophage" includes naturally-occurring and recombinant bacteriophages, unless otherwise indicated. A "naturally-occurring" bacteriophage is a phage isolated from a natural or human-made environment that has not been modified by genetic engineering. A "recombinant bacteriophage" is a phage that comprises a genome that has been genetically modified by insertion of a heterologous nucleic acid sequence into the genome. In some embodiments, the genome of a naturally-occurring phage is modified by recombinant DNA technology to introduce a heterologous nucleic acid sequence into the genome at a defined site.

Bacteriophage genomes may encode as few as four genes, and as many as hundreds of genes. A bacteriophage particle recognizes and binds to its host bacterial cell through its tail fibers and/or other bacteriophage host recognition elements (e.g., tail spikes), causing DNA in the head of the phage to be ejected into the cytoplasm of the bacterial cell where the bacteriophage replicates using either a lytic cycle, which typically results in bacterial cell lysis, or a lysogenic (non-lytic) cycle, which leaves the bacterial cell intact. Differences in bacteriophage host recognition mainly reflect differences in bacterial cell surface receptors. Bacteriophage attachment to bacterial cells requires the binding of host recognition elements to bacterial receptor molecules, and it is typically the host recognition element (e.g., tail fiber) that determines the host range (e.g., different species of host bacterial cells). Thus, altering (e.g., changing or mutating) the host recognition elements of a bacteriophage, in turn, can alter bacteriophage infectivity. Provided herein are methods that can be used to achieve artificial control of bacteriophage infectivity, thereby altering and, in some instances, expanding the range of phage host cells for particular recombinant bacteriophages. As used herein, a "phage host cell" is a cell that can be infected by a phage to yield progeny phage particles.

Bacteriophages

Bacteriophages are obligate intracellular parasites that multiply inside bacteria by making use of some or all of the host biosynthetic machinery. Though different phages may contain different materials, they all contain nucleic acid and protein, and may be covered by a lipid membrane. A bacteriophage genome typically consists of a single, linear or circular, double- or single-stranded nucleic acid. Depending on the phage, the nucleic acid can be either DNA or RNA. Thus, in some embodiments, a bacteriophage of the invention contains DNA, while in other embodiments, a bacteriophage contains RNA. The size of the nucleic acid may vary depending on the phage. A genome of the simplest phages are only a few thousand nucleotides in size, while a genome of more complex phages may be more than 100,000 nucleotides in size, and in rare instances, more than 1,000,000 nucleotides. The number of different kinds of protein and the amount of each kind of protein in the bacteriophage particle may vary depending on the phage. The proteins function in infection and to protect the nucleic acid from nucleases in the environment.

Many bacteriophages range in size from 24-200 nm in diameter. Those having a capsid head may be composed of many copies of one or more different proteins. The nucleic acid is located in the capsid head, which acts as a protective covering for the nucleic acid. For filamentous phage, without capsid heads, the nucleic acid is simply coated with proteins. Many phages have tails attached to the capsid head. The tail is a hollow tube through which the nucleic acid passes during infection. The size of the tail can vary, and in more complex phages, the tail is surrounded by a contractile sheath which contracts during infection of the phage host bacterium. At the end of the tail, phages have a base plate and one or more tail fibers attached to it. The base plate and tail fibers are involved in the adsorption of the phage to the host cell. The main determinant of adsorption and specificity toward bacteria for most phages lies in small appendages surrounding the tail known as tail fibers or tail spikes, depending on their morphology. For phages of the T7 family, the host determinant is encoded by gene gp17, and the mature virus typically has 6 tail fibers each composed of a trimer of Gp17 (Steven, A C et al. *J Mol Biol* 200, 351-365 (1988)).

Some bacteriophage tails may be long, flexible and non-contractile (e.g., Siphoviridae such as lambda). The tail may be connected to the head via a portal complex that may or may not carry side tail fibers. Host recognition proceeds though the tip of the tail fibers (adhesin), thinner fibers located at the very tip of the tail, the tail baseplate, or any combination of the foregoing. Other bacteriophage tails may be long, rigid and contractile (e.g., Myoviridae such as T4, Mu). The tail may have a contractile sheath surrounding the tubular structure of the tail. It may also be attached to the head via a portal complex that may also carry side tail fibers. Host recognition is assumed to proceed primarily through the tip of the tail fiber (e.g., adhesin) or through other recognition elements located at the tip of the tail itself, in the baseplate. Yet other bacteriophage tails may be short, rigid and non-contractile (e.g., Podoviridae such as P22 and T7). The tail may be almost non-existent, but the portal complex is still present. In some instances, a bacteriophage may harbor tail fibers or tail spikes on its portal that are responsible for host recognition.

The first step in the bacteriophage infection process is the adsorption of the phage to the cell membrane. This step is mediated by the tail fibers and/or other bacteriophage host recognition elements and is reversible. For example, the tail fibers attach to specific receptors on the cell and the host specificity of the phage (e.g., the bacteria that it is able to infect) is usually determined by the type of phage tail fibers. The nature of the bacterial receptor varies for different bacteria. Examples of receptors include proteins on the outer surface of the cell, lipopolysaccharide (LPS), pili and lipoprotein.

The attachment of the bacteriophage to the cell through the tail fibers is typically weak and reversible. The irreversible binding of the phage to the cell results in the contraction of the sheath, if present, and delivery of the hollow tail fiber through the bacterial envelope. The nucleic acid from the capsid head then passes through the hollow tail and enters the cell.

The bacteriophages of the invention may be lytic (or virulent) or non-lytic (or lysogenic or temperate). Lytic bacteriophages are phages that can only multiply on bacteria and kill the cell by lysis at the end of the life cycle. Lytic phage, in some embodiments, may be enumerated by a plaque assay. A plaque is a clear area that results in a lawn of bacterial grown on a solid media from the lysis of bacteria. The assay may be performed at a low enough concentration of phage that each plaque arises from a single infectious phage. The infectious particle that gives rise to a plaque is referred to as a PFU (plaque forming unit).

Lysogenic bacteriophages are those that can either multiply through the lytic cycle or enter a quiescent state in the cell. In this quiescent state, most of the phage genes are not transcribed; the phage genome exists in a repressed state. The phage DNA in this repressed state is referred to as a prophage because it has the potential to produce phage. In most cases, the phage DNA actually integrates into the host chromosome and is replicated along with the host chromosome and passed on to the daughter cells. The cell harboring a prophage is not adversely affected by the presence of the prophage, and the lysogenic state may persist indefinitely. The cell harboring a prophage is referred to as a lysogen.

Examples of bacteriophage for use in accordance with the invention include, without limitation, those of the order Myoviridae (T4-like virus; P1-like viruses; P2-like viruses; Mu-like viruses; SPO1-like viruses; phiH-like viruses); Siphoviridae (λ-like viruses, γ-like viruses, T1-like viruses; T5-like viruses; c2-like viruses; L5-like viruses; .psi.M1-like viruses; phiC31-like viruses; N15-like viruses); Podoviridae (T7-like virus; phi29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudivirus); Fuselloviridae (Fusellovirus); Inoviridae (Inovirus, Plectrovirus, M13-like viruses, fd-like viruses); Microviridae (Microvirus, Spiromicrovirus, Bdellomicrovirus, Chlamydiamicrovirus); Leviviridae (Levivirus, Allolevivirus), Cystoviridae (Cystovirus), Ampullaviridae, Bicaudaviridae, Clavaviridae, Globuloviridae, and Guttaviridae. Such phages may be naturally occurring or engineered.

In some embodiments, a bacteriophage genome may comprise at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 325 kb, at least 350 kb, at least 375 kb, at least 400 kb, at least 425 kb, at least 450 kb, at least 475 kb, at least 500 kb, or more.

The bacteriophages of the invention infect bacteria. Bacteria are small (typical linear dimensions of around 1 micron), non-compartmentalized, with circular DNA and ribosomes of 70S. As used herein, the term "bacteria" encompasses all variants of bacteria, including endogenous bacteria. "Endogenous" bacteria naturally reside in a closed system (e.g., bacterial flora) and are typically non-pathogenic. The invention contemplates bacteriophages that infect non-pathogenic and/or pathogenic bacteria. The bacteriophages of the invention may infect bacterial cells of the subdivisions of Eubacteria. Eubacteria can be further subdivided into Gram-positive and Gram-negative Eubacteria, which depend on a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells of the invention include, without limitation, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are *Bacteroides thetaiotaomicron*, *Bacteroides fragilis*, *Bacteroides distasonis*, *Bacteroides vulgatus*, *Clostridium leptum*, *Clostridium coccoides*, *Staphylococcus aureus*, *Bacillus subtilis*, *Clostridium butyricum*, *Brevibacterium lactofermentum*, *Streptococcus agalactiae*, *Lactococcus lactis*, *Leuconostoc lactis*, *Actinobacillus actinobycetemcomitans*, cyanobacteria, *Escherichia coli*, *Helicobacter pylori*, *Selnomonas ruminatium*, *Shigella sonnei*, *Zymomonas mobilis*, *Mycoplasma mycoides*, *Treponema denticola*, *Bacillus thuringiensis*, *Staphlococcus lugdunensis*, *Leuconostoc oenos*, *Corynebacterium xerosis*, *Lactobacillus plantarum*, *Lactobacillus rhamnosus*, *Lactobacillus casei*, *Lactobacillus acidophilus*, *Streptococcus Enterococcus faecalis*, *Bacillus coagulans*, *Bacillus ceretus*, *Bacillus popillae*, *Synechocystis* strain PCC6803, *Bacillus liquefaciens*, *Pyrococcus abyssiSelenomonas nominantium*, *Lactobacillus hilgardii*, *Streptococcus ferus*, *Lactobacillus pentosus*, *Bacteroides fragilis*, *Staphylococcus epidermidis*, *Zymomonas mobilis*, *Streptomyces phaechromogenes*, or *Streptomyces ghanaensis*. Thus, the bacteriophage of the invention may target (e.g., specifically target) a bacterial cell from any one or more of the foregoing genus and/or species of bacteria. In some embodiments, the bacteriophage may target *E. coli* strains BL21, DH5α, DH10B, BW25113, Nissle 1917 and/or MG1655 and/or derivatives of any of the foregoing strains (e.g., a modified strain with, for example, a mutation, insertion and/or plasmid).

In some embodiments, the bacteriophages of the invention infect bacteria of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, *Deinococcus-Thermus*, Dictyoglomi, Elusimicrobia, Fibrobacteres, Firmicutes (e.g., *Bacillus, Listeria, Staphylococcus*), Fusobacteria, Gemmatimonadetes, Nitrospirae, Planctomycetes, Proteobacteria (e.g., *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas*), Spirochaetes, Synergistets, Tenericutes (e.g., *Mycoplasma, Spiroplasma, Ureaplasma*), Thermodesulfobacteria and Thermotogae.

The invention also contemplates, in various aspects and embodiments, substituting bacteriophages for archaeophages (i.e., viruses that infect archaea such as, e.g., φH viruses). Thus, in some embodiments, the phages are able to productively infect archaea. In some embodiments, the archaea is a Euryarcheota. In some embodiments the archaea is a Crenarcheota.

Engineering Recombinant Bacteriophages with Heterologous Tail Fibers

Recombinant bacteriophages of the invention can be engineered by introducing genomic fragments from at least two different bacteriophage genomes into a replicating capture vector with a selectable marker. In some embodiments, the heterologous host recognition particles of the recombinant bacteriophage are encoded by genomic fragments from one type of bacteriophage, while all or most other structures (e.g., capsid head, tail sheath, base plate) are encoded by genomic fragments from a different type of bacteriophage. In general, copies of the linearized capture vector (e.g., YAC) and the set of linear bacteriophage genomic fragments of defined sequence are co-transformed into competent host cells (e.g., yeast cells) and plated on selective media. Cell colonies that grow on the selective media are presumed to contain circularized vector::phage constructs resulting from homologous recombination among the linear bacteriophage genomic fragments and between the linear bacteriophage genomic fragments and the linearized capture vector. The cell colonies are then screened for the presence of junctions between vector DNA and phage DNA, the presence of which indicates successful cloning of the set of linear bacteriophage genomic fragments into the capture vector. Successful cloning results in a recombinant circular nucleic acid molecule that encodes a viable recombinant bacteriophage with heterologous host recognition elements (e.g., heterologous tail fibers).

Phage Genome Isolation

Any suitable method may be used to isolate phage genomes from phage cultures and/or isolated phage and/or concentrated phage preparations. The methods of the invention, in some embodiments, include the use of phage genomes from at least two different types of bacteriophage with a different, or overlapping, host ranges. Examples, of methods that may be used in accordance with the invention to isolate phage genomes include, without limitation, column-based, polyethylene glycol (PEG)-based, filter-based and cesium chloride centrifugation methods. In some embodiments, a phage genome may be isolated by simply boiling phage lysates as a dilution (e.g., 10-fold dilution) in buffer (e.g., TE buffer).

In some embodiments of the invention, a column-based method is used to isolate phage genomes. For example, high-titer lysates of a phage culture may be further concentrated via chromatography based on charge and/or affinity, permitting the concentration of large volumes of lysate into very small volumes. Passing the phages over a column, and then eluting into a small volume provides the material for DNA-harvesting of phages for further genome manipulation.

In some embodiments of the invention, a PEG-based method is used to isolate phage genomes. For example, the presence of high-concentrations of polyethylene glycol permits precipitation of active phage particles from a lower-titer, high volume of phage material.

In some embodiments of the invention, a filter-based method is used to isolate phage genomes. For example, filtering lysates to remove large cell debris, followed by filtration in the 100 kDa size range permits the retention of phage particles, while losing water and salts in the phage lysate preparation.

In some embodiments of the invention, a cesium chloride centrifugation method is used to isolate phage genomes. For example, concentrated lysates may be purified by treating them with DNases to remove contaminating host DNA, followed by centrifugation in a cesium chloride gradient to purify the phage particles away from the cell debris.

Any suitable method may be used to purify phage genomes. In some embodiments, regardless of the purification method, phage lysates may be treated with proteases and chloroform to remove the phage coats, followed by either column-based DNA purification or ethanol precipitation of the recovered DNA. DNA recovered at this step is typically ready for further capture and manipulation.

If the bacteriophage genomic sequence is unknown, the invention contemplates, in some embodiments, methods of generating a complete sequence. For example, next generation sequencing techniques may be used to generate large amounts of data (e.g., contigs) that can be used to assemble contiguous pieces of phage sequence. This sequence is often not sufficient to close an entire phage genome with a single pass, and thus remaining gaps may be filled using PCR-based techniques. Primers designed to anneal to the ends of contigs can be used in combination to amplify the phage genomic DNA. Only primers from contigs that are adjacent to each other will be amplify as a product. These PCR products can be sequenced by traditional Sanger sequencing to close the gaps between contigs.

Modified Sanger sequencing may also be used to directly sequence phage genomic DNA. This technique can be used, in some embodiments, to sequence the ends of the phage given that PCR cannot be used to capture this final sequence. This will complete the phage genomic sequence.

Bacteriophage Genomic Fragments

As used herein, a "genomic fragment" refers to an oligonucleotide isolated from, or synthesized based on, a bacteriophage genome. For brevity, genomic fragments will be referred to in the context of being isolated from a bacteriophage genome; however, any of the genomic fragments for use in accordance with the invention may be synthesized to produce an oligonucleotide that is homologous to (e.g., the same as) an oligonucleotide isolated from a genome of a particular type of bacteriophage. Genomic fragments include, for example, genes, gene fragments, gene cassettes (e.g., more than one gene), origins of replication, and phage packaging signals. In some embodiments, a genomic fragment may have a length of about 50 nucleotides to about 10,000 nucleotides. For example, a genomic fragment may have a length of about 50 nucleotides to about 5,000 nucleotides, about 50 to about 1,000 nucleotides, about 1,000 nucleotides to about 10,000 nucleotides, about 5,000 nucleotides to about 10,000 nucleotides. In some embodiments, a genomic fragment may have a length of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900 or 10000 nucleotides. Other embodiments contemplate larger genomic fragments. Thus, in some embodiments, a genomic fragment may have a length of about 10,000 nucleotides to about 15,000 nucleotides, or more. For example, a genomic fragment may have a length of about 10000, 11000, 12000, 13000, 14000 or 15000 nucleotides, or more.

As used herein, "a set of linear bacteriophage genomic fragments of defined sequence" refers to a set of genomic fragments that, when combined to form a single contiguous nucleic acid, encodes a full length hybrid phage genome, or as much of a hybrid phage genome that is necessary and sufficient to encode a fully functional (e.g., viable and infectious) phage. As used herein, an "infectious" phage refers to a phage that can adsorb to and inject its nucleic acid into a bacterial cell. Thus, a bacteriophage is considered to "infect" a host cell when it adsorbs to and injects its nucleic acid into the cell. In some embodiments, an infectious phage can productively infect, replicate and burst a particular host cell. A "hybrid phage genome," as used herein, refers to a genome comprising genomic fragments from genomes of at least two different types of bacteriophages.

A fully functional phage may require the following: (1) the ability to take control of the host in order to produce phage; (2) an origin of replication and associated replication functions; (3) a complete set of genes permitting capsid assembly; (4) a complete set of genes permitting tail assembly; (5) structures (e.g., tail fibers or tail spikes) for bacteriophage adsorption to the host cell; and/or (6) packaging functions. In some instances, a fully functional phage may also require functions to counteract host defenses such as restriction (e.g., T7 gp0.3, T4 IPI, DNA methylases) or abortive infection (e.g., T4 dmd, T3 gp1.2).

In some embodiments, bacteriophage can use its own transcriptional and translational machinery to produce phage, while in other embodiments, the bacteriophage may utilize the host cell's transcriptional and translational machinery.

In some embodiments, associated replication functions may be provided by the host cell.

In some embodiments, a fully functional bacteriophage may require tail fibers to adsorb to a host cell. For example, T7 and T4 bacteriophages use tail fibers to adsorb to host cells. In other embodiments, a fully functional bacteriophage may require tail spikes to adsorb to a host cell. For example, P22 and K1-5 bacteriophages use tail spikes to adsorb to host cells. In yet other embodiments, a fully functional bacteriophage may require dispensable tail fibers to adsorb to a host cell. For example, lambda bacteriophages use dispensable tail fibers to adsorb to host cells.

Packaging may proceed through various mechanisms depending on the bacteriophage. Some bacteriophages use a site-specific nuclease to initiate cleavage from concatemerized genomes during replication (e.g., COS phages, lambda). Other bacteriophages use a partially site specific nuclease to initiate packaging (e.g., the first cut occurs at a predefined site along the phage genome). The bacteriophages then package, through a "headful mechanism," phage genome monomers from a concatemer generated during replication. The headful mechanism entails the bacteriophage injecting as much DNA inside the capsid as can fit, cutting the DNA, and then continuing the packaging reaction in another capsid (e.g., P22, T4). Still other bacteriophages have long terminal repeats (LTRs) with a packaging enzyme that will recognize two contiguous repeats, cut between them and initiate packaging from the cut site until it encounters another occurrence of two contiguous LTRs (e.g., T7, K1-5).

The linear genomic fragments may be synthesized or amplified (e.g., via polymerase chain reaction (PCR)) from isolated and/or purified bacteriophage genome(s). Sets of PCR primers may be chosen using the following parameters: (1) the set of amplified fragments must span all the genes necessary for a viable phage, and (2) there must be at least 20 base pairs (bp) of homology between each amplified fragment to be assembled (e.g., recombined). In some embodiments, a set of linear bacteriophage fragments is synthesized de novo.

Thus, the set of linear bacteriophage genomic fragments of defined sequences is designed such that each genomic fragment comprises at each end a sequence of at least 20 contiguous nucleotides (referred to herein as an "end sequence"), wherein one of the two end sequences of each bacteriophage genomic fragment is homologous to only one other end sequence of an adjacent genomic fragment. In this way, the genomic fragments can be pieced, or "stitched," together based on homology to form a nucleic acid encoding, in some embodiments, a full length hybrid (or recombinant) phage genome. In some embodiments, each genomic fragment comprises at each end a sequence of at least 30 contiguous nucleotides, at least 35 contiguous nucleotides, at least 40 contiguous nucleotides, at least 45 contiguous nucleotides, at least 50 contiguous nucleotides, or more.

The set of linear bacteriophage genomic fragments of defined sequence and copies of the linearized capture vector are co-transformed into competent host cells. A "host cell," as used herein, refers to a cell into which a recombinant nucleic acid, such as a recombinant vector, has been introduced or produced. Common hosts include, for example, bacteria (e.g., *Escherichia coli, Bacillus subtilis*), yeast (e.g., *Saccharomyces cerevisiae* such as BY4741) and various eukaryotic cell lines. In some embodiments, the set of linear bacteriophage genomic fragments of defined sequence and copies of linearized YAC are co-transformed into competent yeast cells. The set of genomic fragments and linearized capture vector may be combined with an excess of the vector prior to transformation. For example, in some embodiments, an excess of about 50 ng to about 500 ng (e.g., an excess of 50 ng, 100 ng, 200 ng, 250 ng, or 500 ng) of linearized capture vector is used. In some embodiments, an excess of about 100 ng to about 300 ng of linearized capture vector is used.

Heterologous Tail Fibers

The invention contemplates, in some embodiments, tuning bacteriophage host range by engineering recombinant bacteriophage having heterologous tail fibers. As discussed elsewhere herein, host cell specificity of the phage is typically determined by the tail fiber(s). By altering (e.g., swapping and/or mutating) tail fibers, or portions of tail fibers, of a host bacteriophage, the host range, in some embodiments, can be altered (e.g., expanded).

A "host bacteriophage," as used herein, refers to the type of bacteriophage (e.g., T3, T4, T5, T7, K1F, K11, SP6) from which genomic fragments encoding the capsid head (and optionally other non-tail fiber structures) are isolated. As used herein, a "heterologous tail fiber" refers to a tail fiber that does not naturally occur on the host bacteriophage. For example, a heterologous tail fiber may be encoded by genomic fragment(s) isolate from the genome of a type of bacteriophage that is different from the host bacteriophage. Thus, in some embodiments, a recombinant bacteriophage having heterologous tail fibers may have a capsid head from a T7 phage and tail fibers, or portions thereof, from any one or more of T3, T4, T5, K1F, K11, or SP6 phage(s). In some embodiments, a heterologous tail fiber is not a natural phage sequence, while in other embodiments, it is a natural phage sequence, albeit from a different type of phage.

In some embodiments, a recombinant bacteriophage with heterologous tail fibers is encoded by a set of linear bacteriophage genomic fragments of defined sequence that is isolated from the genomes of at least two different types of bacteriophage. For example, a recombinant bacteriophage of the invention may contain a capsid head and tail sheath (and/or other phage structures) encoded by a subset genomic fragments isolated from the genome of one type of bacteriophage and tail fibers encoded by a subset genomic fragments isolated from the genome of another type of bacteriophage.

In other embodiments, a recombinant bacteriophage with heterologous tail fibers is encoded by a set of linear bacteriophage genomic fragments of defined sequence that is isolated from the genomes of at least three, or more, different types of bacteriophage. For example, a recombinant bacteriophage of the invention may contain a capsid head (and/or other phage structures) encoded by a subset of genomic fragments isolated from the genome of one type of bacteriophage (e.g., T3 phage) and tail fibers encoded by multiple subsets genomic fragments, each of the multiple subsets isolated from the genome of different types of bacteriophages (e.g., T4, T5, T7, K1F, K11, or SP6 phage).

Tail fiber proteins typically contain antigenicity determinants and host range determinants. In some embodiments, a heterologous tail fiber may be encoded by a set of genomic fragments isolated from one type of bacteriophage. In other embodiments, the set of genomic fragments may contain subsets of genomic fragments isolated from genomes of different types of bacteriophages. For example, conserved regions of a tail fiber may be encoded by genomic fragments isolated from the genome of the host bacteriophage, while host range determinant regions may be encoded by genomic fragments isolated from the genome of a different type of bacteriophage.

In some embodiments, the recombinant bacteriophages of the invention comprise tail fibers that are completely heterologous. That is, the whole tail fiber is encoded by a nucleic acid that is not present in the host bacteriophage. For example, the heterologous tail fiber of a T3 host bacteriophage may be encoded by gene 17, which is isolated from or stitched together from genomic fragments isolated from T7 phage. Likewise, the heterologous tail fiber of a T7 host bacteriophage may be encoded by gene 17 from T3 phage. In some embodiments, the recombinant bacteriophages of the invention comprise tail fibers that are partially heterologous. That is, only a part of the tail fiber is encoded by a nucleic acid that is not present in the host bacteriophage. For example, the partially heterologous tail fiber of a T3 host bacteriophage may be encoded by a recombinant nucleic acid comprising genomic fragments from T3 phage and genomic fragments from T7. Herein, "partially heterologous tail fibers" are considered to be encompassed by the term "heterologous tail fibers." In some embodiments, at least 10% of the nucleic acid sequence encoding a partially heterologous tail fiber is present in the host bacteriophage. For example, at least 15%, at least 20%, at least 25%, at least 30%, at least 35%, at least 40%, at least 45%, at least 50%, at least 55%, at least 65%, at least 70%, at least 75%, at least 80%, at least 85%, at least 90%, at least 95%, at least 98% or at least 99% of the nucleic acid sequence encoding a partially heterologous tail fiber is present in the host bacteriophage. In other embodiments, at least 10% of the nucleic acid sequence encoding a partially heterologous tail fiber is not present in the host bacteriophage. For example, at least 15%, at least 20%, at least 25%, at least 30%, at least 35%, at least 40%, at least 45%, at least 50%, at least 55%, at least 65%, at least 70%, at least 75%, at least 80%, at least 85%, at least 90%, at least 95%, at least 98% or at least 99% of the nucleic acid sequence encoding a partially heterologous tail fiber is from a bacteriophage that is not the host bacteriophage.

Capture Vectors

As used herein, a "capture vector" refers to a nucleic acid molecule into which a phage genome has been inserted. Examples of capture vectors for use in accordance with the invention include bacterial artificial chromosomes (BACs) and yeast artificial chromosomes (YACs). Bacteriophage for which the genome sequence is known permits recombination of the genome into, for example, a circular vector, such as a YAC, using double strand break repair or other modes of recombination in, for example, yeast such as *Saccharomyces cerevisiae*.

The capture vectors of the invention contain selectable markers. Selectable markers for use herein include, without limitation, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds, genes encoding enzymes with activities detectable by standard assays known in the art (e.g., β-galactosidase, luciferase or alkaline phosphatase), and genes that visibly affect the phenotype of transformed or transfected cells, hosts, colonies, or plaques (e.g., green fluorescent protein). Other selectable markers may be used in accordance with the invention.

The capture vectors are first linearized before inserting a set of linearized bacteriophage genomic fragments of defined sequence. The capture vectors may be linearized by any method known in the art such as, for example, restriction digest.

Phage Genome Capture and Characterization

Any suitable transformation method may be used. The method may depend on the host cell. For example, in some embodiments, a lithium acetate transformation method is used (see e.g., Finlayson, S. D. et al. *Biotechnology Techniques*, 5(1), 13-18 (1991)) to transform yeast cells, followed by heat shock.

Transformed host cells (also referred to herein as "transformants") may be plated on any suitable selective media. The selective media will depend, in part, on the host cell and the selectable marker of the capture vector. For example, if an ampicillin resistance gene is used as the selectable marker, transformants should be plated on selective media containing ampicillin. Only those transformants that contain a circularized recombinant vector that expresses an ampicillin resistance gene will grow.

Presence of a hybrid phage genome, or portions thereof, in a circularized recombinant vector may be confirmed using, for example, PCR-based methods, direct sequencing, restriction digestion or Phi29/sequencing readout. In some embodiments, primers may be used to enable PCR-based confirmation of a hybrid phage genome. For example, if one primer is specific for a portion of the capture vector just outside the region of the hybrid phage genome and another primer is specific for a portion of the hybrid phage genome, these primers should together amplify a band to verify that the proper hybrid phage genome and junctions are present in the circular recombinant vector. In some embodiments, the hybrid phage genome may be directly sequenced to confirm the presence of the hybrid phage DNA inside the vector. The presence of a hybrid phage genome may also be identified and characterized using restriction digestion and gel electrophoresis. In some embodiments, a DNA polymerase from bacteriophage Phi29 can be used to copy the hybrid phage genome in vitro. These substrates may then be used for transformation and sequencing. Further, amplification with Phi29 polymerase allows for analysis with restriction enzymes to identify Restriction Fragment Length Polymorphisms (RFLPs) for rapid whole genome analysis. These products can be run on agarose gels and analyzed by ethidium bromide staining.

Recombinant nucleic acids of the invention may be engineered using, for example, conventional molecular cloning methods (see, e.g., *Current Protocols in Molecular Biology*, Ausubel, F. M., et al., New York: John Wiley & Sons, 2006; *Molecular Cloning: A Laboratory Manual*, Green, M. R. and Sambrook J., New York: Cold Spring Harbor Laboratory Press, 2012; Gibson, D. G., et al., *Nature Methods* 6(5):343-345 (2009), the teachings of which relating to molecular cloning are herein incorporated by reference). The circular nucleic acids encoding the recombinant bacteriophage of the invention may be expressed in any suitable host cells.

Bacteriophage Host Range Engineering with Mutagenesis

The invention also provides high-throughput methods of tuning bacteriophage host range using nucleic acid mutagenesis and, in some embodiments, next-generation sequencing. Thus, various aspect of the invention are directed to methods that comprise providing phagemids, each phagemid containing a nucleic acid that encodes a bacteriophage host recognition element, mutagenizing the nucleic acids that encode the bacteriophage host recognition elements to produce a phagemid library comprising a plurality of nucleic acids that encode a plurality of mutagenized bacteriophage host recognition elements, transforming bacterial cells with (a) lysogenic bacteriophages that are defective in the host recognition element and (b) the phagemid library, and isolating packaged phagemid particles.

As used herein, a "phagemid" is a filamentous phage-derived vector containing the replication origin of a plasmid and the packaging site of a bacteriophage. Examples of phagemids that may be used in accordance with the invention include, without limitation, M13-derived phagemids containing the f1 origin for filamentous phage packaging such as, for example, pBluescript II SK (+/−) and KS (+/−) phagemids, pBC SK and KS phagemids, pADL and P1-based phagemids (see, e.g., Westwater C A et al., *Microbiology* 148, 943-50 (2002); Kittleson J T et al., *ACS*

*Synthetoc Biology* 1, 583-89 (2012); Mead D A et al., *Biotechnology* 10, 85-102 (1988)). Other phagemids may be used in accordance with the invention.

As used herein, a "bacteriophage host recognition element" refers to bacteriophage protein that confers phage host cell specificity. Alterations (e.g., mutations) in a bacteriophage host recognition element can alter the range of phage host cells for a particular host bacteriophage. Thus, in some embodiments, recombinant bacteriophage with heterologous or mutated host recognition elements, are able to infect phage host cells that the host bacteriophage otherwise would not be able to infect. Examples of bacteriophage host recognition elements include, without limitation, long side tail fibers (e.g., T4, lambda), short side tail fibers (e.g., T7, T3), tail spikes (e.g., P22, SP6, K1-5, K1E, K1F), short tail tip fibers (lambda), other parts of the baseplate (e.g., T4), or other host cell receptor recognition proteins. Specific non-limiting examples of bacteriophage host recognition elements include T4 gp37 (e.g., NCBI Accession No. NP_049863.1), gp37 (e.g., NCBI Accession No. AAC61976.1), gp38 (e.g., NCBI Accession No. AAC61977.1), Lambda J (e.g., NCBI Accession No. AAA96553.1), T7 gp17 (e.g., NCBI Accession No. NP_042005.1), T3 gp17 (e.g., NCBI Accession No. CAC86305.1), P22 gp9 (e.g., NCBI Accession No. NP_059644.1), SP6 gp46 (e.g., NCBI Accession No. NP_853609.1), K1-5 gp46 (e.g., NCBI Accession No. YP_654147.1), K1-5 gp47 (e.g., NCBI Accession No. YP_654148.1), K1F gp17 (e.g., NCBI Accession No. YP_338127.1), K1E gp47 (e.g., NCBI Accession No. YP_425027.1), K11 gp17 (e.g., NCBI Accession No. YP_002003830.1), phiSG-JL2 gp17 (e.g., NCBI Accession No. YP_001949790.1), phiIBB-PF7A gp17 (e.g., NCBI Accession No. YP_004306354.1), and 13a gp17 (e.g., NCBI Accession No. YP_002003979.1).

As used herein, the term "nucleic acid" refers to at least two nucleotides covalently linked together, and in some instances, may contain phosphodiester bonds (e.g., a phosphodiester "backbone"). Nucleic acids (e.g., components, or portions, of the nucleic acids) of the invention may be naturally occurring or engineered. Engineered nucleic acids include recombinant nucleic acids and synthetic nucleic acids. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing.

The nucleic acids may be single-stranded (ss) or double-stranded (ds), as specified, or may contain portions of both single-stranded and double-stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xanthine, hypoxanthine, isocytosine, and isoguanine.

Nucleic acids that encode bacteriophage host recognition elements can be mutagenized by any suitable methods. Examples of nucleic acid mutagenesis methods that can be used in accordance with invention include, without limitation, site-directed mutagenesis, PCR mutagenesis and insertional mutagenesis. Non-limiting examples of PCR mutagenesis include: (1) error-prone mutagenesis using manganese or cobalt to increase error rate during elongation, which yields randomly mutagenized host recognition elements; (2) 2-way PCR, which may be used to stitch two non-homologous sequences together; (3) site directed PCR mutagenesis, which uses primers that have selected mutations to amplify the gene of interest; and (4) semi-random primer directed mutagenesis, which uses primers that have randomized nucleotides (e.g., 1-40 nt) that introduce random mutations in a given location of a gene of interest.

In some embodiments, a "bank" of mutagenized DNA fragments (e.g., host recognition elements) may be obtained from a DNA synthesis company.

Any suitable transformation method (e.g., heat shock, electroporation) may be used to transform bacterial cells with the phagemid library and the lysogenic bacteriophages that are defective in the host recognition element.

As discussed elsewhere herein, lysogenic bacteriophages are those that can either multiply via the lytic cycle or enter a quiescent state in the cell. As used herein, lysogenic bacteriophages that are "defective in the host recognition element" are missing the particular host recognition element that is mutagenized in the phagemid library such that a phagemid copy complements the lysogenic bacteriophage.

As used herein, a "packaged phagemid particle" is a bacteriophage (e.g., lysogenic bacteriophage phage defective in the host recognition element) containing a phagemid (e.g., phagemid containing a mutagenized host recognition element).

After isolating the packaged phagemid particles, they may be used to infect bacterial cells. Examples of bacterial cell are provide elsewhere herein and include the following: *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. Bacterial cells infected with the phagemid particles can then be cultured using, for example, conventional bacterial cell culture methods for bacterial cell growth.

The nucleic acid that encodes the mutagenized bacteriophage host recognition elements can be isolated and/or purified from the bacterial cells infected with the phagemid particles using, for example, conventional nucleic acid methods (e.g., combine physical and chemical methods). Examples of nucleic acid extraction/purification methods include, without limitation, ethanol precipitation, phenol chloroform and column purification.

The nucleic acids may be characterized by any suitable means. For example, the nucleic acids may be characterized using a method referred to as "Stichseq" (Yu, et al. *Nature Methods,* 8, 478-480 (2011)). In some instances, the nucleic acids are amplified (e.g., by PCR) together with a nucleic acid that encodes a bacterial 16S sequence to produce a first amplified nucleic acid fragment and a second amplified nucleic acid fragment, respectively. The first and second amplified nucleic acid fragments can then be fused to produce a single amplicon, which can then be used to identify bacterial cell host ranges of the mutagenized bacteriophage host recognition element.

In some embodiments, host range recognition elements (e.g., tail fibers) may be mutated by site-directed mutagenesis and/or random mutagenesis by PCR and/or de novo nucleic acid synthesis.

In some embodiments, after capturing a phage genome in yeast, the host range determinant is replaced with yeast selection marker URA3. Mutated host range recognition elements may be added into yeast cell harboring YAC::phage::URA3. URA3 may be replaced with mutated host range determinant by homologous recombination and transformants selected by 5-FOA counter selection. It should be understood that each mutated host range recognition element has a homologous sequence of upstream and downstream regions of the target gene in the 5' and 3' terminal, respectively.

In some embodiments, a phage with a mutated host range recognition element is captured in one-step with gap-repair cloning. The recognition element may be generated through PCR mutagenesis or other well-known techniques.

Applications

The methods and compositions of the invention may be used in many different applications. For example, in some embodiments, provided herein are "phage cocktails" that comprise the recombinant bacteriophage with heterologous host recognition elements for use in, for example, phage therapy. Phage therapy is a therapeutic use of bacteriophages to treat pathogenic bacterial infections. Because the recombinant bacteriophage of the invention can be tuned to infect a broad range of host bacterial cells, they are a particularly useful alternative to conventional antibiotic therapy against, for example, multi-drug resistant bacteria. Thus, in some embodiments, the invention provides methods of treating bacterial infections (e.g., in humans or other animals) using recombinant bacteriophages with heterologous host recognition elements such as heterologous tail fibers. The methods may comprise administering to a subject with a bacterial infection a composition comprising a recombinant bacteriophage of the invention.

In some embodiments, the recombinant bacteriophages of the invention may be used as delivery vehicles to deliver, to bacterial cells, molecules (e.g., nucleic acids) of interest.

Compositions and Kits

Also provided herein are compositions and kits that comprise any one or more of the bacteriophages, phagemids, nucleic acids and/or libraries of the invention. The compositions and kits may further comprise additional reagents such as buffers, salts and the like. In some embodiments, the compositions are pharmaceutical compositions optionally comprising one or more pharmaceutical carriers and/or excipients.

EXAMPLES

Example 1: Yeast-Based Phage Engineering

A yeast-based phage engineering platform was developed for capturing and engineering phage genomes with unprecedented speed and ease. FIG. 1 depicts one embodiment of the phage engineering method. A phage genome, or all genomic elements, was prepared to be assembled by polymerase chain reaction (PCR) or DNA synthesis, as follows. Each adjacent DNA fragment had homologous overhangs, which were required for gap-repair cloning.

The majority of the phage genome was cloned without alteration and obtained from its own genome by PCR. Purified phage genome was used as PCR template. Phage DNA may also be obtained by simply boiling phage lysates as a 10 fold dilution in TE buffer. A single plaque of the phage of interest (e.g., T7, SP-6, K1-5) was picked from a plate and resuspended in 3 mL lysogeny broth (LB) broth containing about $10^7$ receptor bacteria (the exact strain may vary from phage to phage), and the resulting culture was incubated at 37° C. with shaking until lysis was visible. The lysate was sterilized by the addition of 200 μL of chloroform, with vigorous shaking, followed by a 30-minute incubation period at room temperature. Cellular debris and chloroform were removed by centrifugation and the sterile lysate was transferred to a clean tube. The sterile lysate was then titered for concentration on an appropriate receptor strain.

A 50 mL phage lysate was then started from the stock lysate using the same receptor bacterial strain at the same concentration and a multiplicity of infection of 0.01. The lysate was incubated at 37° C. until complete lysis and was processed as the stock lysate. The lysate was also filtered through a 0.22 μm filter to eliminate as much particulate contaminant as possible. DNaseI and RNaseA were then added to the lysate, incubated 2-3 hours at 37° C., and then chilled to 4° C. To precipitate DNA, 10 mL of an ice-cold solution of 30% PEG6000, 3M NaCl was added to the lysate, and the mixture was incubated at 4° C. for at least 2 hours or overnight. Phage particles were spun down at 10000×g for 30 minutes, the supernatant discarded, and the pellets drained of all remaining liquids. The pellet was then resuspended in 500 μL-1 mL of buffer SM (100 mM NaCl, 8 mM $MgSO_4·7H_2O$, 50 mM Tris-CLAIM (1M, pH 7), 0.002% (w/v) gelatin (2% w/v)) and stored at 4° C. To extract DNA, 200 μL, of the concentrated lysate was processed with the ZR Viral DNA Kit™ using Zymo-Spin™ IC-XL Columns (Zymo Research Corporation).

PCR primers were chosen along the phage genome using the following parameters: (1) span all the genes necessary for a viable phage, and (2) provide at least 30 base pairs (bp) of homology between each PCR product to be assembled. The primers flanking the phage genome contained at least 30 bp homology to the YAC fragment, described below. Examples of primers used to reconstruct several phages are presented in Table 1. The phage genome PCR fragments were amplified using either KAPA HiFi™ or KAPA2G™ Robust polymerase (Kapa Biosystems). Vector maps and sequences of *Enterobacteria* phage T7 (SEQ ID NO:1), *Enterobacteria* phage SP-6 (SEQ ID NO:2), *Enterobacteria* phage K1-5 (SEQ ID NO:3), and pRS415 (SEQ ID NO:34) are shown in FIGS. 7-10, respectively.

TABLE 1

PCR Primers for Phage Reconstructions

| Primer | Sequence (5' → 3') | SEQ ID NO: | Description |
|---|---|---|---|
| T7-3 | GTTTTTGAACACACATGAACAAGGAA GTACAGGTCTCACAGTGTACGGACCTA AAGTTCC | 4 | T7 |

TABLE 1-continued

PCR Primers for Phage Reconstructions

| Primer | Sequence (5' → 3') | SEQ ID NO: | Description |
|---|---|---|---|
| PST227 | TTACGCGAACGCGAAGTCCGACTCTAAGAT | 5 | T7 |
| PST228 | CCAGTTGCACGAGTCTCAATTGGACAAAAT | 6 | T7 |
| PST231 | TCAGTGGCAAATCGCCCAATTAGGACCCAT | 7 | T7 |
| PST84 | CCGAAGGTAAGATGGGTCCTAATT | 8 | T7 |
| PST235 | TTAAATACCGGAACTTCTCCGTAAGTAGTT | 9 | T7 |
| PST236 | GTTCAACACTGTATACATCTTGTCAGATGA | 10 | T7 |
| T7-4 | GAAATGTGCGCGGAACCCCTATTTGTTTATAGGGACACAGAGAGACACTCAAGGTAACAC | 11 | T7 |
| 3'T3-pRS415-F-4 | CAGTATGATAGTACATCTCTATGTGTCCCTTGTCTCATGAGCGGATACATATTTGAATGT | 12 | for capturing T3 genome |
| 5'T3-pRS415-R-2 | GGGGGTACTTTGGGTTCTTGAACTATGAGACCTTGTTCATGTGTGTTCAAAAACGTTATA | 13 | for capturing T3 genome |
| 3'T7-pRS415-F-4 | GTGTTACCTTGAGTGTCTCTCTGTGTCCCTTGTCTCATGAGCGGATACATATTTGAATGT | 14 | for capturing T7 genome |
| 5'T7-pRS415-R-2 | GGGGGAACTTTAGGTCCGTACACTGTGAGACCTTGTTCATGTGTGTTCAAAAACGTTATA | 15 | for capturing T7 genome |
| LUZ19_ASB_Y2_Fw | TCCTGTCGGGTGGTGGTGCGGGAGTGGCTATGTCTCATGAGCGGATACATATTTGAATGT | 16 | for capturing LUZ19 genome |
| LUZ19_ASB_Y2_Rev | GGAAGGGTGGGCTGATACAGAGTCGGGAGGGCCTTGTTCATGTGTGTTCAAAAACGTTATA | 17 | for capturing LUZ19 genome |
| pRS415-F-4 | TGTCTCATGAGCGGATACATATTTGAATGT | 18 | for capturing T3/T7/K11 PCR products |
| pRS415-R-2 | CCTTGTTCATGTGTGTTCAAAAACGTTATA | 19 | for capturing T3/T7/K11 PCR products |
| PST255 | CCTGTACTTCCTTGTTCATGTGTGTTCAAA | 20 | for capturing SP6/K1-5 PCR products |
| PST256 | ATAAACAAATAGGGGTTCCGCGCACATTTC | 21 | for capturing SP6/K1-5 PCR products |
| pRS415-R-2-T3-1-30-F | TATAACGTTTTTGAACACACATGAACAAGGTCTCATAGTTCAAGAACCCAAAGTACCCCC | 22 | T3 |
| T3-9971-10000-R | ACGGAACCTCCTTCTTGGGTTCTTTGACGC | 23 | T3 |
| T3-9961-9990-F | CCAGTGGCTGGCGTCAAAGAACCCAAGAAG | 24 | T3 |
| T3-19931-19960-R | GGAAGTCGGTTCATCGCTAAGCACGATTGC | 25 | T3 |

TABLE 1-continued

PCR Primers for Phage Reconstructions

| Primer | Sequence (5' → 3') | SEQ ID NO: | Description |
|---|---|---|---|
| T3-19921-19950-F | TGGCGATGATGCAATCGTGCTTAGCGATGA | 26 | T3 |
| T3-29891-29920-R | GATGCAACGTTCAGCGCAGCACTTTCGGCA | 27 | T3 |
| T3-29881-29910-F | TTGTAGTTGGTGCCGAAAGTGCTGCGCTGA | 28 | T3 |
| pRS415-F-4-T3-38179-38208-R | ACATTCAAATATGTATCCGCTCATGAGACAAGGGACACATAGAGATGTACTATCATACTG | 29 | T3 |
| T3-33249-33278-R | AACAGCGTCGCGGTCATCCACAGCGTTCGC | 30 | for synthesizing T3-7 |
| T3-T7-gp17-F-1 | GCGAACGCTGTGGATGACCGCGACGCTGTTCCGTTTGGTCAACTAAAGACCATGAACCAG | 31 | for synthesizing T3-7 |
| T3-T7-gp17-R-1 | GTGGACTTAAAGTAGTTCCTTTGATGCTTATTACTCGTTCTCCACCATGATTGCATTAGG | 32 | for synthesizing T3-7 |
| T7-T3-gp17-F-1 | CCTAATGCAATCATGGTGGAGAACGAGTAATAAGCATCAAAGGAACTACTTTAAGTCCAC | 33 | for synthesizing T3-7 |
| pRS415-R-2-1-30-F | TATAACGTTTTTGAACACACATGAACAAGGTCTCACAGTGTACGGACCTAAAGTTCCCCC | 35 | T7 |
| 9971-10000-R | ATTACGCGATGACAGTAGACAACCTTTCCG | 36 | T7 |
| 9960-9989-F | TGCAGCAATACCGGAAAGGTTGTCTACTGT | 37 | T7 |
| 19930-19959-R | ATATGTCTCCTCATAGATGTGCCTATGTGG | 38 | T7 |
| 19920-19949-F | ACTTGTGACTCCACATAGGCACATCTATGA | 39 | T7 |
| 29890-29919-R | GAATAACCTGAGGGTCAATACCCTGCTTGT | 40 | T7 |
| 29880-29909-F | GACATGATGGACAAGCAGGGTATTGACCCT | 41 | T7 |
| pRS415-F-4-39909-39938-R | ACATTCAAATATGTATCCGCTCATGAGACAAGGGACACAGAGAGACACTCAAGGTAACAC | 42 | T7 |
| 35042-35071-R | AACAGCATCGCGGTCATCCACGGCGTTCGC | 43 | for synthesizing T7-3 |
| T7-T3-gp17-F-2 | GCGAACGCCGTGGATGACCGCGATGCTGTTCCGTTTGGTCAACTTAAGACCATGAACCAG | 44 | for synthesizing T7-3 |
| T7-T3-gp17-R-2 | GACTACACGTCTTTCCTTGTGATTTACCAATTACACGTCCTCTACGGCTATTGCTGTTGG | 45 | for synthesizing T7-3 |
| T3-T7-gp17-F-2 | CCAACAGCAATAGCCGTAGAGGACGTGTAATTGGTAAATCACAAGGAAAGACGTGTAGTC | 46 | for synthesizing T7-3 |
| SP6-1 | TTTGAACACACATGAACAAGGAAGTACAGGTCTCTCGGCCTCGGCCTCGCCGGGATGTCC | 47 | SP6 |

TABLE 1-continued

PCR Primers for Phage Reconstructions

| Primer | Sequence (5' → 3') | SEQ ID NO: | Description |
|---|---|---|---|
| SP6-2 | CGTCCTGATGTACTGGTAGGTGAGTGCGGA | 48 | SP6 |
| SP6-3 | ATTTGGTGGATGAAGGAAGGGCCGACGAAT | 49 | SP6 |
| SP6-4 | TTCTCCGTGTAGTTATAGCCTTTCCATATA | 50 | SP6 |
| SP6-5 | CGGCTTGCTTTTTGAGAAGGCATTCCCCGA | 51 | SP6 |
| SP6-6 | AAGATAATAACTTTGAGGTAATCTTTCATC | 52 | SP6 |
| SP6-7 | AGATTATGTGTATGGTCGTGATGTCAAAAT | 53 | SP6 |
| SP6-8 | CTGGAACCTTAGCTGCCTCAATGCGAGGTG | 54 | SP6 |
| SP6-9 | CATTTCAAGCAGTAGGTCTGGCACAAAAGG | 55 | SP6 |
| SP6-10 | CTTGTTTGTCAAAGATTTCAGGTACTTGAC | 56 | SP6 |
| SP6-11 | AGGAGGAGTATTTCTTCATAATGAAGAAGG | 57 | SP6 |
| SP6-12 | CCACATACGCATCTGATTAGCTTCAAAGTT | 58 | SP6 |
| SP6-13 | GCAGTTAAAGAGCGCGATGAAGCGAAGAAG | 59 | SP6 |
| SP6-14 | TCAATCCTCCAATAAGTCTACGCTGGCCTT | 60 | SP6 |
| SP6-15 | GCAAATACGATTGGTGTAGGTCAGATGACC | 61 | SP6 |
| SP6-16 | TAAACCTCCTATTACTATCCAGCCCTCCCC | 62 | SP6 |
| SP6-17 | TTGAGCGGCCTATTACTCACCAGTCTTCAC | 63 | SP6 |
| SP6-18 | GAAATGTGCGCGGAACCCCTATTTGTTTATTAGCCCACGCCCACACACGCTGTCAAGCGG | 64 | SP6 |
| K1-5*1 | GTTTTTGAACACACATGAACAAGGAAGTACAGGTCGCCCTCGCCCTCGCCGGGTTGT | 65 | K1-5 |
| K1-5*2 | GGAGAGTCAGAGGGCTTAAGGTTTACTGCT | 66 | K1-5 |
| K1-5*3 | TGCTATGCTACGCGATGCAGTAGGTGCGAA | 67 | K1-5 |
| K1-5*4 | CAGGGTCACGCATCTCATATGGGTCGAAGA | 68 | K1-5 |
| K1-5*5 | TGGACTTGCTCACCACTGAGGAGTTCCTCT | 69 | K1-5 |
| K1-5*6 | GCTTTGTCAGCCTGCTCAGGGAAGCAAGCA | 70 | K1-5 |
| K1-5*7 | TAACTTCGCTGCTGGTCTGGAGTTCGCTCG | 71 | K1-5 |

TABLE 1-continued

PCR Primers for Phage Reconstructions

| Primer | Sequence (5' → 3') | SEQ ID NO: | Description |
|---|---|---|---|
| K1-5*8 | TGTGCACTTTGTTCTGCATTCCATGAGGCT | 72 | K1-5 |
| K1-5*9 | TGTGCATCTCTTAATAGAGACCCACCACTC | 73 | K1-5 |
| K1-5*10 | AAGAAGCTGAGTGGCTATCTGCTGCGCAGT | 74 | K1-5 |
| K1-5*11 | TCTAAGGATGCAGATCAGACTAAGCTAGCC | 75 | K1-5 |
| K1-5*12 | GCCTTAGCTCGTAACTCTTCTTCCGCAATA | 76 | K1-5 |
| K1-5*13 | TAAAACCGAAGTGTCAGACTTAGGTAAAGC | 77 | K1-5 |
| K1-5*14 | TATTGCCGCCCCAGCTTACATTCTGTTTAA | 78 | K1-5 |
| K1-5*15 | TTGACGGGTTTTATCCAGAAGGATACTTCA | 79 | K1-5 |
| K1-5*16 | GCTATCTCCTATTACTTTCCAACCCTCCCT | 80 | K1-5 |
| K1-5*17 | TTGAGCGGCCTATTACTAGCCAATCTTCAT | 81 | K1-5 |
| K1-5*18 | GAAATGTGCGCGGAACCCCTATTTGTTTATTAGCCCACGCCCTCACACCCTGTCAATCCC | 82 | K1-5 |
| pRS415-R-2-K11-1-30-F | TATAACGTTTTTGAACACACATGAACAAGGTCTCACAGTTTACACTTTTGGTTATCCCCC | 83 | K11 |
| K11-9971-10000-R | ATTAGAAGTCATCGTCTTCTTCGGCTTCGC | 84 | K11 |
| K11-9900-9929-F | AGCGGACGAATCTCGCAGCCGTAAACCTCA | 85 | K11 |
| K11-19961-19990-R | TCATCACCTTCGAGGGCCTTAAGGGCTGAC | 86 | K11 |
| K11-19950-19979-F | ATTGCCGCATGGTCAGCCCTTAAGGCCCTC | 87 | K11 |
| K11-29950-29979-R | CATCGTGTCCTTGAACACATCGTACCCATC | 88 | K11 |
| 29880-29909-F | CGGGGACGCTGCTGAGGCTCAGATTCAGAA | 89 | K11 |
| pRS415-F-4-K11-41152-41181-R | ACATTCAAATATGTATCCGCTCATGAGACAAGGGACACAGAGACATCAACATATAGTGTC | 90 | K11 |

A yeast artificial chromosome (YAC) was also prepared, referred to here as the YAC fragment. Primer PST255 (CCTGTACTTCCTTGTTCATGTGTGTTCAAA; SEQ ID NO:20) and primer PST256 (ATAAACAAATAGGGGTTCCGCGCACATTTC; SEQ ID NO:21) were used to PCR amplify a fragment from pRS415 (FIG. 10, SEQ ID NO:34), which contained a yeast centromeric origin, autonomous replication sequence and LEU2 marker.

All DNA fragments were mixed together with an excess of 100 ng-300 ng of the YAC fragments, and then transformed into yeast BY4741 using a lithium acetate transformation method (e.g., Finlayson, S. D. et al. *Biotechnology Techniques,* 5(1):13-18, 1991). After a 45 minute heat shock, the cells were spun down, resuspended in Synthetic Complete medium and immediately plated onto SC-leu plates. The plates were then incubated for 2-3 days at 30° C. until colonies appeared. Competent yeast may be prepared in advance in large batches, aliquots placed into freezing medium (DMSO 10%, Glycerol 5%), and stored at −80° C. The colonies were streaked again onto fresh SC-leu plates at 30° C. Colonies were then picked, 3 ml liquid SC leu cultures were inoculated with the colonies at 30° C. for 1 to 2 days until saturated.

The cultures were spun down and the supernatant discarded. DNA was obtained using the YeaStar™ Genomic DNA Kit (Zymo Research) according to the manufacturer's instruction, with the exception that more cells than recommended were loaded into the system, and the Zymolyase® incubation period was increased from 2 hours to overnight until cell wall digestion was clearly visible through clearing of the mixture. The final elution volume was 50 µL, which resulted in about 5 µg of DNA total.

Competent cells with a transformation efficiency of about $10^9$ as measured from pUC19 transformation will produce about 1 pfu/ng of DNA when using purified T7 DNA. The yeast genome is about 12 mb and the phage::YAC constructs are about 50 kb, thus it can be assumed that 1/250 of the total DNA extracted from yeast is actual phage::YAC DNA. Thus, 5 µl (500 ng to 1 µg) of total DNA from the yeast clones was than transformed into DH10B electro-competent bacteria for phage expression, and the cells were immediately resuspended in LB. If the phage was able to grow on DH10B (such as T7), the resuspended transformed cells were immediately mixed with 3 mL of top agar and plated onto an LB plate. This yielded between 1 and 50 pfu. If the phage was not able to grow on DH10B (such as SP6 or K1-5), the transformed cells were incubated at 37° C. without shaking for 3 hours. The cells were then killed by chloroform addition, and any debris was spun down. The supernatant was then recovered, mixed with 100 µL, of an appropriate overnight phage recipient culture, and finally plated onto LB plates by way of 3 mL top agar. The 3 hours incubation permitted the successfully transformed cells to go through one burst liberating phages in the supernatant. This yielded hundreds of plaques because the phage amplified in each DH10B that has received a viable phage genome. The bacterial plaques were picked and sequenced, and then the synthetic phages were recovered.

To confirm that purified phage DNA from various Gram-negative phages could be transformed into bacterial hosts to generate functional phages, the "*E. cloni*" 10G strain (10G) was used as a one-time phage propagation host. All phage genomes used in this study were extracted, and up to 4 µg of each genome was electroporated into 10G directly. After incubation, chloroform was added to kill the cells and release phages. Next, supernatant was mixed with overnight culture of natural host bacteria and soft agar, poured onto agar plate, and incubated for 4-18 h to make phage plaques. Except for *Pseudomonas* phage LUZ19, all phage plaques including *Salmonella* and *Klebsiella* phages were found (Table 2), indicating that 10G can be used as an initial host for phage recovering from YAC::phage construct.

TABLE 2

One-time Phage Propagation Assay

| Phage | Propagation in E. cloni 10G | Plaque formation on E. cloni 10G | Host bacteria |
|---|---|---|---|
| T7 | Yes | Yes | E. coli (ex. BL21) |
| T3 | Yes | Yes | E. coli (ex. BL21) |
| K1-5 | Yes | No | IJ1668 (E. coli K-12 hybrid; K1 capsule) |
| SP6 | Yes | No | IJ612 (S. typhimurium LT2) |

TABLE 2-continued

One-time Phage Propagation Assay

| Phage | Propagation in E. cloni 10G | Plaque formation on E. cloni 10G | Host bacteria |
|---|---|---|---|
| LUZ19 | No | No | P. aeruginosa PAO1 |
| gh-1 | Yes | No | P. putida C1S |
| K11 | Yes | No | IJ284 (Klebsiella sp. 390) |

Figure 2:
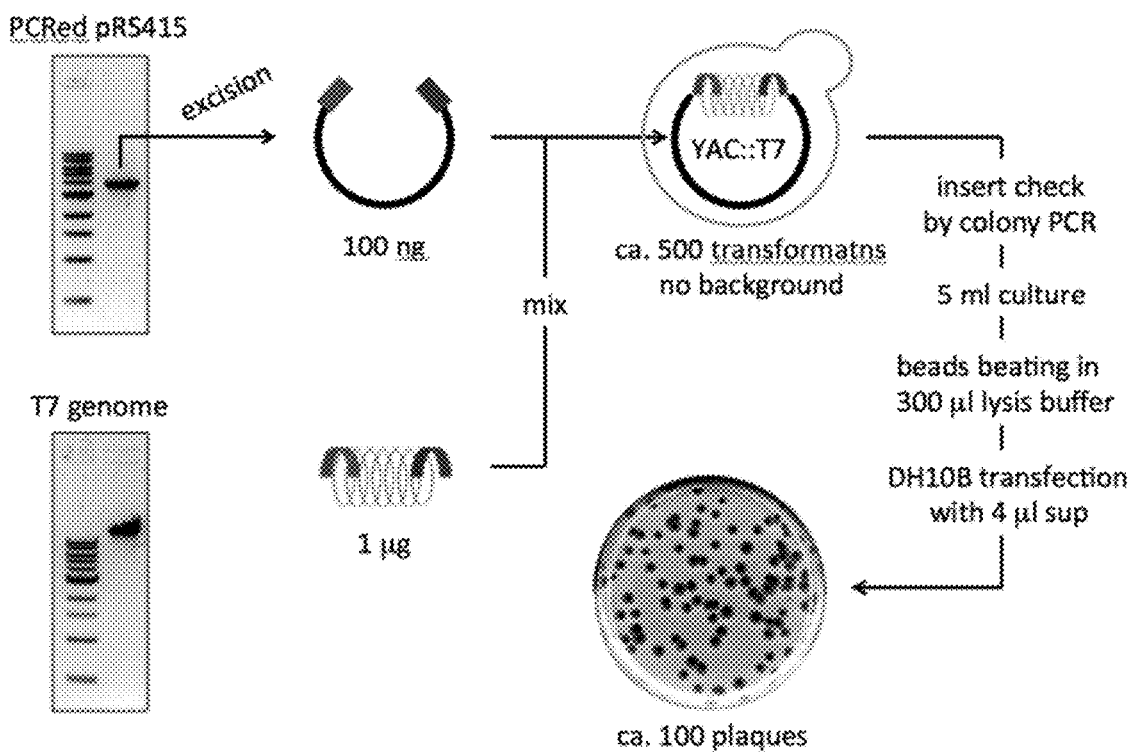
FIG. 2 depicts a yeast-based platform of the present disclosure for capturing a recovering wild-type bacteriophage species.

To validate the yeast-based phage engineering platform and to determine whether phage genomes assembled in yeast remain viable, several wild-type phages (e.g., T3, T4, T5, T7, K1F, K11, and SP6 were captured and recovered. FIG. 2 shows the results of the validation for T7 phage. PCR was used to linearize the YAC pRS415 while also adding overhangs homologous to the ends of the phage genome. To prevent the appearance of false-positive colonies, PCR-amplified YAC was excised and purified from an agarose gel after electrophoresis. Both the amplified and purified YAC and phage genome were co-transformed into yeast. Transformants were suspended in lysis buffer and disrupted by beads beating. The supernatant containing the YAC::phage constructs was used directly for transfection into *E. coli* DH10B cells, which are suitable for maintaining large DNA constructs (Durfee et al., Journal of Bacteriology, 190, 2597 (2008)). Among the 16 yeast transformants selected, all were positive by PCR and produced phage, giving an efficiency of 100%.

Next, wild-type T3 and T7 phages were captured and recovered from each of the four ~10 kbp PCR products plus the YAC. In this case, PCR was used to linearize the YAC but did not add overhangs. Instead, a homologous region was added to the end of the PCR-amplified YAC, specifically to the 5' and 3' terminal of the first and fourth 10 kbp fragments, respectively, to avoid excision and purification of all 10 kbp fragments from the gel. Among the 16 yeast transformants selected, 15 were positive by PCR and all produced phage, giving an efficiency of 94%.

Thus, the yeast-based phage engineering platform of the invention can be used to capture and recover phages efficiently and can be used to engineer desired phages from PCR products in one step.

Materials and Methods

Yeast, bacteria, and phages. *Saccharomyces cerevisiae* BY4741 (MATa his3Δ1 leu2Δ0 met15Δ0 ura3Δ0) was obtained from Thermo Scientific. *Escherichia coli* BL21 [B, F⁻ ompT hsdS$_B$ ($r_B^-m_B^-$) gal dcm], DH5α [K-12, F⁻ λ⁻ Φ80d lacZΔM15 Δ(lacZYA-argF)U169 deoR recA1 endA1 hsdR17 ($r_K^-$ $m_K^+$)phoA supE44 thi-1 gyrA96 relA1], DH10B [K-12, F⁻λ⁻ mcrA Δ(mrr-hsdRMS-mcrBC) Φ80d lacZΔM15 ΔlacX74 deoR recA1 araD139 Δ(ara leu)7697 galU galK rpsL endA1 nupG], BW25113 [K-12, F⁻λ⁻Δ (araD-araB)567 ΔlacZ4787(::rrnB-3) rph-1 Δ(rhaD-rhaB) 568 hsdR514], and MG1655 (K-12, F⁻ λ⁻ ilvG⁻ rfb-50 rph-1) were laboratory stocks. Phage T7 (ATCC BAA-1025-B2) and T3 (ATCC 110303-B3) were laboratory stocks.

Determination of plaque-forming unit (pfu). Serial dilutions of phage performed in 0.95% saline were added to 300 µl overnight bacterial culture in 3.5 ml soft agar, and poured the mixture onto LB plate. After 3 h incubation at 37° C., plaques were counted.

Preparation of yeast competent cells. *S. cerevisiae* BY4741 was grown in 5 ml YPAD medium (e.g., yeast extract, peptone, glucose, adenine hemisulphate, distilled water, cacto-agar) at 30° C. 300 rpm for 24 hours. Overnight culture was added into 50 ml YPAD medium and incubated at 30° C. 300 rpm for 4 hours. Cells were harvested by centrifugation at 3000 g.

Example 2: Model Phages with Tunable Host Ranges

Figure 3:
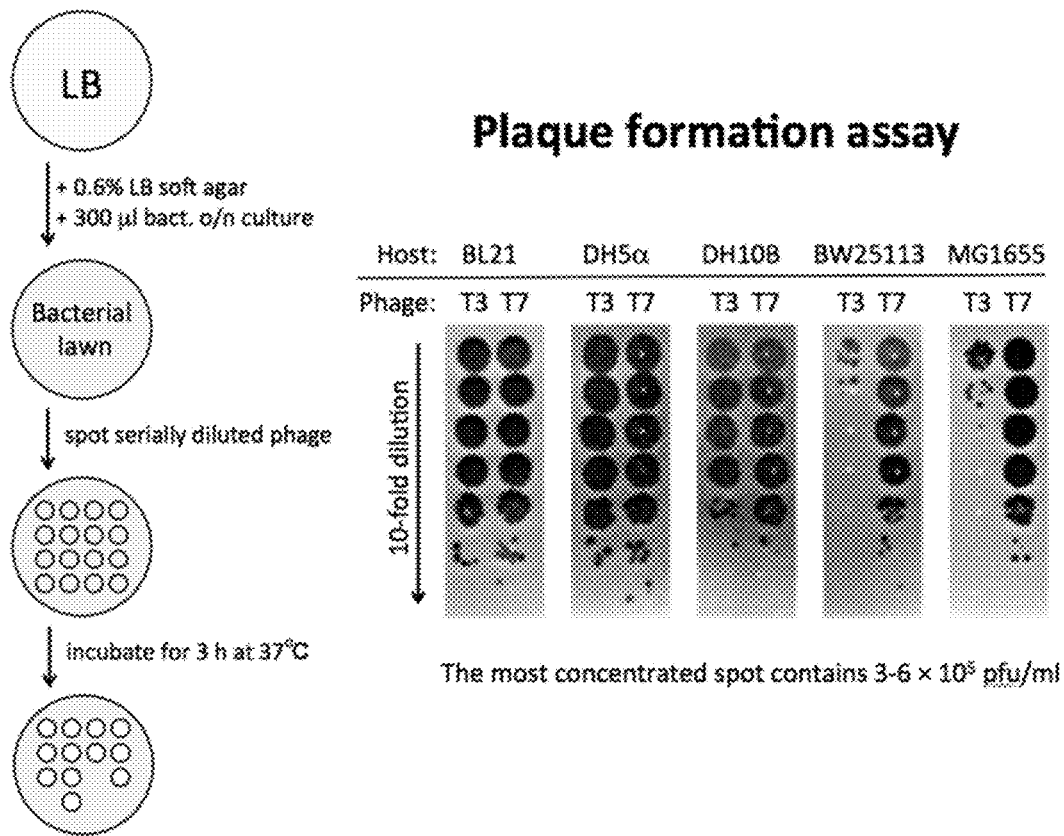
FIG. 3 depicts a plaque formation assay (left) and shows an image of a plaque formation assay using T3 and T7 phage on *Escherichia coli* (*E. coli*) strains BL21, DH5α, DH10B, BW25113 and MG1655 (right).
Figure 4:
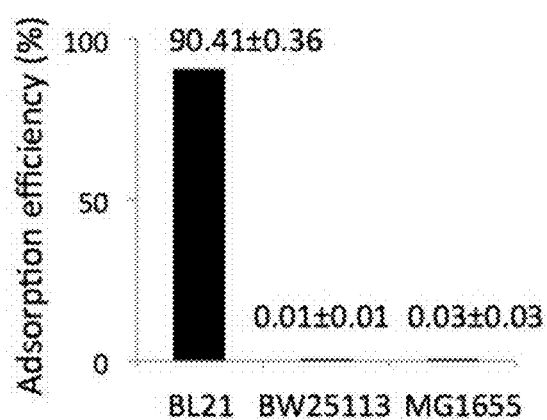
FIG. 4 shows a graph of data from an adsorption assay with T3 phage and *E. coli* BL21 BW25113 and MG1655.

To create engineered model phages with tunable host ranges, T7 and T3 phages were selected. They are obligate lytic phages and were originally isolated as a member of the seven "Type" phages that grow on *E. coli* B (Demerec, M. et al. *Genetics* 30, 119 (1945)). They have almost same size of linear genome (T7, 39937 bp; T3, 38208 bp), similar gene organization, same life cycle, and high homology across the genomes (Dunn, J. J., et al. *Journal of Molecular Biology* 166, 477 (1983); Pajunen, M. I., et al. *Journal of Molecular Biology* 319, 1115 (2002)). Their primary host determinant, tail fiber, consists of single gene product gp17, and importantly, recognizes different host receptors and shows different host ranges (Molineux, U., in *The Bacteriophages*, R. Calendar, Ed. (Oxford Univ. Press, New York, 2006) pp. 277-301). Because there is little information about the difference of host specificities between T7 and T3, their host range was first examined. Based on a previous report that T3 fails to adsorb to many common laboratory *E. coli* K-12 strains (Molineux, U., 2006), plaque formation assays were performed with four K-12 strains. As shown in FIG. 3, T7 can grow efficiently on all strains, while T3 showed poor propagation on BW25113 and MG1655 strains. To assess whether this phenomenon resulted from less adsorption efficiency or post-adsorptive problems, adsorption assays were performed (FIG. 4). Compared with BL21 reference strain, the level of adsorption abilities of T3 on BW25113 and MG1655 were $\sim 10^4$% less efficient, which is consistent with the result of plaque formation assay (FIG. 3). These results indicate that T7 and T3 have different host range, and BW25113 and MG1655 are useful for validating synthetic T7 and T3 phages with engineered tail fiber.

Figure 5A:
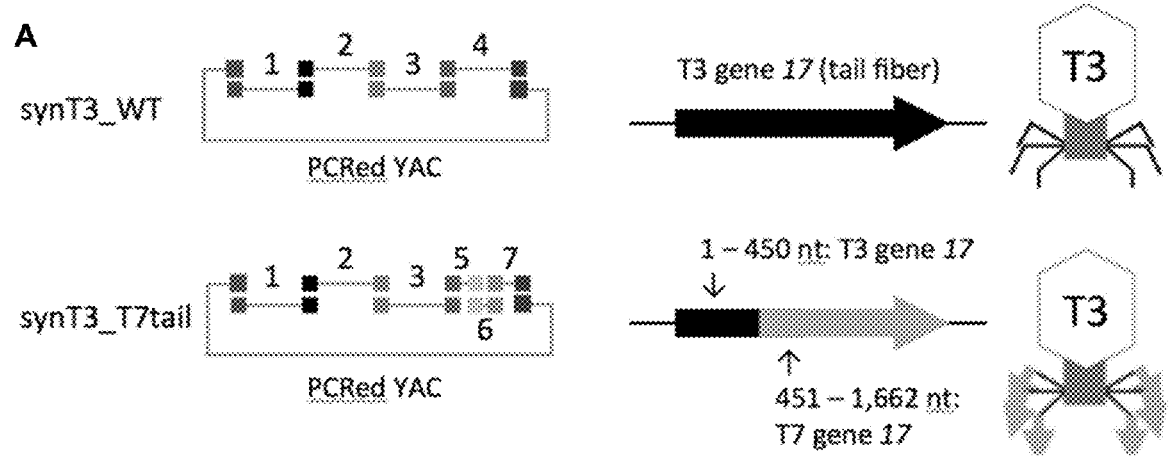
FIG. 5A depicts PCR fragments for engineering a synthetic T3 phage with a T3 tail fiber in a yeast artificial chromosome (YAC) (top) and PCR fragments for engineering a synthetic T3 phage with a T7 tail fiber in a YAC (bottom). Fragments 1, 2, 3 and 4 are from the T3 phage genome, and fragment 6 is from the T7 genome.
Figure 5B:
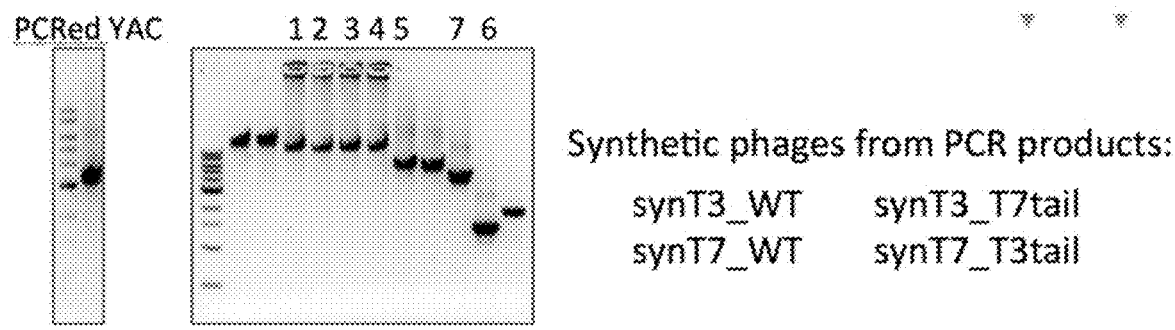
FIG. 5B shows an image of an electrophoresis gel with PCR-amplified fragments from T3 and T7 phage genome.

The tail fibers of T7 and T3 are encoded by gene 17, and the gene product gp17 can be split in two domains. The N-terminal 149 residues are necessary for the tail fiber to bind to the rest of the capsid, while the remaining C-terminal region recognizes the host receptors at bacterial surfaces (Steven, A. C., et al. *Journal of Molecular Biology* 200, 351 (1988)). Between T7 and T3 phages, N-terminal regions have 99% identity while C-termini have 83% in protein level. Similar but clearly different host range among these phages can be explained by differences in the distal portion of the tail fiber gene. This indicated that engineering the C-terminal domain of gp17 with tail fiber modules could produce synthetic phages with altered host ranges. To create synthetic T7 phage with T3 tail fiber (T7-3) and T3 phage with T7 tail fiber (T3-7) in one-step using the yeast-based phage engineering platform, six PCR fragments derived from each phages and PCR-amplified excised YAC were prepared (FIGS. 5A and 5B shows synthetic T3). All fragments were co-transformed into yeast, and transformants were suspended in lysis buffer and disrupted by beads beating. The supernatant containing the engineered phage genome was used directly for transfection into *E. coli* DH10B. By using same method, three synthetic phages (T7-3, T3-7, T7) with wild-type tail fiber (T7-wt) and T3 phage with wild-type tail fiber (T3-wt) were also engineered (FIGS. 5A and 5B).

Figure 5C:
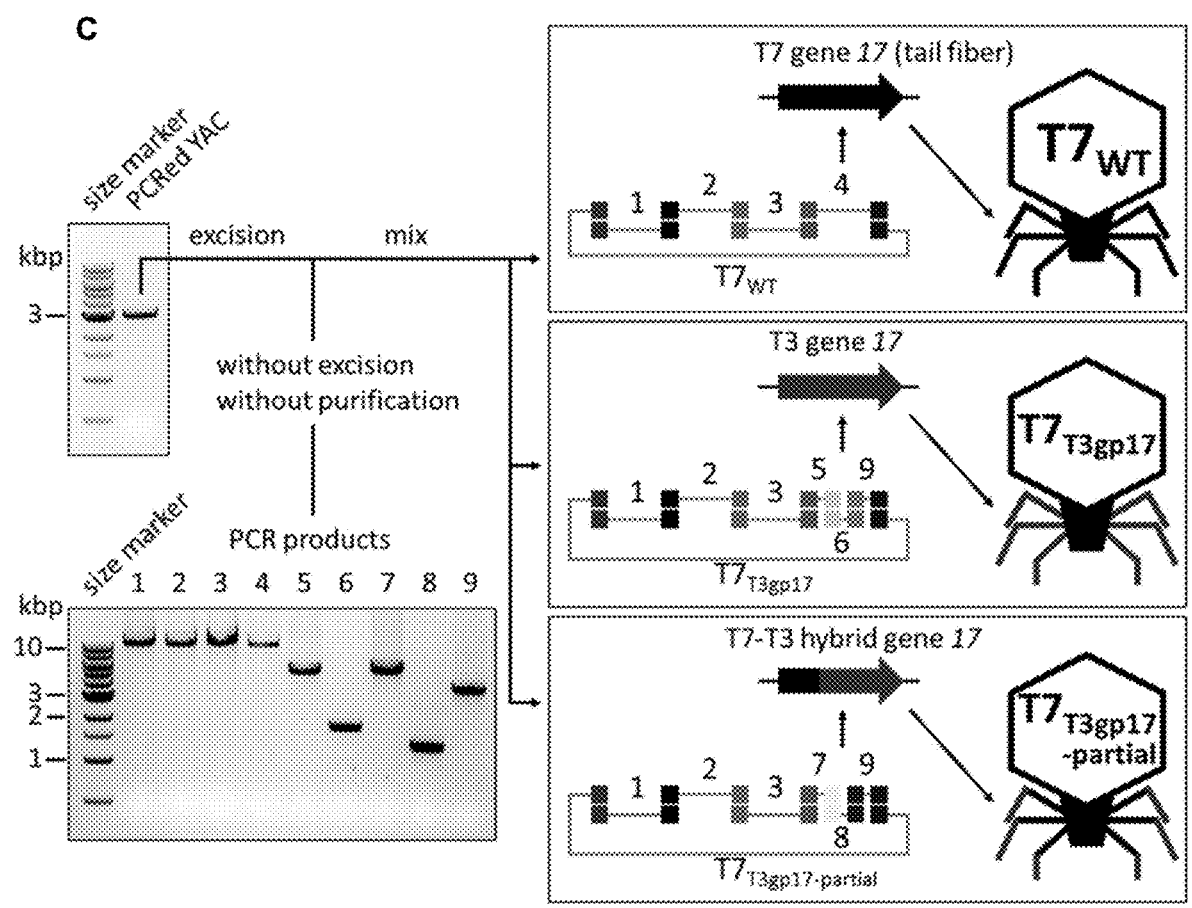
FIG. 5C shows synthetic T7 phages with a T3 tail fibers. As shown in the gel at the bottom left, nine PCR fragments (numbered 1-9), in total, were generated for the three engineered phages. For each T7 phage with T3 tail fibers, six PCR fragments (numbered 1-3, 5, 6 and 9 for $T7_{T3gp17}$, and 1-3 and 7-9 for $T7_{T3gp17\text{-}partial}$) were co-transformed and assembled in yeast. The YAC::phage was extracted and transformed in the bacterial strain designated 10G. As a control, a T7 wild-type phage ($T7_{WT}$) was assembled from four PCR products (1-4).

To create synthetic T7 phages with T3 tail fibers in one-step using the yeast platform system as provided herein, nine PCR fragments derived from each phages plus PCRed-excised YAC were prepared (FIG. 5C for synthetic T7). Fragments were co-transformed into yeast, and transformants were enzymatically disrupted for YAC::phage extraction. The engineered phage genome was used for transformation into bacterial strain 10G. Six synthetic phages (T7 phage with wild-type tail fiber ($T7_{WT}$), T7 phage with C-terminal T3 tail fiber ($T7_{T3gp17\text{-}partial}$), T7 phage with entire T3 tail fiber ($T7_{T3gp17}$), T3 phage with wild-type tail fiber ($T3w_T$), T3 phage with C-terminal T7 tail fiber ($T3_{T7gp17\text{-}partial}$), and T3 phage with entire T7 tail fiber ($T3_{T7gp17}$)) were engineered.

Figure 6A:
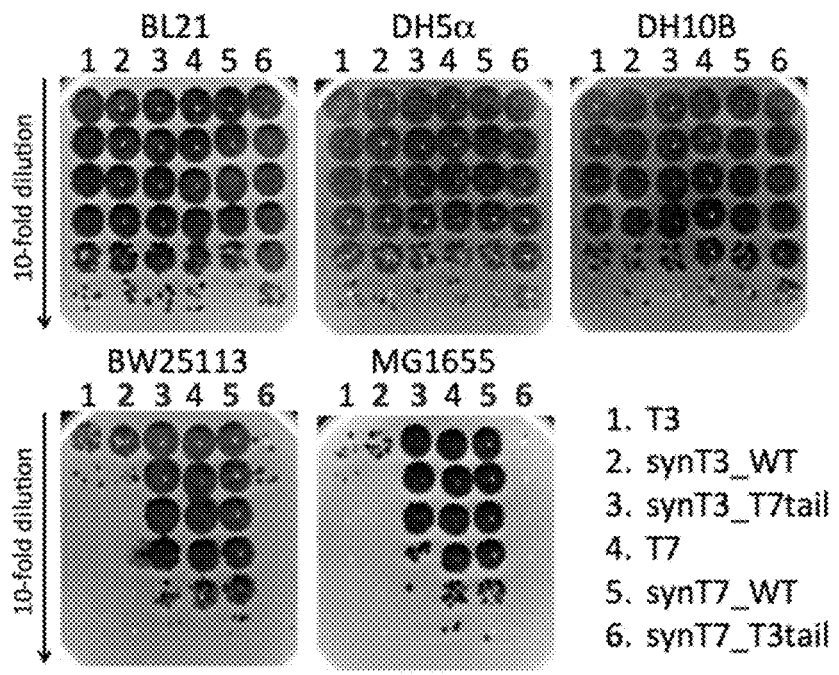
FIG. 6A shows images of plaque formation assays with engineered bacteriophage and *E. coli* strains BL21, DH5α, DH10B, BW25113 and MG1655.

To examine their host specificities, plaque formation assays were performed with K-12 strains described above (FIGS. 6A and 6B). T3-7 phage (e.g., $T3T7_{gp17\text{-}partial}$ and $T3_{T7gp}17$) grew on BW25113 and MG1655 strains with efficiency similar to that of T7, while T3 and T3-wt propagated poorly. By contrast, T7-3 (e.g., $T3_{T7gp17\text{-}partial}$ and $T3_{T7gp17}$) did not grow on BW25113 and MG1655. Plaque formation assays were also performed with two *E. coli* libraries, ECOR group and DECA set, to confirm details of host range of T7, T3, and synthetic phages. As shown in FIG. 6C, T7 phages, T3 phages, and synthetic phages infected ECOR4 and ECOR13. While T3 infected ECOR16, T7 did not, and while $T7_{T3gp17\text{-}partial}$ and $T7T3_{gp17}$ infected ECOR16, $T3_{T7gp17\text{-}partial}$ and $T3_{T7gp17}$ did not. These results clearly indicate that the C-terminal region of gp17 is the host range determinant, and the synthetic engineered phages with different tail fibers acquired tail-fiber-dependent host specificities.

Figure 6B:
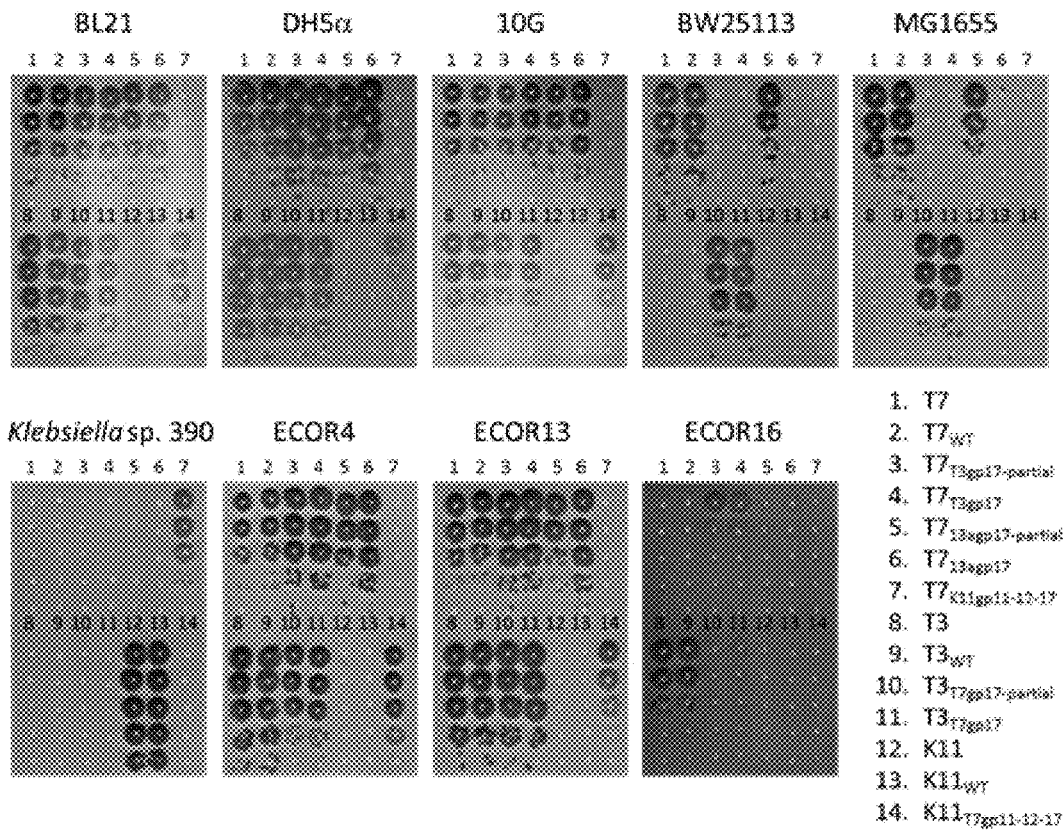
FIG. 6B shows images of plaque formation assays with engineered bacteriophage and bacterial strains BL21, DH5α, 10G, BW25113, MG1655, *Klebsiella* sp. 390, ECOR4, ECOR13 and ECOR16.
Figure 7:
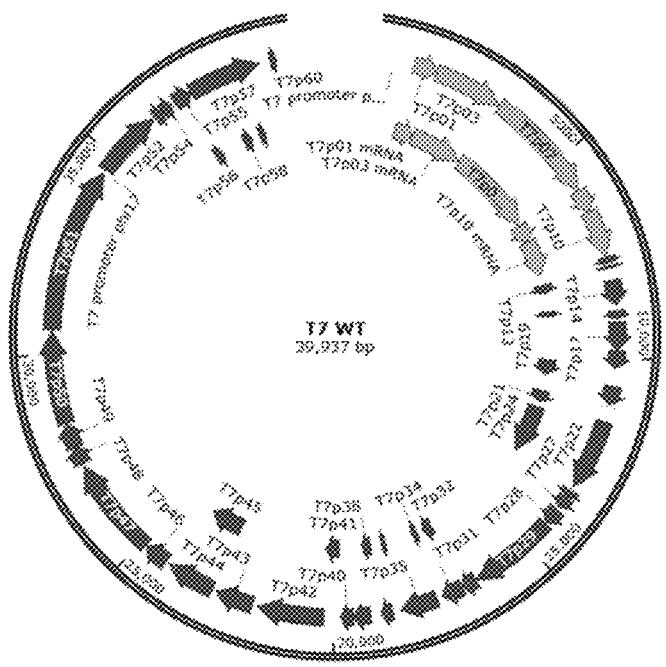
FIG. 7 shows a vector map of *Enterobacteria* phage T7 (SEQ ID NO:1).
Figure 8:
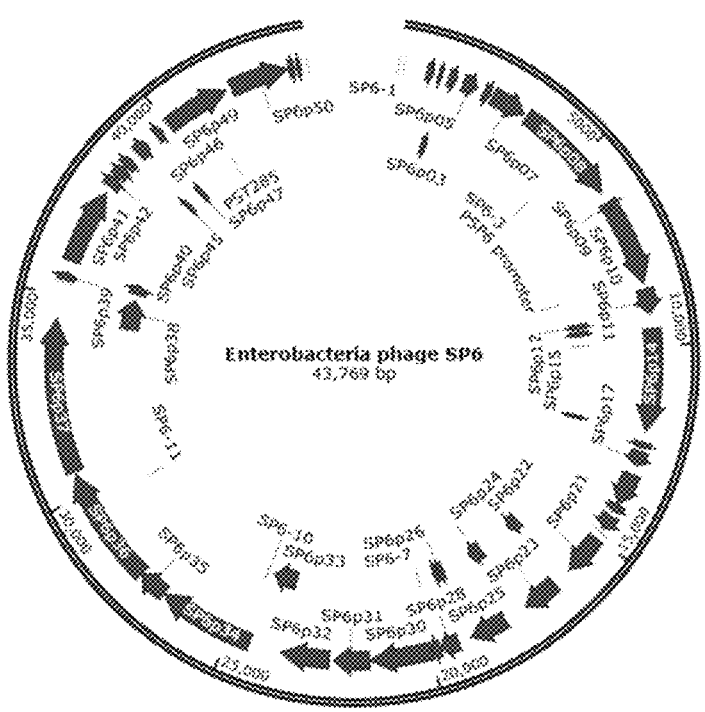
FIG. 8 shows a vector map of *Enterobacteria* phage SP-6 (SEQ ID NO:2).
Figure 9:
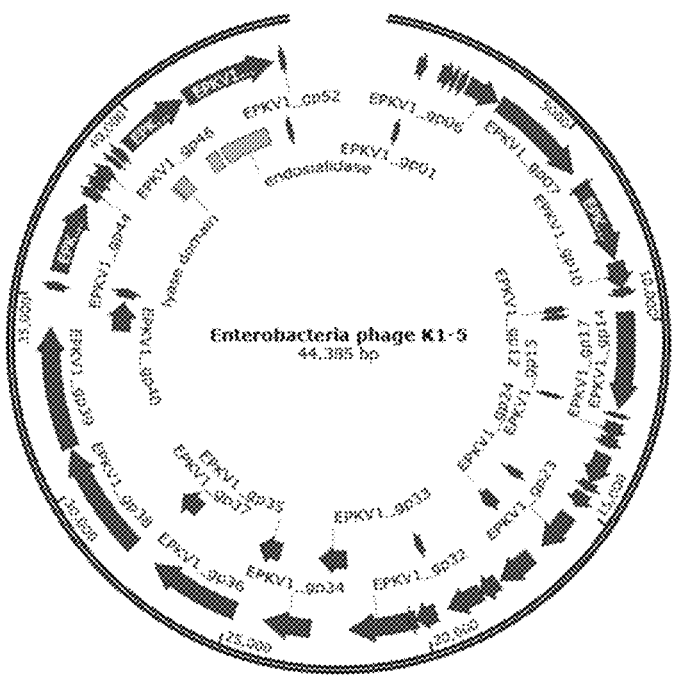
FIG. 9 shows a vector map of *Enterobacteria* phage K1-5 (SEQ ID NO:3).
Figure 10:
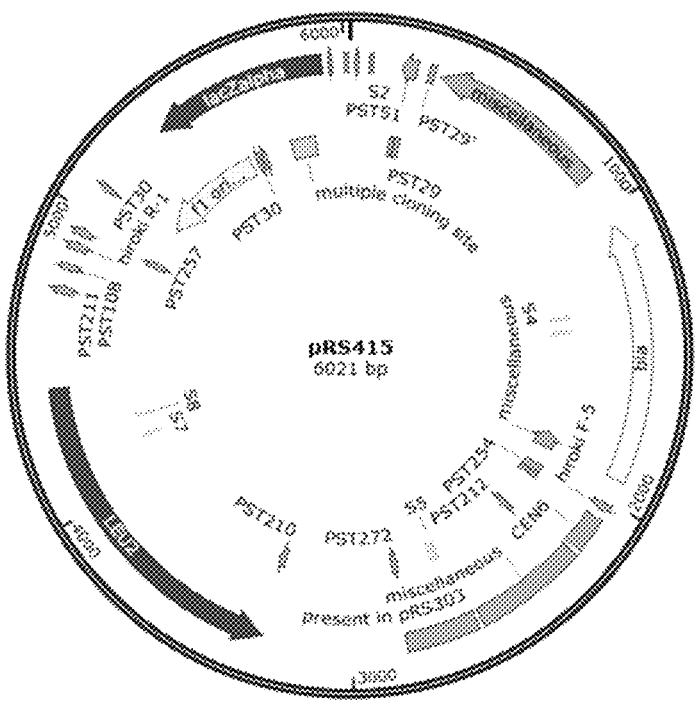
FIG. 10 shows a vector map of pRS415 (SEQ ID NO:34).

Next, phages were engineered with fully synthesized tail fiber. A codon-optimized gene encoding tail fiber was synthesized from the T7-like *Enterobacteria* phage 13a. T7 phage with 13a phage tail fiber was engineered and its functionalities confirmed (FIG. 6B, lanes 5 and 6). $T713a_{gp17\text{-}partial}$ infected BW25113 and MG1655 strains but $T713a_{gp}17$ did not. This result indicates that not only C-terminal part but also N-terminal one are responsible for host specificity.

Example 3: Model Phages with Tunable Host Ranges Between Species

To demonstrate that phages could overcome the species barrier, *Escherichia coli* (*E. coli*) phage T3 and *Yersinia* phage R hybrids were engineered. T3 and R phages have similar gp17 sequences, with the exception of 3 residues; however, while R phage can infect *Yersinia* strains IP2666 and YPIII, T3 cannot. R phage (Rgp17) was engineered by PCR using T3 gp17 and primers having desired mutations. Synthetic T3 with R tail fiber ($T3_{Rgp17}$) was functional and infected *Yersinia* IP2666 and YPIII as well as *E. coli* BL21.

Phages were also engineered with less similarity. *E. coli* phage T7 and *Klebsiella* phage K11 were selected because their host ranges are different and do not overlap. K11 is a T7-like phage and relative to T7 has a similarly sized linear genome, similar gene organization, and similar life cycle. The genome identity between the two strains, however, is low. At the genomic level, T7 and K11 share 59% identity, while T7 and T3 share 72% identify. In the tail fiber gp17, T7 and K11 share only 23% identity, while T7 and T3 share 86%. In addition, K11 has a 322 residue longer tail fiber compared with T7. To create T7 phage with K11 tail fiber and K11 phage with T7 tail fiber, the same strategy was used as described above.

In this experiment, neither synthetic K11 phages with T7 gp17 tail fibers nor synthetic T7 phages with K11 gp17 tail fibers were recovered. Further, hybrid phages with various lengths of gp17 were designed but not recovered. Because the K11 phage is propagated in the 10G strain, as described above, it is unlikely that synthetic K11 phage with T7 gp17 tail fibers can adsorb *E. coli* but cannot produce progeny phages, which indicates that, at least in K11 phage, swapping only the tail fiber is not sufficient to produce a functional synthetic phage.

Figures 11A, 11B:
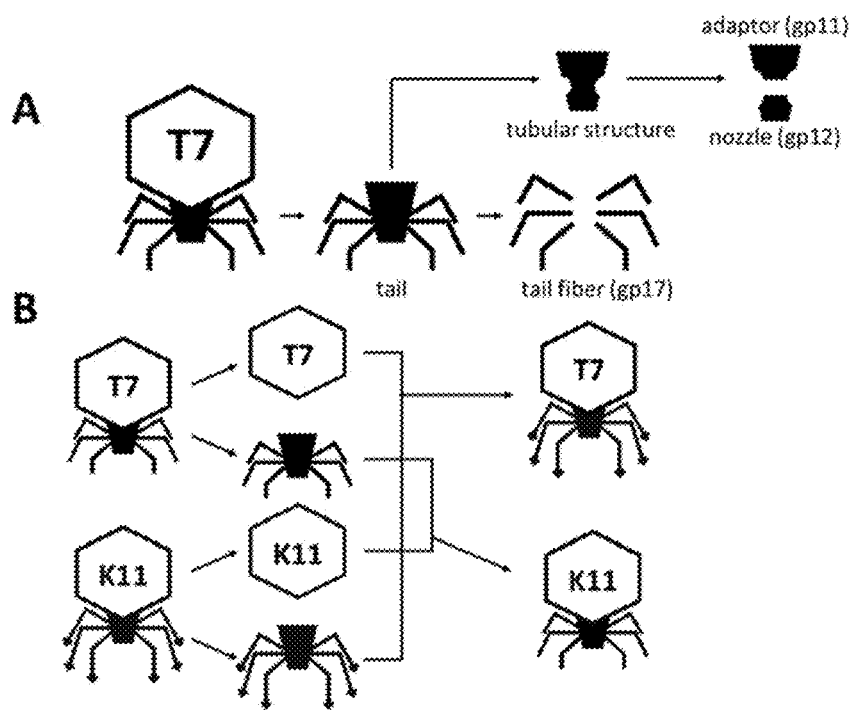
FIG. 11A shows T7 tail complexes. A tail structure contains two components: a tubular structure and tail fibers. The tubular structure contain an adaptor (gp11) and a nozzle (gp12). Tail fiber gp17 interacts with the interface between gp11 and gp12.
FIG. 11B shows a schematic illustration of the combination of head and tail between T7 and K11 phages. T7 head and K11 tail result in T7K11gp1-12-17 and K11 head and T7 tail result in K11T7gp11-12-17.

The tail of T7 phage is formed by a tubular structure (gp11 and gp12) surrounded by six tail fibers (gp17), and the interface between gp11 and gp12 interacts with six gp17 trimers to generate the complete tail (FIG. 11A). In addition, phage K11 spikes contained in the tail have depolymerase activity to degrade host *Klebsiella* capsular polysaccharide for infection. In view of the foregoing, all the tail components (gp11, gp12, and gp17) between T7 and K11 were replaced (FIG. 11B). Surprisingly, both synthetic phages, T7 with K11 tail ($T7_{K11gp11-12-17}$) and K11 with T7 tail ($K11_{T7gp11-12-17}$), were functional and showed tail-dependent host range. $T7_{K11gp11-12-17}$ infected *Klebsiella*, and $K11_{T7gp11-12-17}$ infected *E. coli* (FIG. 6B, lanes 7 and 14).

Figures 12A, 12B:
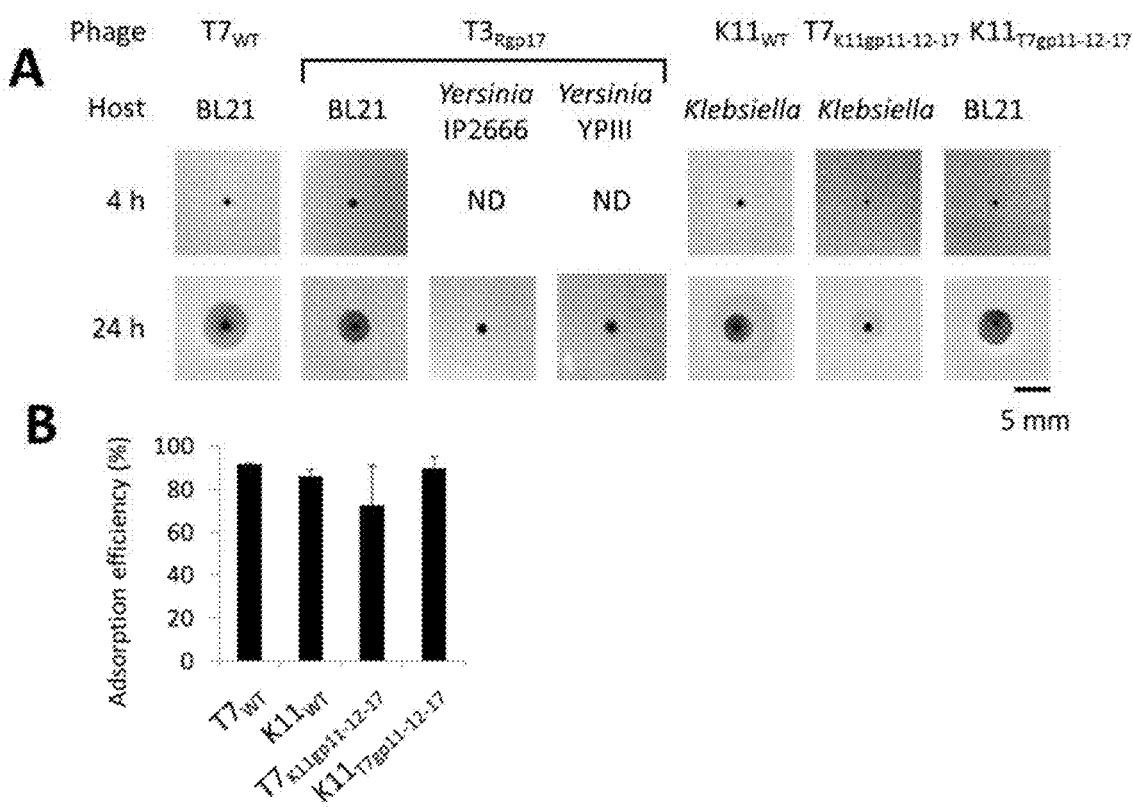
FIG. 12A shows a plaque assay whereby synthetic T3 with R tail fibers ($T3_{Rgp17}$) is capable of infecting *Escherichia coli* strain BL21 and *Yersinia* strains IP2666 and YPIII.
FIG. 12B shows the percent adsorption efficiency of $T7_{WT}$, $K11_{WT}$, $T7_{K11gp11\text{-}12\text{-}17}$, and $K11_{T7gp11\text{-}12\text{-}17}$.
Figure 13:
FIG. 13 shows a schematic summary of synthetic phages engineered using methods of the present disclosure.

The plaque assay, shown in FIG. 12A, demonstrated that synthetic T3 with R tail fiber ($T3_{Rgp17}$) is capable of infecting *Escherichia coli* strain BL21 and *Yersinia* strains IP2666 and YPIII. The plaque assay also demonstrated that synthetic T7 phages with K11 tail fibers ($T7_{K11gp11-12-17}$) are capable of infecting *Klebsiella* and that synthetic K11 phages with T7 tail fibers ($K11_{T7gp11-12-17}$) are capable of infecting BL21. The percent adsorption efficiencies of $T7_{WT}$, $K11_{WT}$, $T7_{K11gp11-12-17}$, and $K11_{T7gp11-12-17}$ are shown in FIG. 12B.

The Example herein demonstrates an efficient and simple yeast-based platform for phage engineering and that phage host range can be altered with synthetic biology techniques. This design may be adapted to be compatible with other phages and viruses. Synthetic biology approaches, described herein, address an important problem for phage-based therapeutics and diagnostics relating to limited phage host range. The methods of the present disclosure may also be used for other applications in biology, veterinary sciences, food sciences and medicine.

Materials and Methods

Strains, vector, and primers. Phages T7 (ATCC BAA-1025-B2) and T3 (ATCC 110303-B3) were laboratory stocks. Phages K1-5 and K11 were provided by University of Texas at Austin. Phage LUZ19 were provided KU Leuven. Phage gh-1 (ATCC 12633-B1) was obtained from ATCC. Synthetic phages are listed in Table 3. *Saccharomyces cerevisiae* BY4741 (MATa his3D1 leu2D0 met15D0 ura3D0) was obtained from Thermo Scientific. *Escherichia coli* BL21 [B, F$^-$ ompT hsdS$_B$ ($r_B^-$ m$_B^-$) gal dcm], DH5a [K-12, F$^-$ l$^-$ F80d lacZDM15 D(lacZYA-argF)U169 deoR recA1 endA1 hsdR17 ($r_K^-$ m$_K^-$)phoA supE44 thi-1 gyrA96 relA1], BW25113 [K-12, F$^-$ l$^-$ D(araD-araB)567 DlacZ4787 (::rrnB-3) rph-1 D(rhaD-rhaB) 568 hsdR514], and MG1655 (K-12, F$^-$ l$^-$ ilvG$^-$ rfb-50 rph-1) were laboratory stocks. *E. cloni* 10G [K-12, F$^-$ D(ara leu)7697 araD139 DlacX74 galU galK F80d lacZDM15 recA1 endA1 nupG1 rpsL (Str$^R$) D(mrr-hsdRMS-mcrBC) tonA] were obtained from Lucigen. 10G is a DH10B derivative and is suitable for maintaining large DNA constructs. Bacterial strains IJ284 *Klebsiella* sp. 390 (O3:K11), IJ1668 K-12 hybrid; K1 capsule, and IJ612 *Salmonella typhimurium* LT2 were provided by University of Texas at Austin. *Yersinia pseudotuberculosis* IP2666 and YPIII were provided by Tufts University. *E. coli* libraries, ECOR group and DECA set, were obtained from Michigan State University. *Pseudomonas putida* (ATCC 23287) was obtained from ATCC. pRS415 yeast centromere vector with LEU2 marker (ATCC 87520) was laboratory stock. Primers are listed in Table 1.

TABLE 3

Synthetic phages

| Phage | Genotype | Description |
| --- | --- | --- |
| T7$_{WT}$ | wild-type | synthesized from PCR fragments |
| T7$_{T3gp17}$ | T7$_{WT}$ Δgene 17 carrying T3 gene 17 | T7 with T3 tail fiber |
| T7$_{T3gp17-partial}$ | T7$_{WT}$ Δgene 17(1-450) carrying T3 gene 17(451-1677) | T7 with T7-T3 hybrid tail fiber |
| T7$_{13agp17}$ | T7$_{WT}$ Δgene 17 carrying 13a gene 17 | T7 with 13a tail fiber |
| T7$_{K11gp11-12-17}$ | T7$_{WT}$ Δgenes 11-12 17 carrying K11 genes 11-12 17 | T7 with K11 tail |
| T3$_{WT}$ | wild-type | synthesized from PCR fragments |
| T3$_{T7gp17}$ | T3$_{WT}$ Δgene 17 carrying T7 gene 17 | T3 with T7 tail fiber |
| T3$_{T7gp17-partial}$ | T3$_{WT}$ Δgene 17(1-450) carrying T7 gene 17(451-1662) | T3 with T3-T7 hybrid tail fiber |
| T3$_{Rgp17}$ | T3$_{WT}$ Δgene 17 carrying R gene 17 | T3 with R tail fiber |
| K11$_{WT}$ | wild-type | synthesized from PCR fragments |
| K11$_{T7gp11-12-17}$ | K11$_{WT}$ Δgenes 11-12 17 carrying T7 genes 11-12 17 | K11 with T7 tail |

Culture conditions. Unless otherwise specified, BY4741 and bacterial strains were cultured in YPD medium [1% Bacto Yeast Extract (BD), 2% Bacto Peptone (BD), 2% dextrose (VWR)] at 30° C. and in LB medium (BD) at 37° C., respectively.

Preparation of linearized pRS415. pRS415 was linearized by using PCR amplification with specific primer sets (Table 1) and KAPA HiFi DNA Polymerase (Kapa Biosystems). For genome capturing, 5' and 3' terminal 30-40 bp of phage homologous sequence were added to the pRS415. Linearized pRS415 was purified from an agarose gel following electrophoresis with QIAquick Gel Extraction Kit (Qiagen).

Preparation of phage genome. After preparation of 200 ml phage lysate ($10^9$-$10^{12}$ cfu/ml), 200 µl chloroform (Sigma) was added to kill the host bacteria and release phages. Lysate was centrifuged at 8,000 g for 5 min and then filtrated with 0.2 µm filter (VWR) to remove cell debris. 216 µl of buffer L1 [20 mg/ml RNase A (Sigma), 6 mg/ml DNase I (NEB), 0.2 mg/ml BSA (NEB), 10 mM EDTA (Teknova), 100 mM Tris-HCl (VWR), 300 mM NaCl (VWR), pH 7.5] was added and incubated at 37° C. for 1 h with gentle shaking. Then 30 ml of ice cold buffer L2 [30% polyethylene glycol (PEG) 6000 (Sigma), 3 M NaCl] was added and stored overnight in 4° C. The sample was centrifuged at 10,000 g for 30 min at 4° C. The phage pellet was suspended in 9 ml buffer L3 (100 mM Tris-HCl, 100 mM NaCl, 25 mM EDTA, pH7.5). Then, 9 ml buffer L4 [4% SDS (VWR)] was added and incubated at 70° C. for 20 min. After cooling down on ice, 9 ml buffer L5 [2.55 M potassium acetate, pH4.8 (Teknova)] was added, and the sample was centrifuged at 10,000 g for 30 min at 4° C. Phage genome in the supernatant was purified by using Qiagen-tip 100 (Qiagen) according to the manufacturer's instructions.

Preparation of PCR products for assembling phage genome. All PCR products were prepared with specific primer sets (Table 1) and KAPA HiFi DNA Polymerase. To avoid excision and purification of all PCR products from an agarose gel, homologous region of the end of linearized pRS415 was added to 5' and 3' terminus of first and last PCR products, respectively.

Preparation of yeast competent cells. S. cerevisiae BY4741 was grown in 5 ml YPD medium at 30° C. for 24 h. Overnight culture was added into 50 ml YPD medium, and incubated at 30° C. for 4 h. Cells were harvested by centrifugation at 3,000 g and washed with 25 ml water and then with 1 ml of 100 mM lithium acetate (LiAc) (Alfa Aesar), and suspended in 400 μl of 100 mM LiAc. Fifty microliter was used for a transformation.

Yeast transformation. All DNA samples and a linearized pRS415 were collected in a tube (0.5-4.0 μg each DNA sample and 100 ng linearized pRS415 in 50 μl water), and mixed with transformation mixture [50 μl yeast competent cell, 240 μl 50% PEG3350 (Sigma), 36 μl M LiAc, 25 μl 2 mg/ml salmon sperm DNA (Sigma)]. The mixture was incubated at 30° C. for 30 min, then at 42° C. for 20 min, centrifuged at 8,000 g for 15 sec, and suspended in 200 μl water. Transformants were selected on complete synthetic defined medium without leucine (SD-Leu) [0.67% YNB+ Nitrogen (Sunrise Science Products), 0.069% CSM-Leu (Sunrise Science Products), 2% dextrose] agar plates at 30° C. for 3 days.

Extraction of captured phage genome. Individual yeast transformants were picked into 2 ml SD-Leu liquid medium and incubated at 30° C. for 24 h. DNA was extracted from these cells using the YeaStar Genomic DNA Kit (Zymo Research) or Yeast Genomic DNA Purification Kit (Amresco) according to the manufacturer's instructions.

Reviving of phage. Except for phage LUZ19, the 10G strain was used as a host bacterium for initial propagation of phage. To revive T7 and T3 phages, 5 μl of extracted DNA were electroporated into 100 μl cells in a 2 mm gap electroporation cuvette (Molecular BioProducts) at 2,500 V, 25 μF, 200Ω using a Gene Pulser Xcell (Bio-Rad). Cells were mixed with 3 ml LB soft agar (LB contains 0.6% agarose) warmed at 55° C., poured onto LB plate, and incubated for 4 h at 37° C. To revive SP6, K1-5, and K11, after electroporation, cells were incubated at 37° C. for 1 h in 1 ml LB medium. Then, some drops of chloroform were added to kill the cells and release phages. After centrifugation at 12,000 g for 1 min, supernatant was mixed with 100 μl overnight culture of natural host bacteria, i.e. IJ612 S. typhimurium LT2 for SP6, IJ1668 K-12 hybrid; K1 capsule for K1-5, and J284 Klebsiella sp. 390 (O3:K11) for K11, and 3 ml LB soft agar, poured onto LB plate, and incubated for 4-18 h at 37° C. For LUZ19, P. aeruginosa PAO1 was used as a host bacterium. All extracted DNA from 2 ml overnight culture was electroporated into competent PAO1 cells with same condition as described above. After electroporation, cells were incubated at 37° C. for 2.5 h in 1 ml LB medium. Cells were mixed with 3 ml LB soft agar, poured onto LB plate, and incubated for 18 h at 37° C.

One-time phage propagation assay. To check the ability of the 10G strain as a one-time phage propagation plant, 0.5-4.0 μg of purified phage genome was electroporated into the cell. The condition of electroporation and the following procedures were exactly same as described in "Reviving of phage".

Adsorption assay. Each 100 μl of 2×10$^8$ cfu/ml E. coli and 1×10$^8$ pfu/ml phage, were miced and incubated at RT for 10 min. Then, 700 μl of 0.95% saline and some drops of chloroform was added to kill the cells and prevent the production of progeny phages. After centrifugation at 11,000 g for 1 min, supernatant was serially diluted and mixed with 100 μl of E. coli BL21 overnight culture and 3 ml LB soft agar, and poured the mixture onto LB plate. After 3 h incubation at 37° C., phage plaques were counted, and adsorption efficiency was calculated. Adsorption efficiency (%)=[1−(pfu of unadsorbed phage/original pfu in the BL21 and phage mixture)]×100

Infection assay. Larvae of the Greater Wax Moth (Galleria mellonella) were purchased in their final larval instar from Vanderhorst Wholesale, Inc. (St. Marys, Ohio, USA). Healthy larvae of around 150-250 mg were sorted from small, darkly colored, or inactive larvae upon receipt and allowed to acclimate at RT in the dark for at least 24 h prior to experiments. For infection assays, an overnight culture of K. pneumoniae was diluted 1:100 into fresh LB and grown to late-log phase at 37° C. for 3 h. Bacteria were washed twice and resuspended in an equal volume of PBS, then further diluted in PBS to yield a final inoculum of approximately 10$^6$ CFU/larva. A KDS100 syringe pump (KD Scientific) was used to inject 10 μl of PBS or the bacterial suspension behind the last left proleg of each randomly chosen larva. Within 1 h of the first injection, a second injection of 10 μl of sterile LB broth or endotoxin-purified phage lysate was administered behind the last right proleg and larvae were incubated at 37° C. in groups of 5 per petri dish. Survival scoring was performed every 12 h for up to 72 h, with mortality confirmed by lack of response to touch. Data were pooled from three experiments each with 10 larvae per treatment group (n=30) and Kaplan-Meier curves were generated and analyzed by log-rank test using GraphPad Prism version 6.0 (GraphPad Software, San Diego, Calif., USA).

```
        Bacteriophage Genome Sequences

SEQ ID NO: 1 - Enterobacteria phage T7
TCTCACAGTGTACGGACCTAAAGTTCCCCCATAGGGGGTACCTAAAGCCC
AGCCAATCACCTAAAGTCAACCTTCGGTTGACCTTGAGGGTTCCCTAAGG
GTTGGGGATGACCCTTGGGTTTGTCTTTGGGTGTTACCTTGAGTGTCTCT
CTGTGTCCCTATCTGTTACAGTCTCCTAAAGTATCCTCCTAAAGTCACCT
CCTAACGTCCATCCTAAAGCCAACACCTAAAGCCTACACCTAAAGACCCA
TCAAGTCAACGCCTATCTTAAAGTTTAAACATAAAGACCAGACCTAAAGA
CCAGACCTAAAGACACTACATAAAGACCAGACCTAAAGACGCCTTGTTGT
TAGCCATAAAGTGATAACCTTTAATCATTGTCTTTATTAATACAACTGAC
TATAAGGAGAGACAACTTAAAGAGACTTAAAAGATTAATTTAAAATTTAT
CAAAAAGAGTATTGACTTAAAGTCTAACCTATAGGATACTTACAGGCATC
GAGAGGGACACGGCGAATAGCCATCCCAATCGACACCGGGGTCAACCGGA
TAAGTAGACAGCCTGATAAGTCGCACGAAAAACAGGTATTGACAACATGA
AGTAACATGCAGTAAGATACAAATCGCTAGGTAACACTAGCAGCGTCAAC
CGGGCGCACAGTGCCTTCTAGGTGACTTAAGCGCACCACGGCACATAAGG
TGAAACAAAACGGTTGACAACATGAAGTAAACACGGTACGATGTACCACA
TGAAACGACAGTGAGTCACCACACTGAAAGGTGATCGGGTCTAACGAAAC
CTGACCTAAGACGCTCTTTAACAATCTGGTAAATAGCTCTTGAGTGCATG
```

| Bacteriophage Genome Sequences |
|---|
| ACTAGCGGATAACTCAAGGGTATCGCAAGGTGCCCTTTATGATATTCACT |
| AATAACTGCACGAGGTAACACAAGATGGCTATGTCTAACATGACTTACAA |
| CAACGTTTTCGACCACGCTTACGAAATGCTGAAAGAAAACATCCGTTATG |
| ATGACATCCGTGACACTGATGACCTGCACGATGCTATTCACATGGCTGCC |
| GATAATGCAGTTCCGCACTACTACGCTGACATCTTTAGCGTAATGGCAAG |
| TGAGGGCATTGACCTTGAGTTCGAAGACTCTGGTCTGATGGCTGACACCA |
| AGGACGTAATCCGCATCCTGCAAGCGCTATCTATGAGCAATTAACGATT |
| GACCTCTGGGAAGACGCAGAAGACTTGCTCAATGAATACTTGGAGGAAGT |
| CGAGGAGTACGAGGAGGATGAAGAGTAATGTCTACTACCAACGTGCAATA |
| CGGTCTGACCGCTCAAACTGTACTTTTCTATAGCGACATGGTGCGCTGTG |
| GCTTTAACTGGTCACTCGCAATGGCACAGCTCAAAGAACTGTACGAAAAC |
| AACAAGGCAATAGCTTTAGAATCTGCTGAGTGATAGACTCAAGGTCGCTC |
| CTAGCGAGTGGCCTTTATGATTATCACTTTACTTATGAGGGAGTAATGTA |
| TATGCTTACTATCGGTCTACTCACCGCTCTAGGTCTAGCTGTAGGTGCAT |
| CCTTTGGGAAGGCTTTAGGTGTAGCTGTAGGTTCCTACTTTACCGCTTGC |
| ATCATCATAGGAATCATCAAAGGGGCACTACGCAAATGATGAAGCACTAC |
| GTTATGCCAATCCACACGTCCAACGGGGCAACCGTATGTACACCTGATGG |
| GTTCGCAATGAAACAACGAATCGAACGCCTTAAGCGTGAACTCCGCATTA |
| ACCGCAAGATTAACAAGATAGGTTCCGGCTATGACAGAACGCACTGATGG |
| CTTAAAGAAAGGTTATATGCCCAATGGCACACTATACGCTGCAAATCGGC |
| GAATAGTGAGAACTTGGCGAGAGAACAACCTCGAACGCCAAGGACAAG |
| AGAGGGCGGCGTGGCATAGACGAAAGGAAAAGGTTAAAGCCAAGAAACTC |
| GCCGCACTTGAACAGGCACTAGCCAACACACTGAACGCTATCTCATAACG |
| AACATAAAGGACACAATGCAATGAACATTACCGACATCATGAACGCTATC |
| GACGCAATCAAAGCACTGCCAATCTGTGAACTTGACAAGCGTCAAGGTAT |
| GCTTATCGACTTACTGGTCGAGATGGTCAACAGCGAGACGTGTGATGGCG |
| AGCTAACCGAACTAAATCAGGCACTTGAGCATCAAGATTGGTGGACTACC |
| TTGAAGTGTCTCACGGCTGACGCAGGGTTCAAGATGCCTGGTAATGGTCA |
| CTTCTCGGCTGCTTATAGTCACCCGCTGCTACCTAACAGAGTGATTAAGG |
| TGGGCTTTAAGAAAGAGGATTCAGGCGCAGCCTATACCGCATTCTGCCGC |
| ATGTATCAGGGTCGTCCTGGTATCCCTAACGTCTACGATGTACAGCGCCA |
| CGCTGGATCATGATGAGTTAACTGGATGGATGGTGAGTTTGTTGAAACT |
| TGTAAACTAATCCGCAAGTTCTTTGAGGGCATCGCCTCATTCGACATGCA |
| TAGCGGGAACATCATGTTCTCAAATGGAGACGTACCATACATCACCGACC |
| CGGTATCATTCTCGCAGAAGAAAGACGGTGGCGCATTCAGCATCGACCCT |
| GAGGAACTCATCAAGGAAGTCGAGGAAGTCGCACGACAGAAAGAAATTGA |
| CCGCGCTAAGGCCCGTAAAGAACGTCACGAGGGGCGCTTAGAGGCACGA |
| GATTCAAACGTCGCAACCGCAAGGCACGTAAAGCACACAAAGCTAAGCGC |
| GAAAGAATGCTTGCTGCGTGGCGATGGGCTGAACGTCAAGAACGGCGTAA |
| CCATGAGGTAGCTGTAGATGTACTAGGGAAGAACCAATAACGCTATGCTCT |
| GGGTCAACATGTTCTCTGGGGACTTTAAGGCGCTTGAGGAACGAATCGCG |
| CTGCACTGGCGTAATGCTGACCGGATGGCTATCGCTAATGGTCTTACGCT |
| CAACATTGATAAGCAACTTGACGCAATGTTAATGGGCTGATAGTCTTATC |
| TTACAGGTCATCTGCGGGTGGCCTGAATAGGTACGATTTACTAACTGGAA |
| GAGGCACTAAATGAACACGATTAACATCGCTAAGAACGACTTCTCTGACA |
| TCGAACTGGCTGCTATCCCGTTCAACACTCTGGCTGACCATTACGGTGAG |
| CGTTTAGCTCGCGAACAGTTGGCCCTTGAGCATGAGTCTTACGAGATGGG |
| TGAAGCACGCTTCCGCAAGATGTTTGAGCGTCAACTTAAAGCTGGTGAGG |
| TTGCGGATAACGCTGCCGCCAAGCCTCTCATCACTACCCTACTCCCTAAG |
| ATGATTGCACGCATCAACGACTGGTTTGAGGAAGTGAAAGCTAAGCGCGG |
| CAAGCGCCCGACAGCCTTCCAGTTCCTGCAAGAAATCAAGCCGGAAGCCG |
| TAGCGTACATCACCATTAAGACCACTCTGGCTTGCCTAACCAGTGCTGAC |
| AATACAACCGTTCAGGCTGTAGCAAGCGCAATCGGTCGGGCCATTGAGGA |
| CGAGGCTCGCTTCGGTCGTATCCGTGACCTTGAAGCTAAGCACTTCAAGA |
| AAAACGTTGAGGAACAACTCAACAAGCGCTAGGGCACGTCTACAAGAAA |
| GCATTTATGCAAGTTGTCGAGGCTGACATGCTCTCTAAGGGTCTACTCGG |
| TGGCGAGGCGTGGTCTTCGTGGCTATAAGGAAGACTCTATTCATGTAGGAG |
| TACGCTGCATCGAGATGCTCATTGAGTCAACCGGAATGGTTAGCTTACAC |
| CGCCAAAATGCTGGCGTAGTAGGTCAAGACTCTGAGACTATCGAACTCGC |
| ACCTGAATACGCTGAGGCTATCGCAACCCGTGCAGGTGCGCTGGCTGGCA |
| TCTCTCCGATGTTCCAACCTTGCGTAGTTCCTCCTAAGCCGTGACTGGC |
| ATTACTGGTGGTGGCTATTGGGCTAACGGTCGTCGTCCTCTGGCGCTGGT |
| GCGTACTCACAGTAAGAAAGCACTGATGCGCTACGAAGACGTTTACATGC |
| CTGAGGTGTACAAAGCGATTAACATTGCGCAAAACACCGCATGGAAATC |
| AACAAGAAAGTCCTAGCGGTCGCCAACGTAATCACCAAGTGGAAGCATTG |
| TCCGGTCGAGGACATCCTGCGATTGAGCGTGAAGACTCCCGATGAAC |
| CGGAAGACATCGACATGAATCCTGAGGCTCTCACCGCGTGGAAACGTGCT |
| GCCGCTGCTGTGTACCGCAAGGACAAGGCTCGCAAGTCTCGCCGTATCAG |
| CCTTGAGTTCATGCTTGAGCAAGCCAATAAGTTTGCTAACCATAAGGCCA |
| TCTGGTTCCCTTACAACATGGACTGGCGCGGTCGTGTTTACGCTGTGTCA |
| ATGTTCAACCCGCAAGGTAACGATATGACCAAAGGACTGCTTACGCTGGC |
| GAAAGGTAAACCAATCGGTAAGGAAGGTTACTACTGGCTGAAAATCCACG |
| GTGCAAACTGTGCGGGTGTCGATAAGGTTCCGTTCCCTGAGCGCATCAAG |
| TTCATTGAGGAAAACCACGAGAACATCATGGCTTGCGCTAAGTCTCCACT |
| GGAGAACACTTGGTGGGCTGAGCAAGATTCTCCGTTCTGCTTCCTTGCGT |
| TCTGCTTTGAGTACGCTGGGGTACAGCACCACGGCCTGAGCTATAACTGC |
| TCCCTTCCGCTGGCGTTTGACGGGTCTTGCTCTGGCATCCAGCACTTCTC |
| CGCGATGCTCCGAGATGAGGTAGGTGGTCGCGCGGTTAACTTGCTTCCTA |
| GTGAAACCGTTCAGGACATCTACGGGATTGTTGCTAAGAAAGTCAACGAG |
| ATTCTACAAGCAGACGCAATCAATGGGACCGATAACGAAGTAGTTACCGT |
| GACCGATGAGAACACTGGTGAAATCTCTGAGAAAGTCAAGCTGGGCACTA |
| AGGCACTGGCTGGTCAATGGCTGGCTTACGGTGTTACTCGCAGTGTGACT |
| AAGCGTTCAGTCATGACGCTGGCTTACGGGTCCAAAGAGTTCGGCTTCCG |
| TCAACAAGTGCTGGAAGATACCATTCAGCCAGCTATTGATTCCGGCAAGG |
| GTCTGATGTTCACTCAGCCGAATCAGGCTGCTGGATACATGGCTAAGCTG |
| ATTTGGGAATCTGTGAGCGTGACGGTGGTAGCTGCGGTTGAAGCAATGAA |
| CTGGCTTAAGTCTGCTGCTAAGCTGCTGGCTGCTGAGGTCAAAGATAAGA |
| AGACTGGAGAGATTCTTCGCAAGCGTTGCGCTGTGCATTGGGTAACTCCT |
| GATGGTTTCCCTGTGTGGCAGGAATACAAGAAGCCTATTCAGACGCGCTT |
| GAACCTGATGTTCCTCGGTCAGTTCCGCTTACAGCCTACCATTAACACCA |
| ACAAAGATAGCGAGATTGATGCACACAAACAGGAGTCTGGTATCGCTCCT |
| AACTTTGTACACAGCCAAGACGGTAGCCACCTTCGTAAGACTGTAGTGTG |
| GGCACACGAAGTACGGAATCGAATCTTTTGCACTGATTCACGACTCCT |
| TCGGTACCATTCCGGCTGACGCTGCGAACCTGTTCAAAGCAGTGCGCGAA |
| ACTATGGTTGACACATATGAGTCTTGTGATGTACTGGCTGATTTCTACGA |
| CCAGTTCGCTGACCAGTTGCACGAGTCTCAATTGGACAAAATGCCAGCAC |
| TTCCGGCTAAAGGTAACTTGAACCTCCGTGACATCTTAGAGTCGGACTTC |
| GCGTTCGCGTAACGCCAAATCAATACGACTCACTATAGAGGGACAAACTC |
| AAGGTCATTCGCAAGAGTGGCCTTTATGATTGACCTTCTTCCGGTTAATA |
| CGACTCACTATAGGAGAACCTTAAGGTTTAACTTTAAGACCCTTAAGTGT |
| TAATTAGAGATTTAAATTAAAGAATTACTAAGAGGACTTTAAGTATGC |
| GTAACTTCGAAAAGATGACCAAACGTTCTAACCGTAATGCTCGTGACTTC |
| GAGGCAACCAAAGGTCGCAAGTTGAATAAGACTAAGCGTGACCGCTCTCA |
| CAAGCGTAGCTGGGAGGGTCAGTAAGATGGGACGTTTATATAGTGGTAAT |
| CTGGCAGCCATTCAAGGCAGCAACAAACAAGCTGTTCCAGTTAGACTTAGC |
| GGTCATTTATGATGACTGGTATGATGCCTATACAAGAAAAGATTGCATAC |
| GGTTACGTATTGAGGACAGGAGTGGAAACCTGATTGATACTAGCACCTTC |
| TACCACCACGACGAGGACGTTCTGTTCAATATGTGTACTGATTGGTTGAA |
| CCATATGTATGACCAGTTGAAGGACTGAGGAAGTAATACGACTCAGTATAGG |
| GACAATGCTTAAGGTCGCTCTCTAGGAGTGGCCTTAGTCATTTAACCAAT |
| AGGAGATAAACATTATGATGAACATTAAGACTAACCCGTTTAAAGCCGTG |
| TCTTTCGTAGAGTCTGCCATTAAGAAGGCTCTGGATAACGCTGGGTATCT |
| TATCGCTGAAATCAAGGTACGATGGGTGTACGCGGGAACATCTGCGTAGACA |
| ATACTGCTAACAGTTACTGGCTCTCTCGTGTATCTAAAACGATTCCGGCA |
| CTGGAGCACTTAAACGGGTTTGATGTTCGCTGGAAGCGTCTACTGAACGA |
| TGACCGTTGCTTCTACAAAGATGGCTTTATGCTTGATGGGGAACTCATGG |
| TCAAGGGCTAGACTTTAACACAGGGTCCGGCCTACTGCGTACCAAATGG |
| ACTGACACGAAGAACCAAGAGTTCATGAAGAGTTATTCGTTGAACCAAT |
| CCGTAAGAAAGATAAAGTTCCCTTTAAGCTGCACACTGGACACCTTCACA |
| TAAAACTGTACGCTATCCTCCCGCTGCACATCGTGGAGTCTGGAGAAGAC |
| TGTGATGTCATGACGTTGCTCATGCAGGAACACGTTAAGAACATGCTGCC |
| TCTGCTACAGGAATACTTCCCTGAAATCGAATGGCAAGCGGCTGAATCTT |
| ACGAGGTCTACGATATGGTAGAACTACAGCAACTGTACGAGCAGAAGCGA |
| GCAGAAGGCCATGAGGGTCTCATTGTGAAAGACCCGATGTGTATCTATAA |
| GCGCGGTAAGAAATCTGGCTGGTGGAAAATGAAACCTGAGAACGAAGCTG |
| ACGGTATCATTCAGGGTCGTGTATGGGTGTACAAAAGGTCTGGCTAATGAA |
| GGTAAAGTGATTGGTTTTGAGGTGCTTCTTGAGAGTGGTCGTTTAGTTAA |
| CGCCACGAATATCTCTCGCGCCTTAATGGATGAGTTCACTGAGACAGTAA |
| AAGAGGCCACCCTAAGTCAATGGGATTCTTTAGCCCATACGGTATTGGC |
| GACAACGGCTTGTACTATTAACCCTTACGATGGCTCTTTGCGGCACCCATCGTTCG |
| TAATGTTCCGTGGCACCGAGGACAACCCTCAAGAGAAATGTAATCACAC |
| TGGCTCACCTTCGGGTGGGCCTTTCTGCGTTTATAAGGAGACACTTTATG |
| TTTAAGAAGGTTGGTAAATTCCTTGGCCCGTTTGGCGACTATCCTGACGCT |
| TGCGTATATTCTTGCGGTATACCCTCAAGTAGCACTAGTAGTAGTTGGCG |
| CTTGTTACTTAGCGGCAGTGTGTGCTTGCGTGTGGAGTATAGTTAACTGG |
| TAATACGACTCACTAAAGGAGGTACACACCATGATGTACTTAATGCCATT |
| ACTCATCGTCATTGTAGGATGCCTTGCCTCCACTGTAGCGATGATGAAA |
| TGCCAGATGGTCACGCTTAATACGACTCACTAAAGGAGCACTATATGTT |
| TCGACTTCATTACAACAAAAAGCGTTAAGAATTTCACGGTTCGCCGTGCTG |
| ACCGTTCAATCGTATGTGCGAGCGAGCGCCGAGCTAAGATACCTCTTATT |
| GGTAACACAGTTCCTTTGGCACCGAGCGTCCACATCATTATCACCCGTTGG |
| TGACTTTGAGAAGACAATAGCAAGAAACGTCCGGTTCTTAGTGGTGCAG |
| TGACCCGCTTCCCGTTCGTCCGTTCGTGTTACTCAAACGAATCAAGGAGGTG |
| TTCTGATGGGACTGTTAGATGGTGAAGCTGGGAAAAAGAAAACCCGCCA |
| GTACAAGCAACTGGGTGTATAGCTTCTTAGAGAAAGATGACCGTTATCC |
| ACACACCTGTAACAAAGGAGCTAACGATATGACCGAACGTGAACAAGAGA |
| TGATCATTAAGTTGATAGACAATAAGAGGTCGCCCAGATGATTTGAA |
| GGCTGCGGTATTCTCTGCTCCAATGTCCCTTGCCACCTCTGCCCCGCAAA |
| TAACGATCAAAAGATAACCTTAGGTGAAATCCGAGCGATGGACCCACGTA |
| AACCACATCTGAATAAACCTGAGGTAACTCCTACAGATGACCAGCCTTCC |
| GCTGAGACAATCGAAGGTGTCACTAAGCCTTCCCACTACATGCTGTTTGA |
| CGACATTGAGGCTATCGAAGTGATTGCTCGTTCAATGACCGTTGAGCAGT |
| TCAAGGGATACTGCTTCGGTAACATCTTAAAGTACAGACTACGTGCTGGT |

| Bacteriophage Genome Sequences |
| --- |
| AAGAAGTCAGAGTTAGCGTACTTAGAGAAAGACCTAGCGAAAGCAGACTT
CTATAAAGAACTCTTTGAGAAACATAAGGATAAATGTTATGCATAACTTC
AAGTCAACCCCACCTGCCGACAGCCTATCTGATGACTTCACATCTTGCTC
AGAGTGGTGCCGAAAGATGTGGGAAGAGACATTCGACGATGCGTACATCA
AGCTGTATGAACTTTGGAAATCGAGAGGTCAATGACTATGTCAAACGTAA
ATACAGGTTCACTTAGTGTGGACAATAAGAAGTTTTGGGCTACCGTAGAG
TCCTCGGAGCATTCCTTCGAGGTTCCAATCTACGCTGAGACCCTAGACGA
AGCTCTGGAGTTAGCCGAATGGCAATACGTTCCGGCTGGCTTTGAGGTTA
CTCGTGTGCGTCCTTGTGTAGCACCGAAGTAATACGACTCACTATTAGGG
AAGACTCCCTCTGAGAAACCAAACGAAACCTAAAGGAGATTAACATTATG
GCTAAGAAGATTTTCACCTCTGCGCTGGGTACCGCTGAACCTTACGCTTA
CATCGCCAAGCCGGACTACGGCAACGAAGAGCGTGGCTTTGGGAACCCTC
GTGGTGTCTATAAAGTTGACCTGACTATTCCCAACAAAGACCCGCGCTGC
CAGCGTATGGTCGATGAAATCGTGAAGTGTCACGAAGAGGCTTATGCTGC
TGCCGTTGAGGAATACGAAGCTAATCCACCTGCTGTAGCTCGTGGTAAGA
AACCGCTGAAACCGTATGAGGGTGACATGCCGTTCTTCGATAACGGTGAC
GGTACGACTACCTTTAAGTTCAAATGCTACGCGTCTTTCCAAGACAAGAA
GACCAAAGAGACCAAGCACATCAATCTGGTTGTGGTTGACTCAAAAGGTA
AGAAGATGGAAGACGTTCCGATTATCGGTGGTGGCTCTAAGCTGAAAGTT
AAATATTCTCTGGTTCCATACAAGTGGAACACTGCTGTAGGTGCAGCGT
TAAGCTGCAACTGGAATCCGTGATGCTGGTCGAACTGGCTACCTTTGGTG
GCGGTGAAGACGATTGGGCTGACGAAGTTGAAGAGAACGGCTATGTTGCC
TCTGGTTCTGCCAAAGCGAGCAAACCACGCGACGAAGAAAGCTGGGACGA
AGACGACGAAGAGTCCGAGGAAGCAGACGAAGACGGAGCTTCTAAGTGG
AACTGCGGGAGAAAATCCTTGAGCGAATCAAGGTGACTTCCTCTGGGTGT
TGGGAGTGGCAGGGCGCTACGAACAATAAAGGGTACGGGCAGGTGTGGTG
CAGCAATACCGGAAAGGTTGTCTACTGTCATCGCGTAATGTCTAATGCTC
CGAAAGGTTCTACCGTCCTGCACTCCTCTGATAATCCATTATGTTGTAAC
CCTGAACACCTATCCATAGGAATCCAAAAGAGAACTCCACTGACATGGT
AAATAAGGGTCGCTCACACAAGGGGTATAAACTTTCAGACGAAGACGTAA
TGGCAATCATGGAGTCCAGCGAGTCCAATGTATCCTTAGCTCGCACCTAT
GGTGTCTCCCAACAGACTATTTGTGATATACGCAAAGAGGCGACATGG
CAGGTTACGGCGCTAAAGGAATCCGAAAGGTTGGAGCGTTTCGCTCTGGC
CTAGAGGACAAGGTTTCAAAGCAGTTGGAATCAAAAGGTATTAAATTCGA
GTATGAAGAGTGGAAAGTGCCTTATGTAATTCCGGCGAGCAATCACACTT
ACACTCCAGACTTCTTACTTCCAAACGGTATTCGTTGAGACAAAGGGT
CTGTGGGAAAGCGATGATAGAAAGAAGCACTTATTAATTAGGGAGCAGCA
CCCCGAGCTAGACATCCGTATTGTCTTCTCAAGCTCACGTACTAAGTTAT
ACAAAGGTTCTCCAACGTCTTATGGAGAGTTCTGCGAAAAGCATGGTATT
AAGTTCGCTGATAAACTGATACCTGCTGAGTGGATAAAGGAACCCAAGAA
GGAGGTCCCCTTTGATAGATTAAAAAGGAAAGGAGGAAAGAAATAATGGC
TCGTGTACAGTTTAAACAACGTGAATCTACTGACGCAATCTTTGTTCACT
GCTCGGCTACCAAGCCAAGTCAGAATGTTGGTGTCCGTGAGATTCGCCAG
TGGCACAAAGAGCAGGGTTGGCTCGATGTGGGATACCACTTTATCATCAA
GCGAGACGGTACTGTGGAGGCAGGCAGATGAGATGCGTAGGCTCTC
ACGCTAAGGGTTACAACCACAACTCTATCGGCGTCTGCCTTGTTGGTGGT
ATCGACGATAAAGGTAAGTTCGACGCTAACTTTACGCCAGCCCAAATGCA
ATCCCTTCGCTCACTGCTTGTCACACTGCTGGCTAAGTACGAAGGCGCTG
TGCTTCGCGCCCATCATGAGGTGGCGCCGAAGGCTTGCCCTTCGTTCGAC
CTTAAGCGTTGGTGGGAGAAGAACGAACTGGTCACTTCTGACCGTGGATA
ATTAATTGAACTCACTAAAGGGAGACCACAGCGGTTTCCCTTTGTTCGCA
TTGGAGGTCAAATAATGCGCAAGTCTTATAAACAATTCTATAAGGCTCCG
AGGAGGCATATCCAAGTGTGGGAGGCAGCCAATGGCCTATCCAACAAAGG
TTATTATATAGACCACATTGACGATAATCCACTCAACGACGCCTTAGACA
ATCTCCGTCTGGCTCTCCCAAAAGAAAACTCATGGAACATGAAGACTCCA
AAGAGCAATACCTCAGGACTAAAGGGACTGAGTTGGAGCAAGGAAAGGGA
GATGTGGAGAGGCACTGTAACAGCTGAGGGTAAACAGCATAACTTTGCTA
GTAGAGATCTATTGGAAGTCGTTCGCGTGGATTTATAGAACTAGGAGGGAA
TTGCATGGACAATTCGCACGATTCCGATAGTGTATTTCTTTACCACATTC
CTTGTGACAACTGTGGGAGTAGTGATGGGAACTCGCTGTTCTCTGACGGA
CACACGTTCTGCTACGTACTGCGAGAAGTGGACTGCTGAGAGAACACAC
TAAAGAGAGGGCTTCAAAACGGAAACCCTCAGGAGGTAAACCAATGACTT
ACAACGTGTGGAACTTCGGGGAATCCAATGGACGCTACTCCGCGTTAACT
GCGAGAGGAATCTCCAAGGAAACCTGTCAGAAGGCTGGCTACTGGATTGC
CAAAGTAGACGGTGTGATGTACCAAGTGGCTGACTATCGGGACCAGAACG
GCAACATTGTGAGTCAGAAGGTTCGAGATAAAGATAAGAACTTTAAGACC
ACTGGTAGTCACAAGGTGACGCTCTGTTCGGGAAGCACTTGTGGAATGA
TGGTAAGAAGATTGTCGTTACAGAAGGTGAAATCGACATGCTTACCGTGA
TGGAACTTCAAGACTGTAAGTATCCTGTAGTGTCGTTGGGTCACGGTGCC
TCTGCCGCTAAGAAGACATGCGCTGCCAACTACGAATACTTTGACCAGTT
CGAACAGATTATCTTAATGTTCGATATGACGAAGCAGGGCGAAGTGGCAGTT
TCGAAGAGGCTGCACAGGTTCTACCTGCTGGTAAGGTACGAGTGGCAGTT
CTTCCGTGTAAGGATGCAAACGAGTGTCACCTAAATGGTCACGACCGTGA
AATCATGGAGCAAGTGTGGAATGCTGGTCCTTGGATTCCTGATGGTGTGG
TATCGGCTCTTTCGTTACGTGAACGAATCCGTGAGCACCTATCGTCCGAG
GAATCAGTAGGTTTACTTTTCAGTGGCTGCACTGGTATCAACGATAAGAC
CTTAGGTGCCCGTGGTGGTGAAGTCATTATGGTCACTTCCGGTTCCGTA | TGGGTAAGTCAACGTTCGTCCGTCAACAAGCTCTACAATGGGGCACAGCG
ATGGGCAAGAAGGTAGGCTTAGCGATGCTTGAGGAGTCCGTTGAGGAGAC
CGCTGAGGACCTTATAGGTCTACACAACCGTGTCCGACTGAGACAATCCG
ACTCACTAAAGAGAGATTATTGAGAACGGTAAGTTCGACCAATGGTTC
GATGAACTGTTCGGCAACGATACGTTCCATCTATATGACTCATTCGCCGA
GGCTGAGACGGATAGACTGCTCGCTAAGCTGGCCTACATGCGCTCAGGCT
TGGGCTGTGACGTAATCATTCTAGACCACATCTCAATCGTCGTATCCGCT
TCTGGTGAATCCGATGAGCGTAAGATGATTGACAACCTGATGACCAAGCT
CAAAGGGTTCGCTAAGTCAACTGGGGTGGTGCTGGTCGTAATTTGTCACC
TTAAGAACCCAGACAAAGGTAAAGCACATGAGGAAGGTCGCCCCGTTTCT
ATTACTGACCTACGTGGTTCTGGCGCACTACGCCAACTATCTGATACTAT
TATTGCCCTTGAGCGTAATCAGCAAGGCGATATGCCTAACCTTGTCCTCG
TTCGTATTCTCAAGTGCCGCTTTACTGGTGATACTGGTATCGCTGGCTAC
ATGGAATACAACAAGGAAACCGGATGGCTTGAACCATCAAGTTACTCAGG
GGAAGAAGAGTCACACTCAGAGTCAACAGACTGGTCCAACGACACTGACT
TCTGACAGGATTCTTGATGACTTTCCAGACGACTACGAGAAGTTTCGCTG
GAGAGTCCCATTCTAATACGACTCACTAAAGGAGACACACCATGTTCAAA
CTGATTAAGAAGTTAGGCCAACTGCTGGTTCGTATGTACAACGTGGAAGC
CAAGCGACTGAACGATGAGGCTCGTAAAGAGGCCACACAGTCACGCGCTC
TGGCGATTCGCTCCAACGAACTGGCTGACAGTGCATCCACTAAAGTTACC
GAGGCTGCCCGTGTGGCAAACCAAGCTCAACAGCTTTCCAAATTCTTTGA
GTAATCAAACAGGAGAAACCATTATGTCTAACGTAGCTGAAACTATCCGT
CTATCCGATACAGCTGACCAGTGGAACCGTCGAGTCCACATCAACGTTCG
CAACGGTAAGGCGACTATGGTTTACCGCTGGAAGGACTCTAAGTCCTCTA
AGAATCACACTCAGCGTATGACGTTGACAGATGAGCAAGCACTGCGTCTG
GTCAATGCGCTTACCAAAGCTGCCGTGACAGCAATTCATGAAGCTGGTCG
CGTCAATGAAGCTATGGCTATCCTCGACAAGATTGATAACTAAGAGTGGT
ATCTCCAAGGTCGCCAAAGTGGTGGCCTTCATGAATACTATTCGACTCAC
TATAGGAGATATTACCATGCGTGACCCTAAAGTTATCCAAGCAGAAATCG
CTAAACTGGAAGCTGAACTGGAGGACGTTAAGTACCATGAAGCTAAGACT
CGCTCCGCTGTTCACATCTTGAAGAACTTAGGCTGGACTTGGACAAGACA
GACTGGCTGGAAGAAACCAGAAGTTTACCAAGCTGAGTCATAAAGGTGTTCG
ATAAGGACACTATGACCCACATCAAGGCTGGTGATTGGGTTAAGGTTGAC
ATGGGAGTTGTTGGTGGATACGGCTACGTCCGCTCAGTTAGTGGCAAATA
TGCACAAGTGTCATACATCACAGGTGTTACTCCACGCGGTGCAATCGTTG
CCGATAAGACCAACATGATTCACAAGGTTTCTTGACAGTTGTTTCATAT
GAAGAGATTGTTAAGTCACGATAATCAATAGGAGAAATCAATATGATCGT
TTCTGACATCGAAGCTAACGCCCTCTTAGAGAGCGTCACTAAGTTCCACT
GCGGGGTTATCTACGACTACTCCACCGCTGAGTACGTAAGCTACCGTCCG
AGTGACTTCGGTGCGTATCTGGATGCGCTGGAAGCCGAGGTTGCACGAGG
CGGTTCTTATTGTGTTCCACAACGGTCACAAGTATGACGTTCCTGCATTGA
CCAAACTGGCAAAGTTGCAATTGAACCGAGAGTTCCACCTTCCTCGTGAG
AACTGTATTGACACCCTTGTGTTGTCACGTTTGATTCATTCCAACCTCAA
GGACACCGATATGGGTCTTCTGCGTTCCGGCAAGTTGCCCGGAAAACGCT
TTGGGTCTCACGCTTTGGAGGCGTGGGGTTATCGCTTAGGCGAGATGAAG
GGTGAATACAAAGACGACTTTAAGCGTATGCTTGAAGAGCAGGGTGAAGA
ATACGTTGACGGAATGGAGTGGTGGAACTTCAACGAAGAGATGATGGACT
ATAACGTTCAGGACGTTGTGGTAACTAAAGCTCTCCTTGAGAAGCTACTC
TCTGACAACATTACTTCCCTCCTGAGATTGACTTTACGGACGTAGGATA
CACTACGTTCTGGTCAGAATCCCTTGAGGCCGTTGACATTGAACATCGTG
CTGCATGGCTGCTCGCTAAACAAGAGCGCAACGGGTTCCCGTTTGACACA
AAAGCAATCGAAGAGTTGTACGTAGAGTTAGCTGCTCGCCGCTCTGAGTT
GCTCGTAAATTGACCGAAAGCTTCGGCTCGTGGTATCAGCCTAAAGGTG
GCACTGAGATGTTCGCCATCCGCGAACAGGTAAGCCACTACCTAAATAC
CCTCGCATTAAGCACCTAAAGTTGGTGGTATCTTTAAGAAGCCTAAGAA
CAAGGCACAGCGAGAAGGCCGTGAGCCTTGCGAACTTGATACCCGCGAGT
ACGTTGCTGGTGCTCCTTACACCCCCAGTTGAACATGTTGGTTTAACCCT
TCGTCTCGTGACCACATTCAGAAGAACTCCAAGAGGCTGGGTGGGTCCC
GACCAAGTACACCGATAAGGGTGCTCCTGTGGTGGACGATGAGGTACTCG
AAGGAGTACGTGTAGATGACCCTGAGAAGCAAGCCGCTATCGACCTCATT
AAAGAGTACTTGATGATTCAGAAGCGAATCGGACAGTCTGCTGAGGGAGA
CAAAGCATGCTTCGTTATGTTGCTGAGGATGGTAAGATTCATGGTTCTG
TTAACCCTAATGGAGCAGTTACGGGTCGTGCGACCCATGCGTTCCCAAAC
CTTGCGCAAATTCCGGGTGTACGTTCTCCTTATGGAGAGCAGTGTCGCGC
TGCTTTTGGCGCTGAGCACCATTTGGATGGGATAACTGGTAAGCCTTGGG
TTCAGGCTGGCATCGACGATCCGGTCTTGAGCTACGCTGCTTGGCTCAC
TTCATGGCTGCTTTGATAACGGCGAGTACGCTCACGAGATTCTTAACGG
CGACATCCACACTAAGAACCAGATAGCTGCTGAACTACCTACCCGAGATA
ACGCTAAGACGTTCATCTATGGGTTCCTCTATGGTGCTGGTGATGAGAAG
ATTGGACAGATTGTTGGTGCTGGTAAAGAGCGCGGTAAGGAACTCAAGAA
GAAATTCCTTGAGAACCCCCGCAGTTGCAGCACTCCGCGAGTCTATCC
AACAGACACTTGTCGAGTCCTTCAATGGGTAGCTGGTGAGCAACAAGTC
AAGTGGAAACGCCGCTGGATTAAAGGTCGGATGGTCGTAAGGTACACGT
TCGTAGTCCTCACGCTGCCTTGAATACCCTACTGCAATCTGCTGGTGCTC
TCATCTGCAAACTGTGGATTATCAAGACCGAAGAGATGCTCGTAGAGAAA
GGCTTGAAGCATGGCTGGGATGGGACTTTGCGTACATGGCATGGGTACA
TGATGAAATCCAAGTAGGCTGCCGTACCGAAGAGATTGCTCAGGTGGTCA |

| Bacteriophage Genome Sequences |
|---|
| TTGAGACCGCACAAGAAGCGATGCGCTGGGTTGGAGACCACTGGAACTTC |
| CGGTGTCTTCTGGATACCGAAGGTAAGATGGGTCCTAATTGGGCGATTTG |
| CCACTGATACAGGAGGCTACTCATGAACGAAAGACACTTAACAGGTGCTG |
| CTTCTGAAATGCTAGTAGCCTACAAATTTACCAAAGCTGGGTACACTGTC |
| TATTACCCTATGCTGACTCAGAGTAAAGAGGACTTGGTTGTATGTAAGGA |
| TGGTAAATTTAGTAAGGTTCAGGTTAAAACAGCCACAACGGTTCAAACCA |
| ACACAGGAGATGCCAAGCAGGTTAGGCTAGGTGGATGCGGTAGGTCCGAA |
| TATAAGGATGGAGACTTTGACATTCTTGCGGTTGTGGTTGACGAAGATGT |
| GCTTATTTTCACATGGGACGAAGTAAAAGGTAAGACATCCATGTGTGTCG |
| GCAAGAGAAACAAAGGCATAAAACTATAGGAGAAATTATTATGGCTATGA |
| CAAAGAAATTTAAAGTGTCCTTCGACGTTACCGCAAAGATGTCGTCTGAC |
| GTTCAGGCAATCTTAGAGAAAGATATGCTGCATCTATGTAAGCAGGTCGG |
| CTCAGGTGCGATTGTCCCCAATGGTAAACAGAAGGAAATGATTGTCCAGT |
| TCCTGACACACGGTATGGAAGGATTGATGACATTCGTAGTACGTACATCA |
| TTTCGTGAGGCCATTAAGGACATGCACGAAGAGTATGCGAAGATAAGGACTC |
| TTTCAAACAATCTCCTGCAACATACGGGAGGTGTTCTGATGTCTGACTA |
| CCTGAAAGTGCTGCAAGCAATCAAAAGTTGCCCTAAGACTTTCCAGTCCA |
| ACTATGTACGGAACAATGCGAGCCTCGTAGCGGAGGCCGCTTCCCGTGGT |
| CACATCTCGTGCCTGACTACTAGTGGACGTAACGTGGCGCTTGGGAAAT |
| CACTGCTTCCGGTACTGCTTTCTGAAACGAATGGGAGGATGTGTCTAAT |
| GTCTCGTGACCTTGTGACTATTCCACGCGATGTGTGGAACGATATACAGG |
| GCTACATCGACTCTCTGGAACGTGAGAACGATAGCCTTAAGAATCAACTA |
| ATGGAAGCTGACGAATACGTAGCGGAACTAGAGGAGAAACTTAATGGCAC |
| TTCTTGACCTTAAACAATTCTATGAGTTACGTGAAGGCTGCGACGACAAG |
| GGTATCCTTGTGATGGACGGCGACTGCTGGTCTTCCAAGCTATGAGTGC |
| TGCTGAGTTTGATGCCTCTTGGGAGGAAGAGATTTGGCACCGATGCTGTG |
| ACCACGCTAAGGCCCGTCAGATTCTTGAGGATTCCATTAAGTCCTACGAG |
| ACCCGTAAGAAGGCTTGGGCAGGTGCTCCAATTGTCCTTGCGTTCACCGA |
| TAGTGTTAACTGGCGTAAAGAACTGGTTGACCCGAACTATAAGGCTAACC |
| GTAAGGCCGTGAAGAAACCTGTAGGGTACTTTGAGTTCCTTGATGCTCTC |
| TTTGAGCGCAAGAGTTCTATTGCATCCGTGAGCCTATGCTTGAGGGTGA |
| TGACGTTATGGGAGTTATTGCTTCCAATCCGTCTGCCTTCGGTGCTCGTA |
| AGGCTGTAATCATCTCTTGCGATAAGGACTTTAAGACCATCCCTAACTGT |
| GACTTCCTGTGGTGTACCACTGGTAACATCCTGACTCAGACCGAAGAGTC |
| CGCTGACTGGTGGCACCTCTTCCAGACCATCAAGGGTGACATCACTGATG |
| GTTACTCAGGGATTGCTGGATGGGTGATACCGCCGAGGACTTCTTGAAT |
| AACCCGTTCATAACCGAGCCTAAAACGTCTGTGCTTAAGTCCGGTAAGAA |
| CAAAGGCCAAGAGGTTACTAAATGGGTTAAACGCGACCCTGAGCCTCATG |
| AGACGCTTTGGGACTGCATTAAGTCCATTGGCGCGAAGGCTGGTATGACC |
| GAAGAGGATATTATCAAGCAGGGCCAAATGGCTCGAATCCTACGGTTCAA |
| CGAGTACAACTTTATTGACAAGGAGATTTACCTGTGGAGACCGTAGCGTA |
| TATTGGTCTGGGTCTTTGTGTTCTCGGAGTGTGCCTCATTTCGTGGGGCC |
| TTTGGGACTTAGCCAGAATAATCAAGTCGTTACACGACACTAAGTGATAA |
| ACTCAAGGTCCCTAAATTAATACGACTCACTATAGGGAGATAGGGGCCTT |
| TACGATTATTACTTTAAGATTAACTCTAAGAGGAATCTTTATTATGTTA |
| ACACCTATTAACCAATTACTTAAGAACCCTAACGATATTCCAGATGTACC |
| TCGTGCAACCGCTGAGTATCTACAGGTTCGATTCAACTATGCGTACCTCG |
| AAGCGTCTGGTCATATAGGACTTATGCGTGCTAATGGTTGTAGTGAGGCC |
| CACATCTTGGGTTTCATTCAGGGCCTACAGTATGCCTCTAACGTCATTGA |
| CGAGATTGAGTTACGCAAGGAACAACTAAGAGATGATGGGGAGGATTGAC |
| ACTATGTGTTTCTCACCGAAAATTAAAACTCCGAAGATGGATACCAATCA |
| GATTCGAGCCGTTGAGCCAGCGCCTCTGACCCAAGAAGTGTCAAGCGTGG |
| AGTTCGGTGGGTCTTCTGATGAGACGGATACCGAGGGCACCGAAGTGTCT |
| GGACGCAAAGGCCTCAAGGTCGAACGTGATGATTCCGTAGCGAAGTCTAA |
| AGCCAGCGGCAATGGCTCCGCTCGTATGAAATCTTCCATCCGTAAGTCCG |
| CATTTGGAGGTAAGAAGTGATGTCTGAGTTCACATGTGTGGAGGCTAAGA |
| GTCGCTTCCGTGCAATCCGGTGGACTGTGGAACAACCTTGGGTTGCCTAAA |
| GGATTCGAAGGACACTTTGTGGGCTACAGCCTCTACGTAGACGAAGTGAT |
| GGACATGTCTGGTTGCCGTGAAGAGTACATTCGGACTCTACCGGAAACAC |
| ATGTAGCGTACTTCGCGTGGTGCGTAAGCTGTGACATTCACCACAAAGGA |
| GACATTCTGGATGTAACGTCCGTTGTCATTAATCCTGACGGACTCTAA |
| GGGCTTACAGCGATTCCTAGCGAAACGCTTTAAGTTACCTTGCGGAACTCC |
| ACGATTGCGATTGGGTGTCTCGTTGTAAGCATGAAGGCGAGACAATGCGT |
| GTATACTTTAAGGAGGTATAAGTTATGGGTAAGAAAGTTAAGAAGGCCGT |
| GAAGAAAGTCACCAAGTCCGTTAAGAAAGTCGTTAAGGAAGGGGCTCGTC |
| CGGTTAAACAGGTTGCTGGCGGTCTAGCTGGTCTGGCTGGCTGGTGGTACTGGT |
| GAAGCACAGATGGTGGAAGTACCACAAGCTGCCGCACAGATTGTTGACGT |
| ACCTGAGAAGAGGTTTCCACTGAGGACGAAGCACAGACAGAAAGCGGAC |
| GCAAGAAAGCTCGTGCTGGCGGTAAGAAATCCTTGAGTGTAGCCCGTAGC |
| TCCGGTGGCGGTATCAACATTTAATCAGGAGGTTATCGTGGAAGACTGCA |
| TTGAATGGACGGAGGTGTCAACTCTAAGGGTTATGGTCGTAAGTGGGTT |
| AATGGTAAACTTGTGACTCCACATAGGCACATCTATGAGGAGACATATGG |
| TCCAGTTCCAACAGGAATTGTGGTGATGCATATCTGCGATAACCCTAGGT |
| GCTATAACATAAAGCACCTTACGCTTGGAACTCCAAAGGATAATTCCGAG |
| GACATGGTTACCAAAGGTAGACAGGCTAAAGGAGAGGAACTAAGCAAGAA |
| ACTTACAGAGTCAGACGTTCTCGCTATACGCTCTTCAACCTTAAGCCACC |
| GCTCCTTAGGAGAACTGTATGGAGTCAGTCAATCAACCATAACGCGAATA |
| CTACAGCGTAAGACATGGAGACACATTTAATGGCTGAGAAACGAACAGGA |
| CTTGCCGGAGGATGGCGCAAAGTCTGTCTATGAGCGTTTAAAGAACGACCG |
| TGCTCCCTATGAGACACGCGCTCAGAATTGCGCTCAATATACCATCCCAT |
| CATTGTTCCCTAAGGACTCCGATAACGCCTCTACAGATTATCAAACTCCG |
| TGGCAAGCCGTGGGCGCTCGTGGTCTGAACAATCTAGCCTCTAAGCTCAT |
| GCTGGCTCTATTCCCTATGCAGACTTGGATGCGACTTACTATATCTGAAT |
| ATGAAGCAAAGCAGTTACTGAGCGACCCCGATGGACTCGCTAAGGTCGAT |
| GAGGGCCTCTCGATGGTAGAGCGTATCATCATGAACTACATTGAGTCTAA |
| CAGTTACCGCGTGACTCTCTTTGAGGCTCTCAAACAGTTAGTCGTAGCTG |
| GTAACGTCCTGCTGTACCTACCGGAACCGGAAGGGTCAAACTATAATCCC |
| ATGAAGCTGTACCGATTGTCTTCTTTATGTGGTCCAACGAGACGCATTCGG |
| CAACGTTCTGCAAATGGTGACTCGTGACCAGATAGCTTTTGGTGCTCTCC |
| CTGAGGACATCCGTAAGGCTGTAGAAGGTCAAGGTGGTGAGAAGAAAGCT |
| GATGAGACAATCGACGTGTACACTCACATCTATCTGGATGAGGACTCAGG |
| TGAATACCTCCGATACGAAGAGGTCGAGGGTATGGAAGTCCAAGGCTCCG |
| ATGGGATTTATCCTAAAGAGGCTTGCCCATACATCCCGATTCGGATGGTC |
| AGACTAGATGGTGAATCCTACGGTCGTTCGTACATTGAGGAATACTTAGG |
| TGACTTACGGTCCCTTGAAAATCTCCAAGAGGCTATCGTCAAGATGTCCA |
| TGATTAGCTCTAAGGTTATCGGCTTAGTGAATCCTGCTGGTATCACCCAG |
| CCACGCCGACTGACCAAAGCTCAGACTGGTGACTTCGTTACTGGTCGTCC |
| AGAAGACATCGTTCCTCCAACTGGAGAAGCAAGCAGACTTTACTGTAG |
| CTAAAGCCGTAAGTGACGCTATCGAGGCTCGCCTTTCGTTTGCCTTTATG |
| TTGAACTCTGCGGTTCAGCGTACAGGTGAACGTGTGACCGCCGAAGAGAT |
| TCGGTCATGGTAGCTTCTGAACATCTTAGGTGGTGTCTACTCTA |
| TCCTTTCTCAAGAATTACAATTGCCTCTGGTACGAGTGCTCTTGAAGCAA |
| CTACAAGCCACGCAACAGATTCCTGAGTTACCTAAGGAAGCCGTAGAGCC |
| AACCATTAGTACAGGTCTGGAAGCAATTGGTCGAGGACAAGACCTTGATA |
| AGCTGGAGCGGTTGTCACTGCGTGGGCTGCACTGGCACCTATGCGGGAC |
| GACCCTGATATTAACCTTGCGATGATTAAGTTACGTATTGCCAACGCTAT |
| CGGTATTGACACTTCTGGTATTCTACTCACCGAAGAACAGAAGCAACAGA |
| AGATGGCCCAACAGTCTATGCAAATGGGTATGGATAATGGTGCTGCTGCG |
| CTGCTCAAGGTATGGCTGCACAACTACAGCTTCACCTGAGGCTATGGC |
| TGCTGCCGCTGATTCCGTAGGTTTACAGCCGGGAATTTAATACGACTCAC |
| TATAGGGAGACCTCATCTTTGAAATGAGCGATGACAAGAGGTTGGAGTCC |
| TCGGTCTTCCTGTAGTTCAACTTTAAGGAGACAATAATAATGGCTGAATC |
| TAATGCAGACGTATATGCACTCTTTTGGCGTGAACTCCGCTGTGATGCTG |
| GTGGTTCCGTTGAGGAACATGAGCAGAACATGCTGGCTCTTCTGATGTTGCT |
| GCCCGTGATGGCGATGATGCAATCGAGTTAGCGTCAGACGAAGTGGAAAC |
| AGAACGTGACCTGTATGACAACTCTGACCCGTTCGGTCAAGAGGATGACG |
| AAGGCCGCATTCAGGTTCGTATCGGTGATGGCTCTGAGCCGACCGATGTG |
| GACACTGGAGAAGAAGGCGTTGAGGGCACCGAAGGTTCCGAAGAGTTTAC |
| CCCACTGGGCGAGACTCCAGAAGAACTGGTAGCTGCCTCTGAGCAACTTG |
| GTGAGCACGAAGAGGCTTCCAAGAGATGATTAACATTGCTGCTGAGCGT |
| GGCATGAGTGTCGAGACCATTGAGGCTATCCAGCGTGAGTACGAGGAGAA |
| CGAAGAGTTGTCCGCCGAGTCCTACGCTAAGCTGGCTGGAAATTGGCTACA |
| CGAAGGCTTTCATTGACTCGTATATCCGTGGTCAAGAAGCTCTGGTGGAG |
| CAGTACGTAAACAGTGTCATTGAGTACGCTGGTGGTCGTGAACGTTTTGA |
| TGCACTGTATAACCACCTTGAGACGCACAACCCTGAGGCTGCACAGTCGC |
| TGGAATAGCGTTGACCAATCGTGACTTAGCGACCGTTAAGCCTATCATC |
| AACTTGGCTGTGAGTCTCGCGCTAAGGCGTTCGGTCGTAAGCCAACTCG |
| TAGTGTGACTAATCGTGCTATTCCGGCTAAACCTCAGGCTACCAAGCGTG |
| AAGGCTTTGCGGACCGTAGCGAGATGATTAAAGCTATGAGTGACCCTCGG |
| TATCGCACAGATGCCAATATCGTCGTCAAGTCGAACAGAAAGTAATCGA |
| TTCGAACTTCTGATAGACTTCGAAATTAATACGACTCACTATAGGGAGAC |
| CACAACGGTTTCCCTCTAGAAATAATTTTGTTTAACTTTAAGAAGGAGAT |
| ATACATATGGCTAGCATGACTGGTGGACAGCAAATGGGTACTAACCAAGG |
| TAAAGGTGTAGTTGCTGCTGGAGATAAACTGGCGTTGTTCTTGAAGGTAT |
| TTGGCGGTGAAGTCCTGACTGCGTTCGCTCGTACCTCCGTGACCACTTCT |
| CGCCACATGGTACGTTCCATCTCCAGCGTGAAATCCGCTCAGTTCCCTGT |
| TCTGGGTCGCACTCAGGCAGCGTATCTGGCTCCGGGCGAGAACCTCGACG |
| ATAAACGTAAGGACATCAAACACCAGAAGGTAATCACCATTGACGGT |
| CTCCTGACGGCTGACGTTCTGATTTATGATATTGAGGACGCGATGAACCA |
| CTACGACGTTCGCTCTGAGTATACCTCTCAGTTGGGTGAATCTCTGGCGA |
| TGGCTGCGGATGGTGCGGTTCTGGCTGAGATTGCCGGTCTGTGTAACGTG |
| GAAAGCAAATATAATGAGAACATCGAGGGCTTAGGTACTGCTACCGTAAT |
| TGAGACCACTCAGAACAAGGCCGACTTACCGACCAAGTTGCGCTGGATA |
| AGGAGATTATTGCGGCTCTGACTAAGGCTCGTGCGCTCTGACCAAGAAC |
| TATGTTCCGGCTGCTGACCGTGTGTTCTACTGTGACCCAGATAGCTACTC |
| TGCGATTCTGGCAGCACTGATGCCGAACGCAGCAAATACGCTGCTCTGA |
| TTGACCCTGAGAAGGGTTCTATCCGCAACGTTATGGGCTTTGAGGTTGTA |
| GAAGTTCCGCACCTCACCGCTGGTGTGCCTGGTACCGCTCGGGGAAGTCA |
| CTGGTTGCTAAGGACAACGTTATCGGCCTGTTCATGCACCGCTCTGCGTA |
| GGTACTGTTAAGCTGCGTGACTTGGCTCTGGAGCGCGCTCGCCGTGCTAA |
| CTTCCAAGCGGACCAGATTATCGCTAAGTACGCAATGGGCCACGGTGGTC |
| TTCGCCCAGAAGCTGCTGGTGCAGTGGTTTTCAAAGTGGAGTAATGCTGG |
| GGGTGGCCTCAACGGTCGCTGCTAGTCCCGAAGAGGCGAGTGTTACTTCA |

| Bacteriophage Genome Sequences |
|---|
| ACAGAAGAAACCTTAACGCCAGCACAGGAGGCCGCACGCACCCGCGCTGC |
| TAACAAAGCCCGAAAGGAAGCTGAGTTGGCTGCTGCCACCGCTGAGCAAT |
| AACTAGCATAACCCCTTGGGGCCTCTAAACGGGTCTTGAGGGGTTTTTTG |
| CTGAAAGGAGGAACTATATGCGCTCATACGATATGAACGTTGAGACTGCC |
| GCTGAGTTATCAGCTGTGAACGACATTCTGGCGTCTATCGGTGAACCTCC |
| GGTATCAACGCTGGAAGGTGACGCTAACGCAGATGCAGCGAACGCTCGGC |
| GTATTCTCAACAAGATTAACCGACAGATTCAATCTCGTGGATGGACGTTC |
| AACATTGAGGAAGGCATAACGCTACTACCTGATGTTTACTCCAACCTGAT |
| TGTATACAGTGACGACTATTTATCCCTAATGTCTACTTCCGGTCAATCCA |
| TCTACGTTAACCGAGGTGGCTATGTGTATGACCGAACGAGTCAATCAGAC |
| CGCTTTGACTCTGGTATTACTGTGAACATTATTCGTCTCCGCGACTACGA |
| TGAGATGCCTGAGTGCTTCCGTTACTGGATTGTCACCAAGGCTTCCCGTC |
| AGTTCAACAACCGATTCTTTGGGGCACCGGAAGTAGAGGGTGTACTCCAA |
| GAAGAGGAAGATGAGGCTAGACGTCTCTGCATGGAGTATGAGATGGACTA |
| CGGTGGGTACAATATGCTGGATGGAGATGCGTTCACTTCTGGTCTACTGA |
| CTCGCTAACATTAATAAATAAGGAGGCTCTAATGGCACTCATTAGCCAAT |
| CAATCAAGAACTTGAAGGGTGGTATCAGCCAACAGCCTGACATCCTTCGT |
| TATCCAGACCAAGGGTCACGCCAAGTTAACGGTTGGTCTTCGGAGACCGA |
| GGGCCTCCAAAAGCGTCCACCTCTTGTTTTCTTAAATACACTTGGAGACA |
| ACGGTGCGTTAGGTCAAGCTCCGTACATCCACCTGATTAACCGAGATGAG |
| CACGAACAGTATTACGCTGTGTTCACTGGTAGCGGAATCCGAGTGTTCGA |
| CCTTTCTGGTAACGAGAAGCAAGTTAGGTATCCTAACGGTTCCAACTACA |
| TCAAGACCGCTAATCCACGTAACGACCTGCGAATGGTTACTGTAGCAGAC |
| TATACGTTCATCGTTAACCGTAACGTTGTTGCACAGAAGAACACAAAGTC |
| TGTCAACTTACCGAATTACAACCCTAATCAAGACGGATTGATTAACGTTC |
| GTGGTGGTCAGTATGGTAGGGAACTAATTGTACACATTAACGGTAAAGAC |
| GTTGCGAAGTATAAGATACCAGATGGTAGTCAACCTGAACACGTAAACAA |
| TACGGATGCCCAATGGTTAGCTGAAGAGTTAGCCAACAGATGCGCACTA |
| ACTTGTCTGATTGGACTGTAAATGTAGGGCAAGGGTTCATCCATGTGACC |
| GCACCTAGTGGTCAACAGATTGACTCCTTCACGACTAAAGATGGCTACGC |
| AGACCAGTTGATTAACCCTGTGACCCACTACGCTCAGTCGTTCTCTAAGC |
| TGCCACCTAATGCTCCTAACGGCTACATGGTGAAAATCGTAGGGGACGCC |
| TCTAAGTCTGCCGACCAGTATTACGTTCGGTATGACGCTGAGCGGAAAGT |
| TTGGACTGAGACTTTAGGTTGGAACACTGAGGACCAAGTTCTATGGGAAA |
| CCATGCCACACGCTCTTGTGCGAGCCGCTGACGGTAATTTCGACTTCAAG |
| TGGCTTGAGTGGTCTCCTAAGTCTTGTGGTGACGTTGACCAACCCTTG |
| GCCTTCTTTTGTTGGTTCAAGTATTAACGATGTGTTCTTCTTCCGTAACC |
| GCTTAGGATTCCTTAGTGGGGAGAACATCATATTGAGTCGTACAGCCAAA |
| TACTTCAACTTCTACCCTGCGTCCATTGCGAACCTTAGTGATGACGACCC |
| TATAGACGTAGCTGTGAGTACCAACCGAATAGCAATCCTTAAGTACGCCG |
| TTCCGTTCTCAGAAGAGTTACTCATCTGGTCCGATGAAGCACAATTCGTC |
| CTGACTGCCTCGGGTACTCTCACATCTAAGTCGGTTGAGTTGAACCTAAC |
| GACCCAGTTTGACGTACAGGACCGAGCGAGACCTTTTGGGATTGGGCGTA |
| ATGTCTACTTTGCTAGTCCGAGGTCCAGCTTCACGTCCATCCACAGGTAC |
| TACGCTGTGCAGGATGTCAGTTCCGTTAAGAATGCTGAGGTCACAGATCC |
| TTGCTGCCAGGATGTCAGTTCCGTTAAGAATGCTGAGGTCACAGATCATC |
| ACACGTTCCTAACTACATCCCTAATGGTGTGTTCAGTATTTGCGGAAGTG |
| GTACGGAAAACTTCTGTTCGGTACTATCTCACGGGGACCCTAGTAAAATC |
| TTCATGTACAAATTCCTGTACCTGAACGAAGAGTTAAGGCAACAGTCGTG |
| GTCTCATTGGGACTTTGGGGAAACGTACAGGTTCTAGCTTGTCAGAGTGA |
| TCAGCTCAGATATGTATGTGATTCTTCGCAATGAGTTCAATACGTTCCTA |
| GCTAGAATCTCTTTCACTAAGAACGCCATTGACTTACAGGGAGAACCCTA |
| TCGTGCCTTTATGGACATGAAGATTCGATACACGATTCCTAGTGGAACAT |
| ACAACGATGACATTCACTACCTCTATTCATATTCCAACAATTTATGGT |
| GCAAACTTCGGGAGGGCAAAATCACTGTATTGGAGCCTGATGGTAAGAT |
| AACCGTGTTTGAGCAACCTACGGCTGGGTGGAATAGCGACCCTTGGCTGA |
| GACTCAGCGGTAACTTGGAGGGACGCATGGTGTACATTGGGTTCAACATT |
| AACTTCGTATATGAGTTCTCTAAGTTCCTCATCAAGCAGACTGCCGACGA |
| CGGGTCTACCTCCACGGAAGACATTGGGCGCTTACAGTTACGCCGAGCGT |
| GGGTTAACTACGAGAACTCTGGTACGTTTGACATTTATGTTGAGAACCAA |
| TCGTCTAACTGGAAGTACACAATGGCTGGTGCCCGATTAGGCTCTAACAC |
| TCTGAGGGCTGGGAGACTGAACTTAGGGACCGGACAATATCGATTCCCTG |
| TGGTTGGTAACGCCAAGTTCAACACTGTATACATCTTGTCAGATGAGAT |
| ACCCCTCTGAACATCATTGGGTGTGGCTGGGAAGGTAACTACTTACGGAG |
| AAGTTCCGGTATTTAATTAAATATTCTCCCTGTGGTGGCTCGAAATTAAT |
| ACGACTCACTATAGGGAGAACAATACGACTACGGGAGGGTTTTCTTATGA |
| TGACTATAAGACACTACTAAAAGTACAGACATTTGAGGTATTCACTCCGAT |
| CACCATGACATTCTTGAAGCTAAGGCTGCTGGTATTGAGCCGCAGTTTCCC |
| TGATGCTTCCGAGTGTGTCACGTTGAGCCTCTATGGGTTCCCTCTAGCTA |
| TCGGTGGTAACTGCGGGGACCAGTGCTGGTTCGTTACGAGCGACCAAGTG |
| TGGCGACTTAGTGGAAAGGCTAAGCGAAAGTTCCGTAAGTTAATCATGGA |
| GTATCGCGATAAGATGCTTGAGAAGTATGATACTCTTTTGGAATTACGTAT |
| GGGTAGGCAATACGTCCCACATTCGTTTCCTCAAGCATATCGGTGCGGTA |
| TTCCATGAAGAGTACACACGAGATGGTCAATTTCAGTTATTTACAATCAC |
| GAAAGGAGGATAACCATATGTGTTGGGCAGCCGCAATACCTATCGCTATA |
| TCTGGCGCTCAGGCTATCAGTGGTCAGAACGCTCAGGCCAAAATGATTGC |
| CGCTCAGACCGCTGCTGGTCGTCGTCAAGCTATGGAAATCATGAGGCAGA |
| CGAACATCCAGAATGCTGACCTATCGTTGCAAGCTCGAAGTAAACTTGAG |

| Bacteriophage Genome Sequences |
|---|
| GAAGCGTCCGCCGAGTTGACCTCACAGAACATGCAGAAGGTCCAAGCTAT |
| TGGGTCTATCCGAGCGGCTATCGGAGAGAGTATGCTTGAAGGTTCCTCAA |
| TGGACCGCATTAAGCGAGTGCACAGAAGACAGTTCATTCGGGAAGCCAAT |
| ATGGTAACTGAGAACTATCGCCGTGACTACCAAGCAATCTTCGCACAGCA |
| ACTTGGTGGTACTCAAAGTGCTGCAAGTCAGATTGACGAAATCTATAAGA |
| GCGAACAGAAACAGAAGAGTAAGCTACAGATGGTTCTGGACCCACTGGCT |
| ATCATGGGGTCTTCCGCTGCGAGTGCTTACGCATCCGGTGCGTTCGACTC |
| TAAGTCCACAACTAAGGCACCTATTGTTGCCGCTAAAGGAACCAAGACGG |
| GGAGGTAATGAGCTATGAGTAAAATTGAATCTGCCCTTCAAGCGGCACAA |
| CCGGGACTCTCTCGGTTACGTGGTGGTGCTGGAGGTATGGGCTATCGTGC |
| AGCAACCACTCAGGCCGAACAGCCAAGGTCAAGCCTATTGGACACCATTG |
| GTCGGTTCGCTAAGGCTGGTGCCGATATGTATACCGCTAAGGACAACGA |
| GCACGAGACCTAGCTGATGAACGCTCTAACGAGATTATCCGTAAGCTGAC |
| CCCTGAGCAACGTCGAGAAGCTCTCAACAACGGGACCCTTCTGTATCAGG |
| ATGACCCATACGCTATGGAAGCACTCCGAGTCAAGACTGGTCGTAACGCT |
| GCGTATCTTGTGGACGATGACGTTATGCAGAAGATAAAAGAGGGTGTCTT |
| CCGTACTCGCGAAGAGATGGAAGAGTATCGCCATAGTCGCCTTCAAGAGG |
| GCGCTAAGGTATACGCTGAGCAGTTCGGCATCGACCCTGAGGACGTTGAT |
| TATCAGCGTGGTTTCAACGGGGACATTACCGAGCGTAACATCTCGCTGTA |
| TGGTGCGCATGATAACTTCTTGAGCCAGCAAGCTCAGAAGGGCGCTATCA |
| TGAACAGCCGAGTGGAACTCAACGGTGTCCTTCAAGACCGTCGATATGCTG |
| CGTCGTCCAGACTCTGCTGACTTCTTTGAGAAGTATATCGACAACGGTCT |
| GGTTACTGGCGCAATCCCATCTGATGCTCAAGCCACACAGCTTATAAGCC |
| AAGCGTTCAGTGACGCTTCTAGCCGTGCTGGTGGTCTTGACTTCCTGATG |
| CGAGTCGGTGACAAGAAGGTAACACTTAACGGAGCCACTACGACTTACCG |
| AGAGTTGATTGGTGAGGAACAGTGGAACGCTCTCATGGTCACAGCACAAC |
| GTTCTCAGTTTGAGACTGACGCGAAGCTGAACGAGCAGTATCGCTTGAAG |
| ATTAACTCTGCGCTGAACCAAGAGGACCCAAGGACAGCTTGGGAGATGCT |
| TCAAGGTATCAAGGCTGAACTAGATAAGGTCCAACCTGATGAGCAGATGA |
| CACCACAACGTGAGTGGCTAATCTCCGCACAGGAACAAGTTCAGAATCAG |
| ATGAACGCATGGACAGAAAGCTCAGGCCAAGGCTCTGGACGATTCCATGAA |
| GTCAATGAACAAACTTGACGTAATCGACAAGCAATTCCAGAAGCGAATCA |
| ACGGTGAGTGGGTCTCAACGGATTTTAAGGATATGCCAGTCAACGAGAAC |
| ACTGGTGAGTTCAAGCATAGCGATATGGTTAACTACGCCAATAAGAAGCT |
| CGCTGAGATTGACAGTATGGACATTCCAGACGGTGCCAAGGATGCTATGA |
| AGTTGAAGTACCTTCCAAGCGGACTCTAAGGGACGGAGCATTCCGTACAGCC |
| ATCGGAACCATGGTCACTGACGCTGGTCAAGAGTGGTCTGCCGCTGTGAT |
| TAACGGTAAGTTACCAGAACGAACCCCAGCTATGGATGCTCTGCGCAGAA |
| TCCGCAATGCTGACCCTCAGTTGATTGCTGCGCTATACCCAGACCAAGCT |
| GAGCTATTCTTGACAGTGGACATGATGGACAAGCAGGGTATTGACCCTCA |
| GGTTATTCTTGATGCCGACCGACTGACTGTTAAGCGGTCCAAAGAGCAAC |
| GCTTTGAGGATGATAAAGCATTCGAGTCTGCACTGAATGCATCTAAGGCT |
| CCTGAGATTGCCCGTATGCCAGCGTCACTGCGCGAATCTGCACGTAAGAT |
| TTATGACTCCGTTAAGTATCGCTCGGGGAACGAAAGCATGGCTATGGAGC |
| AGATGACCAAGGTTCCTTAAGGAATCTACCTACACGTTCACTGGTGATGAT |
| GTTGACGGTGATACCGTTGGTGTGATTCCTAAGAATATGATGCAGGTTAA |
| CTCTGACCCGAAATCATGGGAGCAAGGTCGGGATATTCTGGAGGAAGCAC |
| GTAAGGGAATCATTGCGAGCAACCCTTGGATAACCAATAAGCAACTGACC |
| ATGATATTCTCAAGGTGACTCCATTTACCTTATGGACACCACAGGTCAAGT |
| CAGAGTCCGATACGACAAAGAGTTACTCTCGAAGGTCTGGAGTGAGAACC |
| AGAAGAAACTCGAAGAGAAAGCTCGTGAGAAGGCTCTGGCTGATGTGAAC |
| AAGCGAGCACCTATAGTTGCCGCTACGAAGGCCCGTGAAGCTGCTGCTAA |
| ACGAGTCCGAGAGAAACGTAAACAGACTCCTAAGTTCATCTACGGACGTA |
| AGGAGTAACTAAAGGCTACATAAGGAGGCCTAAATGGATAAGTACGATA |
| AGAACGTACCAAGTGATTATGATGGTCTGTTCCAAAAGGCTGCTGATGCC |
| AACGGGGTCTCTTATGACCTTTTACGTAAAGTCGCTTGGACAGAATCACG |
| ATTTTGCCTACAGCAAAATCTAAGACTGGACCATTAGGCATGATGCAAT |
| TTACCAAGGCAACCGCTCAAGGCCCTCGGTCTGCGAGTTACCGATGGTCCA |
| GACGACGACCGACTGAACCCTGAGTTAGCTATTAATGCTGCCGCTAAGCA |
| ACTTGCAGGTCTGGTAGGGAAGTTTGATGGCGATGAACTCAAAGCTGCCC |
| TTGCGTACAACCAAGGCGAGGGCGCTTGGGTAATCCACAACTTGAGGCG |
| TACTCTAAGGGAGACTTCGCATCAATCTCTGAGGAGGACGTAACTACAT |
| GCGTAACCTTCTGGATGTTGCTAAGTCACCTATGGCTGGACAGTTGGAAA |
| CTTTTGGTGGCATAACCCCAAAGGGTAAAGGCATTCCGGCTGAGGTAGGA |
| TTGGCTGGAATTGGTCACAAGCAGAAAGTAACACAGGAACTTCCTGAGTC |
| CACAAGTTTTGACGTTAAGGGTATCGAACAGGAGGCTACGGCGAAACCAT |
| TCGCCAAGGACTTTTGGGAGACCCACGGAGAAACACTTGACGAGTACAAC |
| AGTCGTTCAACCTTCTTCGGATTCAAAAATGCTGCCGAAGCTGAACTCTC |
| CAACTCAGTCGCTGGGATGGCTTTCCGTGCTGGTCGTCTCGATAATGGTT |
| TTGATGTGTTTAAAGACACCATTACGCCGACTCGCTGGAACTCTCACATC |
| TGGACTCCAGAGGATTAGGAAGAACTGTGAACAGAGGTTAAGAACCCTGC |
| GTACATCAACGTTGTAACTGGTGGTTCCCCTGAGAACCTCGATGACCTCA |
| TTAAATTGGCTAACGAGAACTTTGAGAATGACTCCCGCGCTGCCGAGGCT |
| GGCCTAGGTGCCAACTGAGTGCTGGTATTATTGGTGCTGGTGTGGACCCC |
| GCTTAGCTATGTTCCTATGGTCGGTGTCACTGGTAAGGGCTTTAAGTTAA |
| TCAATAAGGCTCTTGTAGTTGGTGCCGAAAGTGCTGCTCTGAACGTTGCA |
| TCCGAAGGTCTCCGTACCTCCGTAGCTGGTGGTGACGCAGATATGCGGG |

| Bacteriophage Genome Sequences |
|---|
| TGCTGCCTTAGGTGGCTTTGTGTTGGCGCAGGCATGTCTGCAATCAGTG |
| ACGCTGTAGCTGCTGGACTGAAACGCAGTAAACCAGAAGCTGAGTTCGAC |
| AATGAGTTCATCGGTCCTATGATGCGATTGGAAGCCCGTGAGACAGCACG |
| AAACGCCAACTCTGCGGACCTCTCTCGGATGAACACTGAGAACATGAAGT |
| TTGAAGGTGAACATAATGGTGTCCCTTATGAGGACTTACCAACAGAGAGA |
| GGTGCCGTGGTGTTACATGATGGCTCCGTTCTAAGTGCAAGCAACCCAAT |
| CAACCCTAAGACTCTAAAAGAGTTCTCCGAGGTTGACCCTGAGAAGGCTG |
| CGCGAGGAATCAAACTGGCTGGGTTCACCGAGATTGGCTTGAAGACCTTG |
| GGGTCTGACGATGCTGACATCGTAGAGTGGCTATCGACCTCGTTCGCTC |
| TCCTACTGGTATGCAGTCTGGTGCCTCAGGTAAGTTCGGTGCAACAGCTT |
| CTGACATCCATGAGAGACTTCATGGTACTGACCAGCGTACTTATAATGAC |
| TTGTACAAAGCAATGTCTGACGCTATGAAAGACCCTGAGTTCTCTACTGG |
| CGGCGCTAAGATGTCCCGTGAAGAAACTCGATACACTATCTACCGTAGAG |
| CGGCACTAGCTATTGAGCGTCCAGAACTACAGAAGGCACTCACTCCGTCT |
| GAGAGAATCGTTATGGACATCATTAAGGTCTCACTTTGACACCAAGCGTGA |
| ACTTATGGAAAACCCAGCAATATTCGGTAACACAAAGGCTGTGAGTATCT |
| TCCCTGAGAGTCGCCACAAAGGTACTTACGTTCCTCACGTATATGACCGT |
| CATGCCAAGGCGCTGATGATTCAACGCTACGGTGCCGAAGGTTTGCAGGA |
| AGGGATTGCCCGCTCATGGATGAACAGCTACGTCTCCAGACCTGAGGTCA |
| AGGCCAGAGTCGATGAGATGCTTAAGGAATTACACGGGGTGAAGGAAGTA |
| ACACCAGAGATGGTAGAGAAGTACGCTATGGATAAGGCTTATGGTATCTC |
| CCACTCAGACCAGTTCACCAACAGTTCCATAATAGAAGAGAACATTGAGG |
| GCTTAGTAGGTATCGAGAATAACTCATTCCTTGAGGCACGTAACTTGTTT |
| GATTCGGACCTATCCATCACTATGCCAGACGGACAGCAATTCTCAGTGAA |
| TGACCTAAGGGACTTCGATATGTTCCGCATCATGCCAGCGTATGACCGCC |
| GTGTCAATGGTGACATCGCCATCATGGGGTCTACTGGTAAAACCACTAAG |
| GAACTTAAGGATGAGATTTTGGCTCTCAAAGCGAAAGCTGAGGGAGACGG |
| TAAGAGACTGGCGAGGTACATGCTTTAATGGATACGCTTAAGACTCAGTTA |
| CTGGTCGTGCTAGACGCAATCAGGACACTGTGTGGGAAACCTCACTGCGT |
| GCCATCAATGACCTAGGGTTCTTCGCTAAGAACGCCTACATGGGTGCTCA |
| GAACATTACGGAGATTGCTGGGATGATTGTCACTGGTAACGTTCGTGCTC |
| TAGGGCATGGTATCCCAATTCTGCGTGATACACTCTACAAGTCTAAACCA |
| GTTTCAGCTAAGGAACTCAAGGAACTCCATGCGTCTCTGTTCGGGAAGGA |
| GGTGGACCAGTTGATTCGGCCTAAACGTGCTGACATTGTGCAGCGCCTAA |
| GGGAAGCAACTGATACCGGACCTGCCGTGGCGAACATCGTAGGGACCTTG |
| AAGTATTCAACACAGGAACTGGCTGCTCGCTCTCCGTGGACTAAGCTACT |
| GAACGGAACCACTAACTACCTTCTGGATGCTGCGCGTCAAGGTATGCTTG |
| GGGATGTTATTAGTGCCACCCTAACAGGTAAGACTACCCGCTGGGAGAAA |
| GAAGGCTTCCTTCGTGGTGCCTCCGTAACTCCTGAGCAGATGGCTGGCAT |
| CAAGTCTCTCATCAAGGAACATATGGTACGCGGTGAGGACGGGAAGTTTA |
| CCGTTAAGGACAAGCAAGCGGTTCTCTATGGACCCACGGGCTATGGACTTA |
| TGGAGACTGGCTGACAAGGTAGCTGATGAGGCAATGCTGCGTCCACATAA |
| GGTGTCCTTACAGGATTCCCATGCGTTCGGAGCACTAGGTAAGATGGTTA |
| TGCAGTTTAAGTCTTTCACTATCAAGTCCCTTAACTCTAAGTTCCTGCGA |
| ACCTTCTATGATGGATACAAGAACAACCGAGCGATTGACCGCTGCGCTGAG |
| CATCATCACCTCTATGGGTCTCGCTGGTGGTTTCTATGCTATGCGTGCAC |
| ACGTCAAAGCATACGCTCTGCCTAAGGAGAAACGTAAGGAGTACTTGGAG |
| CGTGCACTGGACCCAACCATGATTGCCCACGCTGCGTTATCTCGTAGTTC |
| TCAATTGGGTGCTCCTTTGGCTATGGTTGACCTAGTTGGTGGTGTTTTAG |
| GGTTCGAGTCCTCCAAGATGGCTCGCTCTACGATTCTACCTAAGGACACC |
| GTGAAGGAACGTGACCCAAACAAACCGTACACCTCTAGAGAGGTAATGGG |
| CGCTATGGGTTCAAACCTTCTGGAACAGATGCCTTCGGCTGGCTTTGTGG |
| CTAACGTAGGGGCTACCTTAATGAATGCTGCTGGCGTGGTGCTCAACTCACCT |
| AATAAAGCAACCGAGCAGGACTTCATGACTGGTCTTATGAACTCCACAAA |
| AGAGTTAGTACCGAACGACCCATTGACTCAACAGCTTGTGTTGAAGATTT |
| ATGAGGCAACGGTGTTAACTTGAGGGAGCGTAGGAAATAATACGACTCA |
| CTATAGGGAGAGGCGAAATAATCTTCCCTGTAGTCTCTTGACTTATTACT |
| TTAAGGAGGTCAAATGGCTAACGTAATTAAAACCGTTTTGACTTACCAGT |
| TAGATGGCTCCAATCGTGATTTTAATATCCCGTTTGAGTATCTAGCCCGT |
| AAGTTCGTAGTGGTAACTCTTATTGGTGTAGACCGAAAGGTCCTTACGAT |
| TAATACAGACTATCGCTTTGCTACACGTACTACTATCTCTCTGACAAAGG |
| CTTGGGGTCCAGCCGATGGCTACACGACCATCGAGTTACGTCGAGTAACC |
| TCCACTACCGACCGATTGGTTGACTTTACGGATGGTTCAATCCTCCGCGC |
| GTATGACCTTAACGTCGCTCAGATTCAAACGATGCACGTAGCGGAAGAGG |
| CCCGTGACCTCACTACGGATACTATCGGTGTCAATAACGATGGTCACTTG |
| GATGCTCGTGGTCGTCGAATTGTGAACCTAGCGAACGCCGTGGATGACCG |
| CGATGCTGTTCCGTTTGGTCAACTAAAGACCATGAACCAGAACTCATGC |
| AAGCACGTAATGAAGCCTTACAGTTCCGTAATGAGGCTGAGACTTTCAGA |
| AACCAAGCGGAGGGCTTTAAGAACGAGTCCAGTACCAACGCTACGAACAC |
| AAAGCAGTGGCGCGATGAGACCAAGGGTTTCCGAGACGAAGCCAAGCGGT |
| TCAAGAATACGGCTGGTCAATACGCTACATCTGCTGGGAACTCTGCTTCC |
| GCTGCGCATCAATCTGAGGTAAACGCTGAGAACTCTGCCACACAGCATCCGC |
| TAACTCTGCTCATTTGGCAGAACAGCAAGCAGACCGTGCGGAACGTGAGG |
| CAGACAGCTGGAAAATTACAATGGATTGGCTGGTGCAATTGATAAGGTA |
| GATGGAACCAATGTGTACTGGAAAGGAAATATTCACGCTAACGGGCGCCT |
| TTACATGACCACAAACGGTTTTGACTGTGGCCAGTATCAACAGTTCTTTG |
| GTGGTGTCACTAATCGTTACTCTGTCATGGAGTGGGGAGATGAGAACGGA |
| TGGCTGATGTATGTTCAACGTAGAGAGTGGACAACAGCGATAGGCGGTAA |
| CATCCAGTTAGTAGTAAACGGACAGATCATCACCCAAGGTGGAGCCATGA |
| CCGGTCAGCTAAAATTGCAGAATGGGCATGTTCTTCAATTAGAGTCCGCA |
| TCCGACAAGGCGCACTATATTCTATCTAAAGATGGTAACAGGAATAACTG |
| GTACATTGGTAGAGGGTCAGATAACAACAATGACTGTACCTTCCACTCCT |
| ATGTACATGGTACGACCTTAACACTCAAGCAGGACTATGCAGTAGTTAAC |
| AAACACTTCCACGTAGGTCAGGCCGTTGTGGCCACTGATGGTAATATTCA |
| AGGTACTAAGTGGGGAGGTAAATGGCTGGATGCTTACCTACGTGACAGCT |
| TCGTTGCGAAGTCCAAGGCGTGGACTCAGGTGTGGTCTGGTAGTGCTGGC |
| GGTGGGGTAAGTGTGACTGTTTCACAGGATCTCCGCTTCCGCAATATCTG |
| GATTAAGTGTGCCAACAACTCTTGGAACTTCTTCCGTACTGGCCCCGATG |
| GAATCTACTTCATAGCCTCTGATGGTGGATGGTTACGATTCCAAATACAC |
| TCCAACGGTCTCGGATTCAAGAATATTGCAGACAGTCGTTCAGTACCTAA |
| TGCAATCATGGTGGAGAACGAGTAATTGGTAAATCACAAGGAAAGACGTG |
| TAGTCCACGGATGGACTCTCAAGGAGGTACAAGGTGCTATCATTAGACTT |
| TAACAACGAATTGATTAAGGCTGCTCCAATTGTTGGGACGGGTGTAGCAG |
| ATGTTAGTGCTCGACTGTTCTTTGGGTTAAGCCTTAACGAATGGTTCTAC |
| GTTGCTGCTATCGCCTACACAGTGGTTCAGATTGGTGCCAAGGTAGTCGA |
| TAAGATGATTGACTGGAAGAAAGCCAATAAGGAGTGGATATGTATGGAAAA |
| GGATAAGAGCCTTATTACATTCTTAGAGATGTTGGACACTGCGATGGCTC |
| AGCGTATGCTTGCGGACCTTTCGGACCATGAGCGTGCGCTCTCCGCAACTC |
| TATAATGCTATTAACAAACTGTTAGACCGCCACAAGTTCCAGATTGGTAA |
| GTTGCAGCCGGATGTTCACATCTTAGGTGGCCTTGCTGGTGCTCTTGAAG |
| AGTACAAAGAAGAAGTCGGTGATAACGGTCTTACGGATGATGATAATTTAC |
| ACATTACAGTGATATACTCAAGGCCACTACAGATAGTGGTCTTTATGGAT |
| GTCATTGTCTATACGAGATGCTCCTACGTGAAATCTGAAAGTTAACGGGA |
| GGCATTATGCTAGAATTTTTACGTAAGCTAATCCCTTGGGTTCTCGCTGG |
| GATGCTATTCGGGTTAGGATGGCATCTAGGGTCAGACTCAATGACGCTA |
| AATGGAAACAGGAGGTACAATGAGTACGTTAAGAGAGTTGAGGCTGCG |
| AAGAGCACTCAAAGAGCAATCGATGCGGTATCTGCTAAGTATCAAGAAGA |
| CCTTGCCGCGCTGGAAGGGAGCACTGATAGGATTATTTCTGATTTGCGTA |
| GCGACAATAAGCGGTTGCGCGTCAGAGTCAAAACTACCGGAACCTCCGAT |
| GGTCAGTGTGGATTCGAGCCTGATGGTCGAGCCGAACTTGACGACCGAGA |
| TGCTAAACGTATTCTCGCAGTGACCCAGAAGGGTGACGCATGGATTCGTG |
| CGTTACAGGATACTATTCGTGAACTGCAACGTAAGTAGGAAATCAAGTAA |
| GGAGGCAATAAGCGGTTGTCTACTCAATCGTAATGCGCTCGTAGTGGCGCA |
| ACTGAAAGGAGACTTCGTGGCGTTCCTATTCGTCTTATGGAAGGCGCTAA |
| ACCTACCGGTGCCCACTAAGTGTCAGATTGACATGCTAAGGTGCTGGCG |
| AATGGAGACAACAAGAAGTTCATCTTACAGGCTTTCCGTGGTATCGGTAA |
| GTCGTTCATCACATGTCGTGTTCGTTGTGTGGTCCTTTATGGAGAGACCCTC |
| AGTTGAAGATACTTATCGTATCAGCCTCTAAGGAGCGTGCAGACGCTAAC |
| TCCATCTTTATTAAGAACATCATTGACCTGCTGCCATTCCTATCTGAGTT |
| AAAGCCAAGACCCGGACAGCGTGACTCGGTAATCAGCTTTGATGTAGGCC |
| CAGCCAATCCTGACCACTCTCCTAGTGTGAAATCAGTAGGTATCACTGGT |
| CAGTTAACTGGTAGCCGTGCTGACATTATCATTGCGGATGACGTTGAGAT |
| TCCGTCTAACAGCGCAACTATGGGTGCCCGTGAGAAGCTATGGGACTCTGG |
| TTCAGGAGTTCGCTGCGTTACTTAAACCGCTGCCTTCCTCTCGCGTTATC |
| TACCTTGGTACACCTCAGACAGAGATGACTCTCTATAAGGAACTTGAGGA |
| TAACCGTGGGTACCAACCATTATCTGGCCTGCTCTGTACCCAAGGACAC |
| GTGAAGGAACCTCTATTACTCCAGCGTCCTTGCCTCCTATGTTACGCGCT |
| GAGTACGATGAGAACCCTGAGGCACTTGCTGGGACTCCAACAGACCCAGT |
| GCGCTTTGACCGTGATGACCTGCGCGAGCGTGAGTTGGAATACGGTAAGG |
| CTGGCTTTACGCTACAGTTCATGCTTAACCCTAACCTTAGTGATGCCGAA |
| AAGTACCCGCTGAGGCTTCGTGACGCTATCGTAGCGGCCTTAGACTTAGA |
| GAAGGCCCAATGCATTACCAGTGGCTTCCGAACCGTCAGAACATCATTG |
| AGGACCTTCCTAACGTTGGCCTTAAGGGTGATGACCTGCATACGTACCAC |
| GATTGTTCCAACAACTCAGGTCAGTACCAACAGAAGATTCTGGTCATTGA |
| CCCTAGTGGTCGCCGTGAAGGACGAAACAGGTTACGCTGTGCTGTACACAC |
| TGAACGGTTACATCTACCTTATGGAAGCTGGAGGTTTCCGTGATGGCTAC |
| TCCGATAAGACCCTTGAGTTACTCGCTAAGAAGGCAAAGCAATGGGGAGT |
| CCAGACGGTTGTCTACGAGATGAACTTCGGTGACGTGATGTTCGGTAAGG |
| TATTCAGTCCTATCCTTCTTAAACACCACAATGTGCGATGGAAGAGATT |
| CGTGCCCGTGGTATGAAAGAGATGCGATTTGCGATACCCTTGAGCCAGT |
| CATGCAGACTCACCGCCTTGTAATTCGTGATGAGGTCATTAGGGCCGACT |
| ACCAGTCCGCTCGTGACGTAGACGGTAAGCATGACGTTAAGTACTCGTTG |
| TTCTACCAGATGACCCGTATCACTCGTGAGAAAGGCGCTCTGGCCTCATGA |
| TGACCGATTGGATGCCCTTGCGTTAGGCATTGAGTATCTCCGTGAGTCCA |
| TGCAGTTGGATTCCGTTAAGGTCGAGGGTGAAGTACTTGCTGACTTCCTT |
| GAGGAACATGCCGTCCTACGGTTGCTGCTACGCATATCATTGAGAT |
| GTCTGTGGGAGGAGTTGATGTGTACTCTGAGGACGATGAGGGTTACGGTA |
| CGTCTTTCATTGAGTGGTGATTTATGCATTAGGACTGCATAGGGATGCGAC |
| TATAGACACGGATGGTCAGTTCTTTAAGTTACTGAAAAGAACACGATAAA |
| TTAATACGACTCACTATAGGGAGAGGAGGGACGAAAGGTTACTATATAGA |
| TACTGAATGAATACTTATAGAGTGCATAAAGTATGCATAATGGTGTACCT |
| AGAGTGACCTCAAGAATGGTGATTATATTGTATTAGTATCACCTTAACT |
| TAAGGACCAACATAAAGGGAGGAGACTCATGTTCCGCTTATTGTTGAACC |
| TACTGCGGCATAGAGTCACCTACCGATTTCTTGTGGTACTTTGTGCTGCC |

| Bacteriophage Genome Sequences |
|---|
| CTTGGGTACGCATCTCTTACTGGAGACCTCAGTTCACTGGAGTCTGTCGT |
| TTGCTCTATACTCACTTGTAGCGATTAGGGTCTTCCTGACCGACTGATGG |
| CTCACCGAGGGATTCAGCGGTATGATTGCATCACACCACTTCATCCCTAT |
| AGAGTCAAGTCCTAAGGTATACCCATAAAGAGCCTCTAATGGTCTATCCT |
| AAGGTCTATACCTAAAGATAGGCCATCCTATCAGTGTCACCTAAAGAGGG |
| TCTTAGAGAGGGCCTATGGAGTTCCTATAGGGTCCTTTAAAATATACCAT |
| AAAAATCTGAGTGACTATCTCACAGTGTACGGACCTAAAGTTCCCCCATA |
| GGGGGTACCTAAAGCCCAGCCAATCACCTAAAGTCAACCTTCGGTTGACC |
| TTGAGGGTTCCCTAAGGGTTGGGGATGACCCTTGGGTTTGTCTTTGGGTG |
| TTACCTTGAGTGTCTCTCTGTGTCCCT |
| |
| SEQ ID NO: 2 - Enterobacteria phage SP6 |
| TCTCTCGGCCTCGGCCTCGCCGGGATGTCCCCATAGGGTGCCTGTGGGCG |
| CTAGGGCGGCCTGTGGAGGCCTGAGAGAAGCTCTTAGTGTGGGCCAAAGG |
| GTAACCTGAGGCCTGCCGGAGCGAGCGATAGGGACGCGTGTAGGCCGCTT |
| GACAGCGTGTGTGGGCGTGGGCTATCTGTTCGTTTGCTCCGCTTACGCTA |
| CGCTTCACTCACGGCCTTGTGTACCTTAGGGTCTTCCTTATCGTGTACCT |
| TGGGACAGTCTTAGTAACTACCTTAGTCACTTCCTTAGTAGCTTCCTTAG |
| TGAGTAGCTTAGTGGCTATCTATTGCTGTCTTAGTGTTACCTTAGTGATT |
| GCATAGCTACGCTATAAGATGCGAATAGGTCGCGGTCGGTAGACCGCTAA |
| AGAAAGAGAAGAACAATAAGATGCAGTAGGAGGGACACCAGAATCCTAGC |
| CAGCCTAACCTATCCTAGCTCTGTATCTATTGCTTTTCCTTAGTCCAACA |
| CGTTAGACAACCTATGATTATCTTAGTAGCTGTGACATGTATCACATAAA |
| TAATCTATCTTAGTGAAACTTAGTGTTGACACAGGCAGTAGTCGGTAGTA |
| CATTACAGTCATCGGGAGGCAACCCAGCCGAACGATAGGTAGCTTTGGCT |
| GCCTTGCTCTTTAACAATATGGCTAGTGTCTTGATAGGCTAACTAACTGA |
| GGTTACTATCATGCTCAAAGAGACTCAAATCAAGCACGAAAACGGAAAGT |
| ATTGGGTGTTAGAGGTTAAGAAAGGTATGTATCAGGTGATGATATCTGGC |
| TTAACTCACTCAACTTGTGATAGTGCTTACAACGATCTTAGCTTAGCTAT |
| TTATCGGTGCGATTATCTGGCTAAACGAGCATAAGGTAAGGCTGGCGTAG |
| GCTGGCCTATCAAGGCACTATCCTTGCTCTTTAACAATCTGCTTAGTGTA |
| ACCTATGTAAGCCGTGGTATTACTTATTAACTTAATGAGGTGATACTATG |
| TACGATGAACTGTATGAAGCTTACTTTAACTCTCTGGATGAAGGAGAAGA |
| GGTACTATCCTTTGCTGATTTTGTAGAGGCTAGGGGAGGTGCTGAATGAT |
| GACCTTGAATCTTAGAGAAGCTAGCGCGGTCTTTACTATGTTATGTTGGA |
| TGATACGTAACAACGAAATGATGACCGATGACGAGCTAGCGCTTTACCAC |
| CGCTTTCGTAATGAGGGCTGGGAAGATACAGTGAACAATGTGCGCGACAT |
| ACTGAAGGAGATAATCCATGTTTAAGCACACGATATACACGCAATGCTGC |
| AATTCAGTGGGCATTATGCGTTGGTGGGATGAGTCTAGTGTTAAGTGCTA |
| CAATTTGAATGATGATAGCACTATGTATGAGGTTACTCTCATTAAAAGAT |
| ATAACCACGACACGCTGTTATGGATTCTATCTGAATGGGAACTAACCTAT |
| GAAGATGTGATTACAGAAGAAATTTAAATTAACCATTGACTACCACGGCT |
| TACATAGGTTACATTAAGCACCAACAAGAAGTAACGATCTTTAACAATCT |
| GGATTGAAGCCGATTAGATAGAGGTTAACACATAGGAGGTTTACGAGCCT |
| CCTAGATGGTAACTTACTAAGAGGAAATAGAAATGGCAATGTCTAA |
| CATGACTTACAGCGACGTTTACAACCACGCTTACGGATTGCTGAAAGAAT |
| ACATTCGCTACGATGATGTACGCAACGAGGACGACCTGAGCGATAAATC |
| CACGAGGCCGCTGGTAATGCTGTTCCGCACTGGTACGCTGACATCTTTAG |
| CGTAATGGCTAGTGACGGTATTGACTTGGAGTTCGACGACTCTGGTCTGA |
| TGCCTGACACTAAGGACGTAACGTACATCCTTCAAGCTCGCATCCATGAA |
| CAACTCACGATTGACCTTTACGGGGACGCTGAAGACCTGCTTAATGAGTA |
| TTTAGAAGAGATTGAAGCTGAAGAAGACGAAGAAGAGGACGAATAAATGA |
| ACGGCAAACAATATACCTTTCAATTTTCTGATGGTATTACCTTGAAATGT |
| TCTCTAAGGTTCGCCATGATGCGAGAGGAAACATTAGGAACTAGTTATAA |
| ACTAGTTATGTGACACTATAAGATGATTAACAGGGTATTCTTGCGAGAGT |
| ACCCGATTAATCTAATTTGATGAGGCGATTATGAGTAAAGTAACAAACAT |
| TTTAGTCTCTATTGTAATCCTGTTAGTTGTGCTGTGGTCTGCAATAGGTT |
| CTAACTTCCAGTGGTTTAACACCTGCTATGAAGGAGATTTACACACTAAG |
| CACTTACAGTTTAATGGTGTTACAATATATTCCACCTTTGAAAACCATAA |
| AGATAACCCTTTTCATAAGTAATAGCCTATAGTGTCATTCGTGGCACTAT |
| GTGAAATTACTTAATAACATATGGAGAACATACCATGACTACTGAATACA |
| CCATTGTAACTCTTCGTGAAGCTGCAACCGCTGAAATCAAAGCACATTTA |
| GACACCATCGGCGCTTCCTATATCAAGATTGGTACTTGCTTAAACGAGCT |
| ACGCGCTGACTTTGACGGTCAAAAGGAGTTTTTAGCTTATGTTGAGGCTG |
| AATTCTCAATTAAGAAAGCACAATGCTATCACCTGATGAATGTAGCGCGT |
| GTTTTCGGTGAAGATGAGCGCTTTAAAAGGTGTGGCGATGCGTGTAATGTT |
| GGCGCTTATTCCGGTAGCTGATGAAGCCTCCGTAATGGGTAAGGCCGCAG |
| AACTGGCGGCTAATGGTGAGCTGGATACTAAGGCCGTAAATAAACTGCTT |
| GGAAAGCCTCAGGCCACGCCTAAATCTGAACCTAAGCAATCACATGGCGA |
| CGAAGAGAAAACGCCTGAGAGCGCCGCACAGGGAGCGCCTCAGCCATTGC |
| AGTCAGTACCTGAGGAGGAAGCGCCTTGGGATGAGACACCACGCAA |
| ACTGTGAAAGATGATTCACAGAAAGCACCTGAGACAGCCGCCGCGCCT |
| GGATAACGCTGAGACCGCAGACAGTGCGGCTATGGCTAGCCTGTTAGACC |
| AGATTAGCAAGCTGACAGAACAACTAACATTAGCTAACAACCGCATCGCG |
| GAGTTAACAAGCGCTCGTGAATCCAAGAAAGCAAGCGCTCCAATGCTCCC |
| ACAGTTTAAATCTTCATGTTTCTATGCTCGCTTAGGTCTGAGCGCGGAGG |
| AAGCAACCAAGAAAACAGCAGTTAACAAGGCTAAGCGTGAACTTGTTAAG |

| Bacteriophage Genome Sequences |
|---|
| CTAGGGTATGGTGAAGGTCATGAAGCGTGGGCCTTGATTAGCGAAGCAGT |
| AGAATCCTTAACTAAATAAAGTTGACTTATAGAGCGTCATTAAGTAAGAT |
| GGCGCTCAATTAAGTTTTCTAGTACCGCATGAGGATACAAGATGCAAGAT |
| TTACACGCTATCCAGCTTCAATTAGAAGAAGAGATGTTTAATGGTGGCAT |
| TCGTCGCTTCGAAGCAGATCAACAACGCCAGATTGCAGCAGGTAGCGAGA |
| GCGACACAGCATGGAACCGCCGCCTGTTGTCAGAACTTATTGCACCTATG |
| GCTGAAGGCATTCAGGCTTTATAAAGAAGAGTACGAAGGTAAGAAAGGTCG |
| TGCACCTCGCGCATTGGCTTTCTTACAATGTGTAGAAAATGAAGTTGCAG |
| CATACATCACTATGAAAGTTGTTATGGATATGCTGAATACGGATGCTACC |
| CTTCAGGCTATTGCAATGAGTGTAGCAGAACGCATTGAAGACCAAGTGCG |
| CTTTTCTAAGCTAGAAGGTCACGCCGCTAAATACTTTGAGAAGGTTAAGA |
| AGTCACTCAAGGCTAGCCGTACTAAGTCATATCGTCACGCTCATAACGTA |
| GCTAGTTGCTGAAAAATCAGTTGCAGAAAAGGACGCGGACTTTGACCG |
| TTGGGAGGCGTGGCCAAAAGAAACTCAATTGCAGATTGGTACTACCTTGC |
| TTGAAATCTTAGAAGGTAGCGTTTTCTATAATGGTGAACCTGTATTTATG |
| CGTGCTATGCGCACTTATGGCGGAAAGACTATTTACTACTTACAAACTTC |
| TGAAAGTGTAGGCCAGTGGATTAGCGCATTCAAAGAGCACGTAGCGCAAT |
| TAAGCCCAGCTTATGCCCCTTGCGTAATCCCTCCTCGTCCTTGGAGAACT |
| CCATTTAATGGAGGGTTCCATACTGAGAAGGTAGCTAGCCGTATCCGTCT |
| TGTAAAAGGTAACCGTGAGCATGTACGCAAGTTGACTCAAAAGCAAATGC |
| CAAAGGTTTATAAGGCTATCAACGCATTACAAAATACACAATGGCAAATC |
| AACAAGGATGTATTAGCAGTTATTGAAGAAGTAATCCGCTTAGACCTTGG |
| TTATGGTGTACCTTCCTTCAAGCCACTGATTGACAAGGAGAACAAGCCAG |
| CTAACCCGGTACCTGTTGAATTCCAACACCTGCGCGGTCGTGAACTGAAA |
| GAGATGCTATCACCTGAGCAGTGCAACAATTCATTAACTGGAAAGGCGA |
| ATGCGCGCCTATATACCGCAGAAACTAAGCGCGGTTCAAAGTCCGCC |
| CCGTTGTTCGCATGGTAGGACAGGCCCGTAAATATAGCGCCTTTGAATCC |
| ATTTACTTCGTGTACGCAATGGATAGCCGCAGCCGTGTCTATGTGCAATC |
| TAGCACGCTCTCTCCGCAGTCTAACGACTTAGGTAAGGCATTACTCCGCT |
| TTACCGAGGGACGCCCTGTGAATGGCGTAGAAGCGCTTAAATGGTTCTGC |
| ATCAATGGTGCTAACCTTTGGGGATGGGACAAGAAAACTTTTGATGTGCG |
| CGTGTCTAACGTATTAGATGAGGAATTCCAAGATATGTGTCGAGACATCC |
| CCGCAGACCCTCTCACATTCACCCAATGGGCTAAAGCTGATGCACCTTAT |
| GAATTCCTCGCTTGGTGCTTTGAGTATGCTCAATACCTTGATTTGGTGGA |
| TGAAGGAAGGGCCGACGAATTCCGCACTCACCTACCAGTACATCAGGACG |
| GGTCTTGTTCAGGCATTCGACTATCTGTATGCTTCGCGACGAAGTA |
| GGGGCCAAAGCTGTTAACCTGAAACCCTCCGATGCACCGCAGGATATCTA |
| TGGGGCGGTGGCGCAAGTGGTTATCAAGAAGAATGCGCTATATATGGATG |
| CGGACGATGCAACCACGTTTACTTCTGGTAGCGTCACGCTGTCCGGTACA |
| GAACTGCGAGCAATGGCTAGCGCATGGGATAGTATTGGTATTACCCGTAG |
| CTTAACCAAAAAGCCCGTGATGACCTTGCCATATGGTTCTACTCGCTTAA |
| CTTGCCGTGAATCTGTGATTGATTACATCGTAGACTTAGAGGAAAAAGAG |
| GCGCAGAAGGCAGTAGCGAAGGGCGGACGGCAAACAAGGTACATCCTTT |
| TGAAGACGATCGTCAAGATTACTTGACTCCGGGCGCAGCTTACAACTACA |
| TGACGGCACTAATCTGGCCTTCTATTTCTGAAGTAGTTAAGGCACCGATA |
| GTAGCTATGAAGATGATACGCCAGCTTGCACGCTTTGCAGCGAAACGTAA |
| TGAAGGCTGATGTACACCCTGCCTACTGGCTTCATCTTAGAACAGAAGA |
| TCATGGCAACCGAGATGCTACGCGTGCGTACCTGTCTGATGGGTGATATC |
| AAGATGTCCCTTCAGGTTGAAACGGATATCGTAGATGAAGCCGCTATGAT |
| GGGAGCAGCAGCTCACCTAATTTCGTACACGGTCATGACGCAAGTCACCTTA |
| TCCTTACCGTATGTGAATTGGTAGACAAGGGCGTAACTAGTATCGCTGTA |
| ATCCACGACTCTTTTGGTACTCATGCAGACAACACCCTCACTCTTAGAGT |
| GGCACTTAAAGGGCAGATGGTTGCAATGTATATTGATGGTAATGCGCTTC |
| AGAAATACTGGAGGAGCATGAAGAGCGCTGGATGGTTTGATCAGGTATC |
| GAAGTACCTGAGCAAGGGGAGTTCGACCTTAACGAAATCATGGATTCTGA |
| ATACGTATTTGCCTAATAGAACAATAAATATACAGGTCAGCCTTCGGGCT |
| GGCCTTTCTTTTAACTATTACCTGTAACATTTAATTAACAAGTCCAACG |
| TGTTGGACACGATGCGGATTTAAGGGACACTATAGGACTACCCGTCGGAA |
| ACGGAAAGTAATAGGTAATAAGGAAGTAGTAGGTAAGTAAGGTAATTA |
| TAGGTTACTTAGGTTACTCCTTCCTATTACCTCCTTCTTAATAGGAAGGG |
| CAGACACTAGGTTGTCAACGTGTTGGACAGAACTTATTTACGTGACACT |
| ATTGAACTAATCAACATTCAATTCATTGGAGAATTAATCATGCGTAACTT |
| TGAGAAACTGACCCGTAAGCCTGCTAATCGTTTTGGCATGGAGGAAGGGA |
| AGACAGGCGCCAAGCGTAACAAGCCTACCCGTGACCGTGTATCTAAGCGT |
| GCAGTGTGGGAGTACTAAGTTATGGCTATTATTAACAATATTCCGTGCCC |
| TGCCTGTCAAAAGAATGGACATGAATAAATCTGGCAATCATCTTATGATAT |
| TTGATGATGGCGCTGGTTACTGCAATCGTGACACTTCCATGATAGTGGC |
| AAGCCTTACTACCATAAGCGGAAGGTGGCATCGAAATCACCGAGCTACC |
| CATCACTGGCAATATCAAATACACCTTCTCAATTCAAAGAAATGGAGA |
| AGGAAGGGAAGATAAGTGACCCTAAACTTCGTGCTATCGCCTTGGGTGGT |
| ATGCGTATGAAGATCGTTGGAGGATGCTGATGAATGCGAGAAGAAGGGGA |
| GCAAGAATCTGAATCGCAGCTTGACGTTGAGTGGTTCCTTGAACTTAAAA |
| GGAAGAACCTTGTATCACGACACATTCGCGGAGACATTTGTGCGCTTTAT |
| GACGTCCGAGTAGGTCATGATGGAGAAGGAAGGTTAATAGGCACTACTA |
| CCCTCGCTTCGAAGGTGGCAAACTTGTGGGAGCTAAGTGCCGGACGCTAC |
| CTAAAGATTTCAAGTTTGGACATCTAGGTAAACTGTTTGGCAACAAGAC |
| ATGTTCGGTATGAATACCATGTCTAACGTGTTGGACAAGGGACGAAGGAA |

| Bacteriophage Genome Sequences |
|---|
| AGACACCCTGCTTATCGTGGGAGGTGAACTGGATGCACTAGCAGCACAGC |
| AGATGCTTCTGGATTCTGCCAAAGGTACGAAGTGGGAAGGTCAGCCTTAC |
| CATGTGTGGTCTATCAACAAGGGTGAGGCTTGCCTTGAAGAGATAGTACA |
| GAACCGTGAGCACATCTCTCAGTTCAAGAAGATTATGTGGGCGTTCGACG |
| GTGATGAAATAGGGCAGAAGCTTAACCAACAAGCGGCCCGCCTGTTCCCC |
| GGCAAGTCTTATATCATTGAGTACCCTGCGGGCTGCAAGGATGCTAACAA |
| GGCATTGATGGCTGGCAAATCCAAGGAGTTCGTAGATGCATGGTTCAATG |
| CCAAGTCATCAGATGAGGTTTTCGGTAGCCAGATTAAATCCATCGCCTCT |
| CAAAGGGACAAGCTGAAGGCTGCACGCCCTGAACCGGGATTATCTTGGCC |
| TTGGCCTAGGCTGAACAAGATAACCCTTGGCATCCGTAAGCATCAGCTAA |
| TCATCGTCGGCGCTGGTTCTGGTGTAGGTAAGACTGAGTTCCTCCGCGAA |
| GTAGTGAAGCACCTCATTGAAGAACATGGAGAGTCGGTAGGTATTATCTC |
| CACTGAAGACCCTATGGTTAAGGTCTCCCGCGCATTCATTGGTAAATGGA |
| TTGATAAGCGTATTGAACTACCTCCAACCAATGACCCAAGAGAAGATGGA |
| TACCGTGAGGTCTTTGATTATACCGAAGAGGAAGCCAACGCTGCCATTGA |
| CTACGTTGCTGACACTGGTAAGCTTTTTGTAGCTGACCTTGAAGGTGACT |
| ATTCTATGGAGAAGGTAGAGCAGACGTGCCTTGAGTTTGAGGCAATGGGT |
| ATTTCTAACATCATCATTGATAACTTAACAGGAATTAAATTAGATGAACG |
| AAATTTTGGTGGTAAAGTTGGTGCGCTTGATGAGTGCGTCAAAAGGATTG |
| GCACTATCAAAGACCGACATCCGGTTACTATCTTCCTTGTCTCGCACCTT |
| ACACGTCCTTCAGGACAACGTACCTCACACGAAGAAGGTGGCGAGGTTAT |
| CCTTTCTGACTTCCGAGGCTCAGGGGCTATCGGATTCTGGGCTTCTTACG |
| CCTTGGGGATTGAGCGTAATACAAGAGCTGAAACGCTTGATGAAAGGACT |
| ACCACGTACATCTCATGTGTCAAAGATCGAGACCAAGAGCATTCTACACTGG |
| TACTAAAGTGATGCTCAAAGGGGATGTTAGTACCGGCAGATTAATGGAAC |
| CACAATCACGTACTAAATCATTTGATACAGGTGCTCCAAAAGAGCAAGCT |
| GTGCCTGATGAATTAGGTGACACTATAGAAGAGAACACACAGGAGTTTAA |
| TGGATGATTTAGGTTTTGGTTGTTCGCTACCGTACTACTTGTTATTAACA |
| TAGACAAGGTTGCTATGTTATTCAAATAGTGTACTTATCAGGGTTTGTCT |
| AACATGTTGGACAAACTCTTATTAAGTACATTAACTAACTGGAGATTATT |
| ATGTGTAAATTGCACCTCAACAAATCAGATTGTGTGCGTAACATTAACAA |
| GAGATCTATCCGCTTCGCTGGGAGGGTGTAGTGTTTGAGTAGATGAGA |
| GATACTACCATGTAGTGTATGTAATGGATTACGTCAAACTTATCTGAAG |
| GCTCTGGCGCATCATTACCTTGAACCGATTGAACCAACTAAGAGTAACTG |
| CACCTGTGTACACGATGATCTGTGTGATCGCTGTGCTCGTCAAGTTAATA |
| AGGCATTGACAATCATGGAGCGTTACGGTGCAGGCCACAAGGCAATCTCT |
| GAGGCTGCGTGGACTGTACTCATGTTTGAACGCCCTAATGGTCGTAAGGT |
| GCTGAATCGTGAGCGGCGTAATGTAATCACAGGTCAAGACTTTCGCATCT |
| TAGAGGAGGCTATGTGTAATCCTGGTATTGCTATACGTTATGAGGATGTA |
| GACCATGCTATATCTGAAGGTATCGGTAATCGTTTGGAATTGAATAAGCA |
| TTTTGATCAGGTATTACGTGACACTATAGGTGGGCGCAAAGGTTTTACCT |
| TTGAGCGCGGGCATGTTACATTTAACCCTATCGTTACGGAGGAAACCTAT |
| GTCACGCAATGACAGTAAGTACAGCCTGAAGTTCTTGAGCAGCATGAAG |
| AACTTGCAGCCAAGGTAACTAACCAAGCATTCCTGTTTGCACAACTAACG |
| CTGGCTGAAGCTAAGAACACAGCCTTTACGCGTGAGCAGATTATCAAGGA |
| AGGAACCAAGCGCAGTTAATAAGTCGTGACTTGTCTAACATGTTGGACAG |
| GTCACTCTCATATTAATTGGAGATACATAAATGACTAAAGTAACTAAGTT |
| AACCGAACACCTGATTAAACTAAGTGAAGAACTAAAGAACAGCGAAGTTA |
| GGCTTGAGTATTACTTCATTGACCCAAGGGAAGATGATGCTGAAGAACTT |
| GACTACAAGTTTGAAACGGAGTTAATGTATGAAACATATTAATTGGGCGA |
| AGGAAGCAGAAGGACGTATCCTAGTAATGGATGCGGAGGCTAAAGGCTTA |
| CTTGATGCAATCCGATATGGAAAAGGTAACGATGACGTGCATATAATTTG |
| CTGCATGGACTTGCTCACCACTGAAGAGTTTCTTCTTCAACCCATATG |
| ACCGTCGTGACCCTAACGCCAAGGGAGCACCTGAAGGAGTGGGAATGGTCAT |
| CAGGACGGTGACCTTGAAGATGGTGTGAGATTCCTCAAGCACTGTGAAGC |
| TATCGTGTCACAGAACTTCCTCGGCTATGACGGCTTGCTTTTTGAGAAGG |
| CATTCCCCGATAAGGAAAGGCTATAACTACACGGAGAAGCGCGGCAAA |
| GGCCGTCTGCGGGCCGATCTGTGCCCGGTTAAGGTAATGATAGCCCTTGT |
| CATGTCAAGGCTCCTGAACCCGGATAGGCGACTCCCTCCGCAGGCATACG |
| CTAAGGGTATGGGTAACGTTGCACCTCACTCTATTGAGGCACACGGTATC |
| CGTATAGGTCGCTATAAGCCTGAGACAGGACTGGTCTAAGCTGACAGA |
| CCACATGGTGCACCGAGTACGTGAGGATGTGGCGATCGGTCGTGACCTGT |
| TCCTGTGGCTGTACAACGGCGAGTGGATGGAGCACAAGCGGCGTGGCGTC |
| AATCCAAGGACTGGTCTTGGCATTGAGACAGCCTTCCACATGGAGTCCAT |
| TGTAGCACTGGAGATGTCTCGTCAAGCGGAGCGCGGCTTCCGGCTGGATA |
| TAGACAAGGCACTGGCACGATGCGAGGAGCTTGACCAGAAGATTGACGAG |
| ACTGTTGCAGCCTTCCGGCCTCACATGCCAATGCGCATCAAGTCTAAGCC |
| TTTCAAACCTCAAGAGAAACAGGAGCAAGTAGATGCGGCAAACTCATTTA |
| GTTTACAGAATCATACTGGCGTTACACTTGGAGCCGATGCTTTCATTCAT |
| GCCGAGCGGCGCTCCGATAGAAAGACTGTATGGTCAGTCACTACTAAGTC |
| AGGTGATTGGTCAGCTACTGTCAAGAAAGACTTCCCTCACATCCGAGGA |
| ACATCAATGATACTCCGAGTATTAAACACATCGGGCCATATACACCTGTC |
| ACCTTCGAAGATATCCCGCTTGGTAACCGAGACACAGTTAAGCAGGTTCT |
| GTATGACTTTGGGTGGAGGGGAGTTGAGTTCAACGACACTGAGCAATCTT |
| ATCTGGACGAGCATGGAGTGTTGCCTAAGCCGTGGAGTGGAAAGATAAAT |
| GAGAAGTCCCTTACTTTATGGCAGGAAAGGGCTGCACGTGAAGGTAAGTC |
| AGTACCTGATTGGTGCTTGGGTATCGCTGCATGGTACACTACTCGTATCCC |
| GTCGTGGTCAGATCCTCAACCGTGGTGATGTTGAAACCTTCGATTCAACG |
| GGGCGTTGGCCCTCGCAAGCTGGTGTACGAAAGTGTCGCGGCCTCGTACC |
| TGTAGCCTTTAACAAGGAGCTAGGTATCAATGCACAGGCATACTACGAAA |
| CATATGGCTACTGGCCTACGTCCGACAAGGATGATGGAGAGTGGCGTGTT |
| CCCGCTGTTGCTATTTCTATTGGCACTTCTACGTTCCGTATGCGTCACAG |
| GAATGTGGTTAACATCCCCGCTCGCGGTCTTTACCCTCTTCGTGATTTAT |
| TTATAGCTGGTAAAGGTAAGATGATTCTTGGTTGTGATGGTGCAGGACTG |
| GAGTTGCGTGTGTTATCACACTTCATGAATGACCCTGAATACCAAGAGAT |
| TGTACTGCATGGTGACATCCATACACACAACCAACTTAAGGCTGGTTTAC |
| CTAAGCGTGACATGGCGAAGACTTTTATCTACGCATTCTTGTATGGCTCT |
| GGTATTGCCAACCTTGCCGCTGTATGTGGTGTAACTGAAGATGAGATGAA |
| GGAGGTTGTTGCACGGTTCGAGATCGAACTACCATCACTGGCTCGTCTTC |
| GTGAGAATGTCATCGCTGCTGGTAATAAGTTTGGATACCTGCAAGCACCT |
| GATGGTCATTGGGGCGCATCCGTATGAGTGGTGGTGAGCTTAAAGAACAA |
| CACCATGCTCAACGTATTACTTCACATGACAGGCTCCTTGTGTATGAAAT |
| ATGCTTGGTTAAAGACCTTTGCAGTCATGCGCCGTGAAGGTGTTGCACTG |
| GATAACCTGGGGAATCCGTGTGGCGTGGCTAACGTACACGATGAAATCCA |
| GATGGAAGTGCCAGAAGAGGAGGTGTTATACCTTGACTATGAATTACCTT |
| TCACGTTGGAAGGTTTCGAATCTGAGAAGCAAGCTATCAAAGCTGTGTTC |
| GACCCTGAAGAGAAGACGCGTACATGTGGATTCCGAAGGGCGCATGTGGTC |
| TGCTGCTAACTTGGTTGAAGTGGATACTGCTGCTGGCGTGCTGCGTTGTC |
| AGCGCTGCTACCACAGGGCTGGTCATATTATCGCTGACGCCATGACATGG |
| GCTGGTAAGTACCTGAATATGCGCTGCCCTATGGCTGGCGAGTACAAAAT |
| AGGTGCAAGCTGGAAGGAGACACACTAATGCAAACTGCTCTTATTATTCT |
| TGGAGTGCATATTATTTATGTAGTGTTCTGGGCCTTCTCTGGTATTGACC |
| CAGATTACGATGGTAACTACGACTGAGTTATACTCAAGGTCACTTACGAG |
| TGGCCTTTATGAATAACTTAACTGGAGATTATTATGATTAAATATTGCTT |
| ATCAATTAACTAAAGACCGTAAGAACATTATTGAGGTTAAAGCCTGGAC |
| GCGGGACACATCTCTGTAGTTATAGAGTGCCGCCAAGACAATGGTATGCT |
| GTTAAGAAGCTACCGTTGCTTCACCCAAATTACGCTGCAAAGATTTAACTG |
| AAGAATTATTCTTACGTTGTATTGTTGAATCTATTAAACTTATTAGACCT |
| TACGCTAAGCAAGTTGTAGGTAAGTGTCACAGTGGTAAATTGATTTAGGTG |
| ACACTATAGGAGGAAGACCTAGGTAATCTAGGTTTATAATGTAGTATAGG |
| TAATTAAGTAAATATAGGAGATATAAACATGTCAATGGTAACTACTCTGG |
| TATTCGTGGCTCAATACTTTCGTGGTCTGGCTAATAAGTTCAAGTACAAA |
| GCTATTGAAGCTATTGAGGACCGCATCGAAGCAGTACAGGCAGAACAAGT |
| TGAAGTTGAAGAACATCGTAGTTCTCAAATGATTGACTGCCCATAATCGCT |
| ATTACGCATCTCGTGATGACCTTAATGCACGACAAGTCAAAGAGGTCGAA |
| GAGATGATGGCACGTCACCAGCAAGAGCGTGACAACCTGAAGGCTGACTT |
| TGAAGAGCGCAAGGCATCCATTGCCCTTGTACATCAAGCTGCATCTGACA |
| GCCTGAAGAAAGAGATTGTTACTGCGGAAGGTGAGTTAGACAATCTGACC |
| AAATAATTAGGTGACACTATAGAACAATAGGACGTGGGTTTGTCGGAGAC |
| AGTAAATCCAAGGTGCTCAGTGAGCGTAAAGCCTAAGCACGTCCTATGAT |
| TGTAAAGTGTTGAACCTCTTGTGCATCTTGCACAACCCGATACAGTATCG |
| GGCTTTCTAGTGATACATGCTTGTGCTCAGTACAAAGCTAACAAACAAC |
| AGGAGGAATAAATTAATGGCTCGTAATTTTGATTTTGGTGCTGAGGTTGC |
| TGCTGCTACTGGTGGTGTGTTTAAGAATCCAGAAGTTGGTGATCACGAGG |
| CAGTTATCTCTGGAATCATTCACGTTGGTTCCTTCCAAGACATCTTTAAG |
| AAAGGTAACACTACCGAGGTGAGAAGCCTGCTAACTTCGTTCTTGTTAA |
| GGTTATCCTGATGGGTGACGATGACAAGAACGAGGATGGTTCTCGTATGG |
| AACAGTGGATGGCTGTGCCGCTCAAGTCTGGTGACAAGGCGACGCTGACC |
| AAGTTCCTGAATGCAGTTGACCCTAAAGAATTACTAGGTGGTTTCGATGA |
| CTTCATCGGCGAGTGCATGACTGTGAGCATGGTTGACGATGAAGGAGGTG |
| GCAAGAATGATGACGACGACGCACCTCTCAAGTACGTTAACTGGAAAGGCTTCGGT |
| GGTATGCCGGATAAATTGAAGAAGCTGGTACTGGCTCAGGTAGAGGATGA |
| AGGTCTGGAAATGACTGGTCACATCACCTTTGACAAGCTGACCAAAGATA |
| TCATCGACTCTATTCTGCACCACCTTTACGCAGTACCTCGTGAACGAG |
| ACGCCGCGTGGTAAGAACCTGTCAGTAGTTGGTTCTCATGTAGAGGGTAT |
| CATTGCCGAAGCACGCGCAGCAGACCCTGAGTGGAAGAAGGCCAAGAAGA |
| AAGACAATGAGGCCACCCCTGAAGACCGCAAGACGCTGGACACTGGCGCT |
| GCTGTTCCGCAGGAAGTACCGGAAGCGCAGAATGCCCCGGCACCTGCTAT |
| GGATGAAGATGCTGAATAATAATCAAGGAGGTTTAATGAAAGTAGAAGCA |
| GTAACCCTACACTTCAAGCCCGGCGTAACGTCGCTGGGCGGCACGCAGTT |
| CATTTCTTTTAGCGAGGGCAAGGCCTACCAAGACCTGCACTATATTACCC |
| GTGAGGGGCAGCACGTCGTGAATTACAGCGACCCTGTGACAGGCAAACGT |
| CACGCATTGATTCCCTATGACGGACATCCGTCAGACCAATACAGATTTT |
| GTAAGTCTAACGCGTTGGACAAATCTGTGTCTCTTATTTAGGGGACACTA |
| TAGAAGAGAATTTTAATCGGCGATAATGCCACAATTAACAGAAGGAGA |
| ATTTAAATATGTTCACTATCGAAACTATCGTAAACCGTGTTGTTAAAGGC |
| GCTACCTTGGTATCCGTTGAGTCTTTCATTATCGTCGATGAAGCTGGCTC |
| GCTGGTAGCTGGCACCAAAGCATACGACACCCGCGAAGAAGCTCAAGCTA |
| AGATTGACAGCATGGGTAACTTTGCTACTGGCCTGTCGGAGGTTTTGCGTGCT |
| TGCTTCCCTGAGCAGGCTGACAAAGCACAGATTGGTAAGGCTAACATTGT |
| AGCTGAATATCTGGATTGGATTGCTGCTGGTAAGCAGTGAAAGAAGTTA |
| AGTCTGCTGAAGAAGCTGAAGCTCCGGCAGTGGAAGCTGCACCGGAAGCT |
| CCGGTTAGCGAAGAAGAAGAGTTTTAATTGATGCCCTGTCTGCCTTAGTG |
| TAGGCAGGGTCTTTTTGCGTAATAGTTATTGGAGAATGAATTATGCCGACT |

| Bacteriophage Genome Sequences |
|---|
| ATTAGATCTCGTTTAGTAGCAGATTATGTGTATGGTCGTGATGTCAAAT |
| GATGAAAGATTACCTCAAAGTTATTATCTTGCTTGATGGGGAGTTGTTTC |
| ATACTAAAACCTTCACCCTTCCTGAGTTATTTGACTTAGGATATTGGGGT |
| TATACCTATCAGGCCATAGCAAATAAGGTGCTACTCGATGTATTAAAGGA |
| GTGGCCTACATGCGACCAAACTTCAACTTCGGAGCTACAGTATCGGAAGA |
| CAATAATCTCATCCTGTGGCCGACTGAAGGTAAGAGAATCGCTCTCATAG |
| ATGGAGATATGATTCCATACATCATTGGTTATACTATCAATGAGATGACA |
| CTTGTCCGAGCGATGACCCGCGTTAAGTCAGGGCAAGTAGAGCGCATCGA |
| AGATACACCTGAGTGTAAGCAAGCTTGCGACCGTGTAAACTCTATGCTTA |
| ACTCTTGGGTGTATGGTGCTGAATGTGATGCCGCACGCATCTTCCTCACC |
| AAGTCAGATACTAACTTCCGCCTACGCTTGGCTTTCACGAAACCATACAA |
| AGGTACACGAAAGGCAGACAAGCCTCCTTTCTTCTATGAGATGCGACAAC |
| ACCTGATAAGTGTGCATGGTGCAGAACTGGCAGATGGGGAGGAAGCAGAT |
| GACTTGATGAGTATCGCACAATGGGATAGCCACAACCGATTCTTGCAAGA |
| AGTAGGTAACGAGTTCTCAATAGGAAGCCCTGAGCATAAGGTGTTCTCCG |
| ATACCGTTATTGTATCTGCGGATAAAGACCTGATGATGATACCGGGGTGG |
| CACTTGCAGCCGGGAAGTGAAATGAAGTGGGGTTAAACCTATGGGTTGGCT |
| TGACCTTCGTCGTAAGAATAACGGGCAGGTCAAAGACCTTAAAGGTGCAG |
| GACTAAAGTTCTTCTATGCACAAATGATTATAGGTGACGACATAGATAAC |
| TATGCAGGCATCCCAGGACGTGGGGCCAAGTACGCTTATGACCTCCTTGA |
| TAGTTGCAAGACTGAGAAGGAACTCTATATGCTGTGCTTGGTGCCTACA |
| AGTCTAAGTTTGGAGAAGGGCCAGTCAAGCTCAAGAACCATAGAGGAACC |
| TACCGCATCGGCAAGGCTTTTGATCTGATGTTAGAATGTGGCCGCTTGGC |
| TCATATGGCACAATTCAAAGGTGACATCTGGCGTGCAGGATAAGAATCCAA |
| TTGTGTGGGGAGATGATGATTCATGGCAATCAGATTGAAGGCTTCGGAGG |
| TAGCTGACTACAAGAAAGAGCTACTAGAGAAGCAGAAATGGAAGTGCCCT |
| TTATGTGGCGGCAGCCTCAAGGCTGTCACTGCAATTAACCGTGTACTTGA |
| CCATGACCATGACAGGCTTCTGTCGTGCAGTGGTTTGTCGTGGCTGCA |
| ATGGTGCGGAGGGTAAGATCTTAGGTGTTATTTCTGGTTATGGTAAGGCA |
| GGTAACAATCGCTACTTCCAACTGAAGTGGCTGGAGAACTTGTATACATA |
| CTGGAAGTTACATCAAACACCTCAGACGGATAAGTTGTATCATAAGCATA |
| AGACTGAGGCGGAAGAGCGCGAGGCTCGCAATCGCAAGGCTGCTTGGCA |
| TACGCAAGAAAGAAGGAGGGTAAAGTTGGGTAAGCTACGCTCACTGTATA |
| AGGACTCCGAGGTACTTGATGCAATGAGCAGGCTACCGACGAGAAAGGT |
| AATGTTAATTATAACGAGATGGCTCGCGTACTTTCTGCGCATCCTGTCGG |
| CAAGAAGATTACACGGCAGCTTGCTCGTTACTGGCATGGTCAATTCATGC |
| ATACCAAGAAGAACGGTGACTACTACCAGACTCTTTCTCAGGAGGATAGG |
| CGACTCAAAGAAGCACGTAAGCTCAGGACTCCTGACCGCTATGAGGATCT |
| GGCTATTGTACCATTGCCTGACTCGCCTCATAGAAGTGTACTGGTGATCC |
| CTGATACCCATGCACCTTATGAACACCCAGATACCTTGGAGTTCTTGCA |
| GCAGTGGCGGCACGCTTCCGTCCTGATACGGTGGTTCACTTAGGAGATGA |
| GGCAGACAAACATGCCTTGTCATTCCACGATAGTGACCCTAACCTTGACT |
| CCGCTGGTGTGGAGTTGGAGAAGGCACGTGCCTTCATGCACAAGCTGCAC |
| CGGATGTTCCCGGTCATGCGCCTGTGCCACTCCAATCATGGTTCTATGCA |
| CTTCCGCAAGGCAAGCGCCAAGGGCATCCCTGTCCAATATCTGCGCACTT |
| ACCGAGAAGTCTTCTTCCCGCATGGTGGCGGCGACCAATGGGATTGGCA |
| CACACTCATGTCCTGGAGTTACCTAACGGGGAGCAGGTTGCATTCAAGCA |
| TCAACCAGCAGGTTCTGTGTTAGCAGATGCGGCACATGAGCGAATGAATC |
| TGGTGTGCGGCCACTTGCATGGTAAGATGTCAGTGGAGTTGTCACGTAAC |
| ACACATGAGCAATATTGGGCTGTGCATGGTGGCTGTCTTATTGACGAGTC |
| GTCTCGCGCATTTGCTTATGGCCGTGAGTCCAAGTATAAGCCAGCATTAG |
| GTTGTGTGGTGATTGTAGAGGGTGTACCTCAGATTGTTCCAATGCAGACC |
| AATGCAGAAGGTCGTTGGATTGGCAGGATTTAAGTGACACTATAGAACAA |
| AGGGTCAGGTAATACTTATCGGCTGGCATATCCAAATGATATTGCACTGG |
| CCCTTGATTGTATAGTGAATGGAGGAATTAATTATGTCAGAAATTGATAT |
| TGGTAAGTACGTTGTACGCCGTGCAGCTTATCGAGATGCCTTCTGGAATA |
| AACTGTGTGAAAGCTTAAACAAGCAACCAGATGGGGTGTTCAAAGTGTCC |
| AGTGTAGAACTTAACTACAACTCTATCATGTTAGAAGGTGTGGAGAAACG |
| CGAATGGTATGCACCTTATTTCCAGGTCGTTGACTCCCTGCAAGGCGAAG |
| AGTCCAACATGTTGGACAACAACATGGTTACTAAGCCTAAGCACTATGAG |
| TTCTTCGAGGGTGTCGAGGCAATCACTATCATTGCCCGTAGCATGACCGA |
| GAAGCAATTTGCTGGTTACTGCATGGGTAATGCATTGAAGTACCGTCTGC |
| GTGCAGGTAAGAAGTTCAATACTGAGGAAGACCTGAAGAAACGCAGACTAC |
| TACAAAGACCTGTTCCAGAAGCATCGCCATGAATGTATTGATGAGGATCT |
| CTAATGAATATCTTCCAATTCCTAGGTTTACCTGAAGATCATCGTTCCAA |
| ACCTGTTATGCTGGTTAAGCACAGGGATGAAGTGCCAGAAAGCAAACTTA |
| CATTCCCGGTTTATGCAAGTGAAAAGAGATGGAAATATTTAGTGCTACTA |
| GTTGTGCGTTCTGATGGTACTGTGGGTATCTTTGGTCGCACTGGCAAAAA |
| GCTGGTTAATGTAGAACAACTGGAAGCGTCTTTTATAGGGTGGCCTGCTG |
| GTGTCTACCTCGGTGAGTTGCAATCTATGGCCGTTGATATCTACCTTGAG |
| GCGCTTTCGGGTGTGGTGAATCCAAACAGGACTGAGCCTCTTGACTTCAT |
| AGGACAGCAGATTAAAGATAACCTGTACATTGACTTCTTTGATATGCTGA |
| CTATTAAGGCATTCATCGAAGGGCAGACGGAGGTTACATTCTTAAAGCGA |
| TATGAAGCTCTATGTCGCAGATTGAAAGGTTGCCTTCCACCTGAGAATGC |
| AATCCTGACTATCACACCTTGCCACACCGAGCAAGAGGTAGAGGCGTTTG |
| CACAGAAGCACATTGATGCGGGCGAGAAGGTGCAGTCTTTAAGTTAGAC |
| TGTGACTATGAAGCGGGCCACAAGGGCTTCCGACAGACCAAGATTGTACG |
| CATGGTCTCATACGACTTAACGTGTATTGGTTGGGAAGAGGGGAAAGGTA |
| AATACAAAGGTAAAGTAGCTAATCTTATATTTAAATGGAAGGGTGGCAAG |
| ACAATCAAGGCTATGCTTGGCCGTGGCTGGACACATGAAGATGCCACCCG |
| TATGTATCACGATATTAAACACGGTGGTGAACTGAACGTCATCGGGAAGA |
| TATTCGCTATCAAGGCTCTCCAAGAATCTAGCAAGGGAGTCCTGCGACTT |
| CCCAAGGTTGGAGAGTTGCGCCATGACAAGGAGGAGCCTGATGTCTTTTG |
| ATTCAATGAAAGCGACAAAGGCAGTTGAGGTAGCAGAAGCTATCTTTGAT |
| ATGCTGTCTTGTGGGATTGAAGTCCCTTATACACTTCTGTCTGATGCAGA |
| AGATTTAGGTCTGTCTGTGGAAGCTATCCGCGAGAAAGTGGAGGAGTTGT |
| ATGGCGACGACCAAGAAGCCGACTATCAATATTGAAGGTTGGGATATGCT |
| GGAGAAAATTATACTTGCTCCATCAAGACCTCGACCGGATAAGTCACACG |
| AAGAGTTAGTATGGGATGAAGCCAAGCGCTATATCCTGCTTCTTGTATCAAG |
| CAGCAGTTTGTGGTGCAGCCATGATAAGGCAGGCTTGCTTCCTAGATATC |
| CCTGAGATAATTAATCTAGGGAACAGGTATGTAGAAGAGGAAGTCAAGGT |
| AGTTAAGCATCATTCAGCTACATGGGATGCAGATCAAAGCGCACATCACC |
| TTTGTGCATCCCTTACCAGCAAGGATTTATTTCTATGGGTGGCTGTGGAA |
| GATGGTGTTATCATAGGTTTCCTGTGGGCGGCGGCTCACATCATGGCACC |
| TTGGTCTCCGGCACTTGTGGCTTCTGATCTACTATTCTACATCATACCAG |
| AAAAGCGAGGGTCTCTTGCTGGTGTTGCGCTTGCTCAAAGCTTACAAGTCT |
| TGGGGCCAAGGACGCGGCTGCATAGAGGCAAGGTTGTCTATCGCATCTGG |
| TATCAATGAGGAACGTGTGGGGCGGATGTATAGTCGATTAGGGTTTACTC |
| CGTTCGGTACAGTGTATAACTTGAAGTTTTAAGGAGATAACATGGGTGTA |
| GTTAAGAAGGCATTTCAAGCAGTAGGTCTGGCACAAAAGGCACCTCGCAT |
| TGAGGCAGCTAAGGTTCCAGCACAACAACTTGAGCGGCAGACTGAGGTTA |
| AATCTGAAGACATCCAGATTGGACAAGAGGATGATGCTGCGGCATCTGCT |
| AAGGGCAAGCGTGGCCTTGTGCGCCCTGTAGCCTCTAGCTTAGGAGTTTG |
| ATATGCAAGACACTATACTTGAGTATGGTGGACAGCGATCGAAGATACCT |
| AAACTATGGGAGAAGTTTTCTAAGAAACGCAGTCCCTACCTTGACAGGGC |
| AAAGCATTTCGCTAAGTTAACACTCCCATACCTGATGACAACAAGGGAG |
| ACAATGAGACCTCGCAGAATGGTTGGCAGGGTGTAGGTGCACAAGCTACC |
| AATCACCTAGCTAACAAGCTGGCACAAGTGCTATTCCCTGCGCAACGATC |
| ATTCTTCCGTGTTGATTTAACAGCAAAAGTGGAGAAGGTATTAGATGACC |
| GAGGGCTGAAGAAAACTCAGCTAGCAACCATCTTCGCTCGCGTAGAAACC |
| ACTGCAATGAAGGCGCTGGAGCAAAGGCAATTCCGCCCAGCTATAGTTGA |
| GGTGTTCAAGCACTTAATCGTAGCGGGTAATTGCCTGTTGTACAAACCAA |
| GCAAAGGTGCGATGAGTGCATGAGCCACCACTACGTAGTCAACCGT |
| GACACTAACGCGACTTGATGGATGTAATCCTTCTACAAGAGAAAGCGCT |
| ACGTACATTCGACCCAGCAACTCGCATGGCAATAGAGGTTGGGATGAAAG |
| GTAAGAAGTGCAAAGAGGATGATAACGTCAAACTGTACACTCATGCGCAA |
| TATGCAGGTGAAGGTTTCTGGAAGATTAATCAATCTGCTGACGACATCCC |
| GGTAGGCAAGGAGAGCCGCATCAAGTCCGAGAAGCTACCATTCATTCCAC |
| TTACATGGAAGCGCAGTTATGGCGAGGTTGGGGCCGTCCCTTGGCTGAG |
| GATTATTCTGGTGACTTGTTTGTTATACAGTTCTTATCTGAGGCCATGGC |
| CCGTGGGGCTGCACTGATGGCAGATATCAAGTACCTGATTGGACCCGGTT |
| CACAAACTGATGTTGATCACTTTGTTAACTCAGGTACAGGTGAGGTCATC |
| ACAGGTGTTGCGGAAGACATCCACAATTGTTCAGTTGGGTAAGTATGCAGA |
| CCTGACACCTATCAGCGCTGTGCTGGAAGTATACACCCGACGCATCGGTG |
| TCATCTTCATGATGGAGACCATGACACGCCGTGACGCTGAACGTGTTACT |
| GCCGTAGAAATACATGCGCGCGCTTGAGATTGAGCAGAATATGGGTGG |
| TGTATATTCCCTGTTTGCCATGACCATGCAGACACCTATTGCCATGTGGG |
| GCTTGCAAGAGGCAGGTGATTCATTCACTAGTGAACTGGTAGACCCTGTG |
| ATTGTAACAGGTATTGAAGCACTAGGCCGCATGGCTGAATTGGATAAGCT |
| GGCTAACTTTGCACAGTATATGTCTTACCTCAAACATGGCCTGAACCTG |
| CACAACGTGCAATCCGATGGGTGATTACATGGATTGGGTGCGTGGTCAG |
| ATATCTGCGGAACTCCCATTCCTCAAGTCTGAGGAGGAGATGCAACAAGA |
| AATGGCACAGCAAGCACAGGCCCAGCAAGAGGCCATGCTCAACGAAGGTG |
| TGGCTAAGGCCGTACCGGGTGTTATTCAACAAGAAATGAAGGAGGGTTAA |
| TTAGTGGCCTTTGAATTTGTAGAACCACAATGAAATACCGTCCTGCTCC |
| GGCTGCTGAAGAGAACAAGGAGGTGACTAATGATGTTGCTGGTGTTGACG |
| CTGGTAATACTGGCATTGACGTACAGAATGGTGCAGATGATCAAGGCAAT |
| GAGGACACCGGAGGGAAGCTGTTGGACAGCCTTCAGGAGGGGAGATGG |
| TGAACCGATGGTAAACCTAAGCCAGATGGTTCCACGGATGAGGAAGCGC |
| GATACTTCTTCGGTGAACATGAAGTAATCATTGAAGTGCCTGATGATGTG |
| ACCGAAGCTCTCAAAGAGAAGGGCATCGACGCTATGCAGGTGGCTCGTGA |
| GTTGTATGGTGAAGGTGGTAGATTTGAACTGTCAGAAGAAACCAAGCAGA |
| AACTGTATGATGCATTTGGTAAGTTCGCAGTAGATGCCTACCTATCTGGC |
| CTCAAGGCTCAGAACGAAACCTTTTTCCTCCGTGAAGAAACTGCCGCCAA |
| GGAGGCGGAAGCTGCAAACGCACAGCGCTACACGGATATTGCCAAGGAGG |
| TTGCGGTGACAAGGCTGGAGCCGTCTGGAGGAGTGGGCGCTTGATACT |
| CTTTCTGATGAAGAACTGGAAGCATTTAATGCAGTGATGCAGTCTGGCAA |
| CCAATATCTACAGCAGTACGCTGTGCGCGAGTTGAAGGTCGCCGTAAGG |
| CTGCACAGGGTGACGATAAACCTAACCTTATTGAACCAACGGCTACCGCT |
| GCTGCATCGGAAGATAATGCACCTCTAAGTCGGGAGCAGTACATCCGAGA |
| GATTGCACAGTTAGGCCAGAAGTATGGACGTGACCGCAAAGGGATGGCTG |
| AAGCACAGGCACGTCTGGATGCACGTCGCCGCGCAGGTATGGCTCGCGGT |
| CTTTAATTGCCTATTTAGGTGACACTATAGAAGGGAGGTAGTCCTCCCTA |
| ACCTATCAACTTGATTTATAAGGAGATTATAATACATGTCTACGCCGAAC |

| Bacteriophage Genome Sequences |
|---|
| AACTTGACCAACGTTGCCGTTTCCGCTTCCGGGGAAGTAGATAGTCTTCT
CATTGAGAAGTTCAACGGTAAGGTCAACGAGCAGTACCTGAAGGGCGAAA
ACATCATGTCCTACTTCGACGTGCAGACCTCACGGGAACCAACACTGTG
AGCAACAAATACTTGGGTGAAACCGAGTTGCAGGTATTAGCACCGGGTCA
GTCTCCGGCTGCGACCTCTACTCAGGCCGATAAAAACCAGTTGGTAATCG
ATGCCACTGTTATTGCCCGTAACACAGTTGCACACCTGCACGATGTACAG
GGCGACATTGATAGCCTGAAGCCGCAAGCTGGCTACCAACCAAGCCAAGCA
ACTGAAGCGTATGGAAGATGAGATGCTGATTCAGCAGATGATGTTGGGCG
GTATTGCCAACACTCAAGCTAAACGTACTAACCCGCGTGTTAAGGGTCAT
GGCTTCTCTATCAACGTAGAGGTTGCAGAAGGTGAAGCGCTGGTCAACCC
TCAGTACGTAATGCTGCTGTAGAGTTCGCGCTGGAACAGCAGTTAGAGC
AGGAAGTGGACATCTCCGATGTGGCTATCCTGATGCCGTGGCGCTATTTC
AACGTACTGCGTGATGCAGACCGTATCGTTGACAAGACCTACACCATCAG
TCAGTCTGGTGCAACCATTCAGGGCTTCACCCTGTCCAGCTACAACTGCC
CGGTAATTCCGTCTAACCGTTTCCCTAAATATTCTCAAGGTCAAACTCAT
CACCTGTTGTCCAATGAGGATAACGGCTATCGTTATGACCCGCTCCCGGC
AATGAATGGTGCTATCGCTGTCTTGTTTACGGCGGATGCGCTGCTGGTTG
GTCGCTCTATCGATGTGACTGGTGACATCTTCTATGAGAAGAAAGAGAAG
ACCTACTACATTGATACCTTCATGGCTGAAGGTGCAATCCCTGACCGTTG
GGAGGCTGTGTCTGTTGTTACAACCAAGCGCAACACCACTACTGGAGCAG
TAGAAGGCACTGATGGTGCGCAGCATACTATCGTCAAGAACCGAGCACAG
CGTAAGGCTGTCTATGTCAAGAATGCGGCACCTGTAGCTGCTGCTGCCGC
TAGCCTGTCTGCTGAAGATCTGGTTGCTGCTGTTCGTGCTGTGATGGCTA
ATGCATCAAGCCGACTGCACTGAAGCCGACCGAGGAATAACCTATGCCC
TATCTACCTTGCGTAGGTAGGGTTCTTTTGTTTAGGAGGATTCATGCCTG
TAATTCAACAATCAAGTGATGTAGGTTACATCATGTCCGATGCAAGCTTT
AGCATCATTGATAGCAAGCTAGAGGCCGTCAACCTTTGTATGCGGGCCAT
GGTCGTGAGGGTGTGGATTCCCTTGACTCAGGCGACCTTGATGCTGAAGA
TGCAAGTAAGATGTTGGACATTGTGTCACAGCGCTTCCAATATAATAAAG
GTGGAGGTTGGTGGTTTAATCGTGAGCCTAATTGGCGCATCGTGCCGGAC
ACTAATGGCGAAGTTAACCTGCCTAATAATTGCCTAGCTGTCTTGCAATG
TTATGCATTAGGTGAGCGTAAAGTTCCTATGACAATGCGTGCAGGCAAGC
TGTACTCCACATGGAATCATACGTTTGATATGAGAAGTCATGTGAACAAA
GATGGTGCTATTCGTCGACACTTCTGACATATCTACCTTTCGAACACCT
ACCTACTAGCGTAATGCAAGCAATCGCATATCAGGCTGCGGTGGAGTTCA
TTGTATCTAAGGATGCAGATAAGACCAAGTTGACCACCCATCAGCAGATT
GCAGCACACGCTATTCGTTGATGTTCAATCTGAACAGATGTCCCAGAAGAC
ACTCAACATGTTAGTACACAACCCTACACAGCGTCAGTTTGGTATCATGG
CAGGTGGATCTCAGAACGTACCAGCTTACTCGCATTCACCTTACGATGGT
CATCCACTTAAACCTTGGGAGAGTTATCGCTAATGGAAGTTCAAGGTTCT
TTAGGTCGCCAGATTCAAGGCATAAGCCAGCAACCTCCAGCAGTAAGATT
AGATGGACAGTGTTCAGAAATGGTTAACATGGTGCCTGATGTAGTGGAGG
GAACCAAATCCCGCATGGGTACAACGCATATTGCCAAACTCTTAGAATAT
GGTGAAGATGACATGGCAGTGCATCATTACCGTAGAGGGGGTGAAGGTGA
GGAGGAGTATTTCTTCATAATGAAGAAGGGTCAAGTACCTGAAATCTTTG
ACAAACAAGGACGTAAGTGTATGGTGCAATCACAGGATGCACCTATGACC
TATCTTAGTGAAGTGACTAACCCTAGGGAAGATGTGCAATTTATGACTAT
TGCAGATGTGACCTTCATGTTGAATCGCAAGAAGATCGTCAAGGCCCGAC
CTGAACGCTCCCCTCAAGTAGGTAGCACTGCTATTGTCTTTATGGCCTAT
GGTCAATACGGTACGCACTACAAGATTATTATTGATGGCTAGTGGCTGC
TGGCTATAAGACTAGGGATGGTGCCGAGGCACACCATATTGAAGACATCA
GAACTGAAAGCATAGCTTACAATCTGTACCAGTCACTCCAAAGTTGGGAT
AAGATTGCAGACTATGAAATCCAGTTAGATGGCCATCCTCAATCTATATCAC
AAGGCGGGATGGCTCTACTACCTTCGATATAACCACAGAAGATGGGGCAA
AAGGTAAGGATTGGTAGCCATCAAGTACAAGGTGGCATCTACAGACCTC
TTACCATCACGTGCACCAGAAGGCTACAAGGTGCAAGTCTGGCCTACTGG
CAGTAAGCTGAATCTCGGTACTGGCTGCAAGCTGAGAAGCAGAATGGGA
ACATTGTCTCTTGGAAGGAGACACTGGCCGCCGATGTGTTGATAGGGTTT
GATAAGTCAACCATGCCTTACATTATAGAACGTACAGGGTTTGTTAATGG
AATTGCGCAGTTTAAAATTAGACAAGGCGACTGGGAAGATCGCAAAGTAG
GCGATGACCTGACTAACCCTATGCCTTCATTCATTGATGAGGAAGTGCCT
CAGACATTAGGTGGTATGTTTATGGTGCAGAATCGTCTATGTGTTACTGC
TGGCGAGGCTGTAATTGCAACTCGCACATCTTACTTCTTTGACTTCTTCC
GATATACCGCCGTATCTGCTGTAGCCACTGACCCATTTGATGTATTCTCA
GATGCGAGTGAGGTTTATCAGCTTAAACACGCGGTTACATTGGACGGGTC
TACTGTCTTGTTTGCAGATAAATCTCAGTTCATCCTTCCTGGAGATAAGC
CTCTTGAGAAGTCAAACGTATTGCTCAAGCCTGTAACCACATTTGAAGTT
AACAATAATGTCAAGCCTGTAGCTACAGGTGAGTCCGTAATGTTTGCTAC
AAGTGAAGGTGCTTACTCAGGCATAAGGGAGTTCTACACAGACTCTTATA
GTGATACCAAGAAGGCACAAGCAATAACTAGTCATGTCAATAAGTTGCTA
GAAGGTAATGTTATTATGATGTCAGCCAGTACTAATGTGAACAGGCTGCT
TGTCTTGACCGACAAGTACCGAAACATTATCTACTGCTATGACTGGTTGT
GGCAAGGAACCGAACGTGTACAAGCTGCATGGCATAAATGGGAGTGGCCT
TTGGGTACGTTTATCCGTGGCATGTTCTATTCAGGTGAGCACCTATATTT
GCTCATAGAAAGAGGCAGTACTGGTGTGTATCTTGAGCGCATGGACATGG
GTGATGCGCTTGTATATAACCTGAATGACCGCATCCGTATGGATAGGCAA
GCTGAACTTATCTTTAGACATATCAAGGCAGAAGATGTGTGGGTGTCTGA | GCCGTTACCTTGGCAACCAACCGATGTAACATTGCTTGACTGTGTACTGA
TAGATGGGTGGGACTCTTACATAGGCGGGTCTTTCTTGTTTAGCTATAAC
CCAGGCGATAACACCTTAACTACAACCTTTGATATGCACGATGATGAACA
TGTGAAGGCTAAGGTAGTAGTCGGCCAGTTATACCCACAAGAGTTTGAAC
CTACACAGGTAGTAATACGTGATAACCAAGAGAGGGTGTCTTATATAGAT
GTGCCAACGGTGGGCTTGTTCACCTAAACCTAGACAAATACCCTGACTT
CAAGGTTGAGGTCAAGAATTTGAAGAGTGGCAAAGTACGTAATGTGCTGG
CCTCTAACAGGGTGGGTGGTGCCATAAATAATATTGTTGGCTATGTAGAG
CCGAGAGAAGGTGTGTTCAAATTCCCACTAAGGTCTCTTAGCACCGACAC
AGTTTATCGTGTGATGGTAGAATCGCCTCATACCTTCCAGCTTAGGGATA
TTGAGTGGGAAGGTTCGTACAACCCTACTAAGAGGAGAGTGTAAATGGCA
ATAGGTACTGCTCTTACAGCAGGATTGTCCAGTGTAGCAGGTAGTGCTGC
ATCTGGTGGTTTCCTGTCTTCGTTGGGTGGTGCTATAGGTGCAGAAGGGG
TAATGGGTTCTGCCATGAGTTTCTTAGGCGGAACCACTGGAGGCTTCTCT
AATGCTGGCCTCCTGTCGGCAGGTATGCAAATGCTTAACCCGATAGGAGA
CTACTTCACGCAGAAAGAAACAGCGAAGGCGATGAAGAAGGCGCAAGATG
AGCAATGGCGTCAGCAGTTGATAGCCACAAGGGAGGCTTATGCTTCCGTG
GCTAATGCTGAAAGGTCTGCCTCTAAGCAATACCATTCTGAACTAATAGA
CAATCAGGTATCCTTATTACAGCAACGAGCACAAGTTGCCTTGCTTGCAG
GTGCGAGCGGCACAGGTGGTAACTCTATCACCTCTATGCTGAATGACCTG
ACAGGTGAAGCTGGTAGGAACCAAGCCACCATTATTGACAACTATGAAAC
ACAGTCAGATTAACTTTGCTAACCAGCTCAAGTCTATCCAGAAAGGTGGTC
AGATGATGATGCGCTCCTTTGAGAAGCCATCTGCATTCAGTGCCATAGCC
AAAGGTGTCTGGTATAGGTGAGGCTTACCTGTCTGGTCATCAGAAGGG
TACAGCACTTAGCAAGGCTTGGTCTGACTCTAGGACATATTCATCAGGAA
CAAGAGGAGTTTAAATGGCAATTGAACGTCAAGCTGTACAGGGCTTACGC
CGAGTGCAGTCTACTGGTGGGCCAAGTGCTGCTAGTTTTGCGACTCGTCA
GGTTGGGGTGCAAGAGACTAGTGCATCTGGTAGCCGCTTTCTTGAAGACC
TTGAAATGCTGCTGGCAGTTTGGCGACTGTCACTACTTCTATTCTGAAC
CAAAGAGTGGAAGATGATAAGGTAAGACAATATAATAGGGCGCTTACTGG
CCTAATGCCAACTGAAGATGCAACGGTAGGCGGCACGCGCACACATGC
TTGTTAGTCTACAAAATGACATCATCGCGCAAACTATGCAACTGTCCGAT
GATGCACAACGCTTTGATGGCGATGACAGTCAATGGAAGATCACGTCAT
TAATGCCCGCATGGCTGTGCAAGACCGCCTATGGGATACCTACCCTGAAC
TTCGTGGTGATAAGGAGTCCATGCGGGTAGTTACTAATGCCTTCATGGAG
CAGCAACCTAAAATATTTGCAGCAAGGGAGACCGCCAAGCTGAAGCAGGA
GGCGGAAGCCCGACATCAAGTCTATGGAGTCACGCATTCTGCTGGCTACCC
GTGATGTTCCTGGCGAAGCTATGGGTGATGCCTTGAATCAGTTGCAGAAA
GAAGCTATGGCTATGCAAATCACCAAGCAGGAGTTTGATGCACTGGTTTC
TCAATTGCAGCTAATCGTGCAGCTATTGGTGATGATTCTATGATTCAAG
GAACCAAGTCTCTTAAGGATGAGAATGGAGTATCACTCTATGACCAGATA
GGTCAGTTACAGACAGGAGAGATTCAGGCCAACCGCACATGGGCGGCGCA
GAACCAAGTGGCACTCTTTGAGAAGAAGGATGCTGCAATCAAAGCCTTTG
AAGCTGGACAGCTTAACCGCGAACAGCTACTTCAGGTCATGCAGAACCAC
AATGAAATCTCAGGAGGCCACCGCTTGGTCTGATAGCGAGATCAAATCTTT
ATTTGATAGACAGGCTAAGGCTCGTGCTACGTCTGCCAAGCTGGAAGATT
TGGTGGCCCGTGGTGAACATGGCTCACCCCTAGGCTTGCAAGATATCAGT
AAGGAAGACCGCAAAGCGTATGCTGGTCATTGGTTGATGCCTACACCAA
GTTAGCCAATGACCCAACGATCCACAGGAGCTACTGGTGAAGAAGCTG
AAGCTATCCGTGGCCGCTATGAGCAGATGCGATATGCCAAGCTGGGCCAG
CAGTTGATTGAAGACCCTATCATTAAGAACGGTACGGCTCGCTGATGCA
ACTCTCTTCTGCCAACCTCAAAGATATGAAGATTGAACCTGAAGCATTGC
AGACTATTATGCGCGCCCGCGATTCTATCCCGGAAATGTCCTGCGCGGCG
GTGATGGGTGACAAGGAGTACGCCTTGCGGAGAATTATGATTTGGCGAC
ACGCATGGGTTACACTCCTGGACAGGCTATAGAGTTTGCACAGAATGCAT
CGCGTGGGGACAAGCTTCCCGGTTCTGTTATGAAAGAATTGAATGATGAA
GTAGATGGTGTGGTTTAGTGATGTTGCGAGCGGTAGCTGGCTTACGCGTGG
CGACAACATGAGTGACATGGGTCGTGACCTTATGCTAGAAGAGGCAAACC
AGATTGCTCGCTCTATGAAGGTTGCAGGTCATAACAATGACACCATTAAG
CGTCATCTCAAATCTTTCCTACAGAATCAGTACACTCAGCTATCTGAAGG
TTTCTTCACTCAAGGTGTTCTGGTCAAAGGTGATGTGAGGACGCTAGGTG
ACACTATAGGTGCCAACCAAAAAGACGTACCTACGGTATTACGTCAGTAC
CTTGACAATCATAAGCAAGCATTGCTGGATGCATCTGGCGGTATGGAAGA
AGGAGACTTATACTTTGATGTAGACTTAAGCGCGGTATGTTTACAATAC
GTGCTGGTTCTGGGCGTGTGCCAGTTACTCCAGCTATGCCTTTGTCTGAA
ATCAAGGGACAGGACTTACTGAAGGAGCACTACGAGAAGGCAGTTAAAGA
GCGCGATGAAGCGAAGAAGAATTTGAAGCTAATCAGATGCGTATGTGGG
GTGCTGGTGGTTACCAATCTCCTGCACCAGAAAAGACTACAGCTAAGACT
GTAGGTTCCCGTGGCATCGCTGACTTCCTCATGTCGCCTGCCTTTGCATC
CGGTGAGAATCTACCTTCCAACTTTGAATTCAACTACAAGAGGAATAATA
TGGACTTCTACAATTATGAGTCAAGCAGATGGGGCCAACGTAGGG
TTTGACCGAGTAGCTGGCGTGTACACTCCGTACAAAGATGCACACGGTCA
GTCTGTAGGTTATGGTCACTTCCTCACGGAGGAGGAGAAGAAGAATGGAT
ACATCACTATTGCGAAGATAAAGTACCATTTGCACCGGGACAATCTCAG
TTAACACCTGAGCGGGCAATGCGTCTGCTTGAGCAGGACATGAAGAGCCA
CGTACCTAGCACAAAGGATTGGGCTGTACCTTTTGATGCAATGCATCCGG
GAGTGCAACGTGGCCTCATGGATTATCTTACAACTTAGGAAAGGATGGC |

| Bacteriophage Genome Sequences |
|---|
| ATCAAGAATGCACCGAAAGCCTATGCAGCCTTCAAGGCTGGCAAGTTCAC
CGATGGGTTTATCGAGATGCTGTCTACTGCATCTACTGAAGGTAAGCGTA
GCTCCGGCCTGCTAGTTCGCAGGGCGGAAGCTTATAACCTTGCACAAAGC
GGAGGGTCTGTACCTAAGATTAGCGAAGTTGAGACAAGGGAAGATGGTTC
CATGTACGTTAAGTTCTCAGGTAGCATGTCAGAAGCATTTGTGAGCAAGT
CTATCCTTGGTAAGATAGGTAAAGATGGGTGGATGGAAGTCTACCCTCCT
AAAGCAGGAGCACTTGCAAGCGGCACCAAAGTGGGTCGTATTAAACTGTA
GTGTCATACTCAAGGTTGTCTAACATGTTGGACAGCCTTTATGAATGACA
TTAACTAAGGAGGTAACATGGCTGACGATATTAGCCAAAGCTGGGTGACG
GTATCTCAACGCAGGTTGCCGCCTACCTTTGCACAAGTGGCAGAAGCCGA
GCGTAAGCTTGAAGAACAAAGAGCTAGCGATAAGGTTATGCAGACTGCAC
TGGAAAGCGAATGGGCGCTATACGGTGGTCAGCGTGCTATTGAGCGGCAT
ACAACTGAGTTTGCCGAACAAGAAGGCTACACGGTTCCTGAGTCAACAAA
AGATGAACTATCAAAGATTCATGGTTTTGAAATTGCACAGGATATTGTGA
AGGATGTTAAGTCACCAGAAGAGTTGCAGTTTCGTATGTCCAATGCTATG
GCGGATAAGGAGCGATCGGAGATCCTTGCACGTAATGGGTTTACAGGGTT
TAGCGCTCAGTTAGCTGCTGGTATCTTCGACCCAGTTGGTTGGGCTGCCT
CTATGGTTGCCGCCCCTGTAGCTGGTGCAGTAAAGGTTGCCCGTGTCGGT
CGTATCATAAAGACGGCAGCAGTGGCTGGTGCCGAGAACGCAGCATTGGA
AGCCATCCTAGCCAGCGGTGATTACCAGAAGGGCGCAGATGATGTGCTGG
CTGCTGCTGGCTTTGGTATGATAATGGGCGGCACCATTGGCGCAGCTACA
CGCGAACGCATCGCCAGAAAGCCAGGAGTACAAGGAGTGAATGACGGTGC
TGAGACCGTAGTGGATGACTTAGATACGGTCGTAAAGGGAGCAGATGAGT
TTGATGCATCTGCGGCTAAGGCTGTACGAGAGGCTATGGAGTATGACCGG
TACATGGCTGTGCGTTCCTATGAACCACTGAGGGCTAAGGAAGTGGATAT
GGATGTAGCAATCCTGTCTCACTTAGATGACCTGAAGGCTAACTCTAGCG
TGCGTATGAGTGCCTCCGAGAAAGGTAAACTGAAGGAGCAGATACGCCAG
CTTGAACAGAAGCCGCCACCATTAAAGGCAAGAAGGTAGATGCCGTGGC
AGAAGCTGCTGCTGCTAAGGGTGCGCCTAAGTCTGCTGCTGATAGGCTAG
ACTTGGATGTTAAGAAGAAGGCACTGGCACGTCGCTTTGATGAGCCGCTT
GCCGACATCCAAACAAGACTCGACGAACTTAATGCTAAACTGGCCCGCGT
GGAGAACGTAGGTAAGTCAAAGGAGGAGTTGAAGAGATTCTCTAATCTAA
CTAGGGAGCAGCAAATCAAGGAGCTAGGGTTAGATGCTCCGGCTCGTAAA
GTTGAGATGACAAGTGCGGTACGGGAGGCTCTTGCAGCTATACGTGCTGA
GAAGAAGAAGACACCCACTCAGACTCATGCCGAAGCCAAAGCACAGGCAG
AAGAGGAAGTGCCGCAGAAGCCAGATGACTCTATCGGCGCTAAGCGTGTA
GAGGATTCTGAAATTGCAGGTGAACAATTTGACCTGTCTGATAGCATGGA
AGATCTTATGGATGACCTTGCACGTGAAGCATATCAGTCTGAAGTTAGAC
CTGTAAACCTCAAGGGACTTGGTTCTGTATCTTCCGTGATTCTGAACTCA
AAGAACCCTGTGTTTCGGGGTCTTGGTTTGCGACTGCTGCTGGAGAATGCACA
AGGTGGTGCCTACCAAGGTAAGACCGCTTCTATCTTGTCTAACGTGTATG
GTAACTTGATTCGCTTTGCTGAGAAGAATCGATACAATGATGGCTTCTCT
CAATTCATCAAGGATAACAATTTACGTGCTGTTGATTACCTGAACCCTGC
TGTTACGAGGGATTTTAATAACCAGATTTATACTGCTATTGTCAAAGGAA
TACCTGATGACACGCCACGTGGTGTTAAGCTTGCTGCTGAAGGCATCGCA
GATAAGCTGGCTAAGTCTCTTGAAATCAGAAAGGCTGCTGGTGAGAAGG
CTTCGAAGATGTCAAGTCGGCACGTGATTATATCCCTGTGATATATGATG
GTATCAAGGTGACTGAAGCAGTCAATAGACTTGGTAGTAGCGAGGCTGTT
ATTGCCCTGCTGTCCAAAGGTTATCAGACTGGTAAGTATAAGATGGGTAA
GAAGGCAGCGGATGCACTGGCTAAGGTGCAGTATATTCGCGCCTCCGATT
CTACCTTATCAAGCCGTGTAGCCTTTGACAGGGTAGTTTCTCAGCAGCAA
CAAGCACAGCTTATTGAAGACCTGAAGAGAGCAGGTGTGCCTGATAATAT
CATAGATAACTTCATCGAAGGCACTGAGTTGCAAGAGATGGCGGAATCAG
TGTCTAACCGAGCTAAGGCAAGCATGGGTATCAACACTCAGGCTGAATAT
GGCGGGATGAAGGTTCAGGACTTGCTCAACACTAACGTAGGTGAGTTGGC
GGAGAACTACGCAAGGAGGCAGCAGGTGGTGCAGCTTTGGCGGCTATGG
GGTTCCCGACCCGGCAGTCTGTACTGAATGCAATTGACGCAGCAGAACGC
GCAGGGCGCAATATGCGGGCGCTGACGCCAAGGCAATCAAACAGCTTAG
GGCGGAATCAGAAATGCTCAGGGACTCCGTGAAGCTCATATACGGCAACA
CCATTGACGCAAATCCAAATGCGGGTATCGTCCGAGGGACTCGCCGTGTA
CGTGAGATCACTGGCCTTCTGCGTTTGGGTCAGATGGGCTTTGCGCAGGT
GCCGGAGTTGGCCCGCGCCATTACCAAGATGGGAGTAGGTACAGTGCTGA
AGTCTATCCCTGCCACTAAGTTCTTACGCTCCCGCGCCGGGCGTAAGGGC
GGGACAGCACAAGGTGAGCTACTTGAGCCGGAACTGCGAGAGATGGAAGA
ACTCATAGGTTATATCGGGGAAGATAACTGGCTATCAGGTTGGAACGTAA
GGCACGATGAGTTCGGAGAGACCGCTGACAACATGGGACGTCTGTCTGCC
ATCATCGACAATGGGTTGGCTATGGGTAGCCGTATTAACACATGGCTGTC
TGGCTTCAAGGCGATACAGGGTGGTTCTGAGAAGATCGTAGCACGCTCTA
TCAATAAGCGACTCAAGCAACATTTGATGGGCGAGCGAGAGCTACCTAAG
CGTGACCTTGAAGAGGTTGGCTTGGATGAGGCTACCATGAAGCGACTCAA
GCGCCACTTTGATGAGAACCCGATGTATGCGCCAGTCTGCAGGCGAGGAGG
TTCGAATGATGAACTTTGACGCCATGAGCCAGACTTACAGAGAAATCGTA
GGTGTGGCAGTGCGCCGTATGTCTGGTCGTCTTATTCAGCGTAACTTCAT
TGGTGATGAAGGTATCTGGATGAACAAGTGGTGGGCAAGGCTCTCACTC
AGTTTAAATCATTCTCTATTGTGTCTATTGAGAAACAGCTTATTCACGAC
TTGCCGTGGTGATAAGATTCAGGCAGCACAGATTATGGCATGGTCTTCTT
GCTAGGTTTTGCATCATACGCTACACAGATGCAGATGCAGGCGATTGGAC |
| GAGAAGACCGAGACAAGTTCTTACGGGAGAAGTTTGATACTCAGAACATA
GCTATGGGTGTATTCAATAAACTACCACAAGTGGCTGGCTTTGGCTTAGC
TGGGGATACCTTTGCAACATTCGGCCTTATGCCGGACTCCATGATGCAGG
CACCGGGTCGTATGGGCTTCCGTCAGCAAGGATTGGCGACTTAGTGGCT
GGTGCTGGTGTCATAAGTGATGCTGTGAACTTGTCACAGGCTTTAGTGAA
GTATGCCAATGGAGATGATGATGTCTCCACTAGGCAGTTAGTAGATAAGG
TACGACGCTTGTGCCTTTGGCAAATACGATTGGTGTAGGTCAGATGACC
AAGGCCAGCGTAGACTTATTGGAGGATTGATGAGTTATACTTTCACAGAA
CACACCAGCGGTAGGTTCTCAGACGACTTATCCGTTTAGCTTTGCTGGGCG
CGACAAGGGTTACATTCGCGCATCAGATATTATTGTGGAAGTGTTTCATG
AAGGCGAGTGGAGTATTACACAAGGTTGGGTGCTATCTGGCACTCCACCAG
ATTACCTTCAATGTAGCACTACCAGCAGGGACTAAGTTCCGCATACGTAG
AGATGTAGACAAAGAGTACCCTTACGCGGAGTTTGATAGAGGTGTGGCTC
TTGATATGAAATCATTGAACAACTCATTCATTCATATCTTGCAGATTACA
CAGGAGATTCTTGATGGCTTCTACCCAGAAGGTTACTTCGTCAAACAGAA
TGTGTCTTGGGGTGGGTATAAAATTACTGACCTAGCTGATGGCACAAACC
CTCACGATGCAGTGAATAAGGGGCAGCTTGACGCAATCGACAGGAAGCAT
ACTGAGTGGAATGAACAGCAAGATATTGCAATTGCTGGACTCAAGGCAGG
GATGACATCAGGTCTCTCTCATCGGACAGTACCTTGGGTTACAGTAGCCG
CCGGGGGAGAGCAAGTTATTAGGCCTCCTTACATCTTTTGAATCCGCCTTG
GTTTTCCTTGATGGGGTCTTGCAGCACGAACTGTCAGGTGCAGTTACTAT
AGCTAACAGCACCCTCACCTTCTCCGAGCCTCTACGTCGTGGCACAGAAG
TGTATGTATTGATAGGTAGTCGTATTGCAACCTCTTCACCGGGCCTGCAT
ATGGAGTTTAATAAAGACTTAGGTGCAGGGACTACGGAGGTTAGGATTGG
TATGGCTTTCTCTCATATTGATATCTACCTTGATGGCTTGTTCCAACCTA
AGTCAACATATCAAATAAACGGCGATCTTGTTACATTCTCTGAGGGTGTA
CCAGCTTGCCATATGTCAGCGGATGTAGTCACTTTATAGGAGGTAAGATG
GTTGATTCCGAACTGGTTAGCGGCGGGATGAAGTTAGCGCCATCTGCCTT
AGTATCAGGTGGGTACTTCCTCGGCATCAGTTGGGACAATTGGGTACTGA
TTGCGACATTCATTTATACTGTGTTGCAGATCGGCGATTGGTTCTACAGT
AAATATTCATTATGGAAGGAGAAGAAGCGTGGCAAAACACAATAAACACG
CAGCTACTGAAGACGAGGTAGGTAAGTTACATAGTGCTATCACTAATCTT
TTCAATAAGAAAGCTGCTGCAATCCTAGCTGCGGTAGAAGAAGATCCTGA
TGCAGCAATTGCACTGGTTTCCGGCAAGGACATGGGTGCCATGTGTAAGT
GGGTATTGGATAATGGTATTATGGCTACACCTGCTGCACAGCAAGAAGAG
TCTGCACTATCTAAGCGCCTTGCTAAGATCAAAGCAGCATCTCAAGGTAA
AGTAATCCAATTTGCTAAGGAGGCTTAATGCTAGAGCAAGGGAGTCACA
AGCTGAAGCCCTTGCCCGTTGGGAAGCCCTGCATGAGTTACAGCAAACTT
TTCCGTACACTGTAGCAGGGCTACTCTCATTTGCTCAGGTTGTAATCAAT
AATTTAATCACTGGCAATCCAGACCTGAACCGGGTACAAGCGGATATTCT
GAAATTTCTCTTTGGAGGTAACAAGTATCGAATGGTAGAAGCACAGCGTG
GTCAGGCTAAGACGACCATTGCAGCTATCTACGCTGTGTTCCGTATCATC
CACGAGCCACATAAACGTATCATGATTGTGTCTCAGACAGCGAAGCGAGC
AGAAGAAATCGCTGGGTGGGTTATCAAAATCTTCCGTGGTCTGGACTTCT
TGGGAGTTCATGTTGCCTGATATCTACGCAGGTGACAAGGCTAGTATAAAA
GGTTTTGAAATCCACTACACCTTGCGTGGTAGCGACAAGTCTCCATCAGT
GGCTTGCTACTCCATCGAAGCAGGTATGCAGGGTGCGCGTGCAGATATCA
TCTTGGCGGATGACGTAGAGTCGTTGCAGAACTCTCGTACTGCCGCAGGT
CGTGCTTTACTTGAAGACCTTACCAAGGAGTTTGAATCGATCAACATT
TGGTGATATCATCTACTTGGGTACTCCTCAAAGCGTAAACTCCATCTACA
ACAACCTCCCTGCGCGTGGGTATCAGATTCGCATCTGGCCAGGTCGCTAC
CCTACACTGGAGCAGGAGGCTTGCTATGGGGACTTCCTAGCGCCGATGAT
TCGTCAGGACATGATTGATGACCCCAAGCTCTGCGCTCAGGCTATGGCATAG
ACGGTACAAGGCGCGCCGACTTGTCCTGAAATGTATGATGACGAGAAG
CTCATTGAGAAGGAAATCTCTCAAGGTACAGCTAAGTTCCAGTTGCAGTT
CATGCTGAACACGCGCTTGATGGATGCCGACCGCTACCCTCTTCGTCTTA
ATCAGCTTATCTTAATGAGCTTTGGCACTGACGTAGTGCCGGAGATGCCG
ACTTGGAGTAATGATTCGGTAAACTTATCAGTGATGCGCCACGCTTCGG
GAACAAGCCCACAGATACCTGTATCGGCCTGTGCCGCGTCCGTATGAGT
GGCGGCCTATTCAGCGTAGGTTGATGTATATCGACCCGGCAGGTGGAGGT
AAGAACGGCGACGAGACGGGTGAGCCATTGTGTTCTTGCTTGGAACCTT
TATCTACGTCTACAAAGTCTTCGGCGTACCGGGCGGATACTCAGAATCGG
CCCTCAGTCGCATTGTGAGAGAGGCAAAGCAGGCGGAGGTAAAAGAGGTC
TTCATAGAAGAACTTTGGTCATGGTCGTTTGAGGCGGTAATTAAGCC
ATACTTCGAACGCAATGGCCTGCCGAGTTGAAAGAGGATTACGCCACTG
GTCAGAAAGAGGCCCGCATCATTGAGACACTTGAGCCTCTTATGTCCGCA
CACCGCATCATCTTTAACGCTGAGATGATCAAGCAGGACATCGATAGCGT
TCAGCACTACCCTCTTGAGGTTCGCATGAGCTACAGTCTATTTGCTCAGA
TGTCGAACATCACCCTTGAGAAAGGATGCCTGCGGCACGATGACCGCTTA
GACGCGCTGTATGCGCTATACGGCAACTGACCTCTCAGATAGACTATGA
CGAGGCCAACGGATAAATCGTCTCAGGGCGAAGGAGATGCGCGAATATC
TGGAGATGATGACCGACCCTCTACGTCGCCGGGAGTTCTTCACTGGACAA
GACCACGGGTATCGCAAATCAACTAACGTGTCCAATGCGATGCAGTCTAG
GGTGTTTGGTGGTAGCCGTGTTAAAGTGAAATCAGAAATACCATTTCTT
CAAGAATTTCAAGGACTTGGTAATTAGGGGACACTATAGAAGGAGGCCGA
GGAATAACAGGAAGTTATAGGAGGTCATAGGTATTCCTAGGTAGTATAGG
TACGCCTTAGTGGGAGGTATCCCTACCTCCCTATTCCTTCCTTTATATTAA |

| Bacteriophage Genome Sequences |
| --- |
| CTATAGATAAGGAGTAATAATGCCTAATCGTCCTAATAATTATGGTAATA |
| TGGGTCTGACAGGTAAACCTCGTCGTAAACAAGAGAAGCCTATTGCCACT |
| GCACTGATGGTTCCTTTTGCAGAAGATGAAGCCCATGAGCATGGTGAGAA |
| CATCGAAGTACGTGAGAACCGCATTAATGACCAGACCAAATCAGGTAAGC |
| GCCGTGGTGCTATGCTGCTGACAGACAAGCATGGCCTTGTGGTTGCATCT |
| GGCAGCCGCTTCAATGACATCTGGTATAGCTTTAAATTCGAAGAAATTGG |
| TACAATTCAACCTGCATAAGAAGGAGATAACATATGGCAACTATCAAATA |
| CGGTGATGCTGGTACTGCAACTGGTAAGGCTTTCCTGAAACAGCAACTGG |
| AAACCACAGCGACTGCACTGCCACTTCCAATCGTGTCCAAGTCAGACTTG |
| GGTCGTGCACTGGCACCTATCAATCAGGCTCGCCTGTCTGGTAAGCAGAA |
| GGGTGCTATGGTAATCATGGAAGATGACGGTACGCATGAACTGCACATTG |
| CGGTGGCTGATGGCCCGCTTCCGACTGACGCATGGAACATTTGCAGCCTT |
| GACGGTGAAGTAACTCCGGCACAGGGCCGCTAAGGAGGCTAGATGCTACG |
| ACATCAGATTAACGGGAATCACAACCCGTTACATGTAACAGGCCAACGCT |
| CACGGAGTAATAAGAGTATTGCCATCCAGGAGGGTGTGCCTATTGTACGT |
| GCTTCTGTTCTAGCATCTCCGACATCTTACATCAATGACCCTCACCTGTC |
| AGGTAAGCGTGAAGGTATGATGGTGGCTGTACTGGCACCTGAAGATGGAG |
| ACAAGGCAGGTCTATATCTCTACAGGTGGGCCAGATAAACATAACATCAT |
| TGACCATGCGGTGTTCAAACATTTTGTAACTAACGGCTTGGTTGTAGGCG |
| CTATTGAGACGCACACTGCCACCACTAACAACATCCATGTACGTATGCAC |
| ATCACAGAAGGTTCTACGGGTGCATACACCTTTAGCTTTTCCTTTGAGTG |
| GACATCTGACTTCGACTTACTGGAGTGATAATGTTGAACAAATACTTCAA |
| GCGTAACGAGTTCGCTTGCCGTTGTGGGTGCGGTACATCCACTGTTGACG |
| CGGAACTGTTGCAGGTTGTCACAGATGTCCGTGAATACTTCGGTTACCT |
| GTAGTTATTACATCGGGTCATCGGTGCAGTGACCATAACCGCCGCGTAGG |
| TGGTGCTGCATCTTCCATGCACATGACTGGCAAGGCTGCTGATATTAAAG |
| TGAAAGGGAAGGACGCGAGTGCTATCGCATCCTACTTGGAACACAAGTAC |
| CCTGATAAATATGGTATCGGTCGATACAACTCCTTCACTCACATTAGGCT |
| GCGTGATGGTAAGGCTCGCTGGCGTGGATAACTGCATTGCATGGTGTGAG |
| AAGATGGTTGCTAAGGCATCTGCTGAAGGTAACTATGTTGACTGGCAGAA |
| TTACACCAATCTGCTTAACGAATGGAAATGGAGAGCATTACGATGAAGAA |
| ACTATTCAAGAGCAAGAAGGTGATCGGCGCACTAGTTACACTGATCGTTG |
| CGCTTGTATCGGTATGCTTGGTGTTGACCTAGGCTCAGGTGCGGAGTCT |
| TCTGTTACCGATGTGGTCTGCCAAGTAATTACCTGTGAGTAGGTTACTTG |
| AAGTAGTGGCAGGACTTCTTGGCCTGCTGCTTGCCTATAAGAAGAAGCAA |
| GACCAGAAGGAGGCGCAACATGAAGCAGATCTGGCTAGCGATGACCCTGC |
| TGATTGGTTCGCTGACCATTTCCGGGTGCGGGACGGCGTTACCAGAAACT |
| CAGAAGGTTCGTCCAACCAAACCGACTCTGACGGCAGTTTACGAGAGAGA |
| TGATAGGGTCTGCTTCAGTAAGCCAGATGCTACACAATTAGGCTTGTACA |
| TATTGTCGTTAGAACGCGGCTACAATTAATACATAACCTTATGTATCATA |
| CACATACGATTTAGGTGACACTATAGAATAGAAGTATAGTGCCGTTCTTT |
| TGAGCGGCCTATTACTCACCAGTCTTCACGGGGAGGGCTGGATAGTAATA |
| GGAGGTTTAATGTCATTAACTAAACCACGTTGCTTCAGGAAGGCAAGTTA |
| TCTAAGCCAGTTAGGCACTTTGCAGAATCTGGCTAACACTGGAGATGACG |
| TACTTGTTATCGATGTTGACTACAAGTTCACCAATGGAGACTGTGAGAC |
| TTCAAAGGTCGATTGGTTCGTATAGAATGCGAAGCTAGATTCATAGGCGA |
| TGGAGCTTTAATTTTCACTAATATGGCTAGTGGTTCTGTAGTAGAAAAGC |
| CTTTCATGGAGAGCAAGTCCACACCTTGGGTTATCTACCCTTGGACAGAA |
| GATGGCAAGTGGATTACAGATGCACAGCTGTTGCTGCTACGCTTAAACA |
| ATCTAAGACCGAAGGATATCAACCTGGAGTCAATGATTGGGTCAAGTTCC |
| CAGGACTTGAAGCATTGATACCGCAAGAGGTGAAAGACCAGTATGTAGTA |
| TCAACACTGGACATCCGTGATTGTGTAGGTGTTGAGGTTAGACGTGCTGG |
| TGGGCTTATGGCAGCTTACTTGTTCCGCAACTGTCATCATTGTAAGGTAA |
| TTGATTCTGACACCATCATTGGTGGTAAAGACGGCATCATAACCTTTGAA |
| AACTTAGGTGGTGAATGGGGTATCGGCAACTATGCCATAGGTGGTCGTGT |
| ACATTATGGCTCATGTAGTGGTGTGCAGTTTCTTCGGAACAATGGAGGTG |
| CATCACATAATGGTGGATGTTATTGGTGACCTCATGGCGCGCAGGTGAG |
| TCTGGGTTTAAAACATGGCAAGGTTCTGTAGGTGCAGGTACATCTCGTAA |
| CTATAACCTTCAGTTCCGTGACTCAGTTGCATTATCTCCAGTATGGGACG |
| GCTTTGACTTAGGCTCAGACCCTGGAATGGCACCAGAAGAGGATAGACCG |
| GGAGATTTACCTGTATCTCAATACCCCATGCACCAGTTACCTAATAACCA |
| CATGGTTGATAACATACTTGTTATGAACTCATTAGGTGTAGGTTTAGGTA |
| TGGACGGTAGAGGTGGTTATGTGTCGAATGTTACCGTGCAGGATTGTCA |
| GGCGCAGGTATACTTGCTCATGCATTCAACCGTACCTTCTCTAACATTAC |
| GGTGATTGACTGCAACTACATGAACTTCGATTCAGACCAGATAATCATCA |
| TTGGTGACTGCATCGTGATCCATGGAGCATCCGAGCAGCGGGTATTAAGCCTCAA |
| CCATCCAAAGGCATGATCATCAGTCGACCTCACTCAACCTTGAGCGGTAT |
| TGTGGGTAATGCCGCCAGACCGTATTCTTGCAGGTAACATCCTTGACC |
| CTGTGTTGGGTCATACAAGGATTAATGGGTTTAATAGTGACTCGGCGGAA |
| CTGAGCTTCAGAATCCACAAGCTTACCAAGACCTTGGATAGTGGTGCTAT |
| TCGCTCTACGCTGAACGGTGGGCGGGTACTGGTTCTGCATGGACTGAGAA |
| TGACTGCAATTTCAGGGTCAGCTCCAAATGCTGTCTCGTTGAAGATTAAC |
| CGAGGAGACTTCAAGGCAACTGAGATACCAGTAGCACCTACTGTGCTTCC |
| AGATGAAGCGGTAAGAGCCACAGCTCTATCGCACTTTATTTTGATCAGG |
| AAGCTCTTTGGGCTTTAGTTAAGAAGCCGAACGGAAGCCTCACACGAATG |
| AAGCTTGCTTAATGTAGGCAGCGCGTTAGCGCTGCTTTCACGCGAACTTT |
| TCTTAAAGGTTATCATAGTGGTAGCCTTTCAGAAAAGGAGGTGACATGAT |

| Bacteriophage Genome Sequences |
| --- |
| ACAAAGATTAGGTTCTTCCTTAGTGAAGATGCCAAATGGTATTACATTGA |
| CACAGTGGTTGCAACCTGCAAACATCATCAAGGTAGATGATGCACCATAC |
| AATGGAACCTTATTGCTGCATATAATGTCTATTCCCGTTATAGGTAATTA |
| TGCTTTGGTTCTTACCAACCACACTTACAATGCAGTTGGTTTGTTTGATG |
| CAGGTCGTAACATGAAGCCTAACATCACCATCATTGGTGCTGGTATGCCT |
| CAACTTGCAGATGATAGGTCGTCCTTTGTTGAAGGTTCTGGCACTATCAT |
| TAAAGGCGCAGTCAAGAACTCCGCCAAGGGCTTCCAGATTGGTAACCTAG |
| GTATTGATTGTGGTAACACAGTTAGTCGTACAGACATACCAACCTGCACGC |
| TTCGAAGACCCACTACAGATATACGGGTGTGGCGCTAATGCTAACATCTT |
| TATCGATAACGTGAAGTGCCTTAGTGCAGTTTCTGTAGACGAGAGACCGG |
| GAACACACAGCATTCTGCTTGAGCAAACTGAAGGTGTTACTCTCGGATAT |
| GTAGAGTGCATTGGTGGCTTCCACGGACTTACCATCAAGTGCCGTAACCT |
| ACGTGGCGGGATTGCACATTGCTATGGCCAGTATGGTGATGGCTTCATCA |
| TCAAATCTGACGCTGGTGGTGCAGCGAGTCATATCTACATGGAGCGGATT |
| CAAGTGGGCATCCAGATCAATCTATGTGGCCTGATGTACACTTAGGTGG |
| TATCTACGATGCTCATGATGGAGTGACAATTGACAGTGTTAGTATTGGCG |
| AGTTGCATGTTGTACGAGGGTCTTGGGGCCTGATACCTGCCGGATAACGCC |
| ACGGGTAGTATCACCAACTTCCATATTGGACATTATGAGTGTCACCTTAC |
| TTATGGCAACTACTACTCCCTTGTTATCAACGACAAGGTTGTAGGTTGGA |
| CTATGGGTACTCACAACATCACGACCTGCTCAGGTGGCATCAAGGTAGAC |
| CCTGCATCGGTGTATGTAAACATCGGAACTGGACGCTCCACCAACAACAC |
| TGAGAGTGGGTACTCTCTTGGTGGACACACCCTGATTCATGGTGAACTGA |
| TTGCAGATGCTAATGGTAAGTACGGTGTAGAGTATACAGGTGGCCTAGGT |
| CTTGATGTAAGTAAGATTCATGGGTTCCAGAACCATCTTGGTACTTACTC |
| AGGCTACTCTTCTGCTATCCAATCTCTACTGTGGCCTGACGCTGGGTTTG |
| AAGCGATGGTTACAGGGCGCACTGTGACATTGCGTGGGTCTCTCACGAAA |
| GGTACGACTGCATGGTGTGGTCAGGTACTCGATGCTGTTAAGCCTACACG |
| AGACATTCGTATATACGCATGGGCTGTTGGTCTTGGTGTTCTCTATGGTTC |
| CAGTGGAAGCATGGATTCGTTCTTGCTAATGGAGCTATAGACGTAGTAGGAA |
| AAGGACTCGGTGGGCAAGGGCAGATTGTTAGCTTCACTGGCAGCTACAT |
| ATTCAAGTGAGGTCTGTATGCCATTAGTGAAGTCTATCAAGGAGAAGGCT |
| GTACGCCAGAACACAGAAGAACTCATCAAGTCAGGTCGTCGTGACCCTAAGCA |
| GGCTTATGCAATTGCTAAGGATGTACAACGTCGTGCCCATGAAGAAACCTT |
| CTGCATCTTAGTGTAACCAAAGGGTTGGCTTAGGTTGACCCTTAGTGTAA |
| TCAAAGGAGATAACATGTATATTCCAATGGAAGCAGTAGTAGGTATCGCT |
| TGTTTGCTAGTAGGGTTTGTCATAGGTTTGATAGCACAATAATGGTAGTC |
| ACAAAGTAGCCAAAGTCAAAATTTTGATATAGGCGTGTCAGCTCTCTC |
| GGCCTCGGCCTCGCCGGGATGTCCCCATAGGGTGCCTGTGGGCGCTAGGG |
| CGGCCTGTGGAGGCCTGAGAGAAGCTCTTAGTGTGGGCCAAAGGGTAACC |
| TGAGGCCTGCCGGAGCGAGCGATAGGGACGCGTGTAGGCCGCTTGACAGC |
| GTGTGTGGGCGTGGGCTA |

SEQ ID NO: 3 - *Enterobacteria* phage K1-5
| |
| --- |
| TCGCCCTCGCCCTCGCCGGGTTGTCCCCATAGGGTGGCCTGAGGGAATCC |
| GTCTTCGACGGGCAGGGCTGATGTACTCCTTGTCTAGTACAAGGGAGGCG |
| GAGGGAACGCCTAGGGAGGCCTAGGAATGGCTTAGTGGTGGACAAGGTGA |
| TTACCTTAGTGAAGCCTCTTAGTGCATTCCTGAGGCCATTCAGGGCGTTT |
| ATGAGGGATTGACAGGGTGTGAGGGCGTGGGCTATCTGTTCCTTTGCTCC |
| TCACTTCGTTCGTCGCTGCGGTAGCCTGATGTGTACCTTAGGTTATTCCT |
| TGATGATAGCTTAGGTTAGCCTTAGTGGATTACCTTAGTTAAAGCCTTA |
| GTGCTTCACTTAGTATCAGCTTAGTAGTGTACCTTAGTAAGTCTTAGTGT |
| CTTCTCTTAGTGATTGCACATGCAAGCATGTAAGATGCTAATAGGTCGCG |
| GTCGGCAGACCGCTAAAGAAGAAGGATGTAATAAGATGCAGTAAGAGGAA |
| ACACCAGAAGCCTAGCCAACCTAAGCTATCCTAGCTCTATATCTATTGCT |
| TTTCCTTAGTCTAACACGTTAGACAACCTATCTTATTCTTAGTGATGGTA |
| ACTTAGTGTTGACAAGATAATCTTAGTGTAATACTATGCATCACGTAGGC |
| GGTGCTGAGGCACCTAGTAGCCAGCTAGTAAGGCATACGAAGAGACTAAG |
| GCTTACATTGCTCTTTAACAATTTGCTTAGTGTAACCTATGTATGCCGTG |
| GTTAACTACTTATTGAATGAGGTATTAACTATGACATTAAATAACCGTGA |
| ACTGTCCGTTCTCTTCACTCTGTTGTGCTACATGATTCGTAACAACGAAT |
| TACTTACAGATGATGAGTTAGCCTTGTATCACCGCTTTCTTAACGAAGGT |
| TGGACCATACAGTTAATCACCGTAACATGATAGATGAGTTGAGGGA |
| GGGTAAATAATGTATCAACATGAGGTATTCTTTGAATCAGCTAGCGAAGC |
| TATTCGCTTCCGTGATGATATGATGCAAGCTGGTGTAGGCGTTGATGTGT |
| ATCACTATTTGATAGATTACGACACTGAATATCACCGAGTTACCTTAGTA |
| TCTGATGTGACAACAAGTCATTACCTTAGATCTAGGCAGTGAAGATTA |
| CGATTACGATGAAGTAATCACGACAAATCTCTAAATTAACTGTTGACAGC |
| CACGGCATACAAGGTTACATTAAGCATCAAGACGGCGACGTCTTTAAACA |
| TCCCGCTCTTTAACAATACGGTTTGTGTCTTGATAGGCTAACTAACTAAC |
| TAAGGTAATTATCATGAAAGGGTTAATTTGTAGAACGTATGGTCAATG |
| GTAAACTTGAAATTATTACCACTGAAAACCAATCTAGCTTCAAAGAGTGG |
| TATGCTGTTTTCTCACTGATTTAAGGTAAAGGCTGGCACTAGTCAGCCTA |
| TCAAGGCGCAAACCAAGCTCTTTAACAATTTGGATGGTAGCTTCTTAGTC |
| TGGATAGGTTAAACCTAGGAGATTCTTGAGTCTCCTATAATGTAACCT |
| AACTAACTAAATGAGGATTAAATCATGGAACGCAATGCTAACGCTTACTA |
| CAACCTTCTGGCTGCAACTGTTGAAGCATTCAACGAGCGTATTCAGTTTG |
| ATGAGATTCGCGAAGGTGATGATTACTCTGATGCACTACATGAGGTTGTA |

| Bacteriophage Genome Sequences |
| --- |
| GACAGCAATGTTCCAGTTTATTACAGCGAAATCTTTACAGTGATGGCTGC |
| TGATGGTATTGATGTTGATTTTGAGGATGCTGGTTTGATTCCTGACACGA |
| AGGATGTAACCAAGATTCTACAAGCTCGCATCTATGAAGCTCTTTATAAT |
| GATGTACCAAATGACAGCGATGTAGTTTGGTGTGAAGGCGAAGAAGAGGA |
| AGAATAAGGATGGAAAAGCAATATAACTTTATCTTTTCAGACGGTGTAAC |
| CCTGAAGTGTTCCCTACGATTCGCACAAATTCGTGAGGAAGTACTAGGCA |
| CTACATACAAACTATTTAGCTGACACTATAAGAGAAGGCTTAACAAGGCG |
| TTACTAAGGTAGCGCCTGATTAAACTTTCACTTACTAGGAGTTGAGATTA |
| TGAAAACCTTGATTGGATGCTTCTTGTTGGCTTCTCTTGCTCTGGCATTT |
| ACCGCTAAAGCTGGTTATGACGCTTATAAAGTAGAACAAGCCCAGCAAGA |
| CTGGGCCAAAAAAAAGTTCAACTTGTGCAGCAAGAGCAACACCTACGAGT |
| ACTGCAACAAAACACTAAGACACTTATGGAAAGAGTAACTAGCCTATAGC |
| CCACCTGAGTGGGCTATGTGATATTTACTTAACACTATATAAGGTGATTA |
| CTATGACTACTGAAAACACCCTCGTGTCTGTCCGTGAAGCTGCAACCGCT |
| GAAATCAAGCAACATTTAGACAATATCGGCACTTCTTACATCAAAGTAGG |
| GGCTTGTCTGAATGAGTTACGCGGAGACTTTGAAGGTCAAAAAGAGTTTT |
| TAGCCTATGTTGAAGCAGAGTTTGCCATTAAGAAGGCACAATGTTACAAG |
| CTGATGAGTGTAGCCCGTGTCTTTGAAGGCGATGATCGCTTTAAAGGCGT |
| GGCGATGCGTGTAATGCTGGCGCTTGTTCCTTTCGCTGATGAAAATATAA |
| TCATGGAAAGGCCGCAGAACTCGCCGCAAATGGCAAGCTGGACACTAAT |
| GCCGTAAACGCCCTGATTGAACCTAAGAAAGAGTCAAAGGCCGAAACGGT |
| ACAATCTAAGGCTGAGACAGTAAAACCGCAGGAGAACGCGACTGAGTCCG |
| CAGAATCACATGAAATGCAAGCGCCGCAGGTAGTGCCACCCGCGAGCGAG |
| CAGGAGTCCGACGAATCAGCACTTGGGAAGGAGAAGCAAACCGGAAGC |
| GCCAAAGGCAGCTCCGATGGATAACACGGCTAATACTGAGAATGCCGCTA |
| TTGCTGGTCTGCTGGCACAAATTAAAGCACTGACTGAGCAATTACAGGCA |
| GCCAATGACCGCATCGCCTCCTTAAGTAGCGCACGCGAAAGCAAGAAGGC |
| ATCCGCACCTATGCTGCCGCAGTTCAAATCTTCCTGCTTCTACGCTCGCT |
| TAGGCTTGAGCGCGGAGGAGGCAACGAAGAAAACAGCAGTTAACAAGGCA |
| CGCCGCGAACTGGTTAAGCTGGGATACGGTGAAGGCCATGAGGCATGCC |
| CTTAATCTCTGAGGCAGTAGAAGAGTTGACTAAGTAACCTTATCGGTGGC |
| ATCTTCTTAGGTGTCACCTATTAAGGTTTCTTTCACTAGGAGTAAACAAG |
| ATGCAAGGCCTACACGCTATTCAACTTCAACTTGAAGAAGAAATGTTTAA |
| CGGCGGTATCCGTCGCTTTGAAGCGGACCAACAACGCCAGATTCATCCG |
| GTAATGAATCAGACACGGCATGGAATCGCCGCTTATTGTCCGAGTTAATC |
| GCGCCAATGGCTGAAGGTATTCAGGCATACAAGGAAGAGTAGTGAAGGTAA |
| AAGAGGCCGTGCACCGCGTGCATTAGCTTTCATTAACTGCGTAGAAAACG |
| AAGTGGCAGCATATATCACGATGAAAATCGTTATGGATATGCTGAACACG |
| GATGTAACCTTGCAGGCTATAGCCATGAATGTAGCTGACCGCATTGAGGA |
| CCAAGTACGTTTTAGCAAGCTGGAAGGTCACGCCGCCAAATACTTTGAAA |
| AAGTTAAGAAGTCACTTAAGGCAAGTAAGACTAAATCATATCGCCATGCG |
| CACAACGTAGCGGTAGTGGCTGAGAAGTCAGTAGCTGACCGTGACGCTGA |
| TTTCTCCCGCTGGGAGGCATGGCCTAAAGACACCTTGCTGCAAATTGGGA |
| TGACCTTGCTTGAAATCTTAGAGAATAGCGTATTCTTCAACGGGCAACCT |
| GTCTTCCTCCGCACCTTGCGCACTAATGGCGGCAAACATGGTGTTACTA |
| CCTACAGACTAGTGAACACGTAGGTGAGTGGATAACTGCATTCAAAGAGC |
| ACGTAGCGCAACTGAGTCCTGCCTATGCTCCTTGCGTCATCCCTCCGCGT |
| CCGTGGGTATCACCTTTTAACGGCGGTTTCCACACTGAGAAAGTAGCAAG |
| CCGTATTCGTCTGGTAAAAGGAAACCGCGAACACGTCCGCAACGCTACCA |
| AAAAGCAAATGCCAGAGGTTTACAAGGCTGTTAACGCGTTGCAGGCGACT |
| AAATGGCAGGTTAACAAGGAAGTTTTACAGGTTGTGGAAGACGTCATCCG |
| TCTAGACCTAGGTTATGGTGTACCTTCCTTTAAACCACTCATTGACCGCG |
| AGAACAAGCCAGCTAATCCAGTCGCCGCTAGAATTTCGACACCTACGGGC |
| CGTGAACTGAAAGAAATGCTTACGCCGGAACAATGGCAAGCCTTTATCAA |
| CTGGAAAGGTGAATGTACTAAGCTGTACACCGCTGAAACTAAGCGCGGAA |
| GCAAATCGGCGGCAACCGTTCGCATGGTTGGTCAGGCCCGTAAATATAGC |
| CAGTTCGACGCAATCTACTTCGTGTATGCACTGGACAGCCGCAGCCGCGT |
| CTACGCGCAATCTAGCACACTCTCACCGCAATCAAATGACTTGGGCAAGG |
| CCTTGCTCCGTTTTACCAAGGGCAGCGTCTTGATAGCGCTGAGGCGCTT |
| AAGTGGTTTTGGTGAACGGGCTAATAACTGGGGTTGGGATAAGAAAAC |
| TTTTGACGTGCGCACCGCTAACGTGCTGGATAGTGAATTTCAAGACATGT |
| GCCGCGACATTGCAGCGGATCCGCTGACCTTCACTCAATGGGTAAATGCC |
| GACTCCCCTTACGGCTTCCTTGCATGGTGCTTTGAATATGCGCGTTATCT |
| GGATGCACTGGATGAAGGCACGCAAGACCAATTCATGACGCACCTCCCAG |
| TCCATCAAGATGGTAGTTGTTCTGGTATCCAGCACTACAGTGCTATGCTA |
| CGCGATGCAGTAGGTGCAAAGCAGTAAACCTTAAGCCCTCTGACTCTCC |
| TCAAGATATTTATGGTGCCGTTGCGCAGGTAGTAATTCAGAAGAATTATG |
| CATACATGAATGCAGAGGATGCGGAAACCTTCACTTCTGGCAGCGTGACT |
| TTAACAGGTGCGGAGCTGCGTAGTATGGCTAGTGCGTGGGATATGATAGG |
| AATCACTCGCGGCCTGACCAAAAAGCCCGTAATGACACTACCTTATGGCA |
| GCACAGTCTAACCTGCCGTGAGTCAGTGATTGATTATATCGTTGATTTA |
| GAAGAAAAGAGGCCCAACGGGCTATTGCGGAAGGGCGTACCGCCAATCC |
| TGTACACCCTTTTGATAATGACCGTAAAGACAGCCTGACACCTAGCGCAG |
| CTTATAACTATATGACAGCTTTAATCTGGCCTTCTATTTCGGAAGTGGTT |
| AAAGCCCCTATAGTGGCAATGAAAATGATTCGTCAGCTTGCCCGTTTCGC |
| AGCTAAAAGGAATGAAGGCTTAGAGTATACCCTGCCTACTGGCTTCATCT |
| TGCAACAAAAGATTATGGCTACTGATATGCTCCGCGTATCTACTTGCTTG |

| Bacteriophage Genome Sequences |
| --- |
| ATGGGAGAAATCAAGATGAGTCTACAGATTGAAACAGACGTAGTGGATGA |
| AACGGCAATGATGGGCGCTGCTGCTCCTAACTTTGTGCATGGTCATGATG |
| CCAGCCACCTTATCTTAACAGTCTGCGACCTTGTTGATAAAGGGATTACA |
| TCTATCGCAGTTATTCATGACTCTTTTGGCACTCATGCAGGCCGTACAGC |
| CGACCTTCGTGATAGCTTAAGGGCAGAAATGGTGAAGATGTATCAAGGCC |
| GTAATGCACTGCAAAGCCTGCTAGATGAGCACGAAGAACGCTGGTTAGTT |
| GATACGGAATACAAGTACCAGAGCAAGGGGAGTTTGACCTTAACGAAAT |
| CTTAGTTTCAGACTATTGCTTCGCATAATATTAATAGGCCATTCCTTCGG |
| GAGTGGCCTTTCTTTTACCTACTACCTGTAACATTTCATTAACATAAAAG |
| TGTCTCACATGTGAGACTTATTTACCGGACACTATAGGATAGCCGTCGGA |
| GACGGGAAAGAAAGGGAAGATAAAGGATATAAAGGAAGTAATAGGTATTA |
| AAGGTTATATAGGTTATCTAGGAATACCTATTACCTTCTTCCTTCCTCTT |
| ATTACCACTCAGAGGAAGGGCAGACCTAGGTTGTCTCACATGTGAGACTT |
| CGTATTTACCGGACAGTATAGATAAGATTAACTCACTTTGGAGATTTAAC |
| CATGCGCAACTTTGAGAAGATGGCCCGTAAAGCTAACCGTTTTGACATGG |
| AAGAGGGGCAGAAGAAAGGCAAGAAGCTGAATAAGCCTGTCCGTGACCGT |
| GCATCTAAACGCGCTGCGTGGGAGTTCTAAGTTATGGCTATTATTCAGAA |
| TGTACCGTGTCCTGCCTGTCAAAAGAATGGACATGATATTACTGGCAACC |
| ATCTCATGGATATTTGATGATGGTGCCGGCTACTGTAATCGTGGACACTTT |
| CATGATAATGGTAGACCTTACTATCACAAGCCGGAAGGTGGCATCGAGAT |
| AACCGAGTTATCTATTACTGCAATATCAAATATACACCTTCTCAATTCA |
| AAGAATGGAGAAGGAAGGGAAGATAAGCGACCCTAAATTACGTGCCATC |
| GCACTTGGTGGTATGCGTATGAAAGACCGTTGGGAGGTCATGAATGAACA |
| AGAAAGGGCAGAGCAAGAAGCAGATGGAAACTTGATGTTGAATGGTTCC |
| TCACGCTTAAGCGTAAGAACCTTGTTTCCAGGCACATTCGCGGCGACATT |
| TGCGCATTGTATGATGTACGTGTTGGGCACGATGAAGAGGGTAGAGTCTC |
| ACGGCATTACTATCCGCGCTTCGAAAAAGGTGAGCTAGTAGGCGCTAAGT |
| GTCGCACATTACCTAAAGATTTTAAGTTTGGTCATTTAGGTAAACTCTTT |
| GGTATGCAAGATCTTTTCGGTATGAATACTTTGTCTCCACGTGTTAGACAA |
| GGGAAGACGAAAGGATTGCTTGCTCATTGTCGGCGGCGAACTGGATGCAC |
| TAGCAGCGCAGCAGATGCTCCTTGATTCTGCCAAGGGTACTAAGTGGGAA |
| GGCCAGCCATACCATGTATGGTCTGTCACAAAGGCGAGTCTTGCCTTGA |
| AGAGATAGTGCAGAACCGTGAGCATATCGCCCAATTCAAGAAGATTATAT |
| GGGGTTTTGATGGAGATGAGGTAGGGCAGAAGCAGAATCAGCAAGCGGCT |
| CGCCTGTTTCCTGGTAAATCCTATATCCTTGAATACCCCTCGGTTGCAA |
| AGATGCTAACAAGGCATTGATGGCTGGCAAGGCTAAAGAATTTGTAGATG |
| CATGGTTTAATGCCAAGTCATCTCGATGAAGTCTTTGGTAGCACAGATTAAA |
| TCTATCGCATCTCAAAGGGATAAGCTCAAGGCTGCACGTCCAGAGCAAGG |
| ACTGTCATGGCCTTGGCCTAAGCTGAACAAGGTAACGCTAGGTATTCGTA |
| AGAACCAGCTTATCATTGTAGGTGCAGGGTCTGGTGTAGGTAAGACTGAG |
| TTCCTTCGTGAAGTAGTTAAGCACCTCATTGAAGAACACGGTAGAATCTGT |
| AGGCATCATTTCTACAGAAGACCCGATGGTCAAGGTGTCCCGTGCTTTTA |
| TCGGCAAGTGGATTGATAAGCGTATTGAGTTACCTCCAACCAACGACCCG |
| AAAGAAGACGGATACCGTGAGGTGTTCGACTATACCGAGGAAGAAGCTAA |
| CGCCGCCATTGATTATGACTGTGATAGCAGGTAAGCTGTTTGTAGCTGACC |
| TAGAGGGTGACTATTCGATGGAAAAGGTAGAGCAAACTTGCCTAGAGTTT |
| GAGGCTATGGGTATTTCTAATATCATCATTGATAACTTAACGGGGATTAA |
| ATTAGATGAGCGTGCTTTTGGTGGGAAGGTTGGTGCACTTGATGAATGCG |
| TCAAGCGAGTTGGTACTATCAACACCGACCACCGGTTACTATATTTCTT |
| GTATCACACCTTACACGTCCTCCGGCAAACCGTACCCAACACGAAGAGG |
| TGGCAAGTTATCCTTTCTGACTTCCGAGGCTCAGGCGCTATCGGATTCT |
| GGGCATCTTACGCCTTGGGGATTGAGCGTAATACAAGAGCTGAAACGCTT |
| GACGAAAGGACTACCACGTACATCTCATGTGTCAAAGACCGCGACCAAGG |
| TATCTACACTGGAACCAAGGTCATGCTTAAGGGTGACATTCAAACCGGAC |
| GTTTAATGGAACCACAAGCCCGTACTAAGTCATTTGATACAGGTGAAGCA |
| AGGCAACAAGAAGTACCAGATTTACCGGATACTATAGAGAGACTACCTT |
| CGATGAAGAAAGTGAGTTCTGATTAGTGATTATTATCAGGCTTGTCTCAA |
| TGTGAGACAGGTCTTATTAGACATTAAATAACTGGAGATTGATTATG |
| TATAACTTAGTGTTGAATGTAGGTGACTTTGTACGCAACATCAAGAAAGA |
| TTCAAGTCGCTATCTTTGCCGTGGTGTTGTAACCTTTGTAGGTGAGAACC |
| TGTATTATGTAGAATTCGTTGCGGTTGGTTAAGCAATATTACCACAAGAG |
| ACAGCACATAAATATCTTGAAAAGATTGTAGAGATAAACAATCAATGTAA |
| GTGCATACATGATGAGGTTTGCGATAAATGTGCTCGCCAGATGCTTAAGA |
| ATTTCCTAGCTCCTCTTTATTATGGTGCTGGTCCTCAAACACTAGCAGAG |
| TGCATGGCAGAAAAGAAAACCACACTCAAGAAAGAGCGTCGCAATGTAAT |
| CACTGGTAAGACTCAAAGTGAGATGATTAAGCAATGTGGCACTGCATTAG |
| GTGTTACACAGTTTAATACTCGTGCATTGGGTAAATCCACAGGACAAGCT |
| ATGGTAAAGATTGGAAGCCATGATGCATCCAAATGTACCTGTGCGAATC |
| ATGGATGTTGACCATGCAATCACAGAACAAGGTACGCAACGACGTGTAA |
| TTAATAAGCATTTTGCCGACACTATAGAGGCATTATTCGTAAGCAAGGG |
| TTGAAAGGTCTTCACATCTTAAATGGTGAAGAATTACTGTACCTACCTAT |
| CGTTACTGAAGAAACATACGTGAATATCTAAGGAGTTAATCATGACTAAG |
| GTATTAATTTATATGCGTGGACCTCATAAATGCTATGCAGTTGTAGCACC |
| AAATGGTGTTAAGCCTTATCGTACTTCAAAAAGATTGGCATTAATAGGTG |
| CTAGTAGTAGTGCAAGTTTCCAAATGGAACTTTTTGGTCATTGGACTGAA |
| AGGCAATTCCGTGAGGATTTTAAAGTCATTGGCAGCTTCATGGTGAAATA |
| TGCAGAATAAACATAGTCTTAGAATGTTCGATGGTCATGAAAACCTGCAA |

| Bacteriophage Genome Sequences |
|---|
| GCCAAGATTACTAACCAAGCCTTCCTGTTCGCACAGTTAACTATGGCTGA |
| GGCTAAGAAGAATAGTCTCACTCGTGAACAGGTTATCAAGGAGGCCACTT |
| GGGAACCACACCAAGGTAAATATATGGGCCACAAATTAACTGTAACACGC |
| AGTCGATAAGTCAAGGGTTGTCCAACGTGTTGGACAGCCTTTCATCATAT |
| TGATTGGGAGGTATTAAATGACTAAGTTTACTATGCAAGACCTCATTAAA |
| TTACGTGATGAAATAGAATCACCGGAAGTTAATACAGAGTTTCACTACAT |
| TGATCCACGAGATAAACAGAGATTCCTGATTATCAGATTGAGACGGAGT |
| TAATGTATGAAGATTATTGATTGGAAGAAGGAAGCAGAAGGCCGTATCCT |
| AGTGATGGATGCGGAGGCTAAAGGCCTGCTGGGTGCTATCCGCTACGGTC |
| ATCGTGAAGATGTACACATTATTTGCTGCATGGACTTGCTCACCACTGAG |
| GAGTTCCTCTTCTTCGACCCATATGAGATGCGTGACCCTGAACAAGGGA |
| ACACTTGAAAGAGTGGGAAGGCCATCAAGATGGGACCTTGGTTGATGGTG |
| TTAACTTCCTAAAGCACTGTGAAGCATCGTCTCACAGAACTTCCTAGGC |
| TATGACGGGCTTCTCTTTGAGAAAGCCTTCCCTGACATCTGGAAGGGATT |
| TAACTACACCGAGAGGCGCGGCAAGGGCAGACTACGTGCTGACTTGTGTC |
| CGGTACGCGTCATGGATACGCTGGTCATGAGTCGCCTGTTAAACCCAGAT |
| AGACGCCTTCCTCCGCAAGCATATGCCAAAGGTATGGGTAACGTTGCCCC |
| TCACTCAATTGAGGCGCACGGCATTCGTATAGGCCGTTATAAGCGGAGA |
| ACGAGGATTGGTCTAAACTAACTGACCACATGGTACATCGTGTACGCGAG |
| GACGTGGCGATAGGCCTGACCTATTCCTCTGGCTATTTAACGGAGAATG |
| GACGGAGCACAAACGCCGTGGCGTGAATAAACGCACTGGCCTAGGTATTG |
| AGACAGCCTTCCACATGGAGTCCATTGTGACGCTGGAGATGAGCCGTCAG |
| GCCGAGCGTGGATTCCGTCTGGATATAGATAAAGCATTAGCACGATGCGA |
| GGAATTGGACGCTAAGATTGATGAGACAGTCGCAGCGTTCCGTCCGCCAA |
| TGCCTATGCGTATCAAGTCTAAACCTTTTAAACCGGAAGAAAAGAATGAA |
| GTATGCCAACGCGCAAATGAGTATGGAGCTAGCAACAATATACCTACTGT |
| CCTTGACCCCTCTCACTTTCTTCACGCAGAGAGACGAGGAGATCGCAAGA |
| CAGTATGGAGTGTCACTACTAAGTCTGGTGATTGGTCGGCTAGCGTCAAG |
| AAAGACTTTCCTCACCTTAGAGGAAACCGTAATGACACGCCAAGTGTCAA |
| GTGGATTGGCGCTTACTCGCCTGTTACTTTCGAAGAGATTCCCTTGGGTA |
| ACAGGGATACAGTTAAGCAAGTGCTCTATGATTATGGATGGAAAGGTGTT |
| GAATTTAACGATACCGAGCAAGCGCATCTCGATGAGCATGGCGTATTACC |
| CAAGCCTTGGAGTGGGAAGATAAATGAAAAGTCCCTTACTTTATGGCAAG |
| AGAGAGCCGCACGTGAAGGTAAAACAGTCCCTGATTGGTGCTTGGGTATC |
| GCTGCATGGTACATACTCGTATCCCGTCGTGGTCAGATCCTCAACCGTGG |
| TGACGTTGAAGCCTTCGACCAGAAGGGGGTGTGGCCTTCGCAAGCTGGTA |
| TACGAAAGTGTCGCGGCCTTGTACCGTAGCATTTAACAAGGAGTTAGGA |
| ATCAATGCGCAGCAATACTACGAAAGGTACGGATGCTGGCCTACGTCAGA |
| CAAGGATGACGGAGAATGGCGTGTGCCAGCTATTGCTATTAGTATTGAA |
| CTTCTACGTTCCGTATGCGTCATCGTAACGTGGTTAATATTCCTGCCCGT |
| GGCTTGTATCCTTTACGTGATTTATTCATAGCAGGGAAAAGGCAAGCTAAT |
| CCTTGGTTGTGACGGTGCAGGTCTTGAACTGCGTGTCCTGTCTCACTTCA |
| TGAATGACCCTGAGTACCAAGAGATTGTACTGCACGGTGATATTCATACG |
| CATAACCAGATGAAGGCTGGTCTTCCTAAGCGTGATATGGCGAAGACATT |
| TATATATGCCTTCCTATATGGGTCTGGTATAGCTAACCTTGCAGCAGTAT |
| GTGGTGTTACTGAGGAGAAATGGAGGAAGTTGTGGCAAGATTTGAGGTT |
| GAACTACCATCTCTTGCACGTCTTCGTGAGAATGTTATCGCACAAGGTAA |
| CAAGTTTGGCTACCTACAAGCACCTGATGGTCATTGGGTCGCATCCGTA |
| TGTCTGGTGGTGAACTTAAAGAACACACTATGGCTTAACGTACTACTCAG |
| ATGACTGGTTCTCTGTGTATGAAATACGCATTGGTCAGAGCGTTTGCAGT |
| GATGCGCAAGGAAGGTGTGGCCTTAGATAGCATGGGAAACCCTTGCCGTA |
| TAGCTAACGTGCACGATGAAATCCAGATGGAAGTCCCTGAAGATGAGGTC |
| TTGTATCTCAACTACGACTTGCCTTTCACCTTAGAAGGGTTCGAAAACGAA |
| GAAGGCTGCTGTGAAAGCAGTGTTCGATCAGAGGAGAAACGTGTTCATG |
| TGGATTCTGAAGGACGTATGTGGTCTGCTGCAAATCGTTAGTGTTGAT |
| GCTGGTGTACTTCATTGCCAGCGTCGTTATCACCGTGCAGGGCATATCAT |
| TGCCGACGCAATGACCTGGGCGGGTCAGTACCTGAAGATGCGTTGTCCGA |
| TGGCAGGTGAGTATAAGTTGGTGCAAGTTGGAAGGAAACACACTGATGG |
| ACAGGTTTGATATTGTTTGCCTATTCTCTACCTTCTTTCTTATATTCTT |
| ATGCTTGCTTGCTATGGAAGTATGCGATTAGATATACCTGATGAAGAGGA |
| GGGTTACGATTGATGCAGGCATCTTTTATTATTCTTGAGTCATATTATT |
| TATGGTAGTATTCTGGGCTTTCTCTGGCATTGACCCAGATTGTGATGGTA |
| ACTACGACTGAGTTATACTCAAGGTCACTTACGAGTGGCCTTTATGAATA |
| ACTTATTCCTACTTATTTTGTCTAACATGATTTACTGGACACTATAGAAG |
| GAAAGCATAGGTAATCTAGGTTTATAAGGTAGTATAGGTAATTAAGTAAA |
| TATAGGAGATATAAATATGTCTATGGTAACTACTCTGGTATTCGTGCTC |
| AATACTTTCGTGGTCTTCTAATAAGTTCAAGTCCAAGGCTATCAAAGCT |
| ATTGAGGCTCGCATCGAAGCAGTACAGGCAGAGCAAGTTAAAGTTGAAGA |
| ACATCGTAGTTCTCAAATGATTGACTGTCATAACCGCTACTATGCATCTC |
| GTGATGAACTAAATGCACGTCAAGTCAAAGAGGTAGAAGATATGCTGGCA |
| CGTCACCAGCAAGAGCGTGACAGCCTGAAAGCTGAAGTGAATTGAAGAGACAA |
| GGCATCAATTGCTCTTGTACATCAAGCTGCATCTGACAGTCTGAAGAAAG |
| AGATTGTTATGCTGGAAATCGAACTGGATAACCTGACCAAATAAGGGGGG |
| GTTATGATGGAAGAAGTAATTCAAGCTAAACATGTAGGTATTATCTTTCG |
| CGATCTAGAGCAGCGTAAAGTTGCAGGTCATACTCGTCTGGCTAAAGAGG |
| AAGCACCGCAATCACTACTGTAGAACAAGCAGATGCCTATCGTGGACCA |
| GAGTTCACTCAAGGTGAAACTTGTCACCAATTGAGCCTATCAATTTGTGA |

| Bacteriophage Genome Sequences |
|---|
| CACTATGGCTATTGTAAATGTGCAAGAAGTCGAAGAGGGTGAGTGTGTCA |
| GTTACATCTACCCTTTAGATACTATTGCACGCATTAAGGTAATCCATAAG |
| TAATTACTAGACACTATAGAACAATAGGTCGGCTTAGTTCGGCCTATGAT |
| TGTAAAGTGTTGTTGATGTTGAACCATTGTGCATCTTGCACAACCCGATA |
| CCGTATAGGCTTTCTAGTGAGTACATGCTTGTGCTCAGTACAAAGCTAA |
| CTGACAATAGGAGACTAAATAAATGGCACGTGGTGATTTTGATTTTGGTG |
| CTCAGGTTACTAAATCTGAAGGTAAAGTCTTTAAGAATCCAGAAGTAGGT |
| GATCATGAAGCAGTAATCTCTGGCATCATTCATGTTGGTTCCTTCCAAGA |
| CATCTTTAAGAAAGGTAATACCACTGAAGTTAAGAAGCCAGCAAACTTTG |
| TTCTGGTTAAGATTGTCCTGATGGGTGACGATGACAAGAACGAAGATGGT |
| TCTCGCATGGAACAATGGATGGCTGTGCCTCTGAAGTCTGGTGATAAGGC |
| AACACTGACTAAGTTCCTGAATGCAGTTGACCCTAAAGAGTTGCTGGGTG |
| GCTTCGATGATTTCATTGGTGAATGCCTGACTGCAACGATGGTCGGTTCT |
| GGTGATAAGAATGACGATGGCTCATTCAAGTATGTTAACTGGAAGGGATT |
| TGGTGGTATGCCGGACAAGCTGAAGAAACTGGTCATTGCTCAGGTTGAAG |
| AGGAAGGTCTGTCTATGACAGGTCACATTACCTTCGACAAGCTGACCAAA |
| GAAATCCTTGATGACATCCCAGCCAACTTGGTGCGTCAATACTTCCTGAA |
| CGAGACGCCTCGTGGTAAGAACCTGTCTGTTGCTGGTTCTCACGTAGAAG |
| CAATCATTAAAGCTGCTCGTGAAGAAGACCCAGAATGGAAGAAGGCTAAG |
| AAGAAAGACGAGGAAGATGCTACCCCAGCTAATCGTAAATCTCTGGATAC |
| TGGTGAGTCTGTTCCACAGGAAGTACCTGAAGCAGAAGATACTCCTGCAC |
| CGGAGATGGATGAGGACGCGGAATATTAAGGAGAAAGGATGAAAGTACAA |
| ATCGTAACCCTGCACTGCAAGAAAGGAATTACAACTCTTGGCGGCAACAC |
| TTTTCACTCCTTCTCTGAAGGGACACATATGCCGACCTGCACTCAGGACATCT |
| GGCGCGACGGACGACACGTGGTGAACTACAGCGACCCAGCTACGGGGAAA |
| CGCCACGGCGTATCGCTTCCGGCGCATGACATTGCTCAGGTGAACACAGT |
| TTTATAAAGTCTCACGTGTGAGACAAATCGGTGTCCGGTATTTACTGGAC |
| ACTATAGAAGAGAAAGAAATTTTAATCGGCGATAATGCCATCAACACAAAA |
| GGAGAATTTAATATGTTCAAGATTGAAACATATCGTAAACCGTGTTGTTAA |
| AGGTGCTGCTCTGGTATCCGTTGAGTCTTTCATTATCGTCGATGAAACTG |
| ATCAACTGGTAGCTGGTACTAAGGCTTACGATACCCGTGAAGAAGCTCAG |
| GCTAAGATTGACAGCATGGGTAACTTCGCTGCTGGTCTGGAGTTCGCTCG |
| TGCTTGCTTCCCTGAGCAGGCTGACAAAGCTCAGATTGGTAAGGCTAATA |
| TCGTAGCTGAATATCTGGATTGGGTTGCTGCTGGTAAACCAGTGAAAGAA |
| GTTAAGGCTGCTGAAGAAGCTGAAGCTCCAGCAGAAGAAGTAGCTGCACC |
| GGAAACTCCGGTAAGTGAAGAGGAAGATTTTTGATAATAGCAGGTGTTGC |
| CTCTGTTAGTCCTAGCTGACTATCACGCTCACCTCATCTAATGCCCTGTC |
| TGCCTTAGTGTAGGCAGGGTCTTTTGCGTAATAGTTATTGGAGAATGAAT |
| TATGCCGACTATTGAATCTCGAATTGAACTGGACATTAGCTACAATGCAA |
| TCACCAGACAGTATATTGGGGTTGCCTATGATTACAAAACTGGTGAGAAG |
| CTAGTGGAGGTGAGCAATGGGATGACTATTGGTTAAGACAGAACCTCCA |
| TGATGCGGTGTCCTCCTTCCTGAAGGAGTGGCCTACATGCGACCAAACTT |
| CGACTTCGGAGCTACAGTATCGGAAGACAATAACCTGTTGCTGTGGCCAA |
| CTGAAGGTAATCGAATCGCTTTAATAGATGCTGATATGTTACCTTACATC |
| ATAGGGTATACAATCAGTGATATGACTTATGTACGAGCCCACAACTCGTGT |
| TAAGTCAGGGCAAGTCCCCTCAATCAAAGATACACCTGAGTGTAAGCAAG |
| CGTGTGACCGTGTGAACTCCTTGCTTAACTCTTGGGTGTATGCAGCAGAA |
| TGTGATGCAGCTAAGTTGTTCATGACGAAATCAGAAGCTAACTTCCGTGT |
| CCGCCTAGCATTCACCAAGCCTTATAAAAGGTCAACGTAAGACCGAAGAGC |
| CTCCATTCTTCTATGAATTGCGAGAGCATCTCTTAGAGGGTTCACGGTGCA |
| ATCTTGGCAGATGGAGAGGAAGCAGATGACCTCATGAGTATCGCACAATG |
| GGACAGCCACCGCCGCTTCCAGCAAGATACAGGTAACGAGTTCCCTATCG |
| GTAGTCCAGAGCATAAAGCATTCTCTGATCATTGCATCGTTTTCCTTGGAT |
| AAGGATTTTGATGATTGTTCCCGGTTGGCATCTACAGCCGGGTCAAGAGA |
| GAAATGGGTAGAGCCTATGGGTTGGCTTGAGCTACGCCGTAAGGCTAATG |
| GCAAGTCAAAGATCTAAAAGGTGCTGGCCTCATGTTCCACTATGCACAG |
| ATGATTATCGGTGATGATATTGATACTATGCTGGCATACCAGGTCGTGG |
| TGCTAAATATGCCTATGATCTTCTCAAAGATTGTAAGACAGAGAAAGAGT |
| TGTACATGGCAGTGCTGGGTGCTTACAAGGCTAAGTTCGGGCATGGACAA |
| GTTAAAATTAAGAATTACCGAGGTGGTTATCGTATCGGCAAAGCCTTTGA |
| CCTAATGCTTGAGTGTGGTCGCTTATCTCACATGGCAAGATTCAAGGGTG |
| ATATATGCGAGCCGATAGAACCCAATCTTGTGGGGAGATGATGGCGAA |
| TAGGTTAGCAAATTAAAATCATCGGAGGTGGCAGCTTATAAGAAGGAATTG |
| CTAGATAAGCAAGGATGGAAATGCCCTCTGTGTGGCGGCAGTCTCAAAGC |
| TGTCACACCTGTAAACCGTGTACTTGACCATGACCATGAGACAGGATTCT |
| GCCGCGTCGTTGTATGCCGAGGCTGCAATGGTGCGGAGGGAAGATTAAG |
| GGTGTTATCTCTGGTTATGGTAAGGCTGGTAACAACCGTTACTTCCAGCT |
| TCAATGGTTAGAGCGACTATATGAATACTGGAAGTTACATAGTACGCCTC |
| AGACAGATAAGTTATATCACAAACATCAAACGGAGGCAGAGAAGCGCGAG |
| GCTAAGAACCGTAAGGCACGCCTTGCTTATGCAAGAAGAAGGAGGTTAA |
| AGTTGGGTAAGCTGCGAGCTTGTACAAAGACTCGAGGTACTTGATGCA |
| ATCGACAAGCTACCGACGAGAAAGTAATGTTAACTACAATGAGATGGC |
| ACGTGTATTATCGTGTCATACTGTGGGTAAGAAGATTACCCGCCAGTTGG |
| CTCGATACTGGCATGGTCAATTCAAGAAGACCAAGAAGAATGGTGATTAC |
| TACCAGACCCTTCTGCAAGAAGATAAGCGTATCAAAGAAGAGCGTAAGCT |
| CAGGACTCCTGACCGCTACGAGGATTTGGCTATTGTGCCATTGCCTGACT |
| CGCCTCATCGAAGTGTACTGGTGATCCCTGATACTCATGCACCTTATGAG |

| Bacteriophage Genome Sequences |
|---|
| CACCCAGATACCCTAGAGTTCCTTGCAGCCGTGGCAGCACGTTACCGTCC
AGACACAGTGGTACACCTAGGAGATGAGGCAGACAAACATGCCCTGTCAT
TCCACGATTCGGACCCAAATCTGGATAGTGCTGGCATGGAGTTAGAGAAG
GCTCGTATCTTCATGCACAAATTGCACAAGATGTTCCCTGTGATGCGCCT
GTGTCACTCTAACCACGGCTCTATGCACTTCCGTAAGGCAAGCGCCAAAG
GCATCCCTGTGCAATACCTGCGCACCTATCGTGAAGTCTTCTTCCCGCAG
GGAGGTGGCGACCAGTGGGATTGGCAACATACGCACGTCCTTGAGTTGCC
GAATGGTGAACAAGTGGCATTCAAGCATCAACCTGCTGGCTCTGTCCTAG
CAGATGCAGCGCATGAGCGTATGAACCTTGTGTGTGGTCACTTGCACGGT
AAGATGTCTGTGGAGTACGCACGTAATACACATGAACAGTATTGGGCTGT
GCAAGGTGGCTGCTTAATTGATGAGTCATCCCGTGCATTTGCCTATGGTC
GTGAGTCTAAATACAAGCCAGCATTAGGTTGTGTGGTCATTCTGGAGGGT
GTGCCTCACATTGTCCCGATGCAAACCAATAGCGACAACCGTTGGATTGG
CAAGATTTAGTTGACACTATAGAACAAAGGGCTAGGTAAGACTTTATCGG
CTGGCGTATCCAAATGATATTGCACTAGCCCTTGATTGTATAGTGAATGG
AGGATTCAATATGTCACACTATGAATGTAAGAAGTGTCATAAGCGTTATG
ATTACTGTACTTGTGGTCAAGAGAAAACATCTTTTAAAGTTGGAGACAAG
GTATTTCGTAATGAAAAGATTCGATTCCTTGGAATCAATACTGCAAAGA
AGCTGGTATTGACCCTGATAGCCCTGTAACCATAGATGATATTGATGGCA
TTAACTTGTGCTTTCGTGAGGTGAGGGGTACAGGTTGGGATTCCAAAAAA
TTCAAACTTGCATCTGATAAGTTAGACAACAATATGGTAATTAAGCCTAA
GCACTACGAGTTCTTTGATGGCGTAGAGGCAATCACTATCATTGCCCGCA
GTATGACCGAGAAGCAATTCGCTGGCTATTGCATGGGTAATGCTTTGAAG
TACCGTCTACGTGCAGGTAAGAAGTTCAACACTGAAGAAGACCTGAAGAA
AGCAGATTACTACAAAGAGTTATTCCAGAAGCATCGTCACGAATGTATTG
ATGAGGATATTTGATATGAATATCTTTGAGTTCCTAGGTCTTCCAGAAGA
CCACCGCAATCACCCATTCATGCTGGTGAAGCATCGCGGTGAAGTTCTG
AGAAGAAATTAACTTTTCCATGTTATGCACAGGTGAAACAGAGATGGTATC
TTTTCTGCTGTTGTTGTTCGCACTGATGTGTCGTTGGCATTTTTGGTCG
CACTGGTAAGAAATTGGCAAACACTGAAGGACTCGAACAAGCCTTTGCTA
CCTTTCCGGTTGGCATTTATCTTGGTGAGCTTCAGTCTATGGCCATTGAT
ATCTACCTTGAGGCAATCTCTGGGGTTGTGAACCCCAATCGCACTGAGCC
ACTTGATTTCATAGGCCAGCAGATTAAAGACAACCTGTATATCGACTTCT
TCGATATGTTAACTATTAAGGCATTCCATGATGGATTCACTGATGTTTCT
TATCTCAAACGTTACGATGCTTTACATCGTCGTATCGGCGCTCATCTTAG
CGGGTGCAACGCTATCCTTCCTATCACTCCTTGCCATAATGAGCGAGAAG
TTGAAGCGTTTGCGCAAGAGCAAATATGATCAGGACGTGAGGGTGCTGTA
TTCAAACTGGACTGCGATTATGAAGCAGGACACAAAGGTTATCGTCAGAC
TAAAGAAGTCCGTAAGGTAACCTATGACCTTACTTGTATTGGCTTTGAAG
AAGGTAAAGGCAAATACAAAGGTAAGGTAGCTAACCTCATTTTCAAATGG
AAAGGAGGCAAGACAATCAAAGCTATGTTAGGTAAGGGGTGGACTCATGC
AGATGCAGAGCAGATGTTCCACGACATTAAACATGGTGGACGATTGAATG
TCATTGGTAAAATCTTTGAAGTCAAAGGTCTTCAGGATTCAAGCAAGGGC
AACATTCGTCTGCCCAAAGCGGGAGAATTAAGACATGACAAAGATGAACC
AGATTTCTTTTGATAGCATGAAGGCAACTCGTGCAGTTGAGGTAGCAGAA
GCTATCTTCGAAACTTTATCCTGTGGCATGGAAGTGCCATATACTTTACT
TGCTGATGCAGAAGAACTTGGTCTTTCTGTAGAAGCTATCCAAGAGAAGG
TTGACGAATTATATGGTACAGACGAAGAAGAAACCGACGATTTCATTTGA
AGGAATGGAGATGCTTGAGATGATTCTCAAGCCTTCTTCTCCTAAGGTGA
CTAAGACTCATGAAGAGTTAATCGTTGATGAAGTTAAGCGTTACATCATG
GATTGTGTCAGAGCACAACTGGTGGTCCAATGATACGTCCAGCCTCCTTC
CTAGATATTCCTGAGATTATAAACCTTGGGAATAAATATGTGGAAGAGGA
AGTCAAGGTTGTAGCCCACCACTTAGCCTCATGGAATGCAGAACAAAGTG
CCATAACCTTTGTGCATCTCTTAATAGAGACCCACCACTCAGCCTCATGG
AATGCAGAACAAAGTGCACATAACCTTTGTGCATCTCTTAGTAGAAGAA
TTTATCCCTATGGGTTGCTGTAGATGAAGGGCAGATTGTAGGGTTCCTGT
GGGCTGGCTATCACGAGTTGGCCCCTTGGCACCCTGTAAGAGTTGCCTCT
GACATTCTCTTTTATATTATACCAGAGAGGCGAGGAACACTACTTGGTAT
GCGTCTCATCAAAGCCCTAAAGCAATGGGCTAGTGATAATGAATGCTCTG
AGGTTCGCCTGTCTATCGCCTCTGGTATTAATGAAGAACGTGTCGGACGT
ATGTATAAGCGACTTGGCTTTGAACGTTGGCACTGTGTATAACCTGAA
GTTCTAAGGAGATAACATGGGTGTTGTAAAGAAAGCATTTAAGGCTATCG
GTCTTGCTCAAGATGCACCACGTATTGAAGCAAAGTCCCAGCACAGCAG
CTTGAGCGTAAGCCTGAGACTGAAGCTGAAGATATTCAAATTGGTGCAGG
GGATGATGCTACTGCATCTGCAAAAGGTAAGCGTGGCCTTGTCCGTCCGG
TAGCTTCTAGCTTGAAGTGTAATATGAAACAGAGCATAGATTGGCCTTCAGAT
TGGAGGTAAGCGGTCTAAGATACCTAAGCTATGGGAGAAGTTCTCCAATA
AACGTAGCTCTTTCCTTGATAGGGCGAAGCATTACTCCAAATTAACCTTG
CCCTATCTGATGAATGACAAAGTGATAACGAGACTTCGCAGAATGGATG
GCAAGGTGTAGGTGCTCAGGCAACCAACCATCTAGCCAACAAGCTAGCGC
AAGTACTATTCCCTGCACAGCGTTCCTTCTTCCGTGTAGACTTAACTGCA
CAAGGTGAGAAGGTTCTTAATCAGCGTGGCCTGAAGAAGACAGAGCTAGC
TACCATCTTCGCTCAAGTGGAAACACGGGCAATGAAAGAGTTAGAGCAAC
GTCAATTCCGGCCTGCTGTAGTAGAAGCATTTAAGCATCTTATTGTTGCT
GGCAGCTGTATGCTATACAAGCCGAGCAAAGGTGCAATCAGTGCTATCCC
AATGCATCACTACGTAGTTAACCGTGATACCAATGGCGACCTGTTACACA
TTATCTTGCTACAAGAGAAAGCCTTACGTACCTTTGACCCAGCTACACGT | GCGGTAGTAGAGGTTGGCCTGAAAGGTAAGAAGTGCAAGGAAGATGACAG
CGTTAAGCTGTACACACATGCTAAGTATCTTGGTGATGGATTTTGGGAAC
TCAAGCAATCTGCTGATGATATCCCTGTGGGTAAGGTGAGTAAAATCAAA
TCAGAAAAGCTACCTTTCATCCCATTAACTTGGAAGCGAAGCTATGGTGA
GGATTGGGGTCGACCTCTTGCAGAGGATTACTCCGGTGATTTATTCGTTA
TCCAATTCTTTATCTGAAGCGGTTGCCCGTGGTGCTGCGCTGATGGCAGAT
ATCAAGTACCTGATTCGTCCTGGTGCTCAAACTGATGTTGACCACTTTGT
TAACTCTGGCACTGGTGAGGTTGTCACTGGTGTAGAAGAAGACATCCATA
TTGTACAGTTAGGTAAGTACGCAGACCTCACACCTATTAGCGCGGTTCTA
GAGGTATACACTCGCCGTATCGGTGTTGTCTTCATGATGGAGACAATGAC
ACGCCGTGACGCCGAACGTGTTACTGCTGTAGAAATCCAGCGAGATGCGT
TAGAGATTGAGCAGAACATGGGTGGTGTATACTCCCTCTTTGCTACTACT
ATGCAATCGCCAGTAGCGATGTGGGGTCTGCTGGAGGCAGGGGAGTCCTT
CACTAGTGACTTAGTGGACCCTGTGATTATCACAGGTATTGAAGCTTTAG
GACGCATGGCTGAGTTGGATAAACTGGCTAACTTTGCTCAGTATATGTCA
CTGCCATTACAATGGCCTGAGCCTGTCCTAGCTGCTGTGAAATGGCCTGA
CTATATGGATTGGGTGCGTGGTCAAATCTCTGCTGAACTGCCGTTCCTTA
AATCGGCTGAAGATGGCACAAGAACAGGAAGCACAGATGCAAGCACAG
CAAGCACAGATGCTTGAAGAAGGTGTGGCTAAGGCCGTGCCGGGTGTAAT
TCAACAAGAACTTAAGGAGGCGTAAATGTCTTTCTCATTTACTGAACCGTC
AACCACTCACCCTACTGCTGAAGAGGGTCCGGTAGAAACCAAGGAGGTAA
CAACTGATGCTGCTACTACTGATGCTCCTGCTGACGCTGGCACTTCTGTA
CAAGATGACAATGCTGGTGCACAACCTACTGAAGACACCGGAGGAGAAGC
TTCTGACAGCCTTCAGAAAAAGGAGACAATGGCGGAGAATGGTGAAC
CTAAGCCAGATAGATACCGCGACCGACACTGAGGAAGTGCAATACTTCTTC
GGAGAACATGAAGTAACAGTAGACATCCCACAGGATGTAACTGACAGCCT
TAAAGAGAAAGGCATTGATGCCAAGCAGGTTGCCAAGGAACTCTATTCCA
AAGGTGGCAAGTTTGAACTGTCAGATGCAACAAGCAGAGAATTGTATGAT
GCTTTTGGCAAGTTTGCGGTAGATGCTTACCTATCAGGTCTAAAGGCTCA
AAATGAAGCCTTCTTCCTGAAAGAAGCCAACGCAGCTAAAGAGTTGGAAG
CAGCTAACACCCAACGCTTCTCTGATGTTTCTAAGGAAATTGGTGGCGAA
GAAGGTTGGTCCCGTCTTGAGGAGTGGCGACTTGAAGCGCTGTCTGATGA
CGAACTAATGCATTCAATGCGGTGATGGAATCTGGCAACCAGTACCTGC
AACAATATGCTGTTCGTGAACTGGAGGGTCGTCGTAAGCAGGCACAGGGG
GATGATAAGCCATCCCTGATTGAGCCATCAGCACCTGCTAAGGCTAATGA
AGAGAATGCCCACTGACGCGAGATCAGTACGTTCAAGCAATCGCAACTC
TTAGCCAGAAGTACGCCAATGACCGTAAAGCTATGGCAGAAGCTCAGGCT
AAACTGGACGCCCGTCGCCGTGCTGGCATGGCTCGCGGTATCTAATTCAG
TATTTACTGGACACTATAGAAGGGGAGAAAGTTCTCCCTAGTTATCAATT
TGATTTATAAGGAGATTATAATACATGTCTACACCGAATACTCTGACTAA
CGTTCGTCTATCTCGTCCGGTAGGTTGACAGCCTTCCATTGAGAAGT
TTAATGTAAGGTCAATGAGCAGTACCTGAAAGGTGAGAACATTCTGTCC
TACTTTGATGTACAAACTGTTACTGGCACTAACACAGTGAGCAACAATA
TTTGGGCGAAACTGAGTTGCAGGTGCTAGCACCGGGTCAGTCCCCTAATG
CCACCCTACTCAGGCGGATAAAAACCAGTTGGTAATTGATACCACTGTC
ATTGCTCGTAACACTGTGGCTCACATCCACGATGTACAAGGTGACATCGA
TAGCTGAAACCAAAACTGGCTATGAACAAGCCAAGCAACTGAAACGTC
TGGAAGACCAGATGGCAATTCAGCAGATGCTGTTAGGCGGTATTGCTAAC
ACCAAGACCGAACGTAACAAGCCGCTGTTTAAAGGGCATGGCTTCTCTAT
CAACGTTAACGTAACTGAGAGTGAAGCACTGGCTAACCCTCAGTATGTTA
TGGCTGCGGTAGAGTATGCTCGGAGCAACAGCTTGAGCAGGAAGTGGAC
ATCTCTGATGTAGCTATCATGATGCCGTGGAAGTTCTTCAATGCTTTGCG
TGATGCAGACGAATTGTAGATAAGACTTACACTATCAGCCAGTCTGGTG
CAACCATTAATGGCTTCGTTCTCTCTTCTTATAACTGCCCTGTGATCCCG
CTAACCGATTCCCTACCTTGCTCAGGATCAGGCTCACCACCTGTTGTC
TAATGAAGATAACGGCTATCGTTATGACCCTATCGCAGAGATGAATGGTG
CAGTTGCTGTTCTGTTCACTTCCGACGCACTGCTGGTGGGTCGTACCATT
GAAGTGACTGGTGACATCTTCTATGAGAAGAAGAGAAGACTTATTACAT
TGACACCTTCATGGCTGAGGGTCAATCCCTGACCGTTGGGAAGCAGTGT
CTGTAGTTACCACTAAACGTGATGCAACTACTGGTGATGCTGGAGGTCCT
GGTGATGATCACGCAACCGTACTGGCTCGTGACAGCGTAAGGCTGTATA
TGTCAAAACCGAAGGTGCTGCGGCTGCATTCTCTGCTGCCCCAGCAGTA
TCCAAGCGGAAGACCTTGTAGCGGCGGTACGTGCTGTAATGGCAAATGAC
ATTAAGCCGACTGCAATGAAACCTACTGAGTAACACCTATGCCCTATCTA
CCTTGCGTAGGTAGGGGTTCTTTTTGTTAGGAGGATTCATGCCTGTAATTA
GACAAACCAGTAAATTAGGACATATGATGGAAGATGGTGGCCTTCCAGATT
ATTGATAGTAAGCTGGAAGCGTAAACTTGTGTATGCGAGCTATTGGTCG
TGAGGGTGTGGATTCCCTGACTCAGGGGACTTGGACGCAGAAGATGCAA
GCAAAATGATCGACATCGTATCCCAGCGGTTCCAGTACAACAAAGGAGGT
GGCTGGTGGTTCAATCGTGAACCAAACTGGCAACTTGCACCAGACACTAA
CGGTGAAGTTAATTTACCTAACAACTGCCTAGCAGTATTGCAGTGTTAGA
CTTTAGGTGAAAAGAAAGTACCTATGACTATGCGACAGGTAAGCTCTAC
TCTACTTGGAGTCACACCTTTGATATGCGTAAGCATGTTAATGCTAATGG
TATGATTCGTCTTACCTTACTCACCTTACTACCCCTACGAGCATCTACCTA
CAAGTGTAATGCAGGCTATTGCCTATCAAGCTGCTGTAGAGTTTATTGTG
TCTAAGGATGCAGATCAGACTAAGCTAGCCACTGCGCAGCAGATAGCCAC
TCAGCTTCTTATGGATGTACAATCTGAGCAAATGTCACAGAAGCGATTAA |

Bacteriophage Genome Sequences

```
ACATGCTGGTACATAACCCTACTCAGCGTCAGTTTGGTATCATGGCTGGT
GGCTCTCAGAATGTACCTGCTTACTCTCATTCACCTTATGAGAGTTGGGC
GCTCCGTCCGTGGGAGGATCGTTAATGAAGTACAAGGTTCATTAGGTAG
ACAAATCCAAGGGATTAGCCAGCAGCCGCCAGCGGTACGCTTGGATGGTC
AGTGCACAGCTATGGTTAATATGATACCTGATGTAGTGAATGGTACTCAA
TCACGCATGGGTACAACTCATATTGCAAAGATACTTGATGCGGGACTGA
TGACATGGCTACTCATCATTATCGCAGAGGTGATGGTGATGAAGAGTATT
TCTTCACGTTGAAGAAAGGACAAGTTCCTGAGATATTTGATAAGTATGGG
CGCAAATGTAATGTGACTTCACAAGATGCACCTATGACCTACCTCTCTGA
GGTTGTTAATCCAAGGGAAGATGTGCAATTCATGACGATAGCTGATGTTA
CTTTCATGCTTAATCGTAGGAAAGTAGTTAAAGCTAGTAGCAGGAAGTCA
CCTAAAGTTGGAAACAAAGCCATTGTGTTTTGTGCGTATGGTCAATATGG
TACATCTTATTCCATTGTAATTAATGGGGCCAACGCTGCTAGTTTTAAAA
CACCGGATGGTGGAAGTGCAGACCATGTTGAACAAATTCGAACTGAACGT
ATCACTTCTGAATTGTACTCTAAGTTGCAGCAATGGAGCGGTGTGAGTGA
CTATGAAATACAAAGAGACGGTACTAGTATATTTATCGAGAGACGGGATG
GTGCTAGCTTTACAATAACAACCACCGATGGTGCAAAAGGTAAGGACTTA
GTGGCTATCAAGAATAAAGTTAGCTCTACTGACCTACTCCCTTCTCGTGC
GCCTGCTGGTTATAAAGTACAAGTGTGGCCTACTGGCAGCAAACCTGAGT
CTCGTTACTGGCTGCAAGCTCGAGCCTAAAGAGGGAAACCTTGTGTCTTGG
AAAGAAACAATAGCTGCTGATGTATTACTTGGGTTTGATAAAGGCACAAT
GCCTTACATTATTGAACGTACAGATATCATCAACGGCATAGCTCAATTCA
AGATAAGACAAGGTGATTGGGAAGATCGTAAAGTAGGGGATGACTTGACT
AACCCTATGCCCTCTTTTATTGATGAGGAAGTACCCCAGACAATAGAGGTG
AATGTTCATGGTGCAGAACCGCCTATGCTTTACAGCAGGTGAAGCGGTTA
TTGCTTCTCGTACATCATACTTCTTCGATTTCTTTCGTTATACGGTTATC
TCTGCATTGGCAACTGACCCCTTTGATATTTTCTCAGATGCTAGTGAAGT
CTACCAGCTAAAACATGCAGTGACCTTAGATGGCGCTACCGTGTTGTTCT
CTGATAAGTCACAATTCATCTGCCAGGCGATAAGCCTTTAGAGAAGTCA
AATGCACTGCTTAAGCCTGTTACAACATTTGAAGTGAACAATAAAGTGAA
GCCAGTAGTAACTGGTGAATCGGTAATGTTTGCCACTAATGATGGTTCTT
ACTCTGGTGTACAGAGTTCTATACAGACTCTTATAGTGACACTAAGAAG
GCACAAGCAATCACAAGTCATGTGAATAAAACTCATCGAAGGTAACATTAC
CAACATGGCAGCAAGCACCAATGTCAACAGGTTACTTGTCACTACCGATA
AGTATCGTAACATAATCTACTGCTACGATTGGTTATGGCAAGGAACAGAC
CGTGTACAATCAGCATGGCATGTATGGAAGTGGCCTATAGGTACAAAGGT
GCGAGGTATGTTTTATTCTGGTGAATTACTTTACCTGCTCCTTGAGCGAG
GAGATGGCGTGTATCTGGAGAAGATGGACATGGGTGATGCACTAACCTAC
GGTTTGAATGACCGCATCAGAATGGATAGGCAAGCAGAGTTAGTCTTCAA
GCATTTCAAAGCAGAAGATGAATGGGTATCTGAGCCGCTCCCTTGGGTTC
CTACTAACCCAGAACTTTTAGATTGCATCTTAATCGAGGGTTTGGGATTCA
TATATTGGCGGCTCTTTCTTATTCAAGTACAACCCTAGTGACAATACTTT
GTCTACAACCTTTGATATGTATGATGACAGCCATGTAAAAGCGAAGGTTA
TTGTTGGTCAGATTTACCCTCAAGAGTTTGAACCTACGCCTGTGGTTATC
AGAGACAATCAAGACCGTATCCTACATTGATGTACCAGTTGTAGGATT
GGTTCACCTTAATCTTGACATGTACCCCGATTTCTCCGTAGAAGTTAAGA
ATGTGAAGAGTGGTAAAGTACGTAGAGTATTAGCGTCAAACCGTATAGGT
GGTGCTCTCAATAATACAGTAGGCTATGTTGAACCGAGAGAAGGTGTCTT
CAGATTTCCACTGAGAGCTAAGAGCACGGATGTTGTTTATCGTATTATTG
TAGAGTCACCTCACACATTCCAGCTTCGTGATATTGAGTGGGAAGGGAGC
TACAATCCAACCAAAAGGAGGGTCTAATGGCTATAGGTTCAGCCGTTATG
GCTGGTATGTCTTCTATTGGTAGCATGTTTGCAGGCAGTGGTGCAGCAGC
CGCTGCTGGAGGTGCTGCCGCAGGTGGCGGAGGTTTGCTAGGTTCACTAG
GTGGATTCCTAAGTGGCTCTACTGCTGGTTTCTCTAATGCTGGCCTTCTT
GGTGCTGGCCTTCAAGGGTTAGGCTTGATTGGTGATCTATTTGGTGAAG
TGATGAAGCCAAGGCGATGAAGAAAGCACAAGAAGAGCAATGGCGGCAGC
AGCTTATTGCTACACAAGAGGCGTACAAGACAGTGGCAGACGCAGAACGT
TCTGCTGCTAAACAATATCATGCAGATGCAATCAGTAATCAGGCTTCACT
GCTACAGCAGCGAGCACAGGTTGCATTACTTGCTGGGGCTACTGGTACTG
GTGGTAATTCTGTGTCCTCTATGCTTAATGACTTAGCAGCAGATGGCGGC
AGGAACCAGAGTACTATCATTGATAACTATGAGAATCAGAAGATTATTT
CACCAACCAGCTTAAGTCTATCCAACGTGGTGGTCAGATGCAGATGCGTG
AGTTTAAGAAGCCTTCTGCTATGAATACCTTGGTTAAAGGTATTCCAAGT
CTGGCATCTGCCTATGTAACTGGTAGTAAGTCTGGCAAGGCATTGGGTAA
AGCCTTAACTGATTCTCGCACATATTCATCTGGAACAAGAGGTATTTAAT
GGCAATTGAGCGACAAGCAGTACAAGGTCTGCCACAAGCTGCAAGAGAAT
CTCCTAATGTCATGACCTTTGCACCTCAACAAGTGGGAGGTGTGGAGGCT
GGCGTGGCTTCACCTCCGGTAGTAGGTTTATGAAGACCTTATTCGTGC
AGCAAGCAGCGTGGCTGATGTTACCACTGGTATCCTTAATCAGAAGATTG
AGGAAGATAAGGTTGTTCAAATGGAACGGGCATATAACGGATTAATGCCT
TCTGAGGATGCAACTCGTGGTGGCGCTCGTGCTAACATGCTTGTCAAAGC
TCAACTGCTAGCTAATGATGAAGCAGCACGAATGAAAAGACATGGCTACTC
GTTTCCAAGGAACGGATGACGAATGGACACAACTTATGGTTGACTCTCGT
AATGAGATGCAGAATAAGCTGTTCAGCAATACCCTGAGTTGCAAGGTGA
CAAAGATACTATGCGTATGGTCACTAATGTCTTCCAAGAACAGCAGCCTC
AGATTTGGGCTACACGAACCCAGCATAAACTTGACCGTGAACAAGCGAC
CGTGAGGATACCTTTGACGGGCGAGTGGCTTCTACTTGGGATTCTAATAT
```

```
TGACCCTGAAGCCTCTGGCTATGCTTTACAGGAACGAATCCGCGAAGGTC
TTACTCAAGGATTACTACCTGAACAGATGTACAAGAAGTTAGTCCAGCGA
GCAATTTCACTTGCACAAGGCGGTGATGTTAGCATGGCTGAAGCCCTGAA
GTATGTGAAGGACGATAAGGGTGTTTCTGTTTATGCTAAGAATCCACAGC
TTATCACAGCCATCACTAGTGGTAATGCAGTTTGGGCTAGGAATAATGTA
GCTGATGTAACTCGTATGTCTTTCGAAGTTAAAGAATCCTACCTTGCAGG
TGATTTAACTGATGAAGAATTGTTGGAACGAGCACAGCACATTAATAATC
TGACAGGTAACTCTGTCTTCTCTAATCCAGAACTAGAGGCACTGATGCGC
CAACGGGCTAAGCAGAATGCAGAGCTAGGTGCAATGCAGGATATGCGACG
TGAGCTTTACTCCGACCGCCTGACTGGCTTCCAAGGTAAGACTGATAAAG
AGAAGAAGGCTTACATTGATGTTATCAAACAGGATAGCCAACTTTATGCA
GACCAGCAAATCAAACAACGTGGCTTGGACCCTTACAGTCAAGAGGCTGA
AGCTATTCGTGGTGCAGTGGAAGTGCAGCGCCTGCAATTCATGAACTCCA
AAGGCTTAGTGGATGATACCTTTGAGTCTCGTATCAAAGCCATGGAATCT
ATGCTATCGCCTGAGCACTTTGCCAAGGGCGAACCACAGGAGTTGATGAC
TATTCGCCAGTTGTTGGGAACCAGTTACCAGAAGAGAGCCGAGGTGTCTTTG
GTGACACGGTGAATGGCTACATGGATAACTACAACACTGCTACACAAATG
GGAGAGACACCTTTGCAGGCTGCAAGGTTTGCGCGTAAAGCACAGCAGAA
ATTCTCTCGTACTGAGAAGGAAACCAAGAAGTTCAACTCAGCTATTGGAG
ATGCACTGGATGAGGTATCTGGTGCTGGCTGGTTTGATGGTAAAACCGAA
GTGTCAGACTTAGGTAAAGCTATTGCGGAAGAAGAGTTACGAGCTAAGGC
CAATATGTTGTGGTCTAGTGGTATGCGTAACATGGATTCCATCAAGAAGG
CTTTAATTACTTGGGGCAATAAACGCTACACTCAATCAGAGGATGCAAAG
ACTTCCGGTGGCTATTTCATTAAAGGTGATTACACTTCTGCATCTGATAT
GCTTATGTCAGTTGGGAAAGGCGTAAACCCTACCGATGTACCTCTGGCGC
TTGGTAGGTATGTAGAAACACAGATGCCAGAATTGAAGAAGGAGCTTCAA
GAGGGGGAAACTAAAGATGATATATACATTGATTACAATGAACAGAAAGG
TACTTTCGTGATTCGTGCTGTGCAGCAGGTCGCCCTCTTTCTGGAGTAA
TCCCTGTAACCTCTTTAGATACCACTTCACTACTAGATTCTGCCTATCAG
AAGAAAGTAGAGGAACGAGATAAAGGCGAGTATGTTCACCCGTATCGTAC
AGATATTGGTGCAAGAGCCTATGCCAGCTAAACCAACTGCCAAAGATA
TTGGTAAATTTGGACTAGCTAACTTCTCCATGTCTTCTGCTTTTGCTTCT
GGTGAGAATCTGCCTTCTAACTTCGAGATTAACTATCGAGGTAATATGCA
ACAATTCTATGACAAGCTAGCTATGGATGAGAATAAAGATAAAGTTGGCT
TTAATAAGGCAACTGGAACCTTTACTCCATATAAAGACGCTCACGGTGAG
TCTATCGGTTACGGTCATTTCTTAACGGAAGAAGGAAGCGAAACGGGTA
TATTAAGATTGGCGATGAACTAGTTCCCTATCGAGGGTCTATGCTCAGC
TTACAGAGAGCAAGGCTCGCGCTCTTATGGAGCAAGATGCTAAGAAGCAT
GTGCCTCCTACTCGTGACTGGAAGATTCCGTTTGACCAGATGCACCCTGC
ACAGCAACGTGGCTTGATGGATTTAAGCTACAATTTAGGTAAAGGTGGAA
TCCAGAACTCACCGCGTGCTGTTCTGCATTCAAAGCTGGTAAGCTTACG
GAGGGCTTTATCGAAATGCTGGGCACTGCATCAAGTGAAGGTAAGCGTAT
TCCTGGCCTACTGAAGCGACGCGCTGAGGCATACAATATGGCATCTGCTG
GTGGTGTGCCTAAGATTACCGAAGTGGAGACTCGTGAAGATGGCTCCATG
TGGGTTAGGTTTGGGCACCGACCTATGCCAGCAGGTTCTGTCTCGCATGGA
TCATAAAGTATTGGCGCGATGGTTGGTATCAGGTTATGAGGCTGCAC
CTACCAAGTTAGCTAAAGATTCAAGGTAGGTAAAGTTAAGTTGTAGTAC
CTAACTCAAGGCTTGTCTCACATGTGAGACAGGTCTTTATGATAGGCACT
ATGGAGGAATTATGGAACAAGACATTAAGACTAATTGGGCTGGATATGTC
CAGTCTACTCCTGAGCCGTTTTCTATTGAGGCGGCTCCGGTATCGGCTCC
TACGATACGCCAGCGTAATGAGTTACAAGAGCAAGTTCTTGAAGCTAAAG
CTGACGCTGATATCTTAGGTGCTGTAGGTGCTGCCTTCCAGAATGAGTGG
TTGGCATTCGGAGGCAAGCGGTGGTATAGACCGTGCCACTGCTGATTTCAC
ACCTCAACCAGACTTTAGATACAACCTGAGCAACGTGAAGCACTACGTT
TCAAATATGGTACGGATATGATGCAGACAATCACTGAGGGTGTTCGTTCT
GAGGATGAATTGAACTTCCGTATTCAGAATGCGGATAAGACCTTGAGCG
CAATAAGCCGTTGCTCAGGCTGGCTGGGTTGGCTCTGTGCTGGCGACGATTG
GCGCTGCTGTGCTTGACCCTGTGGGATGGGTTGCCTCTATTCCAACCGGT
GGTGCCGCTAAAGTTGGACTCGTAGGCCGTGCTGTGCGTGGCGCTATCGC
CGCTGGCGTGAGTAATGCCGCTATTGAATCCGTATTGGTCCAAGGTGACA
TGACTCGTGATTTAGATGACATTATGGTAGCACTGGGTTCCGGTATGGCT
ATGGGTGCGTTATTGGCGCTGTAGCGCGTGGGGCCACTAAGCTCAG
TGAGCAAGGTGATGACAGGGCTGCTAGCATTGTGCGCAGTGCAGACGCAG
GGGACCGCTATGTTCGTGCGTTGCCGATGACAGTATCGGTGCGATGCGT
GTTAAGGGCGCAGAGGTTCTCACTGAGGGTGTATTCGATATCTCCAGTAA
GAGTGAAGACCTGCTGAAAACCTTGCAACGAGAAGTGAATGCTGATTGATA
TGACACCTCGCCGTTGGGCTGGAACTATGTCTGCCCCTCGGTACTGTCGTG
CACTCATCTAAAGATGCAAGTATCCGAGGCCTTGGTGCTCGTCTGTTTGA
ATCCCCACAAGGTCTAGGTATGCAGAAGGCATCTGCTAGTCTTATGCAGA
ATACTAACTTAAATCGCCTGAAATCTGCTGATATGAACCGCTTCAATGAT
GGGTTTGATTTGTGGCTTAAAGAGAATAATCAATCCAGTAGCAGGGCA
TACCAACTCTCATTATGTACAGCAATACAATGAAAAGGTGTGGGAGGCAG
TGCGTATTGGCATGGATGAGTCTACACCTAAATCTATCCGCATGGCTGCT
GAGGGACAACAGGCTATGTACAGAGAGGCGCTGGCTTTACGTCAACGTTC
TGGTGAAGCGGGATTTGAAAAGGTAAAGCCGACAACAAATATATGCCTG
ATATCTTTGATAGTATGAAAGCCAGACGTCAATTCGATATGCACGATAAA
GAAGACATCATCGAACTTTTCTCTCGTGCCTACCAGAATGGCGCTCGTAA
```

| Bacteriophage Genome Sequences |
|---|
| GATTCCAAAGGAAGCAGCAGATGAGATTGCACGAGCACAGGTAAATCGCG |
| TTGCTGATGCTACCTTAACTGGAAAGCTTAGTTTTGAAAAGGCAATGTCA |
| GGTCAGACTAAGGCAGAGTATGAAGCTATCATGCGTAAGGCAGGCTTCAG |
| TGATGAAGAAATTGAAAAGATGATAGAAGCTCTGGATAACAAAGAAACCA |
| GAGATAACATCTCTAACCGAGCTAAAATGAGTTTAGGATTAGATGTTACT |
| CAAGAATACAATGGCATTCGTATGCGTGACTTCATGAATACCAACGTGGA |
| AGAGCTAACAGATAACTATATGAAGGAAGCAGCAGGTGGCGCTGCATTGG |
| CTCGCCAAGGCTTCTCTACCTATCAGGCTGCACTTAATGCAATTGACCTT |
| GTAGAGCGAAATGCACGAAACGCGGCTAAGGATAGCAAGGCTAGTTTGGC |
| ATTAGATGAAGAGATTCGTCAGATGCGAGAAGGTCTTCGCCTGATTATGG |
| GCAAGTCGATTGATGCAGACCCACAGGCTATATCTACTAAGATGATGCGT |
| CGTGGTCGTGATATCACAGGTGTGCTTCGCTTAGGTCAAATGGGCTTCGC |
| ACAGCTAGGTGAACTTGCCAACTTTATGGGTGAATTTGGTATTGCTGCAA |
| CTACTATGGCTTTAGGTAAGCAATTCCGCTTCACCTCTAAGGCGTTGCGT |
| AATGGCGATGGCTTCTTCCGAGATAAGAACTTAGCTGAGGTTGAGAGAAT |
| GGTGGGGTACATTGGTGAGGATAACTGGCTAACAACTAAGGGTGCACGTC |
| CTGATGAATTTGGTGATGTAACCACAGTAAGAGGGATGATGGCTCACTTT |
| GACCAATCCATGAACTCAATACGTCGTGCTCAAACCAACCTATCACTCTT |
| CCGCATGGCACAGGGTTCTCTGGAGCGAATGACTAATAGGCAAATAGCTT |
| TGTCTTTCATTGACCACCTTGAAGGCAAGAAGATTATTCCTCAGAAGAAA |
| CTGGAGGAACTTGGTCTTACTCAGGAGTTCATGCTAACCTACAGAAGCA |
| CTATGATGCTAACTCTAAAGGTTCTGGCTTGCTTGGCTTTGATACAATGC |
| CTTATGCCATGGGTGAAACTTTAGCTAATGCTATTCGTCGTAAGTCAGGT |
| CTAATCATCCAACGTAACTTCATTGGTGATGAAGGTATCTGGATGAACAA |
| AGCACTAGGTAAGACATTTGCACAGCTTAAGTCATTCTCTCTTGTATCTG |
| GTGAGAAGCAATTTGGTCGAGGGATTCGCCACGATAAAATTGGTCTTGCT |
| AAGAAGACAGCTTACGGGTTTGCTTTGGGTTCAATAGTGTATGCGGCAAA |
| AGCCTATGTGAACTCTATTGGGCGAGAAGACCAAGATGAATATTTGGAAG |
| AGAAGTTATCGCCTAAAGGGTTGGCCTTTGGTGCAATGGGTATGATGAGT |
| ACAACTGCTGTATTTAGTCTAGGTGGAGATTTCTTAGGTGGCCTAGGTGT |
| TCTACCTTCCGAACTCATTCAATCACGCTATGAAGCAGGTTTCCAAAGTA |
| AGGGTCTGATTGACCAAATACCTCTGGTTGGCGTTGGTGCAGATGCAGTA |
| AATCTGGCTAACTCAATCAAGAAGTATGCAGAAGGTGACACAGAAGGTGT |
| AGATATCGCTAAGCGAGCACTCCGTCTTGTGCCACTTACCAATATAATAG |
| GTGTCCAAAACGCATTGCGTTATGGCTTAGATGAACTGGAGGATTGATGA |
| GTTACATTTCACAGAACATACAGCCAATGGTACGCAAGTCACCTATCCT |
| TTTAGCTTTGCTGGTAGGGATAAAGGTTATCTTCGTGCCTCAGATGTGAT |
| AGTGGAGTCTCTTCAAGGTAACACTTGGATTGAAGTTACATCTGGCTGGC |
| AACTAACTGGCACGCACCAGATTACTTTTGATGTAGCACCAGTTGCAGGT |
| TTGAAGTTCCGTATTCGAAGGGAAGTACAAAAAGAATATCCATACGCTGA |
| GTTTGACCGTGGTGTTACCTTGGATATGAAGTCTTTAAATGGTTCTTTCA |
| TTCATATACTGGAGATTACACAGGAGTTACTTGACGGGTTTTATCCAGAA |
| GGATACTTCATTAAACAGAATGTAAGCTGGGCGGCAATAAGATTACTGA |
| TTTGGCTGATGCACAAATCCGGGAGATGCAGTAAATAAAGGGCAGCTTG |
| ATGCCATCGACAAGAAGCATACAGATTGGAACGCCAACAGGACATTGAG |
| ATTGCTGGCCTTAAGGCTGGTATGACTTCTGGTATTGCGCACAGAACTGT |
| TCCTTGGTACACGATAGCCCAAGGTGGTGAGATTTCCGTAAAACCACCTT |
| ATGAATTTCAAGATGCACTAGTTTTCCTTAATGGGGTATTGCAGCACCAA |
| ATTGTAGGCGCATACTCTATAAGCAACAACACTACTTGCAGACC |
| GCTTGTGGCTGGTACAGAGGTGTATGCTGATTGGTAGTCGTGTGGCTA |
| CATCTGAACCTAATATTCAGTTGGAGTTGAACTTTGACTTAGTAGAAGGC |
| CAACAAGTAGTACAGATTGGCTCTGCATTTAAGTACATTGAGGTCTACCT |
| TGATGGATTATTACAACCTAAACTTGCTTATCAGGTAGACGGTAGGTGACATTG |
| TTACTTTCTCAGAAAGAGTACCAGAATGCCGGATGACTGCTAAGATTATC |
| ACAGCATAAGGAGGTGGGATGATTAACTCCGAACTGGTAGATAGTGGTGT |
| GAAGCTTGCGCCACCTGCACTCATATCAGGTGGGTACTTCCTCGGTATCA |
| GTTGGGATAATTGGGTGTTAATAGCAACATTCATTTATACCGTGTTGCAA |
| ATTGGGGACTGGTTTTATAATAAGTTCAAGATTTTGGAGGGAGAAGCGTGA |
| GCGTACACAATAAACATGCAGCTACGAGGACGAGGTTGGCATTCTGCAT |
| GGTGCTATTACCAAAATCTTCAATAAGAAAGCACAGGCAATACTGGACAC |
| TATAGAAGAGACCCTGATGCAGCATTACATTTAGTGTCTGGTAAGGATA |
| TTGGTGCGATGTGTAAGTGGGTTCTTGATAACGGCATTACCGCCACACCT |
| GCTGCACAGCAGGAAGAGTCCAAGTTATCTAAGCGCCTCAAGGCTATCCG |
| AGAGGCATCCAGTGGTAAGATAATTCAATTCACTAAGGAGGATTGATGGC |
| TAAGGCAAGAGAATCACAAGCGGAGGCTCTTGCCAGATGGGAGATGCTAC |
| AGGAGTTACAGCAGACCTTTCCTTACACCGCGGAAGGTTTGCTTCTCTTT |
| GCAGATACAGTTATTCATAACTTAATTGCAGGCAACCCTCATCTGATTCG |
| TATGCAGGCGGATATCTTGAAGTTCCTATTTTACGGACACAAGTACCGCC |
| TCATCGAAGCGCCTCGTGGTATCGCTAAGACAACACTATCAGCAATCTAT |
| ACGGTATTCCGTATTATTCATGAACCGCATAAGCGTATCATGGTTGTGTC |
| CCAAAACGCAAGCGAGCAGGAGAAATCGCAGGTTGGGTAGTTAAAATCT |
| TCCGTGGCTTAGACTTTCTTGAGTTTATGCTGCCGGATATCTACGCTGGG |
| GACCGTGCATCCGTTAAGGCGTTTGAGATTCATTACACCCTACGTGGTAG |
| TGATAAGTCTCCTTCTGTATCCTGTTACTCAATCGAAGCAGGTATGCAGG |
| GTGCTCGTGCTGATATTATTCTAGCGGATGACGTAGAGTCGATGCAGAAT |
| GCTCGTACGGCAGCGGGCCGTGCCTTGCTTGAGGAGCTGACTAAGGAGTT |
| TGAATCTATCAACCAGTTTGGGGATATCATTTACCTTGGTACACCTCAGA |
| ACGTAAACTCTATCTACAACAACCTACCTGCTCGTGGTTACTCTGTTCGT |
| ATCTGGACTGCGCGTTACCCTTCAGTAGAGCAAGAGCAATGTTATGGCGA |
| CTTCCTTGCACCTATGATTGTTCAAGATATGAAGGACAACCCAGCACTTC |
| GCTCAGGGTACGGGTTGGATGGTAATAGTGGTGCACCTTGTGCCCCTGAA |
| ATGTATGATGATGAAGTCCTGATTGAGAAGGAAATCTCTCAGGGTGCTGC |
| TAAGTTCCAGCTTCAGTTCATGCTTAACACTCGCATGATGGATGCTGACA |
| GATACCCATTACGCCTGAACAATCTAATCTTCACCTCGTTTGGTACAGAG |
| GAAGTCCCTGTGATGCCTACGTGGAGTAATGATTCCATAAACATCATTGG |
| TGATGCACCTAAGTATGGTAACAAGCCTACGGATTTCATGTACAGACCTG |
| TAGCTCGCCCATATGAATGGGGTGCTGTCTCCCGCAAGATTATGTATATT |
| GACCCTGCGGGTGGTGGTAAGAACGGAGATGAGAACGGGTGTAGCCATCGT |
| ATTCCTGCACGGCACATTCATTTATGTGTATCAGTGCTTTGGTGTACCTG |
| GCGGATACCGAGAGTCGTCCCTGAATCGCATTGTGCAGGCCGCAAAGCAG |
| GCGGGTGTTAAAGAGGTATTCATTGAGAAGAACTTTGGTCATGGCGCGTT |
| TGAGGCGGTAATTAAGCCGTACTTTGAACGAGAGTGGCCTGTAACTCTGG |
| AAGAGGATTACGCCACCGGACAGAAAGAGTTGCGTATCATTGAGACGCTG |
| GAGCCGCTCATGGCAGCCCATAGGCTTATCTTCAATGCAGAGATGGTGAA |
| GTCAGACTTTGAGTCGGTACAGCACTATCCGCTTGAACTACGCATGTCCT |
| ACAGTCTTTTCAATCAAATGTCGAACATAACGATTGAGAAGAACAGCCTC |
| CGGCACGATGACCGCCTAGACGCCCTGTATGCGCTATACGGCAATTAAC |
| TTCTCAGATAGACTATGACGAGGTTACAGGGATTAATCGCCTCAGAGCGC |
| AGGAGATGCGCGATTACATCCATGCTATGAACACCTCATCTACGCAGG |
| GCAATGCTATATGGAGATTACGGTACTGAGCGAAGAGTGACCAACACTTC |
| CGTAGCGATGCAGCAGCGAGTTTACGGCAGAACTACCGAAATAAATCGG |
| CAAGCAGAAATACACTTTCTGCAAGGATTTCAAGGACTTATTAATTACTG |
| GACACTATAGAAGGAAGGCCCAGATAATAAGAGAAAATAATAGGTAATAT |
| ATATATAGGTTAACCTAGGTTATATAGGTATGCCTTAGTATGGGTGTACT |
| CCTGTACACCCTATTCCTTACTACCTTACTATATTTACATAATAGGAAGG |
| AGACAATGCTAATGATTATAGTAGTCAACCATTAACAGGTAAGTCTAAG |
| AGAAAGCAGGTACAACCTGTAAGTGAAGAACTAATGCTTCCGGTGCTCAA |
| AAAAGAGGAAGTTAGTAAGAAAAGCAATGTTATTAATGATGCCACCAAAT |
| CAGGTAAACAGAAAGGGCCATGGTGCCTTGAAGTGAAAGGTGGTTA |
| TTGAAGATTGCTATCGCGGTTGATGCAAAGAAGATTCAGAGTGGAAGTT |
| AGTAACAGTGGAACCAACTGTTAACCCAGTTTAAGATAAGGAGGAAGATT |
| ACATGGCTAAATATGGTACTACAGGTTCTGTTACTGGTCAGGCTTTTCGA |
| GTAAAAGCAGTACAAACTATTGCAACGGCAATCCCGATGCCTGTTGTTAA |
| AGAAGAAGACTTAAGAGTAAAGACCACCCTATCACATCAAACATTTAT |
| CAGGTAAACAGAAAGGTGCAATGGTTGCTCTTGAGAAAGGTGACACAACC |
| TTACATATTGCTGTTGCACGTGGTAGTGAACCCACAGACCCTTGGGATGT |
| AACTGGTATGGAAAAAGGACGCTGTTACTCCAGCAGGGTATAATAATGCT |
| TAATAAATACTTCAAGCGTAAAGAGTTTGCCGTTGTGGGTGCGGTA |
| CATCCACTGTTGATGCTGAATTACTACAGGTAGTCACAGATGTGCGTGAG |
| CACTTTGGTTCTCCTGTAGTTATCACTTCGGGTCATCGCTGTGCTAAGCA |
| CAATGCCAATGTAGGTGGCGCTAAGAACTCCATGCATCTTACTGGTAAGG |
| CTGCTGACATTAAAGTGTCTGGCATATTACCTTCTGAAGTGCATAAGTAT |
| CTTACTAGCAAATACCAAGGCAAGTATGGTATAGGTAAGTATAACTCCTT |
| CACTCACATCGATGTACGGGATGGTTGTGCGCGATGGTAAGATGTGTTGA |
| ATGGTGTGAGCGTATGGTTGCCCAAGCTGCCGAGGATGGCAACTATGATG |
| ACTGGAAGACTCTGCTGCTTGGACTCAATGGAAAGGGAGATGCAAT |
| GAAAAAGCTGTTTAAGTCTAAGAAGGTTAGGTGCACTGGTTGCACTTG |
| TTATTGCTCTTGTTTCTGTAGGTCTTGGTGTAGACCTTGGCTCTGGCACG |
| GAATCCTCTGTGACAGATGTGGTCTGCCAAGTGATCACCTGTGAATAAGT |
| TTCTAGAAGTTCTGGCAGGTCTTATTGGCCTGCTTGTCTCGCTAAGAAG |
| AAACAAGAAGAAGGGAGGCACAAAGTGAAGCGAATCATGTTAGTGACAA |
| CCCTTCTGATTGGTTCGCTGACCACTTCCGGGTGTCAGCAGGCGTTACCA |
| GAGAAAGCAATGGTGAAACCTCTGAGGCCGACGCTGACGGCAGTTTACGA |
| GGTAGACGATAAGGTCTGTTTAGTAAGCCTGACGCTACAAACTTGGTT |
| TGTACATTCTCTCGCTAGAACGCGGATACAATTAATACATAGCTTTATGT |
| ATCAGTGTCTTACGATTTACTGGACACTATAGAAGAGGTAAGATAGCGCC |
| GTTCTTTTGAGCGGCCTATTACTAGCCAATCTTCATAGGGAGGGTTGGAA |
| AGTAATAGGAGATAGCATGCTAACAAACCTAATACTGAAGGAA |
| TCTTGCATAAAGGACAATCTTTGTATGAGTACCTTGATGCGAGAGTTTTA |
| ACATCAAAGCCGTTTGGTGCTGCAGGTGACGCCACTACTGATGATACGGA |
| GGTTATAGCTGCTTCATTAAACTCTCAGAAAGCTGTCACAGTCTCAGATG |
| GTGTATTCTCTAGCTCTGGTATTAACAGTAATTACTGTAACTTAGACGGC |
| AGGGGTAGTGGCGTGCTAAGTCACCGTTCAAGTACAGGTAACTACTTAGT |
| ATTTAACAATCTACGTGCAGGTCGCTTAAGTAATATTACGGTAGAAGTA |
| ATAAGGCGACTGATACAACTCAGGGACAGCAGGTATCCCTTGCTGGTGGA |
| AGTGATGTTACTGTAAGTGACGTTAACTTCTCAAACGTTAAAGGTACTGG |
| TTTCAGTTTAATCGCATACCCTAATGATGCGCCACCTGATGGACTTATGA |
| TTAAAGGCATTCAGGGTAGCTATTCCGGCTATGCTACTAATAAGGCAGCC |
| GGATGCGTACTTGCTGATTCCTCAGTTAACTCCCTCATAGATAACGTCAT |
| TGCTAAGAACTACCCTCAGTTCGGAGCAGTAGAGTTGAAAGGTACAGCCA |
| GTTACAACAGTAGTCAGTAATGTTATAGGGACAGATTGCCAGCATGTAACT |
| TACAACGGCACTGAAGGGCCAATAGCTCCTTCTAATAACCTTATCAAGGG |
| GGTGATGGCTAATAACCCTAAGTATGCAGCGGTTGTTGCAGGCAAAGGAA |
| GTACGAACTTAATCTCAGACGTGCTCGTAGATTACTCAACTTCTGATGCT |

| Bacteriophage Genome Sequences |
|---|
| AGGCAGGCTCATGGTGTTACAGTAGAGGGTTCTGATAACGTCATAAATAA |
| TGTGCTTATGTCAGGATGTGATGGTACTAACTCTTTAGGACAAGGGCAGA |
| CTGCTACAATTGCACGCTTTATAGGTACAGCTAATAACAACTATGCGTCT |
| GTATTTCCTAGCTACAGTGCTACAGGTGTTATTACTTTCGAATCCGGCTC |
| TACCCGTAACTTCGTAGAGGTAAAGCACCCTGGCAGGAGAAACGACCTTC |
| TCAGTTCTGCTAGTACTATTGACGGTGCAGCTACTATTGACGGCACTAGT |
| AATAGTAACGTAGTGCACGCACCTGCCTTAGGGCAGTACATAGGTAGTAT |
| GTCAGGTAGGTTCGAATGGCGGATTAAGTCCATGTCACTCCCTTCAGGCG |
| TTCTTACTTCTGCTGATAAGTACAGAATGCTTGGAGATGGTGCTGTGTCA |
| TTAGCTGTAGGTGGGGGCACTTCTTCTCAAGTTCGCCTATTTACTTCTGA |
| TGGTACTTCTCGGACAGTGTCCCTCACCAACGGTAACGTGCGTCTTTCTA |
| CCAGTAGCACAGGCTTTTTGCAGTTAGGTGCTGATGCAATGACCCCAGAC |
| AGTACTGGTACATACGCATTAGGTTCCGCCAGCCGAGCATGGTCTGGCGG |
| TTTTACTCAAGCAGCATTCACTGTTACCTCAGATGCTCGGTGTAAAACAG |
| AACCTCTTACTATCTCAGATGCCTTACTGGATGCTTGGTCTGAAGTTGAC |
| TTTGTGCAGTTTCAGTATTTGGATCGTGTTGAGGAGAAGGGTGCAGACTC |
| AGCTAGATGGCACTTCGGTATCATCGCTCAGCGAGCTAAGGAGGCTTTCG |
| AACGTCACGGTATAGATGCACATCGCTATGGCTTCTTGTGCTTCGACAGT |
| TGGGATGATGTATACGAGGAAGATGCCAATGGCTCTCGTAAACTGATTAC |
| ACCAGCAGGTTCCCGCTACGGTATTCGTTACGAGGAAGTACTGATATTGA |
| AGGCTGCGTTGATGCGGCGGACTATTAAGCGTATGCAGGAAGCACTAGCT |
| TCCCTGCCTAAGTAAGCAACAGGCAGTGCGTAAGCACTGCTTTTAGCGCA |
| ACTTTTCTTAAAGGTTATCACGGTGGTAGCCTTTCAGAAAAGGAGGTTAC |
| ATGATTCAAAGACTAGGTTCTTCATTAGTTAAATTCAAGAGTAAAATAGC |
| AGGTGCAATCTGGCGTAACTTGGATGCAAGCTCACCGAGGTTGTATCGC |
| TTAAAGATTTTGGAGCCAAAGGTGATGGTAAGACAAACGACCAAGATGCA |
| GTAAATGCAGCGATGGCTTCAGGTAAGAGAATTGACGGTGCTGGTGCTAC |
| TTACAAAGTATCATCTTTACCTGATATGGAGCGTATTCTATAACACCCGT |
| TCGTATGGGAACGTTTAGCAGGTCAACCTCTTTACTATGTGAGTAAAGGT |
| TTTATCAATGGTGAACTATATAAAATCACGGATAACCCTTATTACAATGC |
| TTGGCCTCAAGACAAAGCGTTTGTATATGAGAACGTGATATATGCACCTT |
| ACATGGGTAGTGACCGTCATGGTGTTAGTCGTCTGCATGTATCATGGGTT |
| AAGTCTGGTGACGATGGTCAAACATGGTCTACTCCAGATGGTTAACTGA |
| TCTGCATCCAGATTACCCTACAGTGAACTATCATTGTATGAGTATGGGTG |
| TATGTCGCAACCGTCTGTTTGCCATGATTGAAACACGTACTTTAGCCAAG |
| AACAAACTAACCAATTGTGCATTGTGGGATCGCCCTATGCTCTCGTAGTC |
| GCATCTTACTGGTGGTATCACTAAGGCTGCAAATCAGCAATATGCAACAA |
| TACATGTACCAGATCACGGACTATTCGTGGGCGATTTTGTTAACTTCTCT |
| AATTCTGCGGTAACAGGTGTATCAGGTGATATGACTGTTGCAACGGTAAT |
| AGATAAGGACAACTTCACGGTTCTTACACCTAACCAGCAGACTTCAGATT |
| TGAATAACGCTGGAAAGAGTTGGCACATGGGTACTTCTTTCCATAAGTCT |
| CCATGGCGTAAGACAGATCTTGGTCTAATCCCTAGTGTCACAGAGGTGCA |
| TAGCTTTGCTACTATTGATAACAATGGCTTTGTTATGGGCTATCATCAAG |
| GTGATGTAGCTCCACGAGAAGTTGGTCTTTTCTACTTCCCTGATGCTTTC |
| AATAGCCCATCTAATTATGTTCGTCGTCAGATACCATCTGAGTATGAACC |
| AGATGCGTCAGAGCCATGCATCAAGTACTATGACGGTGTATTATACCTTA |
| TCACTCGTGGCACTCTTGGTGACAGACTTGGAAGCTCTTTGCATCGTAGT |
| AGAGATATAGGTCAGACTTGGGAGTCACTGAGATTTCCACATAATGTTCA |
| TCATACTACCCTACCTTTTGCTAAAGTAGGAAGATGACCTTATTATGTTTG |
| GTTCAGAACGTGCAGAAAATGAATGGGAAGCAGGTGCACCAGATGATCGT |
| TACAAGGCATCTTATCCTCGTACCTTCTATGCACGATTGAATGTAAACAA |
| TTGGAATGCAGATGATATTGAATGGGTTAACATCACAGACCAAATCTATC |
| AAGGTGACATTGTGAACTCTAGTGTAGGTGTAGGTTCGGTAGTAGTTAAA |
| GACAGCTACATTTACTATATCTTTGGTGGCGAAAACATTTCAACCCAAT |
| GACTTATGGTGACAACAAAGGTAAAGACCCATTTAAAGGTCATGGACACC |
| CTACTGATATATACTGCTATAAGATGCAGATTGCAAATGACAATCGTGTA |
| TCTCGTAAGTTTACATATGGTGCAACTCCGGGTCAAGCTATACCTACTTT |
| CATGGGTACTGATGGAATACGAAATATCCCTGCACCTTTGTATTTCTCAG |
| ATAACATTGTTACAGAGGTACTAAAGTTGGACACTTAACACTTAAAGCA |
| AGCACAAGTTCCAATATACGATCTGAAGTGCAGATGGAAGGTGAATATGG |
| CTTTATTGGCAAGTCTGTTCCAAAGGACAACCCAACTGGTCAACGTTTGA |
| TTATTTGGTGGAGAAGAGACTTCGTCCTCTTCAGGTGCACAGATAACT |
| TTGCACGGCTCTAATTCAAGTAAGGCTAATCGTATCACTTATAACGAAAA |
| TGAGCACCTATTCCAAGGTGCACCAATCATGCCTGCTGTAGATAACCAGT |
| TTGCTGCTGGTGGACCTAGTAACCGATTCACTACCATCTACCTAGGTAGT |
| GACCCTGTTACAACTTCAGATGCTGACAACAATGACAGTATCTCAGGTA |
| TAATACCAAGGTGTTAAAGGCTTGGAGCAGGGTTGGTTTTAAACAGTATG |
| GTTTGAATAGTGAAGCAGAAGAGGGACCTTGATAGCATACACTTCGGTGTC |
| TTGGCTCAGGATATTGTAGCTGCTTTTGAAGCTGAAGGGTTGGATGCCAT |
| TAAGTATGGAATTGTGTCCTTCGAAGAAGGTAGGTACGGTGTGAGGTATA |
| GTGAAGTTCTAATACTAGAGGCTGCTTATACTCGTTATCGTTTAGACAAG |
| TTAGAGGAGATGTATGCCACTAATAAAATCGTTAAGCAAGCTGCTGTAC |
| TCCAGAACACAGAAGAGCTTATTCAATCAGGACGTGACCCTAAGCAGGCT |
| TATGCCATTGCCAAGGATGTTCAACGTCGTGCCATGAAGAAACCTTCTGC |
| ATCTTCTGCGTAAGCAGGTTAATATCTTAGTATAAACAAGGGCAGACTTA |
| GGTTTGTCCTTAGTGTATTCCAAAGGAGGTAACATGCTGAAAGATGGTTG |
| GGTTTCATATGACCCTACAGACCCTAAGAATTGGCTACAGGTTATCGCTA |

| Bacteriophage Genome Sequences |
|---|
| TAGCTTGTGCAGGTAGCCTATTGGCTGCCCTGATGTATTCATTATGGATG |
| TACACAAAGTAACCAAAGTCAAAATTTTGATGTAGGCGTGTGTCAGCTCT |
| CTCGCCCTCGCCCTCGCCGGGTTGTCCCCATAGGGTGGCCTGAGGGAATC |
| CGTCTTCGACGGGCAGGGCTGATGTACTCCTTGTCTAGTACAAGGGAGGC |
| GGAGGGAACGCCTAGGGAGGCCTAGGAATGGCTTAGTGGTGGACAAGGTG |
| ATTACCTTAGTGAAGCCTCTTAGTGCATTCCTGAGGCCATTCAGGGCGTT |
| TATGAGGGATTGACAGGGTGTGAGGGCGTGGGCTA |

SEQ ID NO: 34 - YAC pRS415
| |
|---|
| TGAGGTAACTCACATTAATTGCGTTGCGCTCACTGCCCGCTTTCCAGTCG |
| GGAAACCTGTCGTGCCAGCTGCATTAATGAATCGGCCAACGCGCGGGGAG |
| AGGCGGTTTGCGTATTGGGCGCTCTTCCGCTTCCTCGCTCACTGACTCGC |
| TGCGCTCGGTCGTTCGGCTGCGGCGAGCGGTATCAGCTCACTCAAAGGCG |
| GTAATACGGTTATCCACAGAATCAGGGGATAACGCAGGAAAGAACATGTG |
| AGCAAAAGGCCAGCAAAAGGCCAGGAACCGTAAAAAGGCCGCGTTGCTGG |
| CGTTTTTCCATAGGCTCCGCCCCCCTGACGAGCATCACAAAAATCGACGC |
| TCAAGTCAGAGGTGGCGAAACCCGACAGGACTATAAAGATACCAGGCGTT |
| TCCCCCTGGAAGCTCCCTCGTGCGCTCTCCTGTTCCGACCCTGCCGCTTA |
| CCGGATACCTGTCCGCCTTTCTCCCTTCGGGAAGCGTGGCGCTTTCTCAT |
| AGCTCACGCTGTAGGTATCTCAGTTCGGTGTAGGTCGTTCGCTCCAAGCT |
| GGGCTGTGTGCACGAACCCCCCGTTCAGCCCGACCGCTGCGCCTTATCCG |
| GTAACTATCGTCTTGAGTCCAACCCGGTAAGACACGACTTATCGCCACTG |
| GCAGCAGCCACTGGTAACAGGATTAGCAGAGCGAGGTATGTAGGCGGTGC |
| TACAGAGTTCTTGAAGTGGTGGCCTAACTACGGCTACACTAGAAGGACAG |
| TATTTGGTATCTGCGCTCTGCTGAAGCCAGTTACCTTCGGAAAAAGAGTT |
| GGTAGCTCTTGATCCGGCAAACAAACCACCGCTGGTAGCGGTGGTTTTTT |
| TGTTTGCAAGCAGCAGATTACGCGCAGAAAAAAAGGATCTCAAGAAGATC |
| CTTTGATCTTTTCTACGGGGTCTGACGCTCAGTGGAACGAAAACTCACGT |
| TAAGGGATTTTGGTCATGAGATTATCAAAAAGGATCTTCACCTAGATCCT |
| TTTAAATTAAAAATGAAGTTTTAAATCAATCTAAAGTATATATGAGTAAA |
| CTTGGTCTGACAGTTACCAATGCTTAATCAGTGAGGCACCTATCTCAGCG |
| ATCTGTCTATTTCGTTCATCCATAGTTGCCTGACTCCCCGTCGTGTAGAT |
| AACTACGATACGGGAGGGCTTACCATCTGGCCCCAGTGCTGCAATGATAC |
| CGCGAGACCCACGCTCACCGGCTCCAGATTTATCAGCAATAAACCAGCCA |
| GCCGGAAGGGCCGAGCGCAGAAGTGGTCCTGCAACTTTATCCGCCTCCAT |
| CCAGTCTATTAATTGTTGCCGGGAAGCTAGAGTAAGTAGTTCGCCAGTTA |
| ATAGTTTGCGCAACGTTGTTGCCATTGCTACAGGCATCGTGGTGTCACGC |
| TCGTCGTTTGGTATGGCTTCATTCAGCTCCGGTTCCCAACGATCAAGGCG |
| AGTTACATGATCCCCCATGTTGTGCAAAAAAGCGGTTAGCTCCTTCGGTC |
| CTCCGATCGTTGTCAGAAGTAAGTTGGCCGCAGTGTTATCACTCATGGTT |
| ATGGCAGCACTGCATAATTCTCTTACTGTCATGCCATCCGTAAGATGCTT |
| TTCTGTGACTGGTGAGTACTCAACCAAGTCATTCTGAGAATAGTGTATGC |
| GGCGACCGAGTTGCTCTTGCCCGGCGTCAATACGGGATAATACCGCGCCA |
| CATAGCAGAACTTTAAAAGTGCTCATCATTGGAAAACGTTCTTCGGGGCG |
| AAAACTCTCAAGGATCTTACCGCTGTTGAGATCCAGTTCGATGTAACCCA |
| CTCGTGCACCCAACTGATCTTCAGCATCTTTTACTTTCACCAGCGTTTCT |
| GGGTGAGCAAAAACAGGAAGGCAAAATGCCGCAAAAAAGGGAATAAGGGC |
| GACACGGAAATGTTGAATACTCATACTCTTCCTTTTTCAATATTATTGAA |
| GCATTTATCAGGGTTATTGTCTCATGAGCGGATACATATTTGAATGTATT |
| TAGAAAAATAAACAAATAGGGGTTCCGCGCACATTTCCCCGAAAAGTGCC |
| ACCTGGGTCCTTTTCATCACGTGCTATAAAAATAATTATAATTTAAATTT |
| TTTAATATAAATATATAAATTAAAAATAGAAAGTAAAAAAAGAAATTAAA |
| GAAAAAATAGTTTTTGTTTTCCGAAGATGTAAAAGACTCTAGGGGGATCG |
| CCAACAAATACTACCTTTTATCTTGCTCTTCCTGCTCTCAGGTATTAATG |
| CCGAATTGTTTCATCTTGTCTGTGTAGAAGACCACACACGAAAATCCTGT |
| GATTTTACATTTTACTTATCGTTAATCGAATGTATATCTATTTAATCTGC |
| TTTTCTTGTCTAATAAATATATATGTAAAGTACGCTTTTTGTTGAAATTT |
| TTTAAACCTTTGTTTATTTTTTTTTCTTCATTCCGTAACTCTTCTACCTT |
| CTTTATTTACTTTCTAAAATCCAAATACAAAACATAAAAATAAATAAACA |
| CAGAGTAAATTCCCAAATTATTCCATCATTAAAAGATACGAGGCGCGTGT |
| AAGTTACAGGCAAGCGATCCGTCCTAAGAAACCATTATTATCATGACATT |
| AACCTATAAAAATAGGCGTATCACGAGGCCCTTTCGTCTCGCGCGTTTCG |
| GTGATGACGGTGAAAACCTCTGACACATGCAGCTCCCGGAGACGGTCACA |
| GCTTGTCTGTAAGCGGATGCCGGGAGCAGACAAGCCCGTCAGGGCGCGTC |
| AGCGGGTGTTGGCGGGTGTCGGGGCTGGCTTAACTATGCGGCATCAGAGC |
| AGATTGTACTGAGAGTGCACCATACGCTACGTGAAGGCGTTTCG |
| ACAGATAAAATTCTTGAGGGAACTTTCACCATTATGGGAAATGGTTCAA |
| GAAGGTATTGACTTAAACTCCATCAAATGGTCAGTCATTGAGTGTTTTT |
| TATTTGTTGTATTTTTTTTTTTTAGAGAAAATCCTCCAATATCAAATTA |
| GGAATCGTAGTTTCATGATTTTCTGTTACACCTAACTTTTTGTGTGGTGC |
| CCTCCTCCTTGTCAATATTAATGTTAAAGTGCAATTCTTTTTCCTTATCA |
| CGTTGAGCCATTAGTATCAATTGCTTACCTGTATTCCTTTACTATCCTC |
| CTTTTTCTCCTTCTTGATAAATGTATGTAGATTGCGTATATAGTTTCGTC |
| TACCCTATGAACATATTCCATTTTGTAATTTCGTGTCGTTTCTATTATGA |
| ATTTCATTTATAAAGTTTATGTACAAATATCATAAAAAAAGAGAATCTTT |
| TTAAGCAAGGATTTTCTTAACTTCTTCGGCGACAGCATCACCGACTTCGG |
| TGGTACTGTTGGAACCACCTAAATCACCAGTTCTGATACCTGCATCCAAA |

Bacteriophage Genome Sequences

```
ACCTTTTTAACTGCATCTTCAATGGCCTTACCTTCTTCAGGCAAGTTCAA
TGACAATTTCAACATCATTGCAGCAGACAAGATAGTGGCGATAGGGTCAA
CCTTATTCTTTGGCAAATCTGGAGCAGAACCGTGGCATGGTTCGTACAAA
CCAAATGCGGTGTTCTTGTCTGGCAAAGAGGCCAAGGACGCAGATGGCAA
CAAACCCAAGGAACCTGGGATAACGGAGGCTTCATCGGAGATGATATCAC
CAAACATGTTGCTGGTGATTATAATACCATTTAGGTGGGTTGGGTTCTTA
ACTAGGATCATGGCGGCAGAATCAATCAATTGATGTTGAACCTTCAATGT
AGGGAATTCGTTCTTGATGGTTTCCTCCACAGTTTTTCTCCATAATCTTG
AAGAGGCCAAAACATTAGCTTTATCCAAGGACCAAATAGGCAATGGTGGC
TCATGTTGTAGGGCCATGAAAGCGGCCATTCTTGTGATTCTTTGCACTTC
TGGAACGGTGTATTGTTCACTATCCCAAGCGACACCATCACCATCGTCTT
CCTTTCTCTTACCAAAGTAAATACCTCCCACTAATTCTCTGACAACAACG
AAGTCAGTACCTTTAGCAAATTGTGGCTTGATTGGAGATAAGTCTAAAAG
AGAGTCGGATGCAAAGTTACATGGTCTTAAGTTGGCGTACAATTGAAGTT
CTTTACGGATTTTTAGTAAACCTTGTTCAGGTCTAACACTACCGGTACCC
CATTTAGGACCACCCACAGCACCTAACAAAACGGCATCAACCTTCTTGGA
GGCTTCCAGCGCCTCATCTGGAAGTGGGACACCTGTAGCATCGATAGCAG
CACCACCAATTAAATGATTTTCGAAATCGAACTTGACATTGGAACGAACA
TCAGAAATAGCTTTAAGAACCTTAATGGCTTCGGCTGTGATTTCTTGACC
AACGTGGTCACCTGGCAAAACGACGATCTTCTTAGGGGCAGACATAGGGG
CAGACATTAGAATGGTATATCCTTGAAATATATATATATATTGCTGAAAT
GTAAAAGGTAAGAAAAGTTAGAAAGTAAGACGATTGCTAACCACCTATTG
GAAAAAACAATAGGTCCTTAAATAATATTGTCAACTTCAAGTATTGTGAT
GCAAGCATTTAGTCATGAACGCTTCTCTATTCTATATGAAAAGCCGGTTC
CGGCCTCTCACCTTTCCTTTTTCTCCCAATTTTTCAGTTGAAAAAGGTAT
ATGCGTCAGGCGACCTCTGAAATTAACAAAAAATTTCCAGTCATCGAATT
TGATTCTGTGCGATAGCGCCCCTGTGTGTTCTCGTTATGTTGAGGAAAAA
AATAATGGTTGCTAAGAGATTCGAACTCTTGCATCTTACGATACCTGAGT
ATTCCCACAGTTAACTGCGGTCAAGATATTTCTTGAATCAGGCGCCTTAG
ACCGCTCGGCCAAACAACCAATTACTTGTTGAGAAATAGAGTATAATTAT
CCTATAAATATAACGTTTTTGAACACACATGAACAAGGAAGTACAGGACA
ATTGATTTTGAAGAGAATGTGGATTTTGATGTAATTGTTGGGATTCCATT
TTTAATAAGGCAATAATATTAGGTATGTGGATATACTAGAAGTTCTCCTC
GACCGTCGATATGCGGTGTGAAATACCGCACAGATGCGTAAGGAGAAAAT
ACCGCATCAGGAAATTGTAAACGTTAATATTTTGTTAAAATTCGCGTTAA
ATTTTTGTTAAATCAGCTCATTTTTTAACCAATAGGCCGAAATCGGCAAA
ATCCCTTATAAATCAAAAGAATAGACCGAGATAGGGTTGAGTGTTGTTCC
AGTTTGGAACAAGAGTCCACTATTAAAGAACGTGGACTCCAACGTCAAAG
GGCGAAAAACCGTCTATCAGGGCGATGGCCCACTACGTGAACCATCACCC
TAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGG
CGAGAAAGGAAGGGAAGAAAGCGAAAGGAGCGGGCGCTAGGGCGCTGGCA
AGTGTAGCGGTCACGCTGCGCGTAACCACCACACCCGCCGCGCTTAATGC
GCCGCTACAGGGCGCGTCGCGCCATTCGCCATTCAGGCTGCGCAACTGTT
GGGAAGGGCGATCGGTGCGGGCCTCTTCGCTATTACGCCAGCTGGCGAAA
GGGGGATGTGCTGCAAGGCGATTAAGTTGGGTAACGCCAGGGTTTTCCCA
GTCACGACGTTGTAAAACGACGGCCAGTGAGCGCGCGTAATACGACTCAC
TATAGGGCGAATTGGGTACCGGGCCCCCCCTCGAGGTCGACGGTATCGAT
AAGCTTGATATCGAATTCCTGCAGCCCGGGGGATCCACTAGTTCTAGAGC
GGCCGCCACCGCGGTGGAGCTCCAGCTTTTGTTCCCTTTAGTGAGGGTTA
ATTGCGCGCTTGGCGTAATCATGGTCATAGCTGTTTCCTGTGTGAAATTG
TTATCCGCTCACAATTCCACACAACATAGGAGCCGGAAGCATAAAGTGTA
AAGCCTGGGGTGCCTAATGAG
```

The Sequence Listing in the accompanying text file entitled "Sequence Listing" (created on Sep. 4, 2014 and having a size of 187 KB) is incorporated by reference herein.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A recombinant bacteriophage comprising:

a. a capsid head encoded by a subset of genomic fragments from a first bacteriophage; and b. tail fibers encoded by at least two subsets of genomic fragments, wherein each of the at least two subsets are from different bacteriophage having different host ranges, wherein the recombinant bacteriophage has a host range that is expanded as compared to the first bacteriophage.

2. The recombinant bacteriophage of claim 1, wherein a first subset of genomic fragments encoding the tail fibers is from a bacteriophage having the same host range as the first bacteriophage; and a second subset of genomic fragments encoding the tail fibers is from a second bacteriophage having a different host range from the first bacteriophage.

3. The recombinant bacteriophage of claim 2, wherein the recombinant bacteriophage has a host range that includes the host range of the first bacteriophage and the host range of the second bacteriophage.

4. The recombinant bacteriophage of claim 1, wherein a first subset of genomic fragments encoding the tail fibers is from a second bacteriophage having a different host range from the first bacteriophage; and a second subset of genomic fragments encoding the tail fibers is from a third bacteriophage different from both the first bacteriophage and the second bacteriophage.

5. The recombinant bacteriophage of claim 4, wherein the recombinant bacteriophage has a host range that includes the host range of the second bacteriophage and the host range of the third bacteriophage.

6. The recombinant bacteriophage of claim 1, wherein each of the different bacteriophage that the subsets of genomic fragments encoding tail fibers are from is selected independently from Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, Ampullaviridae, Bicaudaviridae, Clavaviridae, Globuloviridae, and Guttavirus.

7. The recombinant bacteriophage of claim 1, wherein the bacteriophage infects one or more bacterial species selected from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., and *Lactobacillus* spp.

8. The recombinant bacteriophage of claim 1, wherein bacteriophage infects one or more bacterial species selected from *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinomycetemcomitans, cyanobacteria, Escherichia coli, Helicobacter pylori, Selenomonas ruminantium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnoses, Lactobacillus casei, Lactobacillus acidophilus, Streptococcus Enterococcus faecalis, Bacillus coagulans, Bacillus cereus, Bacillus popilliae, Synechocystis* strain PCC6803, *Bacillus liquefaciens, Pyrococcus abyssi, Lactobacillus hilgardii, Streptococcus ferus, Lactobacillus pentosus, Bacteroides fragilis, Staphylococcus epidermidis, Zymomonas mobilis, Streptomyces phaechromogenes*, and *Streptomyces ghanaensis*.

9. A pharmaceutically acceptable composition comprising the recombinant bacteriophage of claim 1; and a pharmaceutically acceptable carrier.

10. A method of treating a bacterial infection by administering to a subject in need thereof the pharmaceutical composition of claim 9.

11. The method of claim 10, wherein the bacterial infection is caused by a bacteria selected from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., and *Lactobacillus* spp.

12. The method of claim 10, wherein the bacterial infection is caused by one or more bacterial species selected from *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus Enterococcus faecalis, Bacillus coagulans, Bacillus ceretus, Bacillus popillae, Synechocystis* strain PCC6803, *Bacillus liquefaciens, Pyrococcus abyssi Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes*, and *Streptomyces ghanaensis*.

* * * * *